US011952415B2

(12) United States Patent
Platt et al.

(10) Patent No.: US 11,952,415 B2
(45) Date of Patent: Apr. 9, 2024

(54) SCAFFOLD PROTEINS

(71) Applicant: Avacta Life Sciences Limited, Wetherby (GB)

(72) Inventors: Geoffrey William Platt, Wetherby (GB); Graham Robert Pye-Smith Spence, Wetherby (GB)

(73) Assignee: Avacta Life Sciences Limited, Wetherby (GB)

( * ) Notice: Subject to any disclaimer, the term of this patent is extended or adjusted under 35 U.S.C. 154(b) by 260 days.

(21) Appl. No.: 16/623,680

(22) PCT Filed: Jul. 2, 2018

(86) PCT No.: PCT/GB2018/051855
§ 371 (c)(1),
(2) Date: Dec. 17, 2019

(87) PCT Pub. No.: WO2019/008335
PCT Pub. Date: Jan. 10, 2019

(65) Prior Publication Data
US 2020/0181239 A1  Jun. 11, 2020

(30) Foreign Application Priority Data
Jul. 7, 2017  (GB) .................................... 1710973

(51) Int. Cl.
C07K 14/81 (2006.01)
C07K 16/28 (2006.01)
C07K 16/32 (2006.01)
C07K 16/42 (2006.01)
(52) U.S. Cl.
CPC ...... C07K 14/8139 (2013.01); C07K 16/2827 (2013.01); C07K 16/32 (2013.01); C07K 16/42 (2013.01); C07K 2318/20 (2013.01); C07K 2319/30 (2013.01); C07K 2319/31 (2013.01)
(58) Field of Classification Search
CPC ............ C07K 14/8139; C07K 16/2827; C07K 16/32; C07K 16/42; C07K 2318/20; C07K 2319/00; C07K 2319/30; C07K 2319/31
See application file for complete search history.

(56) References Cited

U.S. PATENT DOCUMENTS

| 8,481,491 | B2 | 7/2013 | Woodman et al. |
| 2008/0207509 | A1 | 8/2008 | Woodman et al. |

FOREIGN PATENT DOCUMENTS

| CN | 102056942 B | 5/2017 |
| JP | 2011-520786 A | 7/2011 |
| WO | WO 2006/131749 A2 | 12/2006 |
| WO | WO 2009/136182 A1 | 11/2009 |
| WO | WO 2014/125290 A1 | 8/2014 |
| WO | WO 2019/008335 A1 | 1/2019 |
| WO | WO 2019/197583 A1 | 10/2019 |

OTHER PUBLICATIONS

Katja Skrlec, Non-immunoglobulin scaffolds: a focus on their targets, Trends in Biotechnology, Jul. 2015, vol. 33, No. 7.*
Invitation to Pay Additional Fees dated Aug. 31, 2018 for Application No. PCT/GB2018/051855.
International Search Report and Written Opinion dated Oct. 24, 2018 for Application No. PCT/GB2018/051855.
International Preliminary Report on Patentability dated Jan. 16, 2020 for Application No. PCT/GB2018/051855.
Stadler et al., Structure-function studies of an engineered scaffold protein derived from Stefin A. II: Development and applications of the SQT variant. Protein Eng Des Sel. Sep. 2011;24(9):751-63. doi: 10.1093/protein/gzr019. Epub May 25, 2011.
PCT/GB2018/051855, dated Aug. 31, 2018, Invitation to Pay Additional Fees.
PCT/GB2018/051855, dated Oct. 24, 2018, International Search Report and Written Opinion.
PCT/GB2018/051855, dated Jan. 16, 2020, International Preliminary Report on Patentability.
Woodman et al., Design and validation of a neutral protein scaffold for the presentation of peptide aptamers. J Mol Biol. Oct. 7, 2005;352(5):1118-33.

* cited by examiner

Primary Examiner — Julie Ha
Assistant Examiner — Erinne R Dabkowski
(74) Attorney, Agent, or Firm — Wolf, Greenfield & Sacks, P.C.

(57) ABSTRACT

The invention relates to a polypeptide, such as an Affimer polypeptide, comprising an amino acid sequence having at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 1; characterised in that said polypeptide comprises one or more mutations relative to SEQ ID NO: 1 selected from the group consisting of: T51L, T51V, M65V, N32G, A59I, L38A, V20I, A40I, L38V, A12I, A12V, I16L, V20L, Q26E, E29M, T31K, N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K) and (T83D, Q86E). The invention also relates to various methods and nucleic acids.

32 Claims, 78 Drawing Sheets

Specification includes a Sequence Listing.

| Affimer Working ID | EGFR (FL1-A of QSH01) | mIgG2b (FL1-A of QSH03) | hIgG1 Fc (FL1-A of QSH05) |
|---|---|---|---|
| PBS (BLANK) | 1774 | 1167 | 1230 |
| PBS (BLANK) | 1734 | 1232 | 950 |
| PBS (BLANK) | 1705.5 | 1156 | 1062.5 |
| NEGATIVE - - HA (NEGATIVE) | 1768.5 | 1265.5 | 974 |
| NEGATIVE - - HA (NEGATIVE) | 1667.5 | 1132 | 1025 |
| NEGATIVE - - HA (NEGATIVE) | 1666 | 1136 | 1100 |
| NEGATIVE - - HA (NEGATIVE) | 1637.5 | 1027.5 | 1228.5 |
| MIGG2B G12 - HA (POSITIVE) | 1813 | 158466 | 1095 |
| MIGG2B G12 - HA (POSITIVE) | 1772 | 155424.5 | 1094 |
| MIGG2B G12 - HA (POSITIVE) | 1679 | 118498.5 | 1003 |
| MIGG2B G12 - HA (POSITIVE) | 1668 | 134053 | 1162 |
| 00451_644628 | 1722 | 1235 | 963 |
| 00451_644620 | 1764 | 1110 | 1154 |
| 00451_644599 | 1817 | 1224 | 1055 |
| 00451_644624 | 1717 | 1081.5 | 1144 |
| 00451_644654 | 1642 | 1055 | 1154 |
| 00451_644622 | 1543 | 1213 | 1052 |
| 00451_644633 | 1785 | 1141 | 1062 |
| 00451_644617 | 1750 | 1087 | 998 |
| 00451_644605 | 1736 | 1183 | 1051.5 |
| 00451_644671 | 1536 | 1052 | 1219 |
| 00451_644607 | 1725 | 1188.5 | 1117.5 |
| 00451_644691 | 1779 | 1127.5 | 1130 |
| 00451_644614 | 1768 | 1216 | 1087 |
| 00451_644634 | 1718 | 1142 | 1128.5 |
| 00451_644657 | 1627 | 1093 | 1097 |
| 00451_644644 | 1687.5 | 1174 | 1070 |
| 00451_644696 | 1771 | 1101.5 | 1141 |
| 00451_644670 | 1620 | 1030 | 1086 |
| 00451_644668 | 1689 | 1104.5 | 1115 |
| 00451_644588 | 1726 | 1167 | 1267 |
| 00451_644695 | 1796.5 | 1221 | 1232 |
| 00451_644656 | 1766 | 1134 | 1022 |

FIG. 12

| hPD-L2 (FL1-A of QSH06) | Her2 (R&D) (FL1-A of QSH08) | hPD-L1 (FL1-A of QSH10) | Trastuzumab (FL1-A of QSH11) | hIgG (FL1-A of QSH13) |
|---|---|---|---|---|
| 1303 | 866 | 1413 | 1543 | 1076 |
| 1223.5 | 808 | 1220.5 | 1376.5 | 995.5 |
| 1240 | 882 | 1200 | 1529 | 904.5 |
| 1243 | 822 | 1287 | 1359 | 1076 |
| 1064 | 790 | 1121 | 1252 | 976.5 |
| 1220 | 801 | 1471.5 | 1551.5 | 1033 |
| 1105 | 718 | 1024.5 | 1472 | 1058 |
| 1140 | 868 | 980.5 | 1469 | 1084.5 |
| 1240 | 1053 | 1452.5 | 1446.5 | 1215.5 |
| 1181 | 866 | 1087.5 | 1448 | 1037 |
| 1264 | 1011 | 1297 | 1529 | 1091 |
| 1276 | 2452.5 | 1164 | 1458 | 977.5 |
| 1284 | 2398 | 1282 | 1400 | 1044 |
| 1280.5 | 2129.5 | 1132 | 1495 | 1000 |
| 1152 | 1962 | 1146 | 1373 | 931 |
| 1134 | 1864.5 | 1080 | 1222 | 1003 |
| 1208.5 | 1027.5 | 1265 | 1551 | 1019 |
| 1235 | 930 | 1098 | 1255.5 | 1089.5 |
| 1323.5 | 867.5 | 1108 | 1327 | 979 |
| 1170 | 950.5 | 1178.5 | 1359 | 1084 |
| 1057 | 931 | 1022 | 1319 | 1009 |
| 1275 | 785 | 1052 | 1103 | 962 |
| 1165 | 893 | 1057 | 1470 | 954 |
| 1103 | 868 | 1249 | 1470.5 | 1208 |
| 1310.5 | 858 | 1327 | 1477 | 1038 |
| 1117 | 759 | 1115 | 1280.5 | 1101 |
| 1217 | 864 | 1383.5 | 1453 | 1067 |
| 1260 | 820 | 1197.5 | 1255 | 1043 |
| 1066 | 865.5 | 1205.5 | 1381 | 989 |
| 1248 | 729 | 1186.5 | 1341.5 | 1074 |
| 1167 | 849 | 1210 | 1451 | 1074 |
| 1280.5 | 968.5 | 1323.5 | 1411 | 1089 |
| 1286 | 965.5 | 1499 | 1437 | 1060 |

FIG. 12 (Continued)

| Her2 (Sino) (FL1-A of QSH15) | Her3 (FL1-A of QSH16) | mPD-L1 (FL1-A of QSH18) | No target ctr (FL1-A of QSH22) | Avastin (FL1-A of QSH23) |
|---|---|---|---|---|
| 1046 | 1411 | 1164.5 | 1623 | 1213 |
| 748.5 | 1303 | 1181 | 1373 | 1149 |
| 926 | 1292 | 1177 | 1491 | 1143 |
| 678 | 1343 | 1202 | 1465 | 1027.5 |
| 717.5 | 1408 | 1178 | 1381 | 1154 |
| 874 | 1410.5 | 1182.5 | 1559 | 1019 |
| 879 | 1208 | 1104.5 | 1392.5 | 1091 |
| 872 | 1268 | 1058.5 | 1221 | 1170 |
| 940 | 1370 | 1002.5 | 1506 | 1140.5 |
| 973 | 1431.5 | 1041 | 1408 | 1158.5 |
| 1003 | 1423 | 1229.5 | 1402 | 987 |
| 102773.5 | 1435 | 1272.5 | 1442 | 1092 |
| 91635 | 1435 | 1087.5 | 1485 | 1221.5 |
| 86041 | 1274.5 | 1122 | 1544.5 | 1278 |
| 84281 | 1361.5 | 1057 | 1342 | 1223 |
| 82266 | 1225 | 1117 | 1372 | 1095 |
| 14155 | 1206.5 | 1155 | 1388 | 1173 |
| 13150.5 | 1292 | 1017 | 1359 | 1244 |
| 3728 | 1408 | 1105 | 1336 | 1103 |
| 3138 | 1330 | 1108 | 1493 | 1029 |
| 1550 | 1217.5 | 1114 | 1352.5 | 1100 |
| 1547.5 | 1400 | 1076 | 1513 | 1315.5 |
| 1518 | 1361 | 1013 | 1497.5 | 1363.5 |
| 1434.5 | 1275.5 | 1225 | 1479.5 | 1131.5 |
| 1399.5 | 1370 | 1167 | 1435.5 | 1062 |
| 1356.5 | 1308 | 1114 | 1372 | 1208 |
| 1348 | 1237.5 | 1057 | 1493 | 1123.5 |
| 1348 | 1324 | 1121 | 1502 | 1163.5 |
| 1340 | 1205.5 | 1035 | 1332 | 941.5 |
| 1337 | 1315.5 | 1187 | 1516.5 | 1155.5 |
| 1334 | 1430.5 | 1160 | 1588 | 1189 |
| 1324 | 1528 | 1218.5 | 1350.5 | 1108 |
| 1308 | 1305 | 1141 | 1594 | 1183 |

FIG. 12 (Continued)

| Humira (FL1-A of QSH25) | Rituximab (FL1-A of QSH26) | mPD-L2 (FL1-A of QSH27) | Her4 (FL1-A of QSH28) |
|---|---|---|---|
| 990 | 2200 | 1242 | 1476.5 |
| 969 | 2059.5 | 1185.5 | 1397 |
| 926.5 | 1876.5 | 1181 | 1421 |
| 947.5 | 2073 | 1147.5 | 1254 |
| 863 | 1885 | 1119 | 1303 |
| 1014 | 2079 | 1074.5 | 1461 |
| 906 | 2005 | 1044 | 1375 |
| 853 | 2026.5 | 971 | 1311 |
| 996 | 2145 | 1177 | 1415 |
| 1039.5 | 2147 | 1149 | 1365 |
| 966 | 1998.5 | 1130 | 1462.5 |
| 963 | 2099.5 | 1099.5 | 1387.5 |
| 1108 | 2152 | 1001 | 1521 |
| 960 | 1975 | 1181 | 1345 |
| 1006 | 2023.5 | 1175.5 | 1404 |
| 968 | 1903 | 1081 | 1313.5 |
| 922.5 | 2046 | 1036 | 1466 |
| 985 | 1947 | 1111 | 1326.5 |
| 942 | 1979 | 1183 | 1291 |
| 989 | 2084 | 1181 | 1383 |
| 903.5 | 1929 | 1103 | 1283 |
| 896 | 2036 | 1059.5 | 1513 |
| 1052 | 2096.5 | 1224 | 1342 |
| 1044 | 2108 | 1119 | 1266.5 |
| 906 | 1984 | 1181 | 1406 |
| 855 | 2048.5 | 1183 | 1491 |
| 984 | 1971 | 1114 | 1332 |
| 981 | 2030 | 1197 | 1434 |
| 884 | 2032 | 996.5 | 1346 |
| 969 | 1939 | 1081 | 1293 |
| 1051 | 2005.5 | 1189 | 1418 |
| 861 | 2172 | 1273 | 1484.5 |
| 1004 | 2067 | 1212 | 1324 |

FIG. 12 (Continued)

| | | | |
|---|---|---|---|
| 00451_644719 | 1785 | 1130 | 1158 |
| 00451_644689 | 1663 | 1222 | 1057.5 |
| 00451_644631 | 1548 | 1244.5 | 1181 |
| 00451_644658 | 1693.5 | 1183.5 | 1022 |
| 00451_644717 | 1734 | 1172 | 1087 |
| 00451_644661 | 1753.5 | 1054.5 | 968.5 |
| 00451_644708 | 1780.5 | 1206.5 | 1172.5 |
| 00451_644655 | 1814 | 1155 | 1117 |
| 00451_644706 | 1626 | 993 | 1284 |
| 00451_644629 | 1763.5 | 1125 | 1116 |
| 00451_644619 | 1769.5 | 1122 | 1110 |
| 00451_644652 | 1643 | 1127 | 1041.5 |
| 00451_644609 | 1750 | 1179.5 | 1273 |
| 00451_644659 | 1729 | 1160.5 | 1099 |
| 00451_644703 | 1641.5 | 1061.5 | 939 |
| 00451_644660 | 1714 | 1121 | 1182 |
| 00451_644612 | 1733 | 1262 | 1021.5 |
| 00451_644667 | 1706 | 1261 | 983 |
| 00451_644653 | 1699 | 1132 | 959.5 |
| 00451_644645 | 1716 | 1139.5 | 1057.5 |
| 00451_644596 | 1830.5 | 1235 | 1103 |
| 00451_644643 | 1571 | 1009 | 990 |
| 00451_644697 | 1635.5 | 1127 | 1183.5 |
| 00451_644598 | 1690 | 1266 | 1121 |
| 00451_644707 | 1717 | 1269.5 | 1221 |
| 00451_644583 | 1708 | 1383.5 | 1237 |
| 00451_644714 | 1725 | 1151.5 | 1200 |
| 00451_644642 | 1693 | 1171 | 1150 |
| 00451_644621 | 1590 | 1153 | 1073 |
| 00451_644711 | 1615.5 | 961.5 | 1088 |
| 00451_644636 | 1644.5 | 1175 | 1158 |
| 00451_644632 | 1695 | 1113.5 | 1003.5 |
| 00451_644582 | 1830 | 1154 | 1173 |
| 00451_644722 | 1654 | 1179 | 1196 |
| 00451_644584 | 1736.5 | 1165 | 1100 |

FIG. 12 (Continued)

| | | | | |
|---|---|---|---|---|
| 1149 | 876.5 | 1240 | 1382 | 1077.5 |
| 1190 | 910 | 1141.5 | 1388 | 993 |
| 1375 | 760 | 1115 | 1348 | 969 |
| 1209.5 | 884 | 1224.5 | 1324 | 966.5 |
| 1170 | 977 | 1159 | 1308.5 | 935.5 |
| 1267 | 892 | 1151 | 1513.5 | 979.5 |
| 1198 | 808 | 1130 | 1357 | 1056 |
| 1238 | 907 | 1372.5 | 1222 | 1047 |
| 1246 | 806 | 1162 | 1299 | 949 |
| 1076.5 | 836 | 1322.5 | 1296 | 1139 |
| 1063 | 830 | 1323 | 1248 | 997 |
| 1218 | 917 | 1081 | 1210 | 981 |
| 1053 | 876 | 1227 | 1513 | 1052 |
| 1275 | 802 | 1300 | 1464 | 960 |
| 1119 | 831 | 1039 | 1459.5 | 911.5 |
| 1071 | 839 | 1095 | 1446 | 974 |
| 1243 | 822 | 1078 | 1413 | 1061 |
| 1127 | 923.5 | 1002 | 1388 | 1124 |
| 1149 | 801 | 1042.5 | 1305 | 1012 |
| 1079 | 795 | 1123 | 1434 | 1066.5 |
| 1299.5 | 874 | 1262 | 1411 | 1019 |
| 1100 | 736 | 983 | 1452.5 | 909 |
| 1262 | 860.5 | 1036.5 | 1334.5 | 960 |
| 1194 | 963 | 1282 | 1454 | 1026.5 |
| 1310.5 | 995 | 1278.5 | 1296 | 1038.5 |
| 1215.5 | 720.5 | 1196.5 | 1270 | 1000.5 |
| 1225 | 885 | 989 | 1454.5 | 985 |
| 1309 | 796 | 1097 | 1432 | 1058 |
| 1229.5 | 1028 | 1275.5 | 1256 | 1100 |
| 1095.5 | 831.5 | 1216 | 1319 | 915 |
| 1339.5 | 857 | 1102.5 | 1524.5 | 1057 |
| 1168.5 | 878 | 1079 | 1356 | 1000 |
| 1397 | 1017 | 1413.5 | 1426 | 1170 |
| 1206 | 864 | 1219 | 1306.5 | 976 |
| 1301 | 982 | 1173 | 1534 | 1036 |

FIG. 12 (Continued)

| | | | | |
|---|---|---|---|---|
| 1284 | 1360.5 | 992.5 | 1315 | 1193 |
| 1272.5 | 1287 | 1109 | 1477.5 | 1187 |
| 1268 | 1384.5 | 1030 | 1451 | 1342 |
| 1263 | 1323 | 1103 | 1338 | 1036 |
| 1259 | 1429 | 1219 | 1395.5 | 1128 |
| 1251 | 1337 | 1276 | 1287.5 | 1176 |
| 1245.5 | 1510 | 1140 | 1587 | 1097 |
| 1238 | 1302.5 | 1194 | 1269.5 | 1113 |
| 1237 | 1162 | 1096.5 | 1393 | 965 |
| 1225.5 | 1467 | 1170.5 | 1407 | 1149 |
| 1219 | 1404.5 | 1224 | 1411 | 1181 |
| 1205 | 1224 | 1113 | 1264 | 969 |
| 1195.5 | 1421 | 1153 | 1396 | 1416 |
| 1177.5 | 1442.5 | 1286 | 1380.5 | 1073.5 |
| 1162.5 | 1280 | 1113.5 | 1477.5 | 1111 |
| 1141 | 1365 | 1003 | 1543.5 | 1067.5 |
| 1141 | 1464 | 1213 | 1451 | 1353 |
| 1128 | 1434 | 1117 | 1564 | 1110 |
| 1123.5 | 1211 | 1125 | 1318 | 1125 |
| 1086 | 1439 | 1070.5 | 1410 | 1171 |
| 1084 | 1456.5 | 1162 | 1652 | 1275 |
| 1084 | 1378 | 1004.5 | 1370 | 1198.5 |
| 1081.5 | 1409 | 1174.5 | 1478 | 1075 |
| 1077 | 1507 | 1230 | 1392 | 1179 |
| 1071 | 1422 | 1230.5 | 1470 | 1248 |
| 1068 | 1424 | 1280.5 | 1308 | 1159 |
| 1065 | 1392 | 1154 | 1590.5 | 1228.5 |
| 1052 | 1364 | 1206 | 1472 | 1076 |
| 1051 | 1445 | 1371 | 1435 | 1189 |
| 1049 | 1404 | 1168 | 1360.5 | 1000 |
| 1038 | 1357 | 1115 | 1470.5 | 1103 |
| 1036 | 1297 | 1205 | 1409 | 1039.5 |
| 1035 | 1470 | 1287 | 1411 | 1187 |
| 1030 | 1650 | 1289 | 1537 | 1233.5 |
| 1029 | 1399 | 1217.5 | 1415 | 1162 |

FIG. 12 (Continued)

| | ④ | | | |
|---|---|---|---|---|
| | 977.5 | 2038 | 1078 | 1310.5 |
| | 969 | 1982 | 1146 | 1303.5 |
| | 964 | 2036.5 | 1065 | 1425 |
| | 1024 | 2136 | 981 | 1334.5 |
| | 972 | 2070 | 1123.5 | 1391 |
| | 958 | 2025 | 1144 | 1386 |
| | 884.5 | 2077 | 1105 | 1403.5 |
| | 801 | 2147.5 | 1136.5 | 1416 |
| | 934 | 2086.5 | 1054.5 | 1314.5 |
| | 1068 | 1964 | 1058.5 | 1294 |
| | 972 | 1958 | 1110.5 | 1411 |
| | 888 | 1924 | 1019 | 1440 |
| | 1165 | 2105.5 | 1183.5 | 1240 |
| | 903.5 | 2001 | 1053.5 | 1452.5 |
| | 904 | 2105 | 957 | 1434.5 |
| | 872 | 2057.5 | 1151 | 1362 |
| | 961.5 | 2021 | 1217.5 | 1427 |
| | 853.5 | 1950 | 1085 | 1368.5 |
| | 882.5 | 1901 | 1060 | 1235.5 |
| | 998 | 1927 | 1035.5 | 1286 |
| | 1035 | 2172 | 1121.5 | 1461.5 |
| | 922.5 | 1878 | 1138 | 1308.5 |
| | 897 | 1992 | 1030 | 1329.5 |
| | 927.5 | 2019.5 | 1134 | 1478 |
| | 942 | 2105.5 | 1130 | 1573 |
| | 967.5 | 2089 | 1075 | 1424 |
| | 1004 | 1812.5 | 1275.5 | 1396.5 |
| | 974.5 | 1950.5 | 1112.5 | 1335 |
| | 950 | 2071 | 1148 | 1404 |
| | 963 | 1976 | 1105 | 1367 |
| | 950 | 1922 | 1073 | 1316 |
| | 957 | 2159 | 1094 | 1440 |
| | 954 | 2027 | 1232 | 1504 |
| | 1058.5 | 2024 | 1405 | 1237 |
| | 956 | 2086 | 1179 | 1407 |

| | | | |
|---|---|---|---|
| 00451_644680 | 1976 | 1310 | 1095 |
| 00451_644724 | 1720 | 1272.5 | 1246 |
| 00451_644716 | 1761 | 1069.5 | 1079 |
| 00451_644641 | 1730 | 1200 | 986 |
| 00451_644692 | 1842 | 1135 | 1221 |
| 00451_644682 | 1804 | 1218 | 1130 |
| 00451_644712 | 1752 | 1163 | 1130 |
| 00451_644587 | 1836 | 1170.5 | 1309.5 |
| 00451_644597 | 1846 | 1216 | 1148 |
| 00451_644713 | 1867.5 | 1239.5 | 1191.5 |
| 00451_644585 | 1577 | 1073 | 1349.5 |
| 00451_644592 | 1726 | 1187 | 1211 |
| 00451_644603 | 1604 | 1078 | 1027 |
| 00451_644646 | 1604.5 | 1109 | 1104.5 |
| 00451_644580 | 1824 | 1303 | 1133 |
| 00451_644581 | 1857 | 1221 | 1197 |
| 00451_644702 | 1736 | 1227 | 1018 |
| 00451_644677 | 1848 | 1383 | 1222 |
| 00451_644594 | 1829 | 1112 | 1165.5 |
| 00451_644630 | 1631 | 1074 | 1041 |
| 00451_644676 | 1725 | 1244 | 1160 |
| 00451_644684 | 1644 | 1200 | 1186 |
| 00451_644673 | 1523 | 1073 | 958.5 |
| 00451_644593 | 1678 | 1302 | 1065 |
| PBS (BLANK) | 1939 | 1294 | 1143 |
| 00451_644611 | 1749 | 1232 | 1210 |
| 00451_644613 | 1709 | 1172 | 1058.5 |
| 00451_644710 | 1639 | 1203 | 1124 |
| 00451_644674 | 1663.5 | 1173.5 | 1017 |
| 00451_644726 | 1670 | 1108 | 1202.5 |
| 00451_644600 | 1723 | 1222 | 1052 |
| 00451_644690 | 1638.5 | 1173 | 1138 |
| 00451_644693 | 1599 | 1163 | 1093 |
| 00451_644627 | 1490 | 1144.5 | 1243.5 |
| 00451_644586 | 1749 | 1323 | 1155.5 |

FIG. 12 (Continued)

| | | | | |
|---:|---:|---:|---:|---:|
| 1280.5 | 793 | 1257 | 1217.5 | 1119 |
| 1249 | 885 | 1265 | 1157 | 1016 |
| 1207 | 895 | 1391 | 1211 | 973 |
| 1166.5 | 823.5 | 1450 | 1245 | 1016 |
| 1240 | 735.5 | 1151 | 1227 | 1074 |
| 1266 | 753 | 1214 | 1367.5 | 1101 |
| 1359.5 | 914 | 1310.5 | 1446.5 | 1148 |
| 1240 | 984 | 1316 | 1265 | 1097 |
| 1151 | 927 | 1202 | 1248 | 1020 |
| 1343 | 906 | 1275 | 1367 | 1068 |
| 1014 | 956 | 1019 | 1377 | 1031 |
| 1305 | 1002 | 1364 | 1413 | 1073.5 |
| 1221 | 875.5 | 1282.5 | 1154 | 1050 |
| 1041 | 860 | 1504 | 1181 | 1047 |
| 1295 | 825.5 | 996.5 | 1488.5 | 1127 |
| 1192 | 887 | 1290.5 | 1501 | 1060.5 |
| 1246 | 775.5 | 1295.5 | 1343.5 | 969 |
| 1242 | 913.5 | 1362 | 1287.5 | 1082.5 |
| 1203 | 821.5 | 1002 | 1437 | 958 |
| 1047 | 790 | 1119 | 1245.5 | 960.5 |
| 1265 | 999.5 | 1241 | 1577 | 1003 |
| 1247 | 1008.5 | 1334.5 | 1397 | 1041 |
| 1154 | 795 | 950 | 1251.5 | 971 |
| 1238 | 945.5 | 1354 | 1404.5 | 1085 |
| 1200 | 810 | 1139 | 1187.5 | 963 |
| 1343 | 884 | 1334 | 1362 | 1039 |
| 1138.5 | 868 | 1025 | 1359 | 944 |
| 1176 | 1014 | 1074 | 1315 | 954 |
| 1194 | 782 | 1183 | 1400.5 | 953.5 |
| 1221 | 892 | 1299.5 | 1369.5 | 1095 |
| 1194 | 890.5 | 1127 | 1319 | 1158 |
| 1357 | 880.5 | 1244.5 | 1178.5 | 1125 |
| 1332 | 926.5 | 1093 | 1321 | 1082 |
| 1109 | 1005 | 1143.5 | 1333.5 | 1035 |
| 1281 | 876.5 | 1195.5 | 1414 | 1086 |

FIG. 12 (Continued)

| | | | | |
|---|---|---|---|---|
| 1028 | 1364 | 1270.5 | 1489 | 1073.5 |
| 1025.5 | 1421.5 | 1222 | 1519.5 | 1011.5 |
| 1020 | 1295.5 | 1157 | 1539 | 1213.5 |
| 1012.5 | 1346 | 1199 | 1547 | 1128.5 |
| 1012 | 1577 | 1178 | 1372 | 1283 |
| 1003 | 1551 | 1225.5 | 1403.5 | 1135 |
| 1003 | 1426 | 1206.5 | 1426 | 1132.5 |
| 995 | 1387.5 | 1280 | 1513 | 1129 |
| 991 | 1243 | 1114 | 1230 | 1136 |
| 987 | 1361.5 | 1215.5 | 1453 | 1087 |
| 986 | 1403 | 1186 | 1400 | 1109 |
| 985 | 1352.5 | 1128.5 | 1543 | 1138 |
| 985 | 1384.5 | 1197 | 1184 | 969.5 |
| 984.5 | 1357 | 1113 | 1344.5 | 1081 |
| 983.5 | 1491.5 | 1124 | 1526.5 | 1147.5 |
| 981 | 1293.5 | 1065 | 1488 | 1211 |
| 980.5 | 1381 | 1170 | 1430 | 1092 |
| 974 | 1432 | 1185 | 1594 | 1098.5 |
| 973.5 | 1279.5 | 1305 | 1358.5 | 1149.5 |
| 973 | 1363.5 | 1133.5 | 1311 | 1101 |
| 969.5 | 1446 | 1254 | 1383 | 1203 |
| 968 | 1340.5 | 1241 | 1606 | 1268.5 |
| 967 | 1283 | 1061 | 1330 | 1021 |
| 966 | 1368 | 1041 | 1453 | 1141 |
| 963 | 1343 | 1262 | 1520.5 | 1216 |
| 960 | 1439 | 1205.5 | 1409.5 | 971.5 |
| 954 | 1361.5 | 1189 | 1429.5 | 1117 |
| 953 | 1334 | 1001 | 1285.5 | 1154 |
| 950 | 1238 | 1027 | 1383 | 1172 |
| 947 | 1278 | 1116 | 1470 | 1130 |
| 945 | 1389 | 1251.5 | 1521.5 | 1078 |
| 944.5 | 1292 | 1316 | 1396 | 1362 |
| 941 | 1504 | 1187 | 1543 | 1224 |
| 940 | 1252.5 | 1138 | 1332.5 | 1224.5 |
| 939.5 | 1498.5 | 988.5 | 1324 | 1187.5 |

FIG. 12 (Continued)

| | | | |
|---|---|---|---|
| 1016 | 2116 | 1103 | 1456 |
| 871 | 2112 | 1136 | 1531.5 |
| 1089 | 1925 | 1144 | 1411 |
| 1011 | 2010.5 | 1117 | 1415 |
| 1019.5 | 1991.5 | 1084 | 1561 |
| 1039 | 1995 | 1025 | 1528 |
| 957 | 2162 | 1258 | 1339 |
| 1018.5 | 1935 | 1027 | 1379.5 |
| 990 | 1945 | 1068 | 1307.5 |
| 971 | 2079.5 | 1133 | 1448 |
| 1007.5 | 2025 | 1068 | 1480.5 |
| 1017.5 | 1997.5 | 1093 | 1429 |
| 832 | 1854 | 969 | 1383 |
| 952.5 | 2040 | 1076 | 1210 |
| 1122 | 2102.5 | 1292 | 1489 |
| 971 | 2110.5 | 1095 | 1483 |
| 995.5 | 2115 | 1197.5 | 1290.5 |
| 995.5 | 2086.5 | 1150.5 | 1448 |
| 1069 | 2173 | 1186 | 1397 |
| 952 | 2000 | 990 | 1531 |
| 904 | 1949 | 1045 | 1434 |
| 1065 | 2013.5 | 1052 | 1415 |
| 963 | 1889 | 1108 | 1413 |
| 937 | 1923 | 1167 | 1424.5 |
| 1028 | 1987 | 1224.5 | 1367 |
| 1086 | 2082.5 | 1273 | 1437 |
| 890 | 2061.5 | 1051.5 | 1385 |
| 1007 | 2021.5 | 1177 | 1427 |
| 980.5 | 2054 | 1043 | 1434 |
| 930.5 | 1972.5 | 1122 | 1454 |
| 949 | 2068 | 1076 | 1348 |
| 1077 | 2060 | 1125.5 | 1394 |
| 897.5 | 2173 | 1130 | 1553 |
| 920 | 2078 | 1195 | 1357 |
| 934 | 2066.5 | 1260 | 1519 |

FIG. 12 (Continued)

| | | | |
|---|---|---|---|
| 00451_644648 | 1739 | 1155 | 1114 |
| 00451_644669 | 1823 | 1081 | 1054 |
| 00451_644705 | 1765 | 1058 | 1082 |
| 00451_644604 | 1701 | 1270 | 1184 |
| 00451_644679 | 1848 | 1458 | 1144 |
| 00451_644675 | 1707 | 1152 | 1251 |
| 00451_644623 | 1809 | 1136 | 1037.5 |
| 00451_644595 | 1677 | 1186.5 | 1139.5 |
| 00451_644625 | 1596 | 1159.5 | 1144 |
| 00451_644681 | 1767 | 1183 | 1193 |
| 00451_644683 | 1833 | 1070 | 1139.5 |
| 00451_644601 | 1783.5 | 1046.5 | 1117 |
| 00451_644694 | 1908 | 1108 | 1275.5 |
| 00451_644678 | 1817 | 1108.5 | 1174 |
| 00451_644704 | 1896 | 1158.5 | 1100 |
| 00451_644649 | 1656 | 1131.5 | 1206 |
| 00451_644608 | 1809 | 1136 | 1139.5 |
| 00451_644718 | 1811 | 1098 | 971 |
| 00451_644637 | 1722 | 1294 | 1099.5 |
| 00451_644615 | 1747 | 1227 | 1044 |
| 00451_644699 | 1671.5 | 1161 | 1035.5 |
| 00451_644626 | 1501 | 1101.5 | 1184 |
| 00451_644639 | 1531.5 | 1170 | 1046 |
| 00451_644701 | 1734 | 1159 | 1132 |
| 00451_644723 | 1691 | 1273 | 1175.5 |
| 00451_644610 | 1812 | 1216 | 1215 |
| 00451_644647 | 1737.5 | 1041 | 1077 |
| 00451_644618 | 1817.5 | 1056 | 1079 |
| 00451_644727 | 1761 | 1270 | 1031 |
| 00451_644662 | 1583 | 1150.5 | 1052 |
| 00451_644638 | 1763 | 1100 | 1070.5 |
| 00451_644698 | 1704 | 1173 | 1213 |
| 00451_644709 | 1792 | 1103 | 1023.5 |
| 00451_644602 | 1702.5 | 1121 | 1159 |

FIG. 12 (Continued)

| 10 ↑ | | | | |
|---|---|---|---|---|
| 1030 | 781 | 1088 | 1203.5 | 1036 |
| 1113 | 839 | 1059.5 | 1502 | 1045 |
| 1114 | 877 | 1297.5 | 1476 | 979 |
| 1262 | 928 | 1014 | 1332 | 955 |
| 1332.5 | 826.5 | 1054 | 1414.5 | 1185 |
| 1194 | 998 | 1030.5 | 1308 | 936 |
| 1241.5 | 887 | 1242.5 | 1213.5 | 1106 |
| 1187 | 904 | 1132 | 1098 | 1003.5 |
| 1261 | 946 | 1242 | 1296.5 | 924 |
| 1213.5 | 844 | 1291 | 1353 | 960.5 |
| 1284 | 936 | 1212.5 | 1763 | 1124.5 |
| 1210 | 740.5 | 1108 | 1283 | 1090 |
| 1228 | 818 | 1060 | 1507.5 | 984.5 |
| 1053.5 | 860.5 | 1211 | 1295 | 1011 |
| 1311 | 863 | 1032 | 1558 | 1031 |
| 1175.5 | 890 | 1092.5 | 1345 | 1057 |
| 1125.5 | 808 | 1241 | 1462 | 1022 |
| 1383.5 | 876 | 1131 | 1421 | 973 |
| 1230 | 817 | 1084 | 1472.5 | 1166.5 |
| 1180 | 1027 | 1063 | 1564 | 966 |
| 1041 | 910 | 1258.5 | 1466 | 1238 |
| 1248 | 985 | 1348 | 1187 | 958 |
| 1187.5 | 839 | 1299 | 1329 | 1039 |
| 1171.5 | 810 | 1081 | 1590 | 1084 |
| 1221 | 1087 | 1097 | 1283.5 | 898 |
| 1178 | 885 | 1373 | 1419.5 | 984 |
| 1128 | 742 | 1208 | 1293 | 893 |
| 1163 | 884 | 1419 | 1264.5 | 932 |
| 1228 | 830 | 1060 | 1442 | 950 |
| 1157 | 708.5 | 1050 | 1068 | 899.5 |
| 1213 | 843 | 1126.5 | 1408.5 | 1054.5 |
| 1154 | 829.5 | 793 | 1482.5 | 1053 |
| 1208 | 798 | 1176 | 1360.5 | 893 |
| 1186 | 858 | 1184.5 | 1380.5 | 1113 |
| 1227 | 788 | 1235 | 1466 | 979 |

←J  ⑭↓  FIG. 12 (Continued)  K→

| | | | | |
|---:|---:|---:|---:|---:|
| 938.5 | 1373 | 1065 | 1328 | 955 |
| 938 | 1348.5 | 1132 | 1479 | 1027 |
| 935.5 | 1286 | 1106 | 1265 | 1132 |
| 930.5 | 1423 | 1099 | 1398.5 | 1197 |
| 925 | 1470.5 | 1395 | 1487.5 | 1078 |
| 922 | 1338 | 1300 | 1162 | 1193 |
| 921.5 | 1454.5 | 960 | 1445 | 1144.5 |
| 920 | 1313 | 1171 | 1421 | 1144 |
| 919 | 1337 | 1159.5 | 1300 | 1048 |
| 915 | 1302.5 | 1182.5 | 1515.5 | 1342 |
| 912 | 1329 | 1248.5 | 1534 | 1241 |
| 911.5 | 1318 | 1036.5 | 1443 | 1246 |
| 904.5 | 1477.5 | 1016 | 1329 | 1237.5 |
| 904 | 1353.5 | 937 | 1456 | 974 |
| 904 | 1446 | 1235.5 | 1451 | 1185 |
| 903.5 | 1382.5 | 1045 | 1259 | 1006 |
| 901.5 | 1462 | 1093 | 1488.5 | 963 |
| 901 | 1262 | 1144 | 1388 | 1096.5 |
| 888.5 | 1255 | 1114.5 | 1227.5 | 1097.5 |
| 885 | 1275.5 | 1176 | 1317 | 1090 |
| 878 | 1421 | 1194 | 1415 | 1336 |
| 871.5 | 1378.5 | 1235 | 1515 | 1246 |
| 868 | 1329 | 1140 | 1320 | 1207 |
| 867.5 | 1389.5 | 1216 | 1329 | 1020 |
| 860 | 1434 | 1043.5 | 1305 | 1132 |
| 857 | 1356 | 1368.5 | 1360 | 1149 |
| 853 | 1279.5 | 1092 | 1354 | 1196 |
| 849 | 1265 | 1117 | 1463.5 | 1007.5 |
| 848 | 1308 | 1292 | 1461 | 1042.5 |
| 847 | 1310.5 | 1005.5 | 1381 | 1076 |
| 845.5 | 1329 | 1262 | 1411 | 1124.5 |
| 839 | 1405 | 1056 | 1448 | 1249 |
| 837 | 1366.5 | 1187 | 1318 | 1156 |
| 837 | 1272 | 1198.5 | 1363 | 1157 |
| 833.5 | 1479 | 1122 | 1504 | 1106 |

| | | | |
|---|---|---|---|
| 892 | 1954 | 950 | 1305 |
| 1074 | 1976 | 1113.5 | 1262 |
| 880 | 1880.5 | 1185.5 | 1367 |
| 893 | 2094 | 1145.5 | 1424 |
| 1037 | 2254 | 1181 | 1446 |
| 956 | 1927 | 1164 | 1374.5 |
| 1149 | 1996 | 1176 | 1384 |
| 1019 | 1933 | 1090 | 1308 |
| 928 | 2078.5 | 1220 | 1351 |
| 915 | 1973 | 1035 | 1434 |
| 1006 | 2076 | 1357 | 1427.5 |
| 915 | 2059 | 996 | 1366 |
| 1006 | 2055 | 1163 | 1330 |
| 974 | 2005 | 1010 | 1399 |
| 955 | 2079 | 1176 | 1555 |
| 895.5 | 1967 | 1168.5 | 1456 |
| 952 | 2059 | 1184 | 1507.5 |
| 1024 | 2132 | 1165 | 1435 |
| 964.5 | 2022 | 1227 | 1446 |
| 907 | 2097 | 1200 | 1402 |
| 979 | 2008.5 | 1026.5 | 1310 |
| 926.5 | 2102 | 1105.5 | 1424 |
| 950 | 1908 | 1028 | 1234 |
| 1003 | 2009 | 1105 | 1342 |
| 1012 | 2087 | 1110.5 | 1238 |
| 902 | 1962 | 1213.5 | 1447 |
| 963 | 1900.5 | 1057 | 1217 |
| 959 | 1924.5 | 1073 | 1457.5 |
| 891.5 | 1989 | 1152 | 1356.5 |
| 1008 | 1777 | 963.5 | 1349 |
| 901 | 1979 | 1039 | 1388 |
| 930 | 1998 | 1219 | 1391 |
| 974 | 1821.5 | 1060 | 1204 |
| 963 | 2016 | 1209 | 1334 |
| 934 | 2148 | 1217.5 | 1446.5 |

| | | | | |
|---|---|---|---|---|
| 00451_644700 | | 1600 | 1249 | 1239 |
| 00451_644606 | | 1617 | 1162 | 1107 |
| 00451_644728 | | 1777 | 1198 | 1065 |
| 00451_644635 | | 1702 | 1109 | 1022 |
| 00451_644688 | | 1752.5 | 1263 | 1167 |
| 00451_644616 | | 1774 | 1182.5 | 1043.5 |
| 00451_644725 | | 1837.5 | 1122 | 1200 |
| 00451_644663 | | 1677 | 1108 | 1081.5 |
| 00451_644650 | | 1795 | 1148 | 1052 |
| 00451_644640 | | 1612 | 1206 | 1144.5 |
| 00451_644720 | | 1785 | 1167 | 1073 |
| 00451_644651 | | 1634 | 1188.5 | 1182 |
| 00451_644672 | | 1617 | 1210.5 | 963 |
| 00451_644721 | | 1648 | 1130.5 | 950 |
| 00451_644715 | | 1625 | 1081 | 1101 |

| | | | | |
|---|---|---|---|---|
| 1227 | 788 | 1235 | 1466 | 979 |
| 1252 | 913 | 1235 | 1214 | 1025 |
| 1154 | 923 | 1381 | 1391 | 1011 |
| 1070.5 | 863 | 927 | 1402.5 | 1017 |
| 1164.5 | 769.5 | 1184 | 1235 | 1020 |
| 1222 | 855 | 1117 | 1223.5 | 1047.5 |
| 1283.5 | 912 | 1086 | 1520 | 1122.5 |
| 1364 | 933 | 1233 | 1370 | 1097 |
| 1128 | 1021 | 990.5 | 1505.5 | 892.5 |
| 1232.5 | 818 | 1243 | 1356.5 | 952 |
| 1280 | 789 | 1238 | 1380 | 1157 |
| 1256 | 938.5 | 1165 | 1499 | 807 |
| 1136 | 833.5 | 1030.5 | 1340 | 988 |
| 1098 | 782 | 1183 | 1308.5 | 1033 |
| 1258.5 | 778.5 | 1203.5 | 1434 | 937 |

| | ⑮ | | | | |
|---|---|---|---|---|---|
| 833.5 | 1479 | 1122 | 1504 | 1106 |
| 830 | 1407.5 | 1198 | 1376.5 | 1218 |
| 830 | 1386 | 1284 | 1510 | 1216 |
| 824 | 1375 | 1080 | 1486.5 | 1183.5 |
| 823 | 1434 | 1022 | 1351 | 1216 |
| 816 | 1397.5 | 1095 | 1432 | 1127.5 |
| 811 | 1361 | 1171 | 1477 | 1170 |
| 810 | 1460 | 1124 | 1410 | 1047.5 |
| 792 | 1318 | 1215 | 1397 | 1083 |
| 781 | 1347.5 | 1200 | 1466.5 | 1030 |
| 778.5 | 1349 | 1039 | 1422 | 1197.5 |
| 757 | 1204 | 981 | 1377 | 1087 |
| 753 | 1417 | 1124 | 1402 | 1135 |
| 740.5 | 1429 | 1106 | 1429 | 1033.5 |
| 669 | 1390 | 995 | 1457.5 | 1205 |

FIG. 12 (Continued)

| 934 | 2148 | 1217.5 | 1446.5 |
| 785 | 1955 | 1103 | 1373 |
| 910 | 1936.5 | 1056 | 1380 |
| 962 | 1995 | 962 | 1310 |
| 963 | 1928 | 1210 | 1475 |
| 875.5 | 2065.5 | 1168 | 1393.5 |
| 1000 | 2071 | 1144.5 | 1442 |
| 920 | 2009.5 | 1138 | 1175.5 |
| 833 | 1939 | 998 | 1372.5 |
| 829.5 | 1966 | 1169 | 1536 |
| 893 | 1955 | 1106 | 1421 |
| 930 | 1965 | 1031.5 | 1288 |
| 837.5 | 1925 | 1008 | 1221 |
| 1043 | 2017 | 1089.5 | 1278.5 |
| 855 | 1906 | 1116 | 1371.5 |

FIG. 12 (Continued)

| Affimer Working ID | EGFR (FL1-A of QSH01) | mIgG2b (FL1-A of QSH03) | hIgG1 Fc (FL1-A of QSH05) |
|---|---|---|---|
| 00453_644900 | 1857.5 | 1053.5 | 1830.5 |
| 00453_644808 | 1639.5 | 1022 | 1091.5 |
| 00453_645051 | 1630 | 1108 | 1086.5 |
| 00453_644819 | 1652 | 1198.5 | 1213 |
| 00453_644802 | 1671 | 1029 | 1179.5 |
| 00453_644873 | 1556 | 1036.5 | 1052 |
| 00453_644769 | 1736 | 1245 | 1065.5 |
| 00453_644869 | 1620 | 1086 | 1011.5 |
| 00453_644810 | 1796 | 1164 | 1482 |
| 00453_644809 | 1541.5 | 1119 | 1032.5 |
| 00453_644888 | 1704 | 1099.5 | 1448 |
| 00453_645069 | 1623 | 1230 | 1319.5 |
| 00453_644803 | 1743.5 | 1135 | 1416 |
| 00453_644823 | 1715.5 | 1044 | 1130 |
| 00453_644864 | 1675.5 | 1078 | 1295 |
| 00453_644924 | 1734 | 1272 | 1689 |
| 00453_645089 | 1809 | 1071 | 1466 |
| 00453_644861 | 1691 | 1106 | 1146 |
| 00453_644824 | 1548 | 1099 | 1064.5 |
| 00453_644919 | 1683 | 982.5 | 1205.5 |
| 00453_645036 | 1712 | 1136.5 | 1136 |
| 00453_644833 | 1672 | 1159.5 | 1151 |
| 00453_644851 | 1737.5 | 993 | 1454.5 |
| 00453_644926 | 1936 | 1216 | 1698.5 |
| 00453_645085 | 1679.5 | 1122 | 1213 |
| 00453_645010 | 1842 | 1123.5 | 1710 |
| 00453_644825 | 1796 | 1206.5 | 1248 |
| 00453_644912 | 1648.5 | 1793 | 1091 |
| 00453_644844 | 1878 | 1147 | 1240 |
| 00453_645033 | 1739 | 1033 | 1335 |
| 00453_644772 | 1690 | 1098 | 1239 |
| 00453_644751 | 1842.5 | 1093 | 1284 |
| 00453_644832 | 1752 | 1071 | 1221 |

FIG. 13

| hPD-L2 (FL1-A of QSH06) | Her2 (R&D) (FL1-A of QSH08) | hPD-L1 (FL1-A of QSH10) | Trastuzumab (FL1-A of QSH11) | hIgG (FL1-A of QSH13) |
|---|---|---|---|---|
| 1736.5 | 882 | 1163 | 180145 | 1255.5 |
| 1211.5 | 769 | 1144 | 175577 | 1054 |
| 1119 | 783 | 1178 | 167951 | 1021 |
| 1210.5 | 852.5 | 1230 | 163608.5 | 1100 |
| 1208 | 884.5 | 1035 | 161481 | 1078 |
| 1186 | 863 | 1035 | 150133.5 | 985.5 |
| 1151.5 | 883 | 1357 | 133402.5 | 971 |
| 1134 | 863 | 1148 | 123517.5 | 868 |
| 1423 | 828.5 | 1217.5 | 113116 | 1004 |
| 1109 | 802 | 1206.5 | 108140 | 925 |
| 1383 | 723 | 1138.5 | 106234 | 1073 |
| 1433 | 872 | 1214 | 98995 | 1089 |
| 1411 | 862.5 | 1362 | 98358 | 1140 |
| 1202 | 905.5 | 928 | 97128 | 1146 |
| 1219 | 812 | 1111 | 84553.5 | 967 |
| 1508 | 801.5 | 1250.5 | 83304 | 1035 |
| 1470 | 760 | 1105 | 78338 | 1022 |
| 1178 | 721.5 | 1177 | 77833 | 1068 |
| 1178 | 823 | 1078.5 | 77752 | 1020 |
| 1160 | 802 | 1143 | 75438 | 960 |
| 1163 | 768.5 | 1217.5 | 74310.5 | 995 |
| 1259 | 687 | 1153 | 70321 | 1004 |
| 1337 | 778.5 | 1163.5 | 68725 | 1011 |
| 1536 | 1022 | 1424 | 68205 | 1206 |
| 1227 | 919 | 1328.5 | 64471 | 968 |
| 1337 | 763 | 1264 | 63598 | 1071 |
| 1161 | 935.5 | 1335.5 | 63035.5 | 1063 |
| 1171.5 | 804 | 1003 | 61262 | 1000 |
| 1227 | 695 | 1027 | 59343 | 988 |
| 1456 | 750 | 1152 | 50967 | 1227 |
| 1278 | 787.5 | 1372 | 48521.5 | 982.5 |
| 1216 | 811 | 1232 | 44657 | 1140 |
| 1299 | 1001 | 1062 | 43627 | 992 |

FIG. 13 (Continued)

| Her2 (Sino) (FL1-A of QSH15) | Her3 (FL1-A of QSH16) | mPD-L1 (FL1-A of QSH18) | No target ctr (FL1-A of QSH22) | Avastin (FL1-A of QSH23) |
|---|---|---|---|---|
| 728 | 1502.5 | 1364 | 1387 | 1574.5 |
| 861 | 1324 | 1079 | 1425 | 1132 |
| 748 | 1485.5 | 1092 | 1444 | 1162 |
| 861 | 1427 | 1136.5 | 1580 | 1212.5 |
| 893 | 1418 | 1006 | 1437 | 1202 |
| 785 | 1253.5 | 1145 | 1531 | 1101 |
| 846.5 | 2106 | 1170 | 1512 | 1121 |
| 849 | 1334 | 1080.5 | 1349 | 1012 |
| 927 | 1423.5 | 1268 | 1362 | 1415 |
| 885 | 1354 | 1025.5 | 1400 | 1025 |
| 842 | 1351.5 | 1046.5 | 1216 | 1421 |
| 887 | 1346.5 | 1151.5 | 1405 | 1442 |
| 834 | 1452 | 1161.5 | 1373 | 1418 |
| 868 | 1271.5 | 1033.5 | 1307 | 1140 |
| 718 | 1265 | 1060 | 1326 | 1345 |
| 884.5 | 1547 | 1308 | 1483 | 1515 |
| 922 | 1365 | 1214.5 | 1435.5 | 1402 |
| 793 | 1293 | 1144 | 1402.5 | 1090.5 |
| 842 | 1265 | 1077.5 | 1415 | 1141 |
| 969 | 1330 | 1138 | 1329.5 | 1211 |
| 920 | 1459 | 1148 | 1392 | 1136 |
| 802 | 1387 | 1135 | 1461 | 1171.5 |
| 839.5 | 1329 | 1315.5 | 1287 | 1340 |
| 876 | 1591 | 1524 | 1469 | 1795.5 |
| 752 | 1349 | 1256 | 1391.5 | 1346 |
| 857 | 1521 | 1443 | 1507 | 1646 |
| 927 | 1433 | 1157 | 1546 | 1175 |
| 723 | 1380 | 1095 | 1237 | 1067 |
| 861.5 | 1453 | 1077.5 | 1421 | 1118.5 |
| 817 | 1363.5 | 1233 | 1351 | 1360 |
| 729 | 1431 | 1205 | 1503 | 1265.5 |
| 903 | 1378 | 1221 | 1492 | 1267 |
| 820 | 1321 | 1140 | 1395 | 1241 |

FIG. 13 (Continued)

| Humira (FL1-A of QSH25) | Rituximab (FL1-A of QSH26) | mPD-L2 (FL1-A of QSH27) | Her4 (FL1-A of QSH28) |
|---|---|---|---|
| 1639 | 2222 | 1586 | 1332 |
| 1009 | 1949 | 1189.5 | 1394 |
| 1017 | 1970 | 1227 | 1357 |
| 1041 | 2014 | 1233.5 | 1304.5 |
| 1016 | 1839 | 1192 | 1408 |
| 1019 | 1912.5 | 1075.5 | 1255.5 |
| 1132 | 1970.5 | 1642 | 1492.5 |
| 853 | 2048 | 1197 | 1330 |
| 1278 | 2057 | 1310 | 1357 |
| 1052.5 | 1925 | 1052 | 1303 |
| 1353.5 | 1987 | 1152.5 | 1245 |
| 1168 | 1978.5 | 1138 | 1343 |
| 1291 | 2129 | 1289 | 1396 |
| 901 | 1912 | 1236 | 1295 |
| 1227 | 1954 | 1141 | 1461 |
| 1454 | 2035 | 1251.5 | 1493 |
| 1488 | 2075.5 | 1194 | 1256.5 |
| 901 | 1857 | 1070 | 1384 |
| 884.5 | 2027 | 1006 | 1305 |
| 1113 | 1943.5 | 1060 | 1303 |
| 995 | 1995 | 1171 | 1334.5 |
| 1052 | 1925 | 1290.5 | 1370 |
| 1130 | 2143.5 | 1304 | 1443.5 |
| 1722.5 | 2115.5 | 1526 | 1379.5 |
| 1208 | 2033 | 1290.5 | 1418 |
| 1574 | 2050 | 1411 | 1292 |
| 1071 | 1987 | 1237.5 | 1375 |
| 952 | 1808 | 963 | 1184 |
| 1121 | 1998.5 | 1229.5 | 1432 |
| 1315 | 2110 | 1127 | 1355 |
| 1181 | 2024 | 1216 | 1304 |
| 1238 | 1993 | 1225 | 1264.5 |
| 1095 | 2136.5 | 1272 | 1351 |

FIG. 13 (Continued)

| | | | |
|---|---|---|---|
| 00453_644874 | | 1760 | 1141 | 1243.5 |
| 00453_644887 | | 1642 | 996 | 1122 |
| 00453_644921 | | 1809 | 1241 | 1553.5 |
| 00453_645038 | | 1717 | 1078 | 1561 |
| 00453_645035 | | 1802.5 | 1148 | 1596 |
| 00453_645041 | | 1746.5 | 1204 | 1480.5 |
| 00453_645030 | | 1713 | 1057 | 1112 |
| 00453_644904 | | 1737 | 995 | 1506.5 |
| 00453_644798 | | 1793 | 1120 | 1259 |
| 00453_644753 | | 1720 | 1221 | 986 |
| 00453_644891 | | 1866 | 1159.5 | 1877.5 |
| 00453_644886 | | 1770 | 1117 | 1539 |
| 00453_644853 | | 1803 | 1066 | 1030 |
| 00453_644977 | | 1599 | 1058 | 1393.5 |
| 00453_644777 | | 1708 | 1091 | 1081 |
| 00453_644797 | | 1629.5 | 1205 | 1020.5 |
| 00453_645111 | | 1629 | 999 | 1108 |
| 00453_644754 | | 1737.5 | 1224 | 1417 |
| 00453_644760 | | 1580 | 1127 | 1563 |
| 00453_645094 | | 1860 | 1117 | 1736 |
| 00453_644838 | | 1856 | 1084 | 1508 |
| 00453_644781 | | 1618 | 1059 | 1078 |
| 00453_644759 | | 1652.5 | 1114 | 1084 |
| 00453_644868 | | 1469 | 1012 | 1257 |
| 00453_644792 | | 1645.5 | 1073.5 | 1518 |
| 00453_644991 | | 1692 | 1047 | 1419.5 |
| 00453_644880 | | 1801 | 1074 | 1752.5 |
| 00453_644764 | | 1772 | 1191 | 1590 |
| 00453_644848 | | 1844 | 1103 | 1529 |
| 00453_645043 | | 1614 | 1030 | 1088.5 |
| 00453_644987 | | 1788.5 | 1016 | 1689.5 |
| 00453_644997 | | 1677.5 | 1165 | 1261 |
| 00453_644950 | | 1739 | 1111 | 1367 |

FIG. 13 (Continued)

| | | | | |
|---|---|---|---|---|
| 1453 | 877 | 1302 | 41091.5 | 1019.5 |
| 1206.5 | 810 | 1102.5 | 35642 | 1012 |
| 1369 | 929 | 1148 | 34638 | 1167.5 |
| 1507 | 855 | 1386 | 32862.5 | 1124 |
| 1365.5 | 788.5 | 1119 | 28013 | 1119.5 |
| 1327 | 887 | 1091 | 24984.5 | 1009 |
| 1205 | 837.5 | 1093 | 23350 | 1012 |
| 1489 | 806 | 1431 | 22227 | 1128 |
| 1290 | 710 | 1070.5 | 19871 | 1089 |
| 1323.5 | 862.5 | 1073 | 19301 | 1001.5 |
| 1747 | 826.5 | 1273.5 | 18955.5 | 1152.5 |
| 1519.5 | 786.5 | 1218 | 18790 | 1074.5 |
| 1291 | 910.5 | 1210 | 18587.5 | 1036 |
| 1202.5 | 657 | 1213.5 | 17713 | 964.5 |
| 1227 | 906.5 | 1318 | 17648 | 1006 |
| 1221.5 | 922 | 1189 | 17306 | 953 |
| 1096.5 | 763 | 1090 | 16978 | 1011 |
| 1335.5 | 780 | 1248.5 | 16454 | 1147 |
| 1429 | 890 | 1213 | 16277 | 1071 |
| 1690 | 798.5 | 1207 | 16163 | 1236 |
| 1552.5 | 886 | 1231 | 15900 | 1148 |
| 1210 | 806 | 904 | 15468 | 1020.5 |
| 1152.5 | 849.5 | 1213.5 | 15110 | 1028 |
| 1214.5 | 777 | 1181.5 | 14888 | 1051.5 |
| 1399 | 863 | 1229 | 14886 | 1044 |
| 1359 | 777 | 1082.5 | 14746 | 931 |
| 1600 | 841 | 1222 | 14666.5 | 1011 |
| 1593 | 868 | 1440 | 14637 | 1177 |
| 1364 | 739 | 1288 | 14554 | 1132 |
| 1152 | 829.5 | 1073 | 14458.5 | 1003 |
| 1696 | 775 | 1249.5 | 14342 | 1093 |
| 1086 | 732.5 | 1287.5 | 14283 | 1132 |
| 1434 | 867 | 1244 | 14058.5 | 1168 |

| | | | | | |
|---|---|---|---|---|---|
| | 761 | 1333 | 1251 | 1440 | 1310.5 |
| | 853 | 1445.5 | 1210 | 1524 | 1246 |
| | 984.5 | 1609 | 1288 | 1574.5 | 1499 |
| | 847 | 1399 | 1316.5 | 1472 | 1571 |
| | 702 | 1420 | 1266 | 1570.5 | 1588 |
| | 785 | 1413 | 1303.5 | 1407 | 1316 |
| | 780 | 1363 | 1113.5 | 1356.5 | 1284 |
| | 824 | 1419.5 | 1233.5 | 1415 | 1536 |
| | 755 | 1302.5 | 1063 | 1399.5 | 1264 |
| | 720 | 1286 | 1096.5 | 1450 | 1097 |
| | 880 | 1429 | 1253.5 | 1388 | 1806 |
| | 979 | 1410 | 1324 | 1440 | 1605.5 |
| | 857 | 1354 | 1069.5 | 1467 | 1057.5 |
| | 960.5 | 1363 | 1040 | 1360.5 | 1294 |
| | 973 | 1402 | 1001 | 1432 | 1189.5 |
| | 841.5 | 1362 | 1167 | 1397 | 1045.5 |
| | 850 | 1342.5 | 1138 | 1438 | 1011.5 |
| | 888 | 1405 | 1318 | 1372.5 | 1311 |
| | 888 | 1421 | 1212 | 1516 | 1374 |
| | 874 | 1523 | 1542 | 1491 | 1782 |
| | 778.5 | 1408 | 1302.5 | 1395.5 | 1497 |
| | 783.5 | 1356 | 1189 | 1420.5 | 1235 |
| | 909 | 1210 | 1019.5 | 1472 | 1139 |
| | 904.5 | 1218 | 1045.5 | 1295 | 1169 |
| | 831 | 1295.5 | 1295 | 1410 | 1448 |
| | 774.5 | 1248.5 | 1131.5 | 1353.5 | 1343 |
| | 661 | 1452 | 1322 | 1244 | 1484 |
| | 833 | 1370 | 1383 | 1430.5 | 1666 |
| | 833 | 1424 | 1327 | 1440 | 1475 |
| | 742 | 1290 | 1122 | 1408 | 1086 |
| | 883.5 | 1311 | 1435 | 1450 | 1564 |
| | 726 | 1371 | 1025 | 1349 | 1180 |
| | 851 | 1308.5 | 1335 | 1316 | 1451.5 |

| | | | |
|---|---|---|---|
| 1373 | 2079.5 | 1401.5 | 1428 |
| 1078 | 2017 | 1208 | 1348 |
| 1512 | 2198 | 1780 | 1534 |
| 1436 | 2021 | 1310 | 1533.5 |
| 1513 | 2104.5 | 1365.5 | 1431 |
| 1248.5 | 2086.5 | 1343 | 1437.5 |
| 980 | 1933 | 1020 | 1346 |
| 1446 | 2230 | 1410 | 1494 |
| 1183 | 1965 | 1160.5 | 1278 |
| 990 | 2034.5 | 1016 | 1295 |
| 1793 | 2176 | 1300 | 1515.5 |
| 1528 | 2000.5 | 1342 | 1388 |
| 967 | 2052.5 | 1223.5 | 1348 |
| 1178.5 | 1938 | 1096.5 | 1240.5 |
| 904 | 2038 | 1157 | 1360 |
| 989 | 2043 | 1189 | 1367 |
| 878.5 | 1828 | 1195 | 1359 |
| 1321 | 2119.5 | 1290 | 1446 |
| 1531.5 | 2078 | 1309 | 1245 |
| 1664 | 2081 | 1539.5 | 1564 |
| 1529 | 2081 | 1505 | 1503 |
| 965.5 | 2042.5 | 974 | 1337 |
| 1049 | 1896 | 1097 | 1337 |
| 1046 | 1947.5 | 1197.5 | 1343.5 |
| 1502 | 2053 | 1216 | 1259 |
| 1385 | 1944 | 1256.5 | 1362 |
| 1431 | 2034 | 1308 | 1327 |
| 1755 | 2083 | 1474 | 1357 |
| 1522.5 | 2117.5 | 1391.5 | 1408 |
| 907 | 1847 | 1065 | 1212 |
| 1661 | 2205 | 1435 | 1305 |
| 1078.5 | 2068 | 1081 | 1303 |
| 1291 | 1956 | 1273 | 1310.5 |

| | | | |
|---|---|---|---|
| 00453_645057 | 1723 | 1147.5 | 1010.5 |
| 00453_645048 | 1645 | 1221 | 938 |
| 00453_644892 | 1647.5 | 1113 | 1057 |
| 00453_645037 | 1661 | 1113.5 | 962 |
| 00453_644938 | 1916 | 1125 | 1745 |
| 00453_644925 | 1708 | 1157 | 1145 |
| 00453_644915 | 1672 | 1107 | 1195 |

| 1140.5 | 769.5 | 1114 | 13990 | 809 |
|--------|-------|--------|---------|--------|
| 1196 | 968 | 1218 | 13418 | 1121 |
| 1125 | 725 | 1052 | 13267 | 1002 |
| 1229 | 859 | 1232.5 | 12368.5 | 1012 |
| 1594 | 834 | 1299 | 12235 | 1195.5 |
| 1173.5 | 782 | 1216 | 11288.5 | 1060 |
| 1406 | 835 | 1089 | 3170.5 | 1040.5 |

FIG. 13 (Continued)

| | | | | | |
|---|---|---|---|---|---|
| | 920 | 1337.5 | 1114 | 1301 | 1124 |
| | 664 | 1308.5 | 1154.5 | 1390 | 1235 |
| | 892 | 1219.5 | 1133 | 1406 | 1074 |
| | 892 | 1377 | 1079.5 | 1411 | 1101.5 |
| | 847 | 1439.5 | 1291 | 1432 | 1543 |
| | 807 | 1305 | 1139.5 | 1494 | 1219 |
| | 807 | 1413 | 1292 | 1297 | 1268 |

FIG. 13 (Continued)

| | | | |
|---:|---:|---:|---:|
| 946 | 2060 | 1023.5 | 1337 |
| 1070 | 2108 | 1095 | 1297 |
| 873.5 | 2087 | 1353 | 1335 |
| 975 | 1963 | 1014 | 1359 |
| 1694.5 | 2101 | 1287 | 1432 |
| 1004 | 2140 | 1241 | 1402 |
| 1208 | 2031.5 | 1252 | 1283.5 |

FIG. 13 (Continued)

| Affimer Working ID | EGFR (FL1-A of QSH01) | mIgG2b (FL1-A of QSH03) | hIgG1 Fc (FL1-A of QSH05) |
|---|---|---|---|
| PBS (BLANK) | 1630.5 | 1071 | 1111 |
| PBS (BLANK) | 1710.5 | 1084 | 903 |
| PBS (BLANK) | 1554.5 | 1078 | 1044 |
| PBS (BLANK) | 1543 | 992 | 1043 |
| PBS (BLANK) | 1621 | 1051 | 1093 |
| PBS (BLANK) | 1697 | 1055 | 1000.5 |
| NEGATIVE - - HA (NEGATIVE) | 1656 | 1101 | 1089 |
| NEGATIVE - - HA (NEGATIVE) | 1628 | 996 | 971 |
| NEGATIVE - - HA (NEGATIVE) | 1643.5 | 1116 | 1118 |
| NEGATIVE - - HA (NEGATIVE) | 1640 | 1130 | 1144 |
| NEGATIVE - - HA (NEGATIVE) | 1598.5 | 1055 | 1007 |
| NEGATIVE - - HA (NEGATIVE) | 1664 | 1163 | 1049 |
| ZIKA NS1 C12 () - HA (POSITIVE) | 1663 | 54687 | 1014 |
| ZIKA NS1 C12 () - HA (POSITIVE) | 1588 | 55225 | 1158.5 |
| ZIKA NS1 C12 () - HA (POSITIVE) | 1766 | 43772.5 | 1031 |
| ZIKA NS1 C12 () - HA (POSITIVE) | 1736 | 45644 | 1063 |
| ZIKA NS1 C12 () - HA (POSITIVE) | 1658 | 52196 | 1033.5 |
| ZIKA NS1 C12 () - HA (POSITIVE) | 1734 | 41868 | 1143 |
| 00454_645193 | 1785 | 1090 | 1137 |
| 00454_645325 | 1648 | 1120.5 | 1001 |
| 00454_645324 | 1701 | 1190 | 1101 |
| 00454_645296 | 18689 | 1211 | 108570 |
| 00454_645277 | 1616 | 1097 | 1030 |
| 00454_645140 | 17415.5 | 1071 | 79251 |
| 00454_645250 | 14422 | 1168.5 | 73151 |
| 00454_645222 | 1621 | 1020 | 1109 |
| 00454_645156 | 1726 | 1059 | 1176 |
| 00454_645174 | 1528 | 1100 | 1163.5 |
| 00454_645178 | 1607 | 1219 | 1124.5 |
| 00454_645271 | 1737 | 1265 | 1160 |
| 00454_645234 | 1593 | 1092 | 1177 |
| 00454_645290 | 1725 | 1019 | 1202 |
| 00454_645304 | 1724.5 | 1089 | 1167 |

FIG. 14

| hPD-L2 (FL1-A of QSH06) | Her2 (R&D) (FL1-A of QSH08) | hPD-L1 (FL1-A of QSH10) | Trastuzumab (FL1-A of QSH11) | hIgG (FL1-A of QSH13) |
|---|---|---|---|---|
| 1089 | 820 | 1343 | 1206 | 996 |
| 1094.5 | 830 | 1047 | 1359 | 928 |
| 1132 | 783 | 1062 | 1391 | 884.5 |
| 1122 | 811 | 1087 | 1367 | 1006 |
| 1079 | 810 | 1117 | 1361 | 920 |
| 1088.5 | 863 | 1148 | 1298.5 | 951 |
| 1085 | 957.5 | 990 | 1402 | 1015 |
| 1062 | 861 | 1014 | 1379.5 | 973 |
| 1181 | 745 | 1048 | 1246 | 963.5 |
| 1147 | 909 | 1135 | 1254 | 976 |
| 1215 | 833.5 | 1152 | 1310.5 | 1026 |
| 1132.5 | 850 | 1207.5 | 1431 | 1041 |
| 1062 | 825 | 1034.5 | 1381 | 1009 |
| 1192.5 | 814 | 1028 | 1500.5 | 960.5 |
| 1152 | 766 | 1052 | 1471 | 1038 |
| 1187 | 781.5 | 1063 | 1356.5 | 1041 |
| 1133 | 887 | 1082 | 1262 | 987 |
| 1127 | 969 | 1235 | 1426 | 1082 |
| 1349 | 1004.5 | 29696 | 1539 | 1128 |
| 1264 | 974 | 23210 | 1411 | 1079 |
| 1287 | 1046.5 | 22917.5 | 1504 | 1237 |
| 54516.5 | 1536.5 | 16156 | 139013 | 20297 |
| 1166 | 855 | 15552 | 1272 | 1004 |
| 43622 | 1201.5 | 14844 | 114642 | 16430 |
| 36800 | 1464 | 14150 | 105700 | 13898 |
| 1222 | 815 | 13524 | 1254 | 1045.5 |
| 1119 | 1056 | 13461 | 1284.5 | 1241 |
| 1240 | 937.5 | 13186 | 1493 | 1187.5 |
| 1211.5 | 834 | 13119 | 1450 | 1047.5 |
| 1299 | 887 | 12822 | 1370.5 | 1127 |
| 1280.5 | 1011 | 12603 | 1424 | 1068 |
| 1202 | 990.5 | 12387 | 1347 | 1088.5 |
| 1219 | 899 | 12054 | 1327 | 1025 |

FIG. 14 (Continued)

| Her2 (Sino) (FL1-A of QSH15) | Her3 (FL1-A of QSH16) | mPD-L1 (FL1-A of QSH18) | No target ctr (FL1-A of QSH22) | Avastin (FL1-A of QSH23) |
|---|---|---|---|---|
| 882 | 1276 | 1035 | 1397 | 1075.5 |
| 957 | 1354 | 1093 | 1315 | 1151 |
| 831 | 1267 | 1069 | 1407 | 1012.5 |
| 863 | 1317 | 996.5 | 1349 | 1130 |
| 845 | 1308 | 1114 | 1330 | 1101 |
| 721 | 1349 | 1044 | 1357.5 | 1063 |
| 807 | 1216 | 974 | 1297 | 1121.5 |
| 746 | 1353 | 1022 | 1316 | 1001 |
| 785 | 1289 | 1001 | 1378 | 1041 |
| 833.5 | 1257 | 1047 | 1449.5 | 1027 |
| 715 | 1310 | 1060.5 | 1371.5 | 1093.5 |
| 869.5 | 1276.5 | 1192 | 1316 | 1058.5 |
| 904 | 1295 | 929 | 1513 | 1025 |
| 791 | 1244 | 1196 | 1414.5 | 1140 |
| 969 | 1310 | 1167 | 1465.5 | 1065 |
| 920.5 | 1368.5 | 1124 | 1345 | 1073 |
| 758 | 1313 | 1175 | 1301 | 1118 |
| 930 | 1376 | 1079 | 1451 | 1153.5 |
| 791.5 | 1416 | 1139.5 | 1570.5 | 1213 |
| 755 | 1373 | 1171.5 | 1491 | 1050.5 |
| 1000 | 1446.5 | 1203.5 | 1619 | 1087 |
| 1558 | 9050 | 34447 | 1722 | 80937.5 |
| 977 | 1355 | 998 | 1542 | 1043 |
| 1086 | 7678 | 31591 | 1498 | 67202.5 |
| 1450.5 | 8058 | 26664.5 | 1723 | 59332.5 |
| 966 | 1370 | 1046 | 1411 | 1019.5 |
| 853 | 1402 | 1176 | 1577.5 | 1049.5 |
| 827 | 1402 | 1076 | 1559 | 1103 |
| 912 | 1359.5 | 1179 | 1401 | 1225.5 |
| 835 | 1397 | 1117 | 1483 | 1116 |
| 752 | 1492 | 1087 | 1489.5 | 1187 |
| 758.5 | 1403.5 | 954 | 1521 | 1125.5 |
| 775 | 1356 | 1140 | 1307 | 1133 |

FIG. 14 (Continued)

| Humira (FL1-A of QSH25) | Rituximab (FL1-A of QSH26) | mPD-L2 (FL1-A of QSH27) | Her4 (FL1-A of QSH28) |
|---|---|---|---|
| 848.5 | 1987 | 1148 | 1390.5 |
| 915 | 1962 | 987 | 1355.5 |
| 898 | 1952 | 1111 | 1354 |
| 953.5 | 1862.5 | 1133 | 1316 |
| 981 | 2065 | 1132.5 | 1375 |
| 861 | 1943 | 1125 | 1302 |
| 905 | 1807 | 1073.5 | 1346 |
| 937 | 1874 | 1026 | 1381 |
| 949.5 | 1986 | 1082 | 1291.5 |
| 933.5 | 1936 | 1138 | 1356.5 |
| 827 | 1970 | 1044 | 1334.5 |
| 931.5 | 2066.5 | 1190 | 1407 |
| 874 | 1903 | 1113 | 1278 |
| 961.5 | 1944 | 1095 | 1261 |
| 953.5 | 2009 | 1093 | 1247 |
| 901 | 2010 | 1085 | 1211 |
| 936 | 1989.5 | 1098 | 1413 |
| 996.5 | 1990 | 1104 | 1445 |
| 954 | 2070 | 1114 | 1488 |
| 1045.5 | 2066.5 | 954.5 | 1495.5 |
| 1111 | 2078.5 | 1242 | 1518 |
| 131315 | 22615 | 40253 | 4399 |
| 946 | 2029.5 | 1087 | 1437 |
| 86596 | 19134.5 | 37128 | 3722 |
| 84929 | 15932 | 30973.5 | 3826 |
| 986 | 1978 | 1042 | 1423 |
| 949 | 2012.5 | 1084 | 1502 |
| 1079 | 2023 | 1171 | 1610 |
| 890 | 1882 | 1085 | 1353 |
| 1040 | 2003 | 1138.5 | 1367 |
| 973 | 1957 | 1054 | 1476 |
| 1069 | 1952 | 1101 | 1571 |
| 977.5 | 2025.5 | 1163 | 1357.5 |

| | | | | |
|---|---|---|---|---|
| 36288.5 | 1518 | 11400.5 | 99037 | 18352 |
| 1289 | 828.5 | 10467 | 1437 | 1041 |
| 34870 | 1904 | 10415 | 115321 | 14048 |
| 1267 | 868 | 10265 | 1162 | 1008 |
| 1216 | 933.5 | 10170 | 1174 | 955 |
| 1264 | 1006 | 9941 | 1390 | 1135.5 |
| 1159.5 | 902 | 9151 | 1292 | 1022 |
| 1227 | 960 | 8958 | 1295.5 | 978.5 |
| 1278 | 914 | 8909 | 1477.5 | 1103 |
| 33579 | 1190 | 8875.5 | 117271 | 13220 |
| 1249 | 839 | 8869 | 1356 | 1100 |
| 1133 | 865 | 8848.5 | 1372 | 999.5 |
| 1259 | 987 | 8820.5 | 1415.5 | 1050 |
| 1183 | 893 | 8457 | 1349.5 | 960 |
| 1152.5 | 806 | 8154.5 | 1211 | 1179 |
| 22405 | 1086 | 7967 | 63728.5 | 8146 |
| 1292 | 756 | 7554 | 1364 | 1127 |
| 1202 | 791 | 7548.5 | 1352 | 1079.5 |
| 1222.5 | 781 | 7520 | 1570 | 1093 |
| 19074 | 1135.5 | 7405 | 54490 | 11801.5 |
| 1194 | 990 | 7236 | 1362 | 985 |
| 1136 | 855 | 7152.5 | 1199.5 | 973 |
| 1208 | 864 | 6750 | 1349 | 958.5 |
| 18935 | 1348.5 | 6229 | 57351.5 | 11405 |
| 1151.5 | 807 | 6201 | 1366.5 | 1034.5 |
| 1214.5 | 820 | 5958 | 1390.5 | 1113.5 |
| 18042 | 893 | 5438 | 7352 | 1451 |
| 12215 | 1040 | 5434 | 34368.5 | 8373 |
| 1117 | 756.5 | 5256 | 1075 | 996.5 |
| 1229.5 | 888 | 5184 | 1384 | 1032.5 |
| 1216.5 | 895.5 | 5091 | 1370 | 920 |
| 14030.5 | 834 | 4804.5 | 5806.5 | 1375 |
| 5665 | 750 | 4746 | 2900 | 1123 |
| 1151 | 786 | 4739 | 1260 | 996 |
| 1317 | 919 | 4669.5 | 1658 | 1101 |

FIG. 14 (Continued)

| Col1 | Col2 | Col3 | Col4 | Col5 |
|---|---|---|---|---|
| 1488 | 7688 | 23226.5 | 1687 | 57068 |
| 877 | 1313 | 1125 | 1569.5 | 1126.5 |
| 1731 | 8274.5 | 24038.5 | 2117 | 57839.5 |
| 910.5 | 1273 | 1189 | 1375 | 1117 |
| 775.5 | 1341 | 1062.5 | 1514 | 1102.5 |
| 775.5 | 1437 | 1146 | 1540 | 1175.5 |
| 940.5 | 1311 | 1066 | 1543 | 1194.5 |
| 837 | 1328.5 | 1014 | 1539 | 1125.5 |
| 869 | 1370 | 1095 | 1481 | 1187 |
| 1281 | 8010 | 23969 | 1689 | 57015 |
| 801 | 1421 | 1100 | 1494.5 | 1218 |
| 840 | 1437 | 1049.5 | 1504 | 1108.5 |
| 861 | 1391 | 1000 | 1563 | 1108 |
| 723 | 1392.5 | 1201 | 1440 | 1052 |
| 979 | 1302.5 | 1026 | 1511.5 | 1157 |
| 1287.5 | 5309 | 15791 | 1586 | 35101 |
| 839 | 1359 | 1173 | 1510 | 1019 |
| 812 | 1270 | 1135 | 1435 | 1057 |
| 825 | 1405 | 1162.5 | 1485.5 | 1152.5 |
| 1009 | 4027 | 14606 | 1432 | 29550 |
| 885 | 1310 | 1192 | 1464 | 1178.5 |
| 680 | 1266.5 | 1234.5 | 1450 | 1030 |
| 802.5 | 1418.5 | 1028 | 1435 | 1103 |
| 1330.5 | 4966 | 13374.5 | 1621.5 | 32320 |
| 876 | 1359 | 1117 | 1365 | 1098 |
| 845 | 1354 | 1121 | 1366 | 1121.5 |
| 747 | 2402 | 12293 | 1329.5 | 2428.5 |
| 1166 | 3006 | 9588.5 | 1478 | 19147 |
| 858 | 1235 | 1065 | 1377 | 1062 |
| 737 | 1371 | 1105.5 | 1429 | 1099 |
| 774 | 1342 | 1110 | 1427.5 | 1065 |
| 815.5 | 2308 | 9346 | 1489 | 2161 |
| 671 | 1714.5 | 4103.5 | 1296 | 1417 |
| 771 | 1319 | 1152.5 | 1475 | 1191.5 |
| 830 | 1420.5 | 2127 | 1477.5 | 1565 |

| | | | |
|---:|---:|---:|---:|
| 83437.5 | 16320 | 27748 | 3903 |
| 1009 | 2053 | 1081 | 1467 |
| 99995 | 15617 | 28510 | 4712.5 |
| 996.5 | 2036 | 1094 | 1415 |
| 932 | 1951 | 981 | 1381 |
| 937 | 2059.5 | 1089 | 1338 |
| 938 | 2005.5 | 1125 | 1415 |
| 950 | 1977.5 | 1073 | 1383.5 |
| 952.5 | 2024 | 1172.5 | 1464 |
| 103142 | 13979.5 | 27687 | 3747.5 |
| 992 | 1996.5 | 1163 | 1422.5 |
| 890 | 1958 | 1101.5 | 1333 |
| 868 | 2019 | 1121 | 1467 |
| 1012.5 | 1968.5 | 1225 | 1340.5 |
| 931 | 1957.5 | 1168 | 1356 |
| 53953.5 | 10209 | 19496 | 2849 |
| 922.5 | 2116 | 1112 | 1423 |
| 931 | 2016 | 1007 | 1332 |
| 942 | 2086.5 | 1146 | 1396 |
| 48642 | 10507 | 16577.5 | 2474.5 |
| 962 | 1995 | 1023.5 | 1402.5 |
| 869.5 | 1972 | 1047 | 1399.5 |
| 892 | 1995.5 | 1117 | 1365 |
| 47237.5 | 8831 | 15231 | 2805.5 |
| 845.5 | 1972 | 1159.5 | 1439 |
| 927 | 1958.5 | 1213 | 1497 |
| 7381.5 | 2478 | 14660 | 1834 |
| 31953.5 | 7122.5 | 10349.5 | 2032.5 |
| 936 | 2003.5 | 1071.5 | 1376.5 |
| 890.5 | 1995 | 1004 | 1299 |
| 1028 | 2062 | 1114 | 1357 |
| 5606 | 2375 | 10820 | 1713 |
| 2968 | 2148 | 4891 | 1384 |
| 984.5 | 2021 | 1049 | 1456 |
| 1115.5 | 1931 | 1100 | 1411 |

FIG. 14 (Continued)

| | | | |
|---|---:|---:|---:|
| 00454_645171 | 1620.5 | 1111 | 995 |
| 00454_645142 | 5730 | 1082 | 39717.5 |
| 00454_645276 | 4595 | 1058 | 38717 |
| 00454_645130 | 1683.5 | 1020.5 | 1006 |
| 00454_645162 | 1567 | 998.5 | 1103.5 |
| 00454_645299 | 1655.5 | 1094 | 1141 |
| 00454_645138 | 1674 | 1119 | 1072 |
| 00454_645285 | 1759 | 1173 | 1061 |
| 00454_645282 | 1558 | 1060 | 1123.5 |
| 00454_645165 | 1685 | 1046 | 1173 |
| 00454_645185 | 1720 | 1102.5 | 1092 |
| 00454_645134 | 1699 | 1114 | 1224 |
| 00454_645141 | 1628.5 | 1128 | 1210 |
| 00454_645209 | 1525.5 | 1154 | 1219 |
| 00454_645267 | 1661 | 1198 | 1055.5 |
| 00454_645214 | 1817 | 1151.5 | 1174.5 |
| 00454_645179 | 1545 | 1070 | 879 |
| 00454_645117 | 4995.5 | 1075.5 | 36788 |
| 00454_645157 | 1710 | 1054.5 | 1162 |
| 00454_645213 | 1687.5 | 1097 | 1106 |
| 00454_645180 | 1585.5 | 1012.5 | 1048 |
| 00454_645286 | 1647 | 1059 | 1070 |
| 00454_645259 | 4787 | 1100 | 23727 |
| 00454_645129 | 3095.5 | 1135.5 | 14084 |
| 00454_645242 | 1660 | 1124 | 968 |
| 00454_645145 | 1683 | 1101.5 | 1107 |
| 00454_645170 | 4318 | 1144 | 25645 |
| 00454_645181 | 4500 | 1049 | 25746 |
| 00454_645216 | 1701 | 1221 | 1210 |
| 00454_645201 | 1610 | 1185.5 | 1063 |
| 00454_645261 | 4576 | 1103 | 24225 |
| 00454_645308 | 1759 | 1218 | 1155 |
| 00454_645275 | 1671 | 1049 | 1086 |
| 00454_645264 | 1782 | 1130.5 | 1052 |
| 00454_645249 | 1760 | 1054 | 996 |

| | | | | | |
|---|---|---|---|---|---|
| | 1248.5 | 825 | 4619 | 1385 | 996 |
| | 18126 | 993 | 4612 | 70677 | 7438 |
| | 15884 | 832 | 4555.5 | 6325 | 1396 |
| | 1200 | 922 | 4533 | 1293 | 1019 |
| | 1211 | 992 | 4477 | 1354 | 982 |
| | 1245.5 | 780 | 4372 | 1286 | 920 |
| | 1243 | 936 | 4363 | 1540 | 1135 |
| | 1136.5 | 839 | 4338.5 | 1233.5 | 1019.5 |
| | 1213 | 817.5 | 4301.5 | 1253 | 1020 |
| | 1225 | 849 | 4251 | 1305 | 957.5 |
| | 1157 | 785 | 4239 | 1265.5 | 1011 |
| | 1159 | 917 | 4046 | 1352.5 | 1053 |
| | 1175 | 816.5 | 3967 | 1311 | 1028 |
| | 1159 | 917 | 3951 | 1402 | 1046 |
| | 1125 | 766.5 | 3902 | 1335 | 1043 |
| | 1192.5 | 798.5 | 3898 | 1293.5 | 1019.5 |
| | 1135 | 802 | 3702.5 | 1330 | 1001 |
| | 14948 | 1101.5 | 3633.5 | 67452 | 6348 |
| | 1245 | 787 | 3489 | 1326 | 1044 |
| | 1221 | 929.5 | 3483 | 1423.5 | 995 |
| | 1150 | 936 | 3479 | 1372.5 | 1029 |
| | 1175 | 895 | 3410 | 1423.5 | 1004 |
| | 11702.5 | 855.5 | 3336 | 38104 | 4227.5 |
| | 7087 | 872 | 3294 | 22782 | 2437 |
| | 1133 | 847 | 3258 | 1380.5 | 1070 |
| | 1186 | 740 | 3226 | 1298 | 954 |
| | 8722 | 933.5 | 3199 | 42398 | 4702.5 |
| | 8798.5 | 907 | 3131 | 43687 | 4509 |
| | 1186 | 863 | 3072 | 1365 | 981 |
| | 1116.5 | 854 | 3048.5 | 1458 | 940.5 |
| | 11179 | 985 | 3022 | 35506 | 3754.5 |
| | 1221 | 849.5 | 3005.5 | 1639 | 1142.5 |
| | 1087 | 752.5 | 2982.5 | 1332 | 1081 |
| | 1135 | 775 | 2969 | 1325.5 | 986 |
| | 1221 | 885 | 2954.5 | 1388.5 | 1028 |

FIG. 14 (Continued)

| | | | | |
|---|---|---|---|---|
| 934 | 1278 | 1091 | 1403 | 1120.5 |
| 1014 | 3386 | 12038 | 1446 | 35610 |
| 881 | 2389 | 10949 | 1446.5 | 2113 |
| 856.5 | 1454 | 1130 | 1431.5 | 1146 |
| 868.5 | 1287.5 | 1089 | 1329.5 | 1005.5 |
| 866 | 1404 | 1195 | 1506.5 | 1082 |
| 874 | 1331 | 1094 | 1394.5 | 1151 |
| 906 | 1352.5 | 1063 | 1491 | 1099 |
| 785 | 1423 | 1219 | 1421 | 1204 |
| 820.5 | 1324 | 1036 | 1475 | 1206 |
| 901 | 1372.5 | 1119 | 1453.5 | 1160 |
| 847 | 1341.5 | 1006 | 1369 | 1073 |
| 735.5 | 1386 | 1087 | 1419 | 1039 |
| 888 | 1322 | 1184 | 1351 | 1078 |
| 800.5 | 1368.5 | 1082 | 1432 | 1197 |
| 744 | 1353 | 1187 | 1435.5 | 1155.5 |
| 822 | 1244.5 | 1071 | 1340.5 | 1116 |
| 869 | 3060.5 | 10229 | 1563 | 29634 |
| 902 | 1448 | 1089 | 1403.5 | 1208 |
| 837 | 1318 | 1004.5 | 1399 | 1225 |
| 742.5 | 1332 | 1133 | 1434.5 | 1012 |
| 787 | 1276 | 1122 | 1538.5 | 1148 |
| 960 | 2876.5 | 7656 | 1493.5 | 17120 |
| 890 | 1999 | 4385 | 1376 | 10822.5 |
| 879 | 1337.5 | 1073.5 | 1392 | 922 |
| 825.5 | 1272 | 1192 | 1424 | 1074 |
| 843.5 | 3245 | 6428 | 1325.5 | 16137 |
| 932 | 3301 | 5893 | 1407 | 16338.5 |
| 857 | 1439 | 1092.5 | 1419 | 1181 |
| 837.5 | 1252 | 1040 | 1394 | 1039.5 |
| 955 | 2705 | 7294 | 1443 | 16805 |
| 827.5 | 1415 | 1211 | 1435 | 1233 |
| 728.5 | 1195 | 1090 | 1384 | 1076 |
| 734 | 1315 | 1071 | 1390 | 1082 |
| 989.5 | 1216 | 1169 | 1466 | 1156.5 |

| | | | |
|---|---|---|---|
| 965 | 1968 | 1138 | 1292 |
| 55979.5 | 6651.5 | 14541.5 | 2119 |
| 5959 | 2380 | 12777 | 1672 |
| 989 | 1957 | 1041 | 1461 |
| 893 | 2088 | 1070 | 1314.5 |
| 928 | 1876.5 | 1111.5 | 1446 |
| 976 | 2075 | 1030.5 | 1409 |
| 936 | 1961 | 1099 | 1313 |
| 941.5 | 1922 | 1017 | 1389 |
| 1019.5 | 1919 | 1089.5 | 1310.5 |
| 931.5 | 1966.5 | 1096 | 1348 |
| 876 | 2088 | 1123 | 1324 |
| 1014.5 | 2121.5 | 1219 | 1338.5 |
| 950.5 | 2033 | 1127 | 1452 |
| 885 | 1990 | 1016 | 1284 |
| 902 | 1955 | 1153 | 1442.5 |
| 924 | 2014 | 1049 | 1348.5 |
| 43950 | 5454 | 12677 | 2041 |
| 956.5 | 2000.5 | 1082.5 | 1464 |
| 1004 | 1951 | 1082 | 1424 |
| 888.5 | 1895 | 1151 | 1351.5 |
| 965 | 1942 | 1108 | 1405 |
| 29854 | 4895 | 9021.5 | 2046.5 |
| 16444 | 3619 | 5733 | 1718 |
| 944 | 1995 | 1074 | 1332 |
| 965 | 2028 | 1091.5 | 1405 |
| 37006 | 5461 | 7201 | 2014 |
| 38324.5 | 5263.5 | 7271 | 2179 |
| 1036 | 2011.5 | 1118.5 | 1321 |
| 968 | 2015 | 1138 | 1419 |
| 29575 | 4530 | 8562 | 1782 |
| 1254 | 2008 | 1308 | 1544.5 |
| 949 | 1874 | 1109 | 1409 |
| 937 | 1893.5 | 1185 | 1312.5 |
| 860 | 2092 | 1211.5 | 1372.5 |

| | | | | |
|---|---|---|---|---|
| 00454_645306 | | 1632.5 | 1148 | 1089 |
| 00454_645196 | | 4067 | 1122 | 30337 |
| 00454_645263 | | 1671 | 1114 | 1049 |
| 00454_645188 | | 4239 | 1045.5 | 32917 |
| 00454_645194 | | 4131 | 1108 | 35041 |
| 00454_645190 | | 1742 | 1142 | 1010 |
| 00454_645204 | | 1540 | 1036.5 | 1023.5 |
| 00454_645191 | | 1540.5 | 1114 | 1066.5 |
| 00454_645310 | | 1696 | 1133.5 | 1198.5 |
| 00454_645227 | | 1677 | 1054 | 1047 |
| 00454_645208 | | 3960 | 1100 | 30807 |
| 00454_645311 | | 1701 | 1238 | 1163.5 |
| 00454_645309 | | 3898.5 | 1217.5 | 14158.5 |
| 00454_645224 | | 1674 | 1149 | 1165 |
| 00454_645251 | | 1768.5 | 1116 | 1020 |
| 00454_645319 | | 1634 | 1151 | 1033 |
| 00454_645318 | | 1659.5 | 1177 | 994.5 |
| 00454_645302 | | 1696 | 1019 | 1025 |
| 00454_645307 | | 1727 | 1126.5 | 1093 |
| 00454_645115 | | 2696 | 1147.5 | 8206 |
| 00454_645328 | | 1733 | 1104 | 1233 |
| 00454_645210 | | 1663 | 1139.5 | 1024 |
| 00454_645113 | | 1728 | 1157 | 937.5 |
| 00454_645288 | | 1666 | 1004.5 | 1041 |
| 00454_645303 | | 1590.5 | 1113.5 | 1076 |
| 00454_645317 | | 1769 | 1084 | 1112 |
| 00454_645158 | | 1640.5 | 971 | 1435 |
| 00454_645161 | | 1644 | 1135.5 | 1113.5 |
| 00454_645147 | | 1647 | 1159.5 | 1023.5 |
| 00454_645322 | | 1644 | 1205 | 928 |
| 00454_645177 | | 1738.5 | 1098 | 1114 |
| 00454_645203 | | 1601 | 1154 | 988.5 |
| 00454_645320 | | 1725.5 | 1144 | 1081.5 |
| 00454_645270 | | 1650 | 1100 | 1214.5 |
| 00454_645327 | | 1672 | 1057 | 1115.5 |

| | | | | |
|---|---|---|---|---|
| 1237 | 1019.5 | 2918.5 | 1422.5 | 1106 |
| 10337 | 1011 | 2879 | 46737 | 3621.5 |
| 1057.5 | 897 | 2879 | 1437 | 927 |
| 11244 | 855 | 2871.5 | 48826 | 3399 |
| 11321.5 | 891 | 2855 | 50439 | 3528.5 |
| 1109 | 777 | 2849.5 | 1339.5 | 977.5 |
| 1271.5 | 748 | 2774 | 1341.5 | 998 |
| 1149 | 896 | 2741 | 1357 | 954 |
| 1195 | 1003 | 2668 | 1411 | 1078 |
| 1168 | 782 | 2647 | 1410 | 971 |
| 10297.5 | 943 | 2645.5 | 43612.5 | 3164 |
| 1217.5 | 903 | 2625 | 1448 | 1003.5 |
| 7384 | 922 | 2553 | 23002 | 3768.5 |
| 1173.5 | 773.5 | 2496 | 1142 | 1033 |
| 1273 | 818.5 | 2420 | 1241 | 1046 |
| 1214.5 | 820 | 2369 | 1247 | 1093.5 |
| 1138 | 822 | 2299 | 1295 | 892 |
| 1205 | 814 | 2214 | 1346 | 886 |
| 1278 | 875.5 | 2177 | 1361.5 | 1132 |
| 4630 | 917 | 2151 | 15656 | 1913.5 |
| 1157 | 937.5 | 2028 | 1322 | 982 |
| 1124 | 796 | 2006 | 1356.5 | 990 |
| 1127 | 799 | 1856.5 | 1284 | 869 |
| 1208 | 768 | 1798 | 1252 | 1027.5 |
| 1158.5 | 857.5 | 1720 | 1298.5 | 973 |
| 1124.5 | 812 | 1601 | 1191 | 896 |
| 1914 | 780.5 | 1475 | 1320.5 | 1065.5 |
| 1136 | 863 | 1473.5 | 1429.5 | 1001.5 |
| 1133.5 | 728 | 1354 | 1315 | 963 |
| 1113.5 | 775 | 1326 | 1537 | 1116 |
| 1051 | 734 | 1315 | 1384 | 968 |
| 1130 | 715 | 1310.5 | 1371 | 989.5 |
| 1159.5 | 917 | 1302 | 1255 | 982 |
| 1225 | 856 | 1286 | 1186 | 1011 |
| 1134.5 | 866 | 1279 | 1392.5 | 1086 |

| | | | | | |
|---|---|---|---|---|---|
| | 865 | 1451 | 1072 | 1448 | 1154 |
| | 836 | 2352 | 6982.5 | 1501 | 16918 |
| | 911.5 | 1246 | 1116 | 1472 | 1174.5 |
| | 919.5 | 2354 | 7643 | 1302.5 | 17814.5 |
| | 814.5 | 2414 | 7294 | 1415 | 18413 |
| | 851.5 | 1303 | 1128.5 | 1505 | 1117 |
| | 881 | 1268 | 1035 | 1407.5 | 1076.5 |
| | 809.5 | 1329 | 942 | 1389 | 1112.5 |
| | 880 | 1337 | 1089 | 1476.5 | 1194 |
| | 793.5 | 1332 | 1190 | 1526 | 1105 |
| | 858 | 2289 | 6576 | 1521 | 16966 |
| | 828 | 1372 | 1152.5 | 1329.5 | 1101 |
| | 1104.5 | 2413 | 5281.5 | 1525 | 11538.5 |
| | 831 | 1369 | 1157.5 | 1361 | 1139.5 |
| | 757.5 | 1297 | 1069 | 1474 | 1085.5 |
| | 904 | 1288 | 1065 | 1519.5 | 1192 |
| | 884 | 1319 | 1124.5 | 1341.5 | 1087 |
| | 780 | 1389 | 1173 | 1353.5 | 1087 |
| | 819.5 | 1408.5 | 1070 | 1478 | 1119 |
| | 852 | 1798 | 3035 | 1516 | 6865.5 |
| | 875.5 | 1274.5 | 1063 | 1340 | 1048 |
| | 879.5 | 1405 | 1114 | 1219 | 1066 |
| | 1032.5 | 1334 | 1088 | 1580 | 1177.5 |
| | 978.5 | 1238 | 1018 | 1389 | 1124 |
| | 864.5 | 1369.5 | 1022 | 1411 | 1053.5 |
| | 834 | 1262 | 1008 | 1404.5 | 1128 |
| | 822 | 1387 | 1330 | 1355 | 1068 |
| | 865 | 1322 | 1052 | 1432 | 1166.5 |
| | 815 | 1329 | 1050.5 | 1395.5 | 1154 |
| | 785 | 1248 | 1167 | 1426 | 1039 |
| | 884 | 1309 | 1155.5 | 1523 | 1195 |
| | 795 | 1363 | 1042 | 1270 | 1083.5 |
| | 962 | 1280 | 1108 | 1392 | 1184 |
| | 783 | 1335.5 | 1147.5 | 1382 | 1004 |
| | 788.5 | 1364 | 1178 | 1409 | 1081 |

| | | | | |
|---|---|---|---|---|
| | 1036 | 2072 | 1242 | 1526 |
| | 36622 | 4743 | 8061 | 1950.5 |
| | 919 | 1866 | 1039 | 1346 |
| | 38499 | 4532 | 8273 | 1743.5 |
| | 39260 | 4670 | 8346 | 1698.5 |
| | 955 | 1958 | 1200 | 1329 |
| | 927 | 2001 | 976.5 | 1314.5 |
| | 939 | 1955 | 1118 | 1396 |
| | 971 | 1998 | 1105 | 1452 |
| | 860 | 2045 | 981 | 1423 |
| | 35667 | 4230 | 7843 | 1656 |
| | 988.5 | 1995 | 1093 | 1417.5 |
| | 19026 | 4216 | 5972 | 1831.5 |
| | 966 | 1997 | 1117 | 1380 |
| | 892 | 1906 | 1144 | 1403.5 |
| | 952 | 2002.5 | 988 | 1359 |
| | 885 | 1946 | 1119 | 1315 |
| | 934 | 1955 | 1086 | 1289.5 |
| | 1081 | 2030 | 1142.5 | 1536 |
| | 10547 | 2997.5 | 3834.5 | 1582.5 |
| | 893 | 1938 | 1142.5 | 1378 |
| | 817 | 1951.5 | 1047 | 1380 |
| | 944 | 2048 | 1086 | 1450 |
| | 934 | 2121 | 979.5 | 1362 |
| | 858 | 1931.5 | 1221 | 1230.5 |
| | 770.5 | 1965.5 | 1119 | 1340 |
| | 860 | 1849 | 1462.5 | 1429.5 |
| | 938 | 1969.5 | 1116.5 | 1368.5 |
| | 984 | 1882.5 | 1049 | 1240.5 |
| | 833.5 | 1978.5 | 1004 | 1372 |
| | 887 | 2052 | 1025 | 1342.5 |
| | 831.5 | 1946 | 1167.5 | 1388.5 |
| | 936 | 2086 | 1126.5 | 1345 |
| | 863 | 1922 | 1063 | 1329 |
| | 854 | 1985.5 | 1064 | 1364 |

← (L)    (16)↓    FIG. 14 (Continued)

| | | | |
|---|---|---|---|
| 00454_645128 | 1670.5 | 1112 | 1082 |
| 00454_645151 | 1674 | 1108.5 | 930.5 |
| 00454_645226 | 1696 | 1208 | 1083.5 |
| 00454_645215 | 1759 | 1165 | 1170.5 |
| 00454_645329 | 1820.5 | 1134 | 983.5 |
| 00454_645235 | 1650 | 1008.5 | 1061.5 |
| 00454_645269 | 1668 | 1056 | 1103 |
| 00454_645217 | 1665 | 1106 | 1054 |
| 00454_645237 | 1663.5 | 1229 | 984.5 |
| 00454_645278 | 1706 | 1046 | 1069 |
| 00454_645127 | 1736 | 1157 | 1160 |
| 00454_645253 | 1678.5 | 1127 | 999 |
| 00454_645272 | 1561 | 1081 | 989 |
| 00454_645189 | 1619 | 1188.5 | 1117.5 |
| 00454_645200 | 1550 | 1426 | 1186 |
| 00454_645313 | 1640 | 1066 | 1035 |
| 00454_645148 | 1623 | 1135.5 | 1049 |
| 00454_645258 | 1648 | 1094.5 | 1054 |
| 00454_645206 | 1623 | 1086 | 1082 |
| 00454_645239 | 1682 | 1085.5 | 1056.5 |
| 00454_645187 | 1714 | 1109 | 1051.5 |
| 00454_645150 | 1691 | 1079 | 1027.5 |
| 00454_645323 | 1674 | 1097.5 | 1082 |
| 00454_645135 | 1634.5 | 1055.5 | 1011 |
| 00454_645241 | 1685 | 1152 | 1135 |
| 00454_645186 | 1711.5 | 1106 | 1011 |
| 00454_645153 | 1673.5 | 1208 | 971.5 |
| 00454_645125 | 1724.5 | 1176 | 1149 |
| 00454_645248 | 1593 | 1070 | 1044 |
| 00454_645154 | 1658 | 1099 | 1114.5 |
| 00454_645172 | 1650 | 1108 | 992 |
| 00454_645139 | 1832.5 | 1107.5 | 1022 |
| 00454_645252 | 1737.5 | 1226 | 960 |
| 00454_645321 | 1705.5 | 1118.5 | 1082 |
| 00454_645133 | 1601 | 1151.5 | 1044 |

FIG. 14 (Continued)

| | | | | |
|---|---|---|---|---|
| 1136 | 779 | 1277.5 | 1295 | 909 |
| 1158 | 822.5 | 1270 | 1350 | 1003.5 |
| 1170 | 943.5 | 1265 | 1388 | 1042 |
| 1181 | 886.5 | 1265 | 1189 | 982.5 |
| 1206 | 815 | 1262 | 1330 | 998 |
| 1221.5 | 753 | 1262 | 1360.5 | 853 |
| 1176 | 796 | 1256 | 1381.5 | 979 |
| 1136 | 782.5 | 1255.5 | 1243 | 1014 |
| 1251 | 836 | 1254 | 1367 | 1060 |
| 1123 | 825.5 | 1254 | 1292 | 992 |
| 1288.5 | 868 | 1252 | 1411 | 1074 |
| 1229 | 857.5 | 1250.5 | 1237 | 989 |
| 1230 | 863 | 1250 | 1222 | 998.5 |
| 1074 | 694.5 | 1246 | 1344 | 910 |
| 1153.5 | 701 | 1246 | 1419 | 968.5 |
| 1159 | 813 | 1241 | 1164 | 1063 |
| 1224 | 812 | 1232.5 | 1187.5 | 979 |
| 1044 | 827.5 | 1226.5 | 1318 | 1014 |
| 1152.5 | 799 | 1222 | 1307 | 947 |
| 1311 | 761 | 1220.5 | 1319 | 1068.5 |
| 1110 | 766 | 1216.5 | 1346 | 1031 |
| 1173.5 | 865.5 | 1208 | 1278.5 | 1027.5 |
| 1136 | 735 | 1197 | 1430.5 | 934 |
| 1297 | 685 | 1197 | 1319 | 1036 |
| 1197.5 | 783 | 1194 | 1540 | 1012 |
| 1070.5 | 852 | 1189 | 1321 | 922 |
| 1160 | 787.5 | 1182.5 | 1384 | 979 |
| 1127.5 | 868 | 1174.5 | 1365.5 | 986 |
| 1024 | 780 | 1168 | 1284 | 1024.5 |
| 1100.5 | 869 | 1167.5 | 1341.5 | 936 |
| 1114 | 828.5 | 1166.5 | 1175.5 | 966 |
| 1138 | 814 | 1165 | 1451 | 957 |
| 1089 | 869.5 | 1161.5 | 1425.5 | 1054.5 |
| 1203 | 829 | 1161.5 | 1400 | 987 |
| 1173 | 748.5 | 1148 | 1356 | 974.5 |

| | | | | |
|---|---|---|---|---|
| 643.5 | 1292 | 1162.5 | 1399 | 1200 |
| 790 | 1349 | 1148 | 1445 | 1154 |
| 863 | 1348 | 1136 | 1521 | 1119 |
| 903.5 | 1301 | 1197 | 1435 | 1098 |
| 892.5 | 1233 | 979 | 1521 | 1145 |
| 954 | 1247 | 1185 | 1307 | 1098.5 |
| 890 | 1334 | 1222 | 1439 | 1213 |
| 797.5 | 1297 | 1060 | 1414.5 | 1068 |
| 934 | 1315 | 1083.5 | 1423 | 1115.5 |
| 814 | 1274 | 1076 | 1407 | 1096.5 |
| 874 | 1313 | 1127 | 1533 | 1050.5 |
| 783 | 1374 | 1044 | 1478.5 | 1093 |
| 726 | 1321.5 | 1051 | 1419 | 998 |
| 962 | 1381 | 1041 | 1413 | 1067 |
| 860 | 1272.5 | 1074 | 1322 | 1026.5 |
| 899 | 1364 | 1101 | 1364 | 1045 |
| 812 | 1307 | 987.5 | 1340 | 1024 |
| 790 | 1289 | 1049 | 1367 | 1154 |
| 906 | 1269.5 | 1070 | 1287 | 1115 |
| 896 | 1350.5 | 1022 | 1415 | 1117.5 |
| 854.5 | 1287.5 | 1007.5 | 1294 | 1106 |
| 879.5 | 1332 | 995 | 1412.5 | 1119.5 |
| 809 | 1327.5 | 1091.5 | 1317 | 1109.5 |
| 984.5 | 1318 | 1060 | 1386.5 | 1086 |
| 853 | 1390 | 1108 | 1388 | 1097 |
| 755 | 1268 | 1077.5 | 1415 | 1004 |
| 925 | 1189 | 1025.5 | 1431.5 | 1068 |
| 814 | 1310 | 1143 | 1391 | 1080 |
| 901.5 | 1228 | 1079 | 1494 | 1127.5 |
| 771.5 | 1291 | 1143 | 1478.5 | 1009 |
| 843.5 | 1286.5 | 1256 | 1364.5 | 982 |
| 819.5 | 1380.5 | 1031 | 1453 | 1212 |
| 703 | 1368.5 | 1127 | 1298.5 | 1160.5 |
| 817.5 | 1351 | 1081.5 | 1459 | 1181 |
| 837 | 1302.5 | 1097 | 1454 | 1101 |

| 16 | | | |
|---|---|---|---|
| 904 | 2126 | 1051.5 | 1411 |
| 891.5 | 1896 | 1117 | 1370 |
| 931 | 1979 | 1047 | 1429.5 |
| 896 | 1906 | 1176 | 1391 |
| 853 | 1939.5 | 1127 | 1335 |
| 972.5 | 1986 | 1033 | 1404 |
| 989.5 | 2052.5 | 1175.5 | 1408.5 |
| 893 | 1984 | 1185 | 1287 |
| 888 | 1966 | 1080 | 1264.5 |
| 951 | 1998 | 1184 | 1270.5 |
| 883.5 | 2017 | 1110.5 | 1397 |
| 920 | 2059.5 | 1179 | 1362 |
| 886.5 | 1966 | 1056.5 | 1310 |
| 913 | 1964 | 1118 | 1404 |
| 938.5 | 1864 | 980.5 | 1295 |
| 876 | 1999 | 990 | 1241 |
| 965 | 1876 | 1114 | 1361 |
| 833 | 1769.5 | 1007 | 1370 |
| 1002 | 1920 | 1109 | 1326.5 |
| 965 | 2052.5 | 1111 | 1444.5 |
| 883 | 1931 | 1080 | 1356 |
| 984.5 | 1988.5 | 1155 | 1355.5 |
| 810 | 1990.5 | 997 | 1393 |
| 1036 | 1931 | 1089 | 1369 |
| 928 | 2020 | 1175 | 1353.5 |
| 934.5 | 1979 | 1095 | 1257 |
| 981.5 | 1909 | 1163 | 1335 |
| 966 | 1941 | 1073.5 | 1424 |
| 801 | 1813 | 1051.5 | 1263 |
| 948 | 2009.5 | 1163.5 | 1385.5 |
| 890 | 1931.5 | 1072 | 1257 |
| 914 | 1998 | 1133 | 1332 |
| 841 | 2044.5 | 1186 | 1313 |
| 922 | 2047.5 | 1018 | 1263.5 |
| 922 | 1864 | 1135 | 1357.5 |

FIG. 14 (Continued)

| | | | |
|---|---|---|---|
| 00454_645182 | 1580 | 1157.5 | 1103 |
| 00454_645223 | 1600 | 967.5 | 1127 |
| 00454_645149 | 1651.5 | 1160 | 1143 |
| 00454_645168 | 1622 | 1175 | 1174.5 |
| 00454_645274 | 1646.5 | 1010.5 | 1150.5 |
| 00454_645231 | 1645 | 1082.5 | 1111 |
| 00454_645137 | 1672 | 1165.5 | 1047 |
| 00454_645192 | 1632.5 | 1199 | 1097 |
| 00454_645159 | 1599.5 | 1089.5 | 1100 |
| 00454_645183 | 1799 | 1106 | 1047 |
| 00454_645163 | 1631 | 1124 | 1073 |
| 00454_645305 | 1775 | 1076 | 1166 |
| 00454_645243 | 1663.5 | 1118 | 1055 |
| 00454_645301 | 1630 | 1133 | 1061.5 |
| 00454_645236 | 1768.5 | 1172.5 | 950 |
| 00454_645238 | 1745 | 1234 | 1109.5 |
| 00454_645312 | 1682 | 1086 | 983.5 |
| 00454_645119 | 1677 | 1243 | 1109 |
| 00454_645114 | 1792 | 1143.5 | 1047.5 |
| 00454_645273 | 1571.5 | 1042.5 | 1165 |
| 00454_645256 | 1655 | 1235 | 1064 |
| 00454_645300 | 1612.5 | 1044.5 | 1071 |
| 00454_645232 | 1602 | 1167 | 1008 |
| 00454_645221 | 1674.5 | 1197 | 1138 |
| 00454_645184 | 1620 | 1144 | 1097 |
| 00454_645254 | 1537 | 1133 | 1007.5 |
| 00454_645265 | 1648 | 1148 | 1070.5 |
| 00454_645246 | 1600 | 1128.5 | 1055 |
| 00454_645225 | 1624.5 | 1099.5 | 1071 |
| 00454_645211 | 1617 | 1065.5 | 1093 |
| 00454_645257 | 1648 | 1118 | 1106 |
| 00454_645229 | 1620 | 1155 | 1020 |
| 00454_645228 | 1596 | 1115 | 976.5 |
| 00454_645283 | 1699 | 1138.5 | 1118 |
| 00454_645292 | 1588.5 | 1097 | 1148 |

| | | | | |
|---|---|---|---|---|
| 1195 | 825 | 1145 | 1396 | 1037.5 |
| 1155 | 723 | 1143 | 1154 | 1043.5 |
| 1111 | 831.5 | 1142 | 1292.5 | 965 |
| 1248 | 868 | 1138 | 1317 | 985 |
| 1155.5 | 804 | 1134 | 1273 | 1068 |
| 1162.5 | 862.5 | 1133.5 | 1356 | 899.5 |
| 1157 | 885 | 1132 | 1399 | 968 |
| 1115 | 795.5 | 1128.5 | 1371 | 1047 |
| 1162.5 | 812 | 1125 | 1294 | 878 |
| 1149.5 | 831.5 | 1124 | 1318 | 1028 |
| 1108 | 804.5 | 1122 | 1307 | 985.5 |
| 1168.5 | 874.5 | 1122 | 1335 | 1074 |
| 1159.5 | 807 | 1121.5 | 1361.5 | 987 |
| 1107.5 | 778 | 1120.5 | 1280 | 1044 |
| 1127 | 895.5 | 1120 | 1302 | 942 |
| 1269 | 808 | 1119 | 1321 | 847 |
| 1200 | 920 | 1119 | 1486 | 886.5 |
| 1124 | 836 | 1118.5 | 1426 | 989 |
| 1240 | 857 | 1109 | 1311 | 1041 |
| 1141.5 | 756 | 1108.5 | 1260 | 956 |
| 1200.5 | 887 | 1103 | 1235 | 952 |
| 1184 | 851.5 | 1102.5 | 1353 | 1019 |
| 1108 | 863 | 1101 | 1340.5 | 931 |
| 1159 | 871 | 1100 | 1254 | 995 |
| 1127 | 799 | 1091 | 1332 | 998.5 |
| 1073.5 | 853 | 1087 | 1254.5 | 998.5 |
| 1174 | 852 | 1086 | 1369 | 1029 |
| 1179.5 | 908 | 1086 | 1287 | 1028.5 |
| 1252 | 910.5 | 1085.5 | 1586 | 1065 |
| 1135.5 | 761 | 1084 | 1385 | 1006 |
| 1202 | 717 | 1076 | 1252 | 933 |
| 1197 | 794.5 | 1065 | 1218.5 | 1006 |
| 1130 | 857 | 1060 | 1108 | 1016 |
| 1190 | 815 | 1059 | 1225.5 | 942 |
| 1079 | 793 | 1055 | 1325 | 974.5 |

FIG. 14 (Continued)

| | | | | |
|---|---|---|---|---|
| 885 | 1311 | 944 | 1441 | 1105 |
| 828 | 1264 | 950 | 1481.5 | 1060 |
| 864.5 | 1216 | 1213.5 | 1438.5 | 1068.5 |
| 888.5 | 1246 | 1141 | 1364 | 1105 |
| 933 | 1421 | 1200 | 1321 | 1236 |
| 825 | 1248.5 | 1110 | 1275 | 1089 |
| 772 | 1359 | 1166 | 1301 | 1100 |
| 890 | 1349 | 1008.5 | 1435 | 1096 |
| 814 | 1243 | 1078 | 1321 | 1084 |
| 790 | 1328 | 1137 | 1505 | 1175 |
| 753 | 1319.5 | 1068 | 1376.5 | 1148 |
| 877 | 1375 | 1186 | 1475 | 1141 |
| 815 | 1259 | 1161.5 | 1492 | 1033 |
| 823.5 | 1424 | 1122 | 1440 | 1122 |
| 833 | 1278.5 | 1014 | 1458 | 1073 |
| 800.5 | 1314.5 | 1006.5 | 1326 | 1019 |
| 837 | 1311 | 1196 | 1475 | 1133 |
| 885 | 1362 | 1109 | 1512.5 | 1061 |
| 901 | 1314 | 1099 | 1416 | 1159.5 |
| 909 | 1327 | 1056 | 1402 | 1068 |
| 745.5 | 1339.5 | 1037 | 1370 | 983 |
| 915.5 | 1278 | 1124 | 1407 | 957 |
| 830 | 1277 | 1070.5 | 1361 | 1045 |
| 894 | 1378 | 1206.5 | 1421 | 1148 |
| 841 | 1273.5 | 971 | 1351 | 1151 |
| 820 | 1295.5 | 1079 | 1323 | 1186 |
| 814 | 1344 | 1154 | 1367 | 1039 |
| 739.5 | 1280.5 | 1075 | 1299.5 | 1125 |
| 792 | 1284 | 1035 | 1423.5 | 1167 |
| 948 | 1347 | 1141 | 1459 | 1047 |
| 798 | 1373 | 1128 | 1432.5 | 1038 |
| 917.5 | 1251 | 965 | 1370.5 | 1173 |
| 892 | 1433 | 983.5 | 1202 | 1098.5 |
| 801 | 1402 | 1182 | 1348.5 | 1043 |
| 835 | 1324 | 947 | 1531.5 | 987 |

| 964 | 2008 | 1082 | 1321.5 |
| 899 | 1898 | 1152 | 1372.5 |
| 941.5 | 2006 | 1224 | 1307 |
| 949.5 | 1943 | 996 | 1259.5 |
| 952 | 1988 | 1170.5 | 1359 |
| 993 | 1882 | 1211 | 1321.5 |
| 917 | 1974 | 1127.5 | 1287 |
| 958 | 2018 | 1003 | 1337 |
| 887.5 | 1896 | 1105 | 1254 |
| 865 | 2049 | 1030 | 1356 |
| 879 | 1928.5 | 998 | 1278 |
| 837 | 1973.5 | 1197 | 1346 |
| 872 | 2031 | 1054 | 1332 |
| 968 | 1949 | 1033 | 1259 |
| 891.5 | 1938 | 1162 | 1297.5 |
| 927 | 2065.5 | 1125 | 1370 |
| 930 | 1860 | 1197 | 1447 |
| 949 | 2012.5 | 1326 | 1402 |
| 779 | 2053.5 | 1106 | 1297 |
| 850.5 | 1944 | 1115.5 | 1365 |
| 942 | 1939 | 1095 | 1315 |
| 868 | 1858 | 965 | 1359 |
| 880 | 1844 | 1012 | 1264 |
| 899 | 2015.5 | 1148 | 1485.5 |
| 852.5 | 1880 | 991.5 | 1325.5 |
| 836.5 | 1960 | 1101 | 1378 |
| 901 | 2005 | 1202 | 1386 |
| 919.5 | 1910 | 1099 | 1356 |
| 872.5 | 1908 | 1225 | 1366 |
| 962.5 | 2003.5 | 1179 | 1415 |
| 867 | 1887.5 | 1092 | 1388 |
| 841 | 1960 | 1101 | 1258 |
| 914 | 1948 | 1062.5 | 1243 |
| 895.5 | 1925.5 | 1030 | 1362 |
| 936 | 2010.5 | 1100.5 | 1248 |

FIG. 14 (Continued)

| | | | |
|---|---:|---:|---:|
| 00454_645255 | 1710 | 1024 | 1092 |
| 00454_645245 | 1666.5 | 1119 | 1088.5 |
| 00454_645266 | 1679 | 1022 | 913 |
| 00454_645126 | 1683 | 1135 | 1139 |
| 00454_645146 | 1704.5 | 971 | 936.5 |
| 00454_645233 | 1704 | 1063 | 1117 |
| 00454_645230 | 1744 | 971 | 1208 |
| 00454_645279 | 1726.5 | 1108 | 1109 |
| 00454_645207 | 1762 | 1115 | 995 |
| 00454_645240 | 1756 | 1088 | 1098 |
| 00454_645247 | 1620.5 | 1094.5 | 936 |
| 00454_645176 | 1553 | 1138 | 941 |

FIG. 14 (Continued)

| 1099.5 | 740 | 1051.5 | 1283 | 941 |
| 1165.5 | 779.5 | 1041 | 1400.5 | 1018 |
| 1121 | 834 | 1039 | 1275 | 1017 |
| 1130 | 841.5 | 1027 | 1271.5 | 960 |
| 1200 | 872.5 | 1000 | 1099 | 1049 |
| 1130 | 822 | 996 | 1398 | 1022 |
| 1215.5 | 858 | 981.5 | 1233 | 1065 |
| 1183 | 853.5 | 971 | 1303 | 1054 |
| 1236 | 782 | 962 | 1364 | 953 |
| 1017 | 789.5 | 960 | 1170 | 1027 |
| 1206.5 | 830 | 949 | 1397 | 998 |
| 1034 | 700 | 941 | 1327 | 887.5 |

FIG. 14 (Continued)

| | ㉓ | | | |
|---:|---:|---:|---:|---:|
| 838.5 | 1279 | 1112 | 1370 | 1105 |
| 909 | 1319 | 1068 | 1463.5 | 1041 |
| 981 | 1295 | 1025 | 1443 | 1218 |
| 875 | 1364 | 1095 | 1521.5 | 1130 |
| 818 | 1351.5 | 1167 | 1450.5 | 1126 |
| 884 | 1434.5 | 1122 | 1400 | 1124 |
| 884 | 1174 | 1135 | 1410 | 1202 |
| 877 | 1240 | 1011 | 1356 | 1182.5 |
| 802 | 1340 | 1062 | 1365 | 1051.5 |
| 802 | 1218 | 1105 | 1306 | 947.5 |
| 863 | 1290.5 | 995 | 1368 | 982 |
| 755 | 1279.5 | 1024 | 1426 | 955 |

FIG. 14 (Continued)

| 876.5 | 1962 | 1198 | 1421 |
| 1019 | 1933 | 1141 | 1311 |
| 866 | 1847 | 1114 | 1318.5 |
| 874 | 2027 | 960 | 1412.5 |
| 896 | 2000 | 1071 | 1280 |
| 971 | 2075.5 | 1180.5 | 1404 |
| 902.5 | 1981 | 950 | 1360.5 |
| 851 | 1965 | 969 | 1304 |
| 946 | 1927 | 1159 | 1287 |
| 912 | 1868 | 1024 | 1273 |
| 896.5 | 1979 | 1166 | 1443 |
| 787.5 | 1904.5 | 1062.5 | 1261.5 |

FIG. 14 (Continued)

| Affimer Working ID | Canine PDL_1 (FL1-A of QSH02) | Human VEGFR2 (FL1-A of QSH04) |
|---|---:|---:|
| 00492_655534 | 487686 | 1046.5 |
| 00492_655606 | 300170 | 968 |
| 00492_655478 | 265975 | 973 |
| 00492_655610 | 198066 | 1053 |
| 00492_655494 | 192523.5 | 1148 |
| 00492_655614 | 185154.5 | 1134.5 |
| 00492_655480 | 174787 | 1126.5 |
| 00492_655573 | 157161 | 962.5 |
| 00492_655572 | 156490.5 | 1171 |
| 00492_655611 | 150997.5 | 1025 |
| 00492_655638 | 139829 | 1028.5 |
| 00492_655648 | 133745 | 963 |
| 00492_655481 | 116414.5 | 1016.5 |
| 00492_655608 | 114909 | 949 |
| 00492_655505 | 109482.5 | 1066.5 |
| 00492_655533 | 107343 | 1116 |
| 00492_655652 | 106006 | 1052 |
| 00492_655495 | 105968 | 882 |
| 00492_655472 | 100676 | 979 |
| 00492_655585 | 100161 | 1178 |
| 00492_655521 | 99513.5 | 896.5 |
| 00492_655468 | 99499 | 1070 |
| 00492_655552 | 99086.5 | 984 |
| 00492_655471 | 98638 | 961.5 |
| 00492_655519 | 92743 | 843 |

| SMA(4A6)+BA-Peptide (FL1-A of QSH05) | Human FC (FL1-A of QSH10) | Canine PD1 (FL1-A of QSH18) | Amine Peg11 (FL1-A of QSH15) |
|---|---|---|---|
| 1515 | 1362 | 1976 | 1057.5 |
| 1441 | 1235 | 1489 | 1087.5 |
| 1268 | 1569 | 1512 | 1031 |
| 1270 | 1458.5 | 1414 | 1163 |
| 1341.5 | 1284 | 1467.5 | 966.5 |
| 1489 | 1330 | 1602 | 1180 |
| 1248 | 1364 | 1371 | 1173 |
| 1132 | 1338 | 1404 | 1112 |
| 1558 | 1510 | 1332 | 1105.5 |
| 1343 | 1202.5 | 1261 | 914 |
| 1502.5 | 1299 | 1623 | 970.5 |
| 1310 | 1254 | 1448 | 976 |
| 1190 | 1149 | 1241 | 934 |
| 1334 | 1346.5 | 1406 | 1055 |
| 1278 | 1245 | 1357 | 1086 |
| 1275 | 1252 | 1278 | 920 |
| 1196 | 1205 | 1178 | 858 |
| 1254 | 1178.5 | 1427 | 1031.5 |
| 1297 | 1301.5 | 1319 | 928.5 |
| 1585.5 | 1233 | 1291.5 | 1140 |
| 1262 | 1197 | 1186 | 935 |
| 1308 | 1324 | 1259.5 | 999 |
| 1224 | 1232 | 1168 | 967.5 |
| 1389.5 | 1462.5 | 1245 | 1066.5 |
| 1245 | 1179 | 1346 | 1148 |

FIG. 17 (Continued)

| mIgG2b (Control) (FL1-A of QSH21) | No Target (Control) (FL1-A of QSH26) | Fumonisin B1 (FL1-A of QSH29) | SMA (2A9) + BA-Peptide (FL1-A of QSH22) |
|---|---|---|---|
| 2661 | 2272 | 1297 | 2172 |
| 2557.5 | 2138 | 1283 | 2493 |
| 2674 | 2396 | 1466 | 2397.5 |
| 2872.5 | 2102 | 1257 | 1679 |
| 2447 | 2272 | 1182.5 | 2143 |
| 2378 | 2214 | 1250.5 | 1848 |
| 2598 | 2221.5 | 1300.5 | 1982 |
| 2609 | 2267 | 2566 | 2648 |
| 2811 | 2219.5 | 1763 | 2302 |
| 2345 | 1946.5 | 1558.5 | 2286 |
| 2722.5 | 2202.5 | 1674 | 2299.5 |
| 2672 | 2157 | 1741.5 | 2216.5 |
| 2397.5 | 2214 | 1271 | 1734 |
| 2642 | 2091 | 1561 | 1972 |
| 2429 | 2129 | 1295 | 2071 |
| 2432 | 2019 | 1349 | 1992 |
| 2302 | 2075 | 1173.5 | 2039.5 |
| 2234 | 2034 | 1047 | 1874 |
| 2647 | 2243 | 1255.5 | 2030 |
| 2459.5 | 2375 | 2440 | 2723.5 |
| 2497 | 2138 | 1315.5 | 1929 |
| 2589.5 | 2040.5 | 1406 | 1850 |
| 2214.5 | 2029 | 1233 | 1693 |
| 2359 | 1979 | 1089 | 2259 |
| 2217 | 2110 | 1311.5 | 1739 |

FIG. 17 (Continued)

| | | | |
|---|---|---|---|
| 00492_655541 | ☐ | 89444 | 1081.5 |
| 00492_655601 | ☐ | 84042 | 1041.5 |
| 00492_655551 | ☐ | 81090.5 | 1011 |
| 00492_655639 | ☐ | 81068.5 | 941 |
| 00492_655465 | ☐ | 80613.5 | 1054 |
| 00492_655477 | ☐ | 77681.5 | 1065 |
| 00492_655520 | ☐ | 75087 | 1121 |
| 00492_655591 | ☐ | 75010 | 958 |
| 00492_655627 | ☐ | 71011.5 | 1057 |
| 00492_655605 | ☐ | 67170 | 1096 |
| 00492_655654 | ☐ | 65882 | 971.5 |
| 00492_655563 | ☐ | 60901 | 1081 |
| 00492_655574 | ☐ | 56010.5 | 1122 |
| 00492_655562 | ☐ | 54184.5 | 1021.5 |
| 00492_655625 | ☐ | 53675 | 1036 |
| 00492_655612 | ☐ | 52102 | 1092 |
| 00492_655488 | ☐ | 51106.5 | 947 |
| 00492_655583 | ☐ | 50260.5 | 965.5 |
| 00492_655530 | ☐ | 50008.5 | 1019 |
| 00492_655514 | ☐ | 49577 | 1040 |
| 00492_655650 | ☐ | 48880 | 1038 |
| 00492_655482 | ☐ | 48521 | 994 |
| 00492_655643 | ☐ | 46995.5 | 1035 |
| 00492_655511 | ☐ | 44026 | 951.5 |
| 00492_655518 | ☐ | 43791 | 1001 |
| 00492_655576 | ☐ | 42227 | 1021 |
| 00492_655641 | ☐ | 38459 | 1173 |
| 00492_655628 | ☐ | 37765 | 918.5 |
| 00492_655607 | ☐ | 36757.5 | 985 |

FIG. 17 (Continued)

| | | | |
|---|---|---|---|
| 1434 | 1286 | 1268 | 1021 |
| 1428 | 1302 | 1338 | 1147.5 |
| 1119 | 1204 | 1157 | 1095.5 |
| 1154.5 | 950 | 1211 | 856 |
| 1316 | 1280 | 1268 | 1130 |
| 1543.5 | 1354 | 1270 | 1132.5 |
| 1723 | 1338 | 1023 | 1151.5 |
| 1202 | 1206 | 1093 | 793 |
| 1141 | 1292 | 1142 | 893 |
| 1286.5 | 1150.5 | 1474 | 1071 |
| 1247 | 1291.5 | 1152 | 1062 |
| 1435.5 | 1086 | 1329 | 925 |
| 1550 | 1430.5 | 1243 | 938.5 |
| 1356 | 1234.5 | 1348 | 1041 |
| 1513.5 | 1307.5 | 1524 | 1116 |
| 1208 | 1216 | 1232 | 853 |
| 1723 | 1199 | 1340 | 1049 |
| 1111 | 1233.5 | 1211.5 | 1130 |
| 1410 | 1459.5 | 1193 | 1008 |
| 1315.5 | 1203 | 1252 | 989 |
| 1057 | 1139 | 938 | 987 |
| 1297 | 1198 | 1275 | 973 |
| 1208 | 1216.5 | 1109 | 999 |
| 1154 | 1165.5 | 1225 | 1022.5 |
| 1186.5 | 1211.5 | 1217 | 1068 |
| 1193 | 1272 | 1393 | 1160 |
| 1532 | 1380.5 | 1197.5 | 983 |
| 1119 | 1154 | 1220 | 767 |
| 1351 | 1333.5 | 1537 | 1130 |

FIG. 17 (Continued)

| | | | |
|---:|---:|---:|---:|
| 2462.5 | 2247 | 1293.5 | 1992.5 |
| 2552 | 2248 | 1226 | 1736 |
| 3043 | 2218 | 1353.5 | 1772.5 |
| 2304 | 1895.5 | 917 | 1619.5 |
| 2676 | 2252 | 1289 | 1798 |
| 2385 | 2254 | 2714 | 2759.5 |
| 2493 | 2052.5 | 1216 | 2159 |
| 2653.5 | 2086 | 1303 | 2215.5 |
| 2275.5 | 1914 | 1383.5 | 1774 |
| 2437 | 2154 | 1806 | 2519.5 |
| 2076.5 | 2154 | 1324 | 2008 |
| 2887 | 2277 | 1685 | 2102 |
| 2672 | 2234 | 2642 | 2933 |
| 2631 | 2201 | 1846 | 2153 |
| 2727 | 2260 | 2297.5 | 2626.5 |
| 2380 | 2167.5 | 1356.5 | 2405 |
| 2926.5 | 2227 | 2009 | 2996.5 |
| 2570 | 2164 | 1303 | 1991 |
| 2100.5 | 2078 | 1273 | 1655.5 |
| 2536 | 2027.5 | 1308.5 | 1981.5 |
| 2538.5 | 2073 | 1297 | 1935 |
| 2655 | 2183.5 | 1276 | 2234 |
| 2237 | 1869.5 | 1326 | 1768 |
| 2639 | 2044.5 | 1272.5 | 1788 |
| 2514.5 | 1901 | 1198.5 | 1779 |
| 2509 | 2100.5 | 1539.5 | 2086 |
| 2756 | 2237 | 2259 | 4318 |
| 2252 | 1761.5 | 1712 | 1900 |
| 2315 | 2038 | 1326 | 1757 |

FIG. 17 (Continued)

| | | | |
|---|---|---|---|
| 00492_655529 | | 32520.5 | 1035 |
| 00492_655567 | | 31602 | 1066 |
| 00492_655528 | | 29826 | 1039 |
| 00492_655557 | | 27151 | 981.5 |
| 00492_655564 | | 25662 | 877 |
| 00492_655582 | | 25377 | 992 |
| 00492_655613 | | 24028.5 | 1218 |
| 00492_655485 | | 21284.5 | 928 |
| 00492_655501 | | 20252 | 1077 |
| 00492_655634 | | 20036 | 1079 |
| 00492_655543 | | 19493 | 1022 |
| 00492_655587 | | 19437 | 975 |
| 00492_655577 | | 18999.5 | 1113 |
| 00492_655633 | | 16266 | 1014 |
| 00492_655594 | | 15210.5 | 1010 |
| 00492_655542 | | 12009 | 1021 |
| 00492_655655 | | 10450 | 1018 |
| 00492_655609 | | 8522 | 1073.5 |
| 00492_655490 | | 7667 | 1136 |
| 00492_655584 | | 6709 | 1021.5 |
| 00492_655487 | | 4646 | 960 |

| | | | |
|---|---|---|---|
| 1151.5 | 1206 | 1454 | 1136.5 |
| 1015.5 | 1183 | 1250.5 | 1185.5 |
| 1285 | 1178 | 1510 | 1095 |
| 1321 | 1189 | 1170 | 923 |
| 1114 | 1130 | 1400 | 1000.5 |
| 1174.5 | 1153 | 1199 | 957 |
| 1566 | 1448 | 1323 | 1116 |
| 1380 | 1170 | 1175 | 1052 |
| 1206 | 1145.5 | 1204.5 | 1046 |
| 2175.5 | 1472 | 1252.5 | 1168 |
| 1702.5 | 1305.5 | 1319 | 1008 |
| 1089 | 1137 | 1065 | 834 |
| 1335 | 1273 | 1446 | 1065 |
| 1380.5 | 1260 | 1161 | 1141 |
| 1133 | 1304.5 | 1119 | 1029 |
| 1646.5 | 1493 | 1329 | 892.5 |
| 1211 | 1190 | 1192.5 | 1018 |
| 1319 | 1338.5 | 1289 | 1057 |
| 1218 | 1204 | 1253 | 938.5 |
| 1482 | 1484.5 | 1316 | 989 |
| 1571 | 1163 | 1158.5 | 912 |

| | | | |
|---:|---:|---:|---:|
| 2536 | 2199.5 | 1440.5 | 2305 |
| 2299 | 2203 | 1276 | 1742.5 |
| 2622.5 | 2121.5 | 1349 | 1942 |
| 2292 | 1892 | 1251 | 1724 |
| 2399 | 1935.5 | 1214 | 1623 |
| 2510 | 1922 | 1194 | 2507.5 |
| 2504 | 2278 | 1285 | 2286 |
| 2386 | 2078.5 | 1213 | 2206.5 |
| 2456 | 2211 | 1309.5 | 1639 |
| 2509 | 2216 | 3030.5 | 4665 |
| 2343 | 2054 | 2326 | 2610 |
| 2431 | 2052 | 1077.5 | 1520 |
| 2680.5 | 2226 | 2042 | 2366 |
| 2951 | 1986 | 2174 | 2346 |
| 2597 | 2017 | 1805.5 | 2535.5 |
| 2466 | 2195.5 | 1311.5 | 2585 |
| 2647 | 2038 | 1515 | 2277 |
| 2525 | 2159 | 1426.5 | 2049 |
| 2763 | 2213 | 1385.5 | 2079 |
| 2540 | 2195 | 2603.5 | 2525 |
| 2677.5 | 1989.5 | 1224 | 2006 |

FIG. 17 (Continued)

SEQUENCE LISTING

```
<160> NUMBER OF SEQ ID NOS: 127

<210> SEQ ID NO 1
<211> LENGTH: 98
<212> TYPE: PRT
<213> ORGANISM: Homo sapiens

<400> SEQUENCE: 1

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
                20                  25                  30

Glu Thr Tyr Gly Lys Leu Glu Ala Val Gln Tyr Lys Thr Gln Val Val
            35                  40                  45

Ala Gly Thr Asn Tyr Tyr Ile Lys Val Arg Ala Gly Asp Asn Lys Tyr
        50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 2
<211> LENGTH: 294
<212> TYPE: DNA
<213> ORGANISM: Artificial Sequence
<220> FEATURE:
<223> OTHER INFORMATION: Synthetic

<400> SEQUENCE: 2
```

```
atgattcctg gtggtttgtc ggaagccaaa ccggctactc cggaaatcca ggagattgtg    60
gacaaagtca aaccgcaact ggaggaaaag accaatgaaa cctatggcaa actcgaagcg   120
gtacagtaca aaacccaagt cgttgcgggt acgaactact acatcaaagt acgcgcagga   180
gataacaagt atatgcatct gaaagtgttc aaaagcttac agggcagaa tgaggatctg    240 gttcttacgg gctatcaggt ggataagaac aaagacgatg aactgacagg ctttt        294
```

<210> SEQ ID NO 3
<211> LENGTH: 98
<212> TYPE: PRT
<213> ORGANISM: Canis familiaris

<400> SEQUENCE: 3

Met Met Pro Gly Gly Leu Thr Glu Ala Lys Pro Ala Thr Pro Glu Val
1               5                   10                  15

Gln Glu Ile Ala Asn Glu Val Lys Pro Gln Leu Glu Glu Lys Thr Asn
            20                  25                  30

Glu Thr Tyr Gln Glu Phe Glu Ala Val Glu Tyr Lys Thr Gln Val Val
        35                  40                  45

Ala Gly Ile Asn Tyr Tyr Ile Lys Val Arg Val Gly Asp Asn Ser Tyr
    50                  55                  60

Ile His Leu Lys Ile Phe Lys Gly Leu Pro Gly Gln Asn Pro Thr Leu
65                  70                  75                  80

Thr Leu Thr Gly Tyr Gln Thr Asp Lys Ser Lys Asp Glu Leu Thr
                85                  90                  95

Gly Phe

<210> SEQ ID NO 4
<211> LENGTH: 227
<212> TYPE: PRT
<213> ORGANISM: Artificial Sequence
<220> FEATURE:
<223> OTHER INFORMATION: Synthetic

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 225
<212> TYPE: PRT
<213> ORGANISM: Artificial Sequence
<220> FEATURE:
<223> OTHER INFORMATION: Synthetic

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 6
<211> LENGTH: 227
<212> TYPE: PRT
<213> ORGANISM: Artificial Sequence
<220> FEATURE:
<223> OTHER INFORMATION: Synthetic

<400> SEQUENCE: 6

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 7
<211> LENGTH: 227
<212> TYPE: PRT
<213> ORGANISM: Artificial Sequence
<220> FEATURE:
<223> OTHER INFORMATION: Synthetic

<400> SEQUENCE: 7

Asp Lys Thr His Thr Cys Pro Pro Cys Pro Ala Pro Glu Ala Glu Gly
1               5                   10                  15

Ala Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ser Ser Ile
                100                 105                 110

Glu Lys Thr Ile Ser Lys Ala Lys Gly Gln Pro Arg Glu Pro Gln Val
            115                 120                 125

```
Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 232
<212> TYPE: PRT
<213> ORGANISM: Artificial Sequence
<220> FEATURE:
<223> OTHER INFORMATION: Synthetic

<400> SEQUENCE: 8

Glu Pro Lys Ser Ser Asp Lys Thr His Thr Cys Pro Pro Cys Pro Ala
1               5                   10                  15

Pro Glu Ala Glu Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 9
```

<211> LENGTH: 227
<212> TYPE: PRT
<213> ORGANISM: Artificial Sequence
<220> FEATURE:
<223> OTHER INFORMATION: Synthetic

<400> SEQUENCE: 9

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 10
<211> LENGTH: 226
<212> TYPE: PRT
<213> ORGANISM: Artificial Sequence
<220> FEATURE:
<223> OTHER INFORMATION: Synthetic

<400> SEQUENCE: 10

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly

```
             85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 11
<211> LENGTH: 227
<212> TYPE: PRT
<213> ORGANISM: Artificial Sequence
<220> FEATURE:
<223> OTHER INFORMATION: Synthetic

<400> SEQUENCE: 11

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gln Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
```

```
            210                 215                 220

Pro Gly Lys
225

<210> SEQ ID NO 12
<211> LENGTH: 227
<212> TYPE: PRT
<213> ORGANISM: Artificial Sequence
<220> FEATURE:
<223> OTHER INFORMATION: Synthetic

<400> SEQUENCE: 12

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ser Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 13
<211> LENGTH: 227
<212> TYPE: PRT
<213> ORGANISM: Artificial Sequence
<220> FEATURE:
<223> OTHER INFORMATION: Synthetic

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

```
Glu Asp Pro Glu Val Lys Phe Asn Trp Tyr Val Asp Gly Val Glu Val
 50                  55                  60

His Asn Ala Lys Thr Lys Pro Arg Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: Synthetic

<400> SEQUENCE: 14

Asp Lys Thr His Thr Cys Pro Pro Cys Pro Ala Pro Glu Leu Leu Gly
 1                5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr His Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 233
<212> TYPE: PRT
<213> ORGANISM: Artificial Sequence
<220> FEATURE:
<223> OTHER INFORMATION: Synthetic

<400> SEQUENCE: 15

Asp Lys Arg Val Glu Ser Lys Tyr Gly Pro Pro Cys Pro Ser Cys Pro
1               5                   10                  15

Ala Pro Glu Phe Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 16
<211> LENGTH: 233
<212> TYPE: PRT
<213> ORGANISM: Artificial Sequence
<220> FEATURE:
<223> OTHER INFORMATION: Synthetic

<400> SEQUENCE: 16

Asp Lys Arg Val Glu Ser Lys Tyr Gly Pro Pro Cys Pro Cys Pro
1               5                   10                  15
```

```
Ala Pro Glu Phe Leu Gly Gly Pro Ser Val Phe Leu Phe Pro Pro Lys
             20                  25                  30

Pro Lys Asp Thr Leu Met Ile Ser Arg Thr Pro Glu Val Thr Cys Val
         35                  40                  45

Val Val Asp Val Ser Gln Glu Asp Pro Glu Val Gln Phe Asn Trp Tyr
 50                  55                  60

Val Asp Gly Val Glu Val His Asn Ala Lys Thr Lys Pro Arg Glu Glu
 65                  70                  75                  80

Gln Phe Asn Ser Thr Tyr Arg Val Val Ser Val Leu Thr Val Leu His
                 85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
210                 215                 220

Lys Ser Leu Ser Leu Ser Leu Gly Lys
225                 230

<210> SEQ ID NO 17
<211> LENGTH: 585
<212> TYPE: PRT
<213> ORGANISM: Homo sapiens

<400> SEQUENCE: 17

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
             20                  25                  30

Gln Cys Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
```

```
            145                 150                 155                 160
Tyr Lys Ala Ala Phe Thr Glu Cys Cys Gln Ala Ala Asp Lys Ala Ala
                    165                 170                 175

Cys Leu Leu Pro Lys Leu Asp Glu Leu Arg Asp Glu Gly Lys Ala Ser
                    180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575
```

```
Ala Ala Ser Gln Ala Ala Leu Gly Leu
            580                 585

<210> SEQ ID NO 18
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (81)..(89)
<223> OTHER INFORMATION: Xaa can be any naturally occurring amino acid

<400> SEQUENCE: 18

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Lys Glu Thr Gly
            20                  25                  30

Lys Thr Trp Gly Lys Leu Glu Ala Val Glu Tyr Lys Thr Gln Val Asp
        35                  40                  45

Xaa Xaa Xaa Xaa Xaa Xaa Xaa Xaa Xaa Gly Leu Asn Tyr Tyr Ile Lys
    50                  55                  60

Val Arg Val Gly Asn Lys Tyr Ile His Leu Lys Val Phe Lys Ser Leu
65                  70                  75                  80

Xaa Xaa Xaa Xaa Xaa Xaa Xaa Xaa Xaa Glu Asp Leu Val Leu Thr Gly
                85                  90                  95

Tyr Gln Val Asp Lys Asn Lys Asp Asp Glu Leu Thr Gly Phe
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (81)..(89)
<223> OTHER INFORMATION: Xaa can be any naturally occurring amino acid

<400> SEQUENCE: 19

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Lys Glu Thr Gly
            20                  25                  30

Lys Thr Trp Gly Lys Leu Glu Ala Val Glu Tyr Lys Thr Gln Val Asp
        35                  40                  45

Xaa Xaa Xaa Xaa Xaa Xaa Xaa Xaa Xaa Gly Leu Asn Tyr Tyr Ile Lys
    50                  55                  60

Val Arg Val Asn Gly Lys Tyr Ile His Leu Lys Val Phe Lys Ser Leu
65                  70                  75                  80

Xaa Xaa Xaa Xaa Xaa Xaa Xaa Xaa Xaa Glu Asp Leu Val Leu Thr Gly
                85                  90                  95
```

```
Tyr Gln Val Asp Lys Asn Lys Asp Asp Glu Leu Thr Gly Phe
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (82)..(90)
<223> OTHER INFORMATION: Xaa can be any naturally occurring amino acid

<400> SEQUENCE: 20

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Gly
            20                  25                  30

Glu Thr Tyr Gly Lys Leu Glu Ala Val Gln Tyr Lys Thr Gln Val Asp
        35                  40                  45

Xaa Xaa Xaa Xaa Xaa Xaa Xaa Xaa Xaa Gly Thr Asn Tyr Tyr Ile Lys
    50                  55                  60

Val Arg Ala Gly Asp Asn Lys Tyr Met His Leu Lys Val Phe Lys Ser
65                  70                  75                  80

Leu Xaa Xaa Xaa Xaa Xaa Xaa Xaa Xaa Glu Asp Leu Val Leu Thr
            85                  90                  95

Gly Tyr Gln Val Asp Lys Asn Lys Asp Asp Glu Leu Thr Gly Phe
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (82)..(90)
<223> OTHER INFORMATION: Xaa can be any naturally occurring amino acid

<400> SEQUENCE: 21

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Gly
            20                  25                  30

Glu Thr Tyr Gly Lys Leu Glu Ala Val Gln Tyr Lys Thr Gln Val Asp
        35                  40                  45

Xaa Xaa Xaa Xaa Xaa Xaa Xaa Xaa Xaa Gly Thr Asn Tyr Tyr Ile Lys
    50                  55                  60

Val Arg Ala Gly Asp Asn Lys Tyr Ile His Leu Lys Val Phe Lys Ser
65                  70                  75                  80

Leu Xaa Xaa Xaa Xaa Xaa Xaa Xaa Xaa Glu Asp Leu Val Leu Thr
            85                  90                  95

Gly Tyr Gln Val Asp Lys Asn Lys Asp Asp Glu Leu Thr Gly Phe
```

100                 105                 110

<210> SEQ ID NO 22
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (82)..(90)
<223> OTHER INFORMATION: Xaa can be any naturally occurring amino acid

<400> SEQUENCE: 22

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Gly
            20                  25                  30

Glu Thr Tyr Gly Lys Leu Glu Ala Val Gln Tyr Lys Thr Gln Val Asp
        35                  40                  45

Xaa Xaa Xaa Xaa Xaa Xaa Xaa Xaa Xaa Gly Leu Asn Tyr Tyr Ile Lys
    50                  55                  60

Val Arg Ala Gly Asp Asn Lys Tyr Ile His Leu Lys Val Phe Lys Ser
65                  70                  75                  80

Leu Xaa Xaa Xaa Xaa Xaa Xaa Xaa Xaa Xaa Glu Asp Leu Val Leu Thr
                85                  90                  95

Gly Tyr Gln Val Asp Lys Asn Lys Asp Asp Glu Leu Thr Gly Phe
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (82)..(90)
<223> OTHER INFORMATION: Xaa can be any naturally occurring amino acid

<400> SEQUENCE: 23

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Gly
            20                  25                  30

Glu Thr Tyr Gly Lys Leu Glu Ala Val Glu Tyr Lys Thr Gln Val Asp
        35                  40                  45

Xaa Xaa Xaa Xaa Xaa Xaa Xaa Xaa Xaa Gly Thr Asn Tyr Tyr Ile Lys
    50                  55                  60

Val Arg Ala Gly Asp Asn Lys Tyr Ile His Leu Lys Val Phe Lys Ser
65                  70                  75                  80

Leu Xaa Xaa Xaa Xaa Xaa Xaa Xaa Xaa Xaa Glu Asp Leu Val Leu Thr
                85                  90                  95

Gly Tyr Gln Val Asp Lys Asn Lys Asp Asp Glu Leu Thr Gly Phe
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(57)
<223> OTHER INFORMATION: Xaa can be any naturally occurring amino acid
<220> FEATURE:
<221> NAME/KEY: misc_feature
<222> LOCATION: (82)..(90)
<223> OTHER INFORMATION: Xaa can be any naturally occurring amino acid

<400> SEQUENCE: 24

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Gly
            20                  25                  30

Glu Thr Tyr Gly Lys Leu Glu Ala Val Glu Tyr Lys Thr Gln Val Asp
        35                  40                  45

Xaa Xaa Xaa Xaa Xaa Xaa Xaa Xaa Xaa Gly Leu Asn Tyr Tyr Ile Lys
    50                  55                  60

Val Arg Ala Gly Asp Asn Lys Tyr Ile His Leu Lys Val Phe Lys Ser
65                  70                  75                  80

Leu Xaa Xaa Xaa Xaa Xaa Xaa Xaa Xaa Glu Asp Leu Val Leu Thr
                85                  90                  95

Gly Tyr Gln Val Asp Lys Asn Lys Asp Asp Glu Leu Thr Gly Phe
            100                 105                 110

<210> SEQ ID NO 25
<211> LENGTH: 18
<212> TYPE: PRT
<213> ORGANISM: Artificial Sequence
<220> FEATURE:
<223> OTHER INFORMATION: Synthetic

<400> SEQUENCE: 25

Met Lys Trp Val Thr Phe Ile Ser Leu Leu Phe Leu Phe Ser Ser Ala
1               5                   10                  15

Tyr Ser

<210> SEQ ID NO 26
<211> LENGTH: 22
<212> TYPE: PRT
<213> ORGANISM: Artificial Sequence
<220> FEATURE:
<223> OTHER INFORMATION: Synthetic

<400> SEQUENCE: 26

Met Asp Met Arg Ala Pro Ala Gly Ile Phe Gly Phe Leu Leu Val Leu
1               5                   10                  15

Phe Pro Gly Tyr Arg Ser
            20

<210> SEQ ID NO 27
<211> LENGTH: 19
<212> TYPE: PRT
<213> ORGANISM: Artificial Sequence
<220> FEATURE:
<223> OTHER INFORMATION: Synthetic

```
<400> SEQUENCE: 27

Met Thr Arg Leu Thr Val Leu Ala Leu Leu Ala Gly Leu Leu Ala Ser
1               5                   10                  15

Ser Arg Ala

<210> SEQ ID NO 28
<211> LENGTH: 19
<212> TYPE: PRT
<213> ORGANISM: Artificial Sequence
<220> FEATURE:
<223> OTHER INFORMATION: Synthetic

<400> SEQUENCE: 28

Met Glu Leu Gly Leu Ser Trp Ile Phe Leu Leu Ala Ile Leu Lys Gly
1               5                   10                  15

Val Gln Cys

<210> SEQ ID NO 29
<211> LENGTH: 19
<212> TYPE: PRT
<213> ORGANISM: Artificial Sequence
<220> FEATURE:
<223> OTHER INFORMATION: Synthetic

<400> SEQUENCE: 29

Met Glu Leu Gly Leu Arg Trp Val Phe Leu Val Ala Ile Leu Glu Gly
1               5                   10                  15

Val Gln Cys

<210> SEQ ID NO 30
<211> LENGTH: 19
<212> TYPE: PRT
<213> ORGANISM: Artificial Sequence
<220> FEATURE:
<223> OTHER INFORMATION: Synthetic

<400> SEQUENCE: 30

Met Lys His Leu Trp Phe Phe Leu Leu Leu Val Ala Ala Pro Arg Trp
1               5                   10                  15

Val Leu Ser

<210> SEQ ID NO 31
<211> LENGTH: 19
<212> TYPE: PRT
<213> ORGANISM: Artificial Sequence
<220> FEATURE:
<223> OTHER INFORMATION: Synthetic

<400> SEQUENCE: 31

Met Asp Trp Thr Trp Arg Ile Leu Phe Leu Val Ala Ala Ala Thr Gly
1               5                   10                  15

Ala His Ser

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Met Asp Trp Thr Trp Arg Phe Leu Phe Val Val Ala Ala Ala Thr Gly
1               5                   10                  15
```

Val Gln Ser

<210> SEQ ID NO 33
<211> LENGTH: 19
<212> TYPE: PRT
<213> ORGANISM: Artificial Sequence
<220> FEATURE:
<223> OTHER INFORMATION: Synthetic

<400> SEQUENCE: 33

Met Glu Phe Gly Leu Ser Trp Leu Phe Leu Val Ala Ile Leu Lys Gly
1               5                   10                  15

Val Gln Cys

<210> SEQ ID NO 34
<211> LENGTH: 19
<212> TYPE: PRT
<213> ORGANISM: Artificial Sequence
<220> FEATURE:
<223> OTHER INFORMATION: Synthetic

<400> SEQUENCE: 34

Met Glu Phe Gly Leu Ser Trp Val Phe Leu Val Ala Leu Phe Arg Gly
1               5                   10                  15

Val Gln Cys

<210> SEQ ID NO 35
<211> LENGTH: 26
<212> TYPE: PRT
<213> ORGANISM: Artificial Sequence
<220> FEATURE:
<223> OTHER INFORMATION: Synthetic

<400> SEQUENCE: 35

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 36
<211> LENGTH: 22
<212> TYPE: PRT
<213> ORGANISM: Artificial Sequence
<220> FEATURE:
<223> OTHER INFORMATION: Synthetic

<400> SEQUENCE: 36

Met Asp Met Arg Val Pro Ala Gln Leu Leu Gly Leu Leu Leu Leu Trp
1               5                   10                  15

Leu Ser Gly Ala Arg Cys
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic

<400> SEQUENCE: 37

Met Lys Tyr Leu Leu Pro Thr Ala Ala Ala Gly Leu Leu Leu Leu Ala
1               5                   10                  15

Ala Gln Pro Ala Met Ala

```
                       20

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Met Gly Val Lys Val Leu Phe Ala Leu Ile Cys Ile Ala Val Ala Glu
1               5                   10                  15

Ala

<210> SEQ ID NO 39

<400> SEQUENCE: 39

000

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Met Ala Phe Leu Trp Leu Leu Ser Cys Trp Ala Leu Leu Gly Thr Thr
1               5                   10                  15

Phe Gly

<210> SEQ ID NO 41
<211> LENGTH: 14
<212> TYPE: PRT
<213> ORGANISM: Artificial Sequence
<220> FEATURE:
<223> OTHER INFORMATION: Synthetic

<400> SEQUENCE: 41

Met Gln Leu Leu Ser Cys Ile Ala Leu Ile Leu Ala Leu Val
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

Met Asn Leu Leu Leu Ile Leu Thr Phe Val Ala Ala Val Ala
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic

<400> SEQUENCE: 43

Met Pro Leu Leu Leu Leu Leu Pro Leu Leu Trp Ala Gly Ala Leu Ala
1               5                   10                  15
```

```
<210> SEQ ID NO 44
<211> LENGTH: 30
<212> TYPE: PRT
<213> ORGANISM: Artificial Sequence
<220> FEATURE:
<223> OTHER INFORMATION: Synthetic

<400> SEQUENCE: 44

Met Asp Ser Lys Gly Ser Ser Gln Lys Gly Ser Arg Leu Leu Leu Leu
1               5                   10                  15
Leu Val Val Ser Asn Leu Leu Leu Cys Gln Gly Val Val Ser
            20                  25                  30

<210> SEQ ID NO 45
<211> LENGTH: 23
<212> TYPE: PRT
<213> ORGANISM: Artificial Sequence
<220> FEATURE:
<223> OTHER INFORMATION: Synthetic

<400> SEQUENCE: 45

Met Asp Ala Met Lys Arg Gly Leu Cys Cys Val Leu Leu Leu Cys Gly
1               5                   10                  15
Ala Val Phe Val Ser Pro Ser
            20

<210> SEQ ID NO 46
<211> LENGTH: 16
<212> TYPE: PRT
<213> ORGANISM: Artificial Sequence
<220> FEATURE:
<223> OTHER INFORMATION: Synthetic

<400> SEQUENCE: 46

Met Leu Leu Leu Leu Leu Leu Leu Leu Leu Ala Leu Ala Leu Ala
1               5                   10                  15

<210> SEQ ID NO 47
<211> LENGTH: 21
<212> TYPE: PRT
<213> ORGANISM: Artificial Sequence
<220> FEATURE:
<223> OTHER INFORMATION: Synthetic

<400> SEQUENCE: 47

Met Trp Trp Arg Leu Trp Trp Leu Leu Leu Leu Leu Leu Leu Leu Trp
1               5                   10                  15
Pro Met Val Trp Ala
            20

<210> SEQ ID NO 48
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: may repeat 1-10 times

<400> SEQUENCE: 48

Gly Gly Gly Gly Ser
1               5

<210> SEQ ID NO 49
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 49

Gly Gly Gly Gly Gly Gly Gly Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic

<400> SEQUENCE: 50

Gly Gly Gly Gly Gly Gly
1               5

<210> SEQ ID NO 51
<211> LENGTH: 18
<212> TYPE: PRT
<213> ORGANISM: Artificial Sequence
<220> FEATURE:
<223> OTHER INFORMATION: Synthetic

<400> SEQUENCE: 51

Lys Glu Ser Gly Ser Val Ser Ser Glu Gln Leu Ala Gln Phe Arg Ser
1               5                   10                  15

Leu Asp

<210> SEQ ID NO 52
<211> LENGTH: 14
<212> TYPE: PRT
<213> ORGANISM: Artificial Sequence
<220> FEATURE:
<223> OTHER INFORMATION: Synthetic

<400> SEQUENCE: 52

Glu Gly Lys Ser Ser Gly Ser Gly Ser Glu Ser Lys Ser Thr
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Gly Ser Ala Gly Ser Ala Ala Gly Ser Gly Glu Phe
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: may repeat 1-10 times

<400> SEQUENCE: 54
```

Glu Ala Ala Ala Lys
1               5

<210> SEQ ID NO 55
<211> LENGTH: 46
<212> TYPE: PRT
<213> ORGANISM: Artificial Sequence
<220> FEATURE:
<223> OTHER INFORMATION: Synthetic

<400> SEQUENCE: 55

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 56
<211> LENGTH: 5
<212> TYPE: PRT
<213> ORGANISM: Artificial Sequence
<220> FEATURE:
<223> OTHER INFORMATION: Synthetic

<400> SEQUENCE: 56

Pro Ala Pro Ala Pro
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic

<400> SEQUENCE: 57

Ala Glu Ala Ala Ala Lys Glu Ala Ala Ala Lys Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Ala Pro Ala Pro Ala Pro Ala Pro Ala Pro
1               5                   10

<210> SEQ ID NO 59
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(2)
<223> OTHER INFORMATION: may repeat 1-12 times

<400> SEQUENCE: 59

Gly Gly Ser Gly
1

```
<210> SEQ ID NO 60
<211> LENGTH: 4
<212> TYPE: PRT
<213> ORGANISM: Artificial Sequence
<220> FEATURE:
<223> OTHER INFORMATION: Synthetic

<400> SEQUENCE: 60

Gly Ser Gly Ser
1

<210> SEQ ID NO 61
<211> LENGTH: 4
<212> TYPE: PRT
<213> ORGANISM: Artificial Sequence
<220> FEATURE:
<223> OTHER INFORMATION: Synthetic

<400> SEQUENCE: 61

Gly Gly Gly Ser
1

<210> SEQ ID NO 62
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (2)..(4)
<223> OTHER INFORMATION: may repeat 1-7 times

<400> SEQUENCE: 62

Ser Gly Gly Ser
1

<210> SEQ ID NO 63
<211> LENGTH: 7
<212> TYPE: PRT
<213> ORGANISM: Artificial Sequence
<220> FEATURE:
<223> OTHER INFORMATION: Synthetic

<400> SEQUENCE: 63

Gly Gly Gly Ser Gly Gly Gly
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

Glu Ser Gly Gly Gly Gly Val Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Leu Glu Ser Gly Gly Gly Gly Val Thr
```

```
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic

<400> SEQUENCE: 66

Gly Arg Ala Gln Val Thr
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic

<400> SEQUENCE: 67

Trp Arg Ala Gln Val Thr
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Ala Arg Gly Arg Ala Gln Val Thr
1               5

<210> SEQ ID NO 69
<211> LENGTH: 33
<212> TYPE: PRT
<213> ORGANISM: Artificial Sequence
<220> FEATURE:
<223> OTHER INFORMATION: Synthetic

<400> SEQUENCE: 69

Ser Gly Thr Thr Ser Gly Thr Thr Arg Leu Leu Ser Gly His Thr Cys
1               5                   10                  15

Phe Thr Leu Thr Gly Leu Leu Gly Thr Leu Val Thr Met Gly Leu Leu
            20                  25                  30

Thr

<210> SEQ ID NO 70
<211> LENGTH: 26
<212> TYPE: PRT
<213> ORGANISM: Artificial Sequence
<220> FEATURE:
<223> OTHER INFORMATION: Synthetic

<400> SEQUENCE: 70

Ser Gly Thr Ser Pro Gly Leu Ser Ala Gly Ala Thr Val Gly Ile Met
1               5                   10                  15

Ile Gly Val Leu Val Gly Val Ala Leu Ile
            20                  25

<210> SEQ ID NO 71
<211> LENGTH: 24
<212> TYPE: PRT
```

```
<213> ORGANISM: Artificial Sequence
<220> FEATURE:
<223> OTHER INFORMATION: Synthetic

<400> SEQUENCE: 71

Ser Ala Pro Val Leu Ser Ala Val Ala Thr Val Gly Ile Thr Ile Gly
1               5                   10                  15

Val Leu Ala Arg Val Ala Leu Ile
            20

<210> SEQ ID NO 72
<211> LENGTH: 24
<212> TYPE: PRT
<213> ORGANISM: Artificial Sequence
<220> FEATURE:
<223> OTHER INFORMATION: Synthetic

<400> SEQUENCE: 72

Ser Ser Pro Asp Leu Ser Ala Gly Thr Ala Val Ser Ile Met Ile Gly
1               5                   10                  15

Val Leu Ala Gly Met Ala Leu Ile
            20

<210> SEQ ID NO 73
<211> LENGTH: 25
<212> TYPE: PRT
<213> ORGANISM: Artificial Sequence
<220> FEATURE:
<223> OTHER INFORMATION: Synthetic

<400> SEQUENCE: 73

Thr Leu Gly Gly Asn Ser Ala Ser Tyr Thr Phe Val Ser Leu Leu Phe
1               5                   10                  15

Ser Ala Val Thr Leu Leu Leu Leu Cys
            20                  25

<210> SEQ ID NO 74

<400> SEQUENCE: 74

000

<210> SEQ ID NO 75

<400> SEQUENCE: 75

000

<210> SEQ ID NO 76
<211> LENGTH: 16
<212> TYPE: PRT
<213> ORGANISM: Artificial Sequence
<220> FEATURE:
<223> OTHER INFORMATION: Synthetic

<400> SEQUENCE: 76

Asp Lys Thr His Thr Cys Pro Pro Cys Pro Ala Pro Glu Leu Leu Gly
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 77

Gly Ser Thr His Thr Cys Pro Pro Cys Pro Ala Pro Glu Leu Leu Gly
1               5                   10                  15

<210> SEQ ID NO 78
<211> LENGTH: 21
<212> TYPE: PRT
<213> ORGANISM: Artificial Sequence
<220> FEATURE:
<223> OTHER INFORMATION: Synthetic

<400> SEQUENCE: 78

Glu Pro Lys Ser Cys Asp Lys Thr His Thr Cys Pro Pro Cys Pro Ala
1               5                   10                  15

Pro Glu Leu Leu Gly
            20

<210> SEQ ID NO 79
<211> LENGTH: 24
<212> TYPE: PRT
<213> ORGANISM: Artificial Sequence
<220> FEATURE:
<223> OTHER INFORMATION: Synthetic

<400> SEQUENCE: 79

Glu Pro Lys Ser Cys Asp Lys Thr His Thr Cys Pro Pro Cys Pro Ala
1               5                   10                  15

Pro Glu Leu Leu Gly Gly Pro Ser
            20

<210> SEQ ID NO 80
<211> LENGTH: 24
<212> TYPE: PRT
<213> ORGANISM: Artificial Sequence
<220> FEATURE:
<223> OTHER INFORMATION: Synthetic

<400> SEQUENCE: 80

Glu Pro Lys Ser Ser Asp Lys Thr His Thr Cys Pro Pro Cys Pro Ala
1               5                   10                  15

Pro Glu Leu Leu Gly Gly Pro Ser
            20

<210> SEQ ID NO 81
<211> LENGTH: 24
<212> TYPE: PRT
<213> ORGANISM: Artificial Sequence
<220> FEATURE:
<223> OTHER INFORMATION: Synthetic

<400> SEQUENCE: 81

Glu Pro Lys Ser Ser Asp Lys Thr His Thr Cys Pro Pro Cys Pro Ala
1               5                   10                  15

Pro Glu Leu Leu Gly Gly Ser Ser
            20

<210> SEQ ID NO 82
<211> LENGTH: 24
<212> TYPE: PRT
<213> ORGANISM: Artificial Sequence
<220> FEATURE:
<223> OTHER INFORMATION: Synthetic

<400> SEQUENCE: 82
```

```
Glu Pro Lys Ser Ser Gly Ser Thr His Thr Cys Pro Pro Cys Pro Ala
1               5                   10                  15

Pro Glu Leu Leu Gly Gly Ser Ser
            20

<210> SEQ ID NO 83
<211> LENGTH: 19
<212> TYPE: PRT
<213> ORGANISM: Artificial Sequence
<220> FEATURE:
<223> OTHER INFORMATION: Synthetic

<400> SEQUENCE: 83

Asp Lys Thr His Thr Cys Pro Pro Cys Pro Ala Pro Glu Leu Leu Gly
1               5                   10                  15

Gly Pro Ser

<210> SEQ ID NO 84
<211> LENGTH: 19
<212> TYPE: PRT
<213> ORGANISM: Artificial Sequence
<220> FEATURE:
<223> OTHER INFORMATION: Synthetic

<400> SEQUENCE: 84

Asp Lys Thr His Thr Cys Pro Pro Cys Pro Ala Pro Glu Leu Leu Gly
1               5                   10                  15

Gly Ser Ser

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000
```

<210> SEQ ID NO 91

<400> SEQUENCE: 91

000

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

```
Gly Gly Ser Gly Gly Ser Gly Gly Ser
1               5
```

<210> SEQ ID NO 93
<211> LENGTH: 97
<212> TYPE: PRT
<213> ORGANISM: Artificial Sequence
<220> FEATURE:
<223> OTHER INFORMATION: Synthetic

<400> SEQUENCE: 93

```
Met Met Pro Gly Gly Leu Thr Glu Ala Lys Pro Ala Thr Pro Glu Val
1               5                   10                  15

Gln Glu Ile Ala Asn Glu Val Lys Pro Gln Leu Glu Lys Glu Thr Gly
            20                  25                  30

Lys Thr Trp Gln Glu Phe Glu Ala Val Glu Tyr Lys Thr Gln Val Asp
        35                  40                  45

Ala Gly Leu Asn Tyr Tyr Ile Lys Val Arg Val Asn Gly Lys Tyr Ile
    50                  55                  60

His Leu Lys Ile Phe Lys Gly Leu Pro Gly Gln Asn Pro Thr Leu Thr
65                  70                  75                  80

Leu Thr Gly Tyr Gln Thr Asp Lys Ser Lys Asp Asp Glu Leu Thr Gly
                85                  90                  95

Phe
```

<210> SEQ ID NO 94
<211> LENGTH: 110
<212> TYPE: PRT
<213> ORGANISM: Artificial Sequence
<220> FEATURE:
<223> OTHER INFORMATION: Synthetic

<400> SEQUENCE: 94

```
Met Met Pro Gly Gly Leu Thr Glu Ala Lys Pro Ala Thr Pro Glu Val
1               5                   10                  15

Gln Glu Ile Ala Asn Glu Val Lys Pro Gln Leu Glu Lys Glu Thr Gly
            20                  25                  30

Lys Thr Trp Gln Glu Phe Glu Ala Val Glu Tyr Lys Thr Gln Val Asp
        35                  40                  45

Gly Gly Ser Gly Gly Ser Gly Gly Ser Leu Asn Tyr Tyr Ile Lys
    50                  55                  60

Val Arg Val Asn Gly Lys Tyr Ile His Leu Lys Ile Phe Lys Gly Leu
65                  70                  75                  80

Gly Gly Ser Gly Gly Ser Gly Gly Ser Pro Thr Leu Thr Leu Thr Gly
                85                  90                  95

Tyr Gln Thr Asp Lys Ser Lys Asp Asp Glu Leu Thr Gly Phe
                100                 105                 110
```

```
<210> SEQ ID NO 95
<211> LENGTH: 98
<212> TYPE: PRT
<213> ORGANISM: Artificial Sequence
<220> FEATURE:
<223> OTHER INFORMATION: Synthetic

<400> SEQUENCE: 95

Met Ile Pro Gly Gly Leu Thr Glu Ala Lys Pro Ala Thr Pro Glu Val
1               5                   10                  15

Gln Glu Ile Ala Asn Glu Val Lys Pro Gln Leu Glu Glu Lys Thr Gly
            20                  25                  30

Glu Thr Tyr Gln Glu Phe Glu Ala Val Glu Tyr Lys Thr Gln Val Asp
        35                  40                  45

Ala Gly Ile Asn Tyr Tyr Ile Lys Val Arg Val Gly Asp Asn Ser Tyr
    50                  55                  60

Ile His Leu Lys Ile Phe Lys Gly Leu Pro Gly Gln Asn Pro Thr Leu
65                  70                  75                  80

Thr Leu Thr Gly Tyr Gln Thr Asp Lys Ser Lys Asp Asp Glu Leu Thr
                85                  90                  95

Gly Phe

<210> SEQ ID NO 96
<211> LENGTH: 98
<212> TYPE: PRT
<213> ORGANISM: Artificial Sequence
<220> FEATURE:
<223> OTHER INFORMATION: Synthetic

<400> SEQUENCE: 96

Met Ile Pro Gly Gly Leu Thr Glu Ala Lys Pro Ala Thr Pro Glu Val
1               5                   10                  15

Gln Glu Ile Ala Asn Glu Val Lys Pro Gln Leu Glu Glu Lys Thr Gly
            20                  25                  30

Glu Thr Tyr Gln Glu Phe Glu Ala Val Glu Tyr Lys Thr Gln Val Asp
        35                  40                  45

Ala Gly Ile Asn Tyr Tyr Ile Lys Val Arg Val Gly Asp Asn Ser Tyr
    50                  55                  60

Ile His Leu Lys Ile Phe Lys Ser Leu Pro Gly Gln Asn Glu Asp Leu
65                  70                  75                  80

Thr Leu Thr Gly Tyr Gln Thr Asp Lys Ser Lys Asp Asp Glu Leu Thr
                85                  90                  95

Gly Phe

<210> SEQ ID NO 97
<211> LENGTH: 98
<212> TYPE: PRT
<213> ORGANISM: Artificial Sequence
<220> FEATURE:
<223> OTHER INFORMATION: Synthetic

<400> SEQUENCE: 97

Met Ile Pro Gly Gly Leu Thr Glu Ala Lys Pro Ala Thr Pro Glu Val
1               5                   10                  15

Gln Glu Ile Val Asn Glu Val Lys Pro Gln Leu Glu Glu Lys Thr Gly
            20                  25                  30

Glu Thr Tyr Gln Glu Leu Glu Ala Val Glu Tyr Lys Thr Gln Val Asp
        35                  40                  45
```

Ala Gly Ile Asn Tyr Tyr Ile Lys Val Arg Val Gly Asp Asn Ser Tyr
 50                  55                  60

Ile His Leu Lys Ile Phe Lys Gly Leu Pro Gly Gln Asn Pro Thr Leu
65                  70                  75                  80

Thr Leu Thr Gly Tyr Gln Thr Asp Lys Ser Lys Asp Asp Glu Leu Thr
                85                  90                  95

Gly Phe

<210> SEQ ID NO 98
<211> LENGTH: 98
<212> TYPE: PRT
<213> ORGANISM: Artificial Sequence
<220> FEATURE:
<223> OTHER INFORMATION: Synthetic

<400> SEQUENCE: 98

Met Ile Pro Gly Gly Leu Thr Glu Ala Lys Pro Ala Thr Pro Glu Val
1               5                   10                  15

Gln Glu Ile Val Asn Glu Val Lys Pro Gln Leu Glu Glu Lys Thr Gly
                20                  25                  30

Glu Thr Tyr Gln Glu Leu Glu Ala Val Glu Tyr Lys Thr Gln Val Asp
            35                  40                  45

Ala Gly Ile Asn Tyr Tyr Ile Lys Val Arg Val Gly Asp Asn Ser Tyr
 50                  55                  60

Ile His Leu Lys Ile Phe Lys Ser Leu Pro Gly Gln Asn Glu Asp Leu
65                  70                  75                  80

Thr Leu Thr Gly Tyr Gln Thr Asp Lys Ser Lys Asp Asp Glu Leu Thr
                85                  90                  95

Gly Phe

<210> SEQ ID NO 99
<211> LENGTH: 111
<212> TYPE: PRT
<213> ORGANISM: Artificial Sequence
<220> FEATURE:
<223> OTHER INFORMATION: Synthetic

<400> SEQUENCE: 99

Met Ile Pro Gly Gly Leu Thr Glu Ala Lys Pro Ala Thr Pro Glu Val
1               5                   10                  15

Gln Glu Ile Ala Asn Glu Val Lys Pro Gln Leu Glu Glu Lys Thr Gly
                20                  25                  30

Glu Thr Tyr Gln Glu Phe Glu Ala Val Glu Tyr Lys Thr Gln Val Asp
            35                  40                  45

Gly Gly Ser Gly Gly Ser Gly Gly Ser Gly Ile Asn Tyr Tyr Ile Lys
 50                  55                  60

Val Arg Val Gly Asp Asn Ser Tyr Ile His Leu Lys Ile Phe Lys Gly
65                  70                  75                  80

Leu Gly Gly Ser Gly Gly Ser Gly Gly Ser Pro Thr Leu Thr Leu Thr
                85                  90                  95

Gly Tyr Gln Thr Asp Lys Ser Lys Asp Asp Glu Leu Thr Gly Phe
            100                 105                 110

<210> SEQ ID NO 100
<211> LENGTH: 111
<212> TYPE: PRT
<213> ORGANISM: Artificial Sequence
<220> FEATURE:

<223> OTHER INFORMATION: Synthetic

<400> SEQUENCE: 100

Met Ile Pro Gly Gly Leu Thr Glu Ala Lys Pro Ala Thr Pro Glu Val
1               5                   10                  15

Gln Glu Ile Ala Asn Glu Val Lys Pro Gln Leu Glu Glu Lys Thr Gly
            20                  25                  30

Glu Thr Tyr Gln Glu Phe Glu Ala Val Glu Tyr Lys Thr Gln Val Asp
        35                  40                  45

Gly Gly Ser Gly Gly Ser Gly Gly Ser Gly Ile Asn Tyr Tyr Ile Lys
    50                  55                  60

Val Arg Val Gly Asp Asn Ser Tyr Ile His Leu Lys Ile Phe Lys Ser
65                  70                  75                  80

Leu Gly Gly Ser Gly Gly Ser Gly Gly Ser Glu Asp Leu Thr Leu Thr
                85                  90                  95

Gly Tyr Gln Thr Asp Lys Ser Lys Asp Glu Leu Thr Gly Phe
            100                 105                 110

<210> SEQ ID NO 101
<211> LENGTH: 111
<212> TYPE: PRT
<213> ORGANISM: Artificial Sequence
<220> FEATURE:
<223> OTHER INFORMATION: Synthetic

<400> SEQUENCE: 101

Met Ile Pro Gly Gly Leu Thr Glu Ala Lys Pro Ala Thr Pro Glu Val
1               5                   10                  15

Gln Glu Ile Val Asn Glu Val Lys Pro Gln Leu Glu Glu Lys Thr Gly
            20                  25                  30

Glu Thr Tyr Gln Glu Leu Glu Ala Val Glu Tyr Lys Thr Gln Val Asp
        35                  40                  45

Gly Gly Ser Gly Gly Ser Gly Gly Ser Gly Ile Asn Tyr Tyr Ile Lys
    50                  55                  60

Val Arg Val Gly Asp Asn Ser Tyr Ile His Leu Lys Ile Phe Lys Gly
65                  70                  75                  80

Leu Gly Gly Ser Gly Gly Ser Gly Gly Ser Pro Thr Leu Thr Leu Thr
                85                  90                  95

Gly Tyr Gln Thr Asp Lys Ser Lys Asp Glu Leu Thr Gly Phe
            100                 105                 110

<210> SEQ ID NO 102
<211> LENGTH: 111
<212> TYPE: PRT
<213> ORGANISM: Artificial Sequence
<220> FEATURE:
<223> OTHER INFORMATION: Synthetic

<400> SEQUENCE: 102

Met Ile Pro Gly Gly Leu Thr Glu Ala Lys Pro Ala Thr Pro Glu Val
1               5                   10                  15

Gln Glu Ile Val Asn Glu Val Lys Pro Gln Leu Glu Glu Lys Thr Gly
            20                  25                  30

Glu Thr Tyr Gln Glu Leu Glu Ala Val Glu Tyr Lys Thr Gln Val Asp
        35                  40                  45

Gly Gly Ser Gly Gly Ser Gly Gly Ser Gly Ile Asn Tyr Tyr Ile Lys
    50                  55                  60

Val Arg Val Gly Asp Asn Ser Tyr Ile His Leu Lys Ile Phe Lys Ser

```
                65                  70                  75                  80
Leu Gly Gly Ser Gly Gly Ser Gly Gly Ser Glu Asp Leu Thr Leu Thr
                    85                  90                  95
Gly Tyr Gln Thr Asp Lys Ser Lys Asp Asp Glu Leu Thr Gly Phe
                100                 105                 110
```

<210> SEQ ID NO 103
<211> LENGTH: 97
<212> TYPE: PRT
<213> ORGANISM: Artificial Sequence
<220> FEATURE:
<223> OTHER INFORMATION: Synthetic

<400> SEQUENCE: 103

```
Met Met Pro Gly Gly Leu Thr Glu Ala Lys Pro Ala Thr Pro Glu Val
1               5                   10                  15

Gln Glu Ile Ala Asn Glu Val Lys Pro Gln Leu Glu Lys Glu Thr Gly
                20                  25                  30

Lys Thr Trp Gln Glu Phe Glu Ala Val Glu Tyr Lys Thr Gln Val Asp
            35                  40                  45

Ala Gly Leu Asn Tyr Tyr Ile Lys Val Arg Val Gly Asn Lys Tyr Ile
        50                  55                  60

His Leu Lys Ile Phe Lys Gly Leu Pro Gly Gln Asn Pro Thr Leu Thr
65                  70                  75                  80

Leu Thr Gly Tyr Gln Thr Asp Lys Ser Lys Asp Asp Glu Leu Thr Gly
                85                  90                  95

Phe
```

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

```
Gly His His His His His His
1               5
```

<210> SEQ ID NO 105
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (50)..(58)
<223> OTHER INFORMATION: Xaa can be any naturally occurring amino acid
<220> FEATURE:
<221> NAME/KEY: misc_feature
<222> LOCATION: (84)..(92)
<223> OTHER INFORMATION: Xaa can be any naturally occurring amino acid

<400> SEQUENCE: 105

```
Met Ser Ala Ala Thr Gly Val Arg Ala Val Pro Gly Asn Glu Asn Ser
1               5                   10                  15

Leu Glu Ile Glu Glu Leu Ala Arg Phe Ala Val Asp Glu His Asn Lys
                20                  25                  30

Lys Glu Asn Ala Leu Leu Glu Phe Val Arg Val Val Lys Ala Lys Glu
            35                  40                  45

Gln Xaa Xaa Xaa Xaa Xaa Xaa Xaa Xaa Xaa Thr Met Tyr Tyr Leu Thr
```

```
                     50                  55                  60
Leu Glu Ala Lys Asp Gly Gly Lys Lys Leu Tyr Glu Ala Lys Val
 65                  70                  75                  80

Trp Val Lys Xaa Xaa Xaa Xaa Xaa Xaa Xaa Xaa Asn Phe Lys Glu
                 85                  90                  95

Leu Gln Glu Phe Lys Pro Val Gly Asp Ala Ala Ala His His
            100                 105                 110

His His His Gly
        115

<210> SEQ ID NO 106
<211> LENGTH: 106
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (50)..(58)
<223> OTHER INFORMATION: Xaa can be any naturally occurring amino acid
<220> FEATURE:
<221> NAME/KEY: misc_feature
<222> LOCATION: (84)..(92)
<223> OTHER INFORMATION: Xaa can be any naturally occurring amino acid

<400> SEQUENCE: 106

Met Ser Ala Ala Thr Gly Val Arg Ala Val Pro Gly Asn Glu Asn Ser
  1               5                  10                  15

Leu Glu Ile Glu Glu Leu Ala Arg Phe Ala Val Asp Glu His Asn Lys
                 20                  25                  30

Lys Glu Asn Ala Leu Leu Glu Phe Val Arg Val Val Lys Ala Lys Glu
             35                  40                  45

Gln Xaa Xaa Xaa Xaa Xaa Xaa Xaa Xaa Thr Met Tyr Tyr Leu Thr
         50                  55                  60

Leu Glu Ala Lys Asp Gly Gly Lys Lys Leu Tyr Glu Ala Lys Val
 65                  70                  75                  80

Trp Val Lys Xaa Xaa Xaa Xaa Xaa Xaa Xaa Xaa Asn Phe Lys Glu
                 85                  90                  95

Leu Gln Glu Phe Lys Pro Val Gly Asp Gly
            100                 105

<210> SEQ ID NO 107
<211> LENGTH: 134
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa may be Gly, Ala, Val, Arg, Lys, Asp or Glu
<220> FEATURE:
<221> NAME/KEY: misc_feature
<222> LOCATION: (50)..(69)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa may be Gly, Ala, Val, Ser or Thr
<220> FEATURE:
<221> NAME/KEY: misc_feature
<222> LOCATION: (91)..(91)
<223> OTHER INFORMATION: Xaa may be Arg, Lys, Asn, Gln, Ser or Thr
<220> FEATURE:
<221> NAME/KEY: misc_feature
<222> LOCATION: (92)..(92)
```

```
<223> OTHER INFORMATION: Xaa may be Gly, Ala, Val, Ser or Thr
<220> FEATURE:
<221> NAME/KEY: misc_feature
<222> LOCATION: (93)..(93)
<223> OTHER INFORMATION: Xaa may be Ala, Val, Ile, Leu, Gly or Pro
<220> FEATURE:
<221> NAME/KEY: misc_feature
<222> LOCATION: (94)..(113)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa may be Gly, Ala, Val, Asp or Glu
<220> FEATURE:
<221> NAME/KEY: misc_feature
<222> LOCATION: (116)..(116)
<223> OTHER INFORMATION: Xaa may be Ala, Val, Ile, Leu, Arg or Lys

<400> SEQUENCE: 107

Met Ile Pro Xaa Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Xaa Xaa Xaa Xaa Xaa Xaa Xaa Xaa Xaa Xaa Xaa Xaa
    50                  55                  60

Xaa Xaa Xaa Xaa Xaa Xaa Thr Asn Tyr Tyr Ile Lys Val Arg Ala Gly
65                  70                  75                  80

Asp Asn Lys Tyr Met His Leu Lys Val Phe Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Asp Xaa Val Leu Thr Gly Tyr Gln Val Asp Lys Asn Lys Asp
            115                 120                 125

Asp Glu Leu Thr Gly Phe
        130

<210> SEQ ID NO 108
<211> LENGTH: 10
<212> TYPE: PRT
<213> ORGANISM: Artificial Sequence
<220> FEATURE:
<223> OTHER INFORMATION: Synthetic

<400> SEQUENCE: 108

Lys Ser Leu Pro Gly Gln Asn Glu Asp Leu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic

<400> SEQUENCE: 109

Asn Gly Pro Pro Gly Gln Asn Ala Asp Arg
1               5                   10

<210> SEQ ID NO 110
<211> LENGTH: 98
<212> TYPE: PRT
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (12)..(12)
<223> OTHER INFORMATION: Xaa may be A, I or V
<220> FEATURE:
<221> NAME/KEY: misc_feature
<222> LOCATION: (16)..(16)
<223> OTHER INFORMATION: Xaa may be I or L
<220> FEATURE:
<221> NAME/KEY: misc_feature
<222> LOCATION: (20)..(20)
<223> OTHER INFORMATION: Xaa may be V, I or L
<220> FEATURE:
<221> NAME/KEY: misc_feature
<222> LOCATION: (26)..(26)
<223> OTHER INFORMATION: Xaa may be Q or E
<220> FEATURE:
<221> NAME/KEY: misc_feature
<222> LOCATION: (29)..(29)
<223> OTHER INFORMATION: Xaa may be E or M
<220> FEATURE:
<221> NAME/KEY: misc_feature
<222> LOCATION: (30)..(30)
<223> OTHER INFORMATION: Xaa may be any naturally occurring amino acid
<220> FEATURE:
<221> NAME/KEY: misc_feature
<222> LOCATION: (31)..(31)
<223> OTHER INFORMATION: Xaa may be T or K
<220> FEATURE:
<221> NAME/KEY: misc_feature
<222> LOCATION: (32)..(32)
<223> OTHER INFORMATION: Xaa may be N, G, D or H
<220> FEATURE:
<221> NAME/KEY: misc_feature
<222> LOCATION: (33)..(33)
<223> OTHER INFORMATION: Xaa may be any naturally occurring amino acid
<220> FEATURE:
<221> NAME/KEY: misc_feature
<222> LOCATION: (34)..(34)
<223> OTHER INFORMATION: Xaa may be T, V, R, D or P
<220> FEATURE:
<221> NAME/KEY: misc_feature
<222> LOCATION: (38)..(38)
<223> OTHER INFORMATION: Xaa may be L, A or V
<220> FEATURE:
<221> NAME/KEY: misc_feature
<222> LOCATION: (40)..(40)
<223> OTHER INFORMATION: Xaa may be A, I or V
<220> FEATURE:
<221> NAME/KEY: misc_feature
<222> LOCATION: (42)..(42)
<223> OTHER INFORMATION: Xaa may be Q or D
<220> FEATURE:
<221> NAME/KEY: misc_feature
<222> LOCATION: (45)..(45)
<223> OTHER INFORMATION: Xaa may be T, I, V
<220> FEATURE:
<221> NAME/KEY: misc_feature
<222> LOCATION: (48)..(48)
<223> OTHER INFORMATION: Xaa may be V, E, G or A
<220> FEATURE:
<221> NAME/KEY: misc_feature
<222> LOCATION: (51)..(51)
<223> OTHER INFORMATION: Xaa may be T, F, V, L or A
<220> FEATURE:
<221> NAME/KEY: misc_feature
<222> LOCATION: (54)..(54)
<223> OTHER INFORMATION: Xaa may be any naturally occurring amino acid
<220> FEATURE:
<221> NAME/KEY: misc_feature
<222> LOCATION: (59)..(59)
<223> OTHER INFORMATION: Xaa may be A, L or I
<220> FEATURE:
<221> NAME/KEY: misc_feature
<222> LOCATION: (60)..(60)
<223> OTHER INFORMATION: Xaa may be any naturally occurring amino acid
<220> FEATURE:
<221> NAME/KEY: misc_feature
```

```
<222> LOCATION: (61)..(61)
<223> OTHER INFORMATION: Xaa may be D or absent
<220> FEATURE:
<221> NAME/KEY: misc_feature
<222> LOCATION: (62)..(62)
<223> OTHER INFORMATION: Xaa may be any naturally occurring amino acid
<220> FEATURE:
<221> NAME/KEY: misc_feature
<222> LOCATION: (65)..(65)
<223> OTHER INFORMATION: Xaa may be M or V
<220> FEATURE:
<221> NAME/KEY: misc_feature
<222> LOCATION: (67)..(67)
<223> OTHER INFORMATION: Xaa may be L or I
<220> FEATURE:
<221> NAME/KEY: misc_feature
<222> LOCATION: (83)..(83)
<223> OTHER INFORMATION: Xaa may be any naturally occurring amino acid
<220> FEATURE:
<221> NAME/KEY: misc_feature
<222> LOCATION: (86)..(86)
<223> OTHER INFORMATION: Xaa may be any naturally occurring amino acid

<400> SEQUENCE: 110

Met Ile Pro Gly Gly Leu Ser Glu Ala Lys Pro Xaa Thr Pro Glu Xaa
1               5                   10                  15

Gln Glu Ile Xaa Asp Lys Val Lys Pro Xaa Leu Glu Xaa Xaa Xaa Xaa
            20                  25                  30

Xaa Xaa Tyr Gly Lys Xaa Glu Xaa Val Xaa Tyr Lys Xaa Gln Val Xaa
        35                  40                  45

Ala Gly Xaa Asn Tyr Xaa Ile Lys Val Arg Xaa Xaa Xaa Xaa Lys Tyr
    50                  55                  60

Xaa His Xaa Lys Val Phe Lys Ser Leu Pro Gly Gln Asn Glu Asp Leu
65                  70                  75                  80

Val Leu Xaa Gly Tyr Xaa Val Asp Lys Asn Lys Asp Asp Glu Leu Thr
            85                  90                  95

Gly Phe

<210> SEQ ID NO 111
<211> LENGTH: 98
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: Xaa may be E or M
<220> FEATURE:
<221> NAME/KEY: misc_feature
<222> LOCATION: (30)..(30)
<223> OTHER INFORMATION: Xaa may be any naturally occurring amino acid
<220> FEATURE:
<221> NAME/KEY: misc_feature
<222> LOCATION: (32)..(32)
<223> OTHER INFORMATION: Xaa may be N or G
<220> FEATURE:
<221> NAME/KEY: misc_feature
<222> LOCATION: (33)..(33)
<223> OTHER INFORMATION: Xaa may be any naturally occurring amino acid
<220> FEATURE:
<221> NAME/KEY: misc_feature
<222> LOCATION: (34)..(34)
<223> OTHER INFORMATION: Xaa may be T, V or R
<220> FEATURE:
<221> NAME/KEY: misc_feature
<222> LOCATION: (45)..(45)
<223> OTHER INFORMATION: Xaa may be T, I or V
<220> FEATURE:
<221> NAME/KEY: misc_feature
<222> LOCATION: (51)..(51)
```

<223> OTHER INFORMATION: Xaa may be T, F, V or L
<220> FEATURE:
<221> NAME/KEY: misc_feature
<222> LOCATION: (59)..(59)
<223> OTHER INFORMATION: Xaa may be A, L or I
<220> FEATURE:
<221> NAME/KEY: misc_feature
<222> LOCATION: (60)..(60)
<223> OTHER INFORMATION: Xaa may be any naturally occurring amino acid
<220> FEATURE:
<221> NAME/KEY: misc_feature
<222> LOCATION: (61)..(61)
<223> OTHER INFORMATION: Xaa may be D or absent
<220> FEATURE:
<221> NAME/KEY: misc_feature
<222> LOCATION: (62)..(62)
<223> OTHER INFORMATION: Xaa may be any naturally occurring amino acid
<220> FEATURE:
<221> NAME/KEY: misc_feature
<222> LOCATION: (65)..(65)
<223> OTHER INFORMATION: Xaa may be M or V
<220> FEATURE:
<221> NAME/KEY: misc_feature
<222> LOCATION: (67)..(67)
<223> OTHER INFORMATION: Xaa may be L or I

<400> SEQUENCE: 111

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Xaa Xaa Thr Xaa
            20                  25                  30

Xaa Xaa Tyr Gly Lys Leu Glu Ala Val Gln Tyr Lys Xaa Gln Val Val
        35                  40                  45

Ala Gly Xaa Asn Tyr Tyr Ile Lys Val Arg Xaa Xaa Xaa Lys Tyr
    50                  55                  60

Xaa His Xaa Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 112
<211> LENGTH: 98
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa may be A, I or V
<220> FEATURE:
<221> NAME/KEY: misc_feature
<222> LOCATION: (16)..(16)
<223> OTHER INFORMATION: Xaa may be I or L
<220> FEATURE:
<221> NAME/KEY: misc_feature
<222> LOCATION: (20)..(20)
<223> OTHER INFORMATION: Xaa may be V, I or L
<220> FEATURE:
<221> NAME/KEY: misc_feature
<222> LOCATION: (26)..(26)
<223> OTHER INFORMATION: Xaa may be Q or E
<220> FEATURE:
<221> NAME/KEY: misc_feature
<222> LOCATION: (31)..(31)
<223> OTHER INFORMATION: Xaa may be T or K
<220> FEATURE:
<221> NAME/KEY: misc_feature
<222> LOCATION: (32)..(32)
<223> OTHER INFORMATION: Xaa may be N, D or H

```
<220> FEATURE:
<221> NAME/KEY: misc_feature
<222> LOCATION: (34)..(34)
<223> OTHER INFORMATION: Xaa may be T, D or P
<220> FEATURE:
<221> NAME/KEY: misc_feature
<222> LOCATION: (38)..(38)
<223> OTHER INFORMATION: Xaa may be L, A or V
<220> FEATURE:
<221> NAME/KEY: misc_feature
<222> LOCATION: (40)..(40)
<223> OTHER INFORMATION: Xaa may be A, I or V
<220> FEATURE:
<221> NAME/KEY: misc_feature
<222> LOCATION: (42)..(42)
<223> OTHER INFORMATION: Xaa may be Q or D
<220> FEATURE:
<221> NAME/KEY: misc_feature
<222> LOCATION: (48)..(48)
<223> OTHER INFORMATION: Xaa may be V, E, G or A
<220> FEATURE:
<221> NAME/KEY: misc_feature
<222> LOCATION: (51)..(51)
<223> OTHER INFORMATION: Xaa may be T or A
<220> FEATURE:
<221> NAME/KEY: misc_feature
<222> LOCATION: (54)..(54)
<223> OTHER INFORMATION: Xaa may be any naturally occurring amino acid
<220> FEATURE:
<221> NAME/KEY: misc_feature
<222> LOCATION: (60)..(60)
<223> OTHER INFORMATION: Xaa may be any naturally occurring amino acid
<220> FEATURE:
<221> NAME/KEY: misc_feature
<222> LOCATION: (61)..(61)
<223> OTHER INFORMATION: Xaa may be any naturally occurring amino acid
<220> FEATURE:
<221> NAME/KEY: misc_feature
<222> LOCATION: (62)..(62)
<223> OTHER INFORMATION: Xaa may be any naturally occurring amino acid
<220> FEATURE:
<221> NAME/KEY: misc_feature
<222> LOCATION: (83)..(83)
<223> OTHER INFORMATION: Xaa may be any naturally occurring amino acid
<220> FEATURE:
<221> NAME/KEY: misc_feature
<222> LOCATION: (86)..(86)
<223> OTHER INFORMATION: Xaa may be any naturally occurring amino acid

<400> SEQUENCE: 112

Met Ile Pro Gly Gly Leu Ser Glu Ala Lys Pro Xaa Thr Pro Glu Xaa
1               5                   10                  15

Gln Glu Ile Xaa Asp Lys Val Lys Pro Xaa Leu Glu Lys Xaa Xaa
            20                  25                  30

Glu Xaa Tyr Gly Lys Xaa Glu Xaa Val Xaa Tyr Lys Thr Gln Val Xaa
        35                  40                  45

Ala Gly Xaa Asn Tyr Xaa Ile Lys Val Arg Ala Xaa Xaa Xaa Lys Tyr
    50                  55                  60

Met His Leu Lys Val Phe Lys Ser Leu Pro Gly Gln Asn Glu Asp Leu
65                  70                  75                  80

Val Leu Xaa Gly Tyr Xaa Val Asp Lys Asn Lys Asp Asp Glu Leu Thr
                85                  90                  95

Gly Phe

<210> SEQ ID NO 113
<211> LENGTH: 98
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (12)..(12)
<223> OTHER INFORMATION: Xaa may be A, I or V
<220> FEATURE:
<221> NAME/KEY: misc_feature
<222> LOCATION: (16)..(16)
<223> OTHER INFORMATION: Xaa may be I or D
<220> FEATURE:
<221> NAME/KEY: misc_feature
<222> LOCATION: (20)..(20)
<223> OTHER INFORMATION: Xaa may be V, A, I or L
<220> FEATURE:
<221> NAME/KEY: misc_feature
<222> LOCATION: (26)..(26)
<223> OTHER INFORMATION: Xaa may be Q or E
<220> FEATURE:
<221> NAME/KEY: misc_feature
<222> LOCATION: (29)..(29)
<223> OTHER INFORMATION: Xaa may be E or M
<220> FEATURE:
<221> NAME/KEY: misc_feature
<222> LOCATION: (30)..(30)
<223> OTHER INFORMATION: Xaa may be any naturally occurring amino acid
<220> FEATURE:
<221> NAME/KEY: misc_feature
<222> LOCATION: (31)..(31)
<223> OTHER INFORMATION: Xaa may be T or K
<220> FEATURE:
<221> NAME/KEY: misc_feature
<222> LOCATION: (32)..(32)
<223> OTHER INFORMATION: Xaa may be N, G, D or H
<220> FEATURE:
<221> NAME/KEY: misc_feature
<222> LOCATION: (33)..(33)
<223> OTHER INFORMATION: Xaa may be any naturally occurring amino acid
<220> FEATURE:
<221> NAME/KEY: misc_feature
<222> LOCATION: (34)..(34)
<223> OTHER INFORMATION: Xaa may be T, V, R, K, D or P
<220> FEATURE:
<221> NAME/KEY: misc_feature
<222> LOCATION: (38)..(38)
<223> OTHER INFORMATION: Xaa may be L, A, V or F
<220> FEATURE:
<221> NAME/KEY: misc_feature
<222> LOCATION: (40)..(40)
<223> OTHER INFORMATION: Xaa may be A, I or V
<220> FEATURE:
<221> NAME/KEY: misc_feature
<222> LOCATION: (42)..(42)
<223> OTHER INFORMATION: Xaa may be Q, E or D
<220> FEATURE:
<221> NAME/KEY: misc_feature
<222> LOCATION: (45)..(45)
<223> OTHER INFORMATION: Xaa may be T, I or V
<220> FEATURE:
<221> NAME/KEY: misc_feature
<222> LOCATION: (48)..(48)
<223> OTHER INFORMATION: Xaa may be V, E, D, G, A or L
<220> FEATURE:
<221> NAME/KEY: misc_feature
<222> LOCATION: (50)..(50)
<223> OTHER INFORMATION: Xaa may be G or S
<220> FEATURE:
<221> NAME/KEY: misc_feature
<222> LOCATION: (51)..(51)
<223> OTHER INFORMATION: Xaa may be T, F, V, L, I or A
<220> FEATURE:
<221> NAME/KEY: misc_feature
<222> LOCATION: (54)..(54)
<223> OTHER INFORMATION: Xaa may be any naturally occurring amino acid
<220> FEATURE:
<221> NAME/KEY: misc_feature
<222> LOCATION: (59)..(59)
<223> OTHER INFORMATION: Xaa may be A, L, I or V
<220> FEATURE:
<221> NAME/KEY: misc_feature
<222> LOCATION: (60)..(60)
<223> OTHER INFORMATION: Xaa may be any naturally occurring amino acid
```

```
<220> FEATURE:
<221> NAME/KEY: misc_feature
<222> LOCATION: (61)..(61)
<223> OTHER INFORMATION: Xaa may be D or absent
<220> FEATURE:
<221> NAME/KEY: misc_feature
<222> LOCATION: (62)..(62)
<223> OTHER INFORMATION: Xaa may be any naturally occurring amino acid
<220> FEATURE:
<221> NAME/KEY: misc_feature
<222> LOCATION: (63)..(63)
<223> OTHER INFORMATION: Xaa may be K or R
<220> FEATURE:
<221> NAME/KEY: misc_feature
<222> LOCATION: (65)..(65)
<223> OTHER INFORMATION: Xaa may be M, V or I
<220> FEATURE:
<221> NAME/KEY: misc_feature
<222> LOCATION: (67)..(67)
<223> OTHER INFORMATION: Xaa may be L or I
<220> FEATURE:
<221> NAME/KEY: misc_feature
<222> LOCATION: (83)..(83)
<223> OTHER INFORMATION: Xaa may be any naturally occurring amino acid
<220> FEATURE:
<221> NAME/KEY: misc_feature
<222> LOCATION: (86)..(86)
<223> OTHER INFORMATION: Xaa may be any naturally occurring amino acid
<220> FEATURE:
<221> NAME/KEY: misc_feature
<222> LOCATION: (90)..(90)
<223> OTHER INFORMATION: Xaa may be N or T

<400> SEQUENCE: 113

Met Ile Pro Gly Gly Leu Ser Glu Ala Lys Pro Xaa Thr Pro Glu Xaa
1               5                   10                  15

Gln Glu Ile Xaa Asp Lys Val Lys Pro Xaa Leu Glu Xaa Xaa Xaa Xaa
            20                  25                  30

Xaa Xaa Tyr Gly Lys Xaa Glu Xaa Val Xaa Tyr Lys Xaa Gln Val Xaa
        35                  40                  45

Ala Xaa Xaa Asn Tyr Xaa Ile Lys Val Arg Xaa Xaa Xaa Xaa Xaa Tyr
50                  55                  60

Xaa His Xaa Lys Val Phe Lys Ser Leu Pro Gly Gln Asn Glu Asp Leu
65                  70                  75                  80

Val Leu Xaa Gly Tyr Xaa Val Asp Lys Xaa Lys Asp Asp Glu Leu Thr
            85                  90                  95

Gly Phe

<210> SEQ ID NO 114
<211> LENGTH: 73
<212> TYPE: PRT
<213> ORGANISM: Artificial Sequence
<220> FEATURE:
<223> OTHER INFORMATION: Synthetic

<400> SEQUENCE: 114

Met Ile Pro Gly Gly Leu Ser Glu Ala Lys Pro Thr Pro Glu Gln Glu
1               5                   10                  15

Ile Asp Lys Val Lys Pro Leu Glu Tyr Gly Lys Glu Val Tyr Lys Gln
            20                  25                  30

Val Ala Gly Asn Tyr Ile Lys Val Arg Lys Tyr His Lys Val Phe Lys
        35                  40                  45

Ser Leu Pro Gly Gln Asn Glu Asp Leu Val Leu Gly Tyr Val Asp Lys
    50                  55                  60

Asn Lys Asp Asp Glu Leu Thr Gly Phe
65                  70
```

<210> SEQ ID NO 115
<211> LENGTH: 73
<212> TYPE: PRT
<213> ORGANISM: Artificial Sequence
<220> FEATURE:
<223> OTHER INFORMATION: Synthetic

<400> SEQUENCE: 115

Met Met Pro Gly Gly Leu Thr Glu Ala Lys Pro Thr Pro Gln Glu
1               5                   10                  15

Ile Asn Glu Val Lys Pro Leu Glu Tyr Gln Glu Val Tyr Lys Gln
                20                  25                  30

Val Ala Gly Asn Tyr Ile Lys Val Arg Ser Tyr His Lys Ile Phe Lys
            35                  40                  45

Gly Leu Pro Gly Gln Asn Pro Thr Leu Thr Leu Gly Tyr Thr Asp Lys
        50                  55                  60

Ser Lys Asp Asp Glu Leu Thr Gly Phe
65                  70

<210> SEQ ID NO 116
<211> LENGTH: 98
<212> TYPE: PRT
<213> ORGANISM: Artificial Sequence
<220> FEATURE:
<223> OTHER INFORMATION: Synthetic

<400> SEQUENCE: 116

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
                20                  25                  30

Glu Thr Tyr Gly Lys Leu Glu Ala Val Gln Tyr Lys Thr Gln Val Leu
            35                  40                  45

Ala Ser Thr Asn Tyr Tyr Ile Lys Val Arg Ala Gly Asp Asn Lys Tyr
        50                  55                  60

Met His Leu Lys Val Phe Asn Gly Pro Pro Gly Gln Asn Ala Asp Arg
65                  70                  75                  80

Val Leu Thr Gly Tyr Gln Val Asp Lys Asn Lys Asp Asp Glu Leu Thr
                85                  90                  95

Gly Phe

<210> SEQ ID NO 117
<211> LENGTH: 94
<212> TYPE: PRT
<213> ORGANISM: Artificial Sequence
<220> FEATURE:
<223> OTHER INFORMATION: Synthetic
<220> FEATURE:
<221> NAME/KEY: NON_CONS
<222> LOCATION: (49)..(50)
<223> OTHER INFORMATION: heterologous peptide sequence in Loop2
<220> FEATURE:
<221> NAME/KEY: NON_CONS
<222> LOCATION: (74)..(75)
<223> OTHER INFORMATION: heterologous peptide sequence in Loop4

<400> SEQUENCE: 117

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
                20                  25                  30

```
Glu Thr Tyr Gly Lys Leu Glu Ala Val Gln Tyr Lys Thr Gln Val Leu
         35                  40                  45

Ala Ser Thr Asn Tyr Tyr Ile Lys Val Arg Ala Gly Asp Asn Lys Tyr
 50                  55                  60

Met His Leu Lys Val Phe Asn Gly Pro Ala Asp Arg Val Leu Thr Gly
 65                  70                  75                  80

Tyr Gln Val Asp Lys Asn Lys Asp Asp Glu Leu Thr Gly Phe
                 85                  90
```

<210> SEQ ID NO 118
<211> LENGTH: 2
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: REPEAT
<222> LOCATION: (1)..(2)
<223> OTHER INFORMATION: may repeat 1-10 times

<400> SEQUENCE: 118

Xaa Pro
1

<210> SEQ ID NO 119
<211> LENGTH: 6
<212> TYPE: PRT
<213> ORGANISM: Artificial Sequence
<220> FEATURE:
<223> OTHER INFORMATION: Synthetic

<400> SEQUENCE: 119

Arg Gly Val Phe Arg Arg
1               5

<210> SEQ ID NO 120
<211> LENGTH: 12
<212> TYPE: DNA
<213> ORGANISM: Artificial Sequence
<220> FEATURE:
<223> OTHER INFORMATION: Synthetic

<400> SEQUENCE: 120
accgttgccg gt                                                             12

<210> SEQ ID NO 121
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(9)
<223> OTHER INFORMATION: n is a, c, g or t

<400> SEQUENCE: 121
accnnnnnng gt                                                             12

<210> SEQ ID NO 122
<211> LENGTH: 92
<212> TYPE: PRT

```
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(49)
<223> OTHER INFORMATION: Xaa may be A, S, absent
<220> FEATURE:
<221> NAME/KEY: misc_feature
<222> LOCATION: (50)..(50)
<223> OTHER INFORMATION: Xaa may be T or absent
<220> FEATURE:
<221> NAME/KEY: misc_feature
<222> LOCATION: (72)..(72)
<223> OTHER INFORMATION: Xaa may be P or A
<220> FEATURE:
<221> NAME/KEY: misc_feature
<222> LOCATION: (73)..(73)
<223> OTHER INFORMATION: Xaa may be D or absent
<220> FEATURE:
<221> NAME/KEY: misc_feature
<222> LOCATION: (74)..(74)
<223> OTHER INFORMATION: Xaa may be L or absent

<400> SEQUENCE: 122

Met Ile Pro Arg Gly Leu Ser Glu Ala Lys Pro Ala Thr Pro Glu Ile
1               5                   10                  15

Gln Glu Ile Val Asp Lys Val Lys Pro Gln Leu Glu Lys Thr Asn
            20                  25                  30

Glu Thr Tyr Gly Lys Leu Glu Ala Val Gln Tyr Lys Thr Gln Val Leu
        35                  40                  45

Xaa Xaa Asn Tyr Tyr Ile Lys Val Arg Ala Gly Asp Asn Lys Tyr Met
    50                  55                  60

His Leu Lys Val Phe Asn Gly Xaa Xaa Xaa Val Leu Thr Gly Tyr Gln
65                  70                  75                  80

Val Asp Lys Asn Lys Asp Asp Glu Leu Thr Gly Phe
                85                  90

<210> SEQ ID NO 123
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(49)
<223> OTHER INFORMATION: Xaa may be A or L
<220> FEATURE:
<221> NAME/KEY: misc_feature
<222> LOCATION: (70)..(70)
<223> OTHER INFORMATION: Xaa may be L or E
<220> FEATURE:
<221> NAME/KEY: misc_feature
<222> LOCATION: (71)..(71)
<223> OTHER INFORMATION: Xaa may be D or absent
<220> FEATURE:
<221> NAME/KEY: misc_feature
<222> LOCATION: (72)..(72)
<223> OTHER INFORMATION: Xaa may be L or absent

<400> SEQUENCE: 123

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Lys Glu Thr Gly
            20                  25                  30

Lys Thr Trp Gly Lys Leu Glu Ala Val Glu Tyr Lys Thr Gln Val Asp
        35                  40                  45
```

```
Xaa Asn Tyr Tyr Ile Lys Val Arg Val Asn Gly Lys Tyr Ile His Leu
    50                  55                  60

Lys Val Phe Lys Ser Xaa Xaa Xaa Val Leu Thr Gly Tyr Gln Val Asp
 65              70                  75                  80

Lys Asn Lys Asp Asp Glu Leu Thr Gly Phe
                85                  90

<210> SEQ ID NO 124
<211> LENGTH: 91
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(49)
<223> OTHER INFORMATION: Xaa may be A or T
<220> FEATURE:
<221> NAME/KEY: misc_feature
<222> LOCATION: (71)..(71)
<223> OTHER INFORMATION: Xaa may be L or E
<220> FEATURE:
<221> NAME/KEY: misc_feature
<222> LOCATION: (72)..(72)
<223> OTHER INFORMATION: Xaa may be D or absent
<220> FEATURE:
<221> NAME/KEY: misc_feature
<222> LOCATION: (73)..(73)
<223> OTHER INFORMATION: Xaa may be L or absent

<400> SEQUENCE: 124

Met Ile Pro Gly Gly Leu Ser Glu Ala Lys Pro Ala Thr Pro Glu Ile
 1               5                  10                  15

Gln Glu Ile Val Asp Lys Val Lys Pro Gln Leu Glu Glu Lys Thr Gly
                20                  25                  30

Glu Thr Tyr Gly Lys Leu Glu Ala Val Glu Tyr Lys Thr Gln Val Asp
             35                  40                  45

Xaa Asn Tyr Tyr Ile Lys Val Arg Ala Gly Asn Lys Tyr Ile His
    50                  55                  60

Leu Lys Val Phe Lys Ser Xaa Xaa Xaa Val Leu Thr Gly Tyr Gln Val
 65                  70                  75                  80

Asp Lys Asn Lys Asp Asp Glu Leu Thr Gly Phe
                 85                  90

<210> SEQ ID NO 125
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa may be A, G or L
<220> FEATURE:
<221> NAME/KEY: misc_feature
<222> LOCATION: (5)..(12)
<223> OTHER INFORMATION: Xaa may be GSGGSGGS or absent
<220> FEATURE:
<221> NAME/KEY: NON_CONS
<222> LOCATION: (12)..(13)
<220> FEATURE:
<221> NAME/KEY: misc_feature
<222> LOCATION: (19)..(19)
<223> OTHER INFORMATION: Xaa may be L, G or E
<220> FEATURE:
<221> NAME/KEY: misc_feature
<222> LOCATION: (20)..(20)
<223> OTHER INFORMATION: Xaa may be G, D or absent
```

```
<220> FEATURE:
<221> NAME/KEY: misc_feature
<222> LOCATION: (21)..(21)
<223> OTHER INFORMATION: Xaa may be S, L or absent
<220> FEATURE:
<221> NAME/KEY: misc_feature
<222> LOCATION: (22)..(27)
<223> OTHER INFORMATION: Xaa may be GGSGGS or absent

<400> SEQUENCE: 125

Gln Val Asp Xaa Xaa Xaa Xaa Xaa Xaa Xaa Xaa Asn Tyr Tyr Phe
1               5                   10                  15

Lys Ser Xaa Xaa Xaa Xaa Xaa Xaa Xaa Xaa Xaa Val Leu Thr
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa may be G or absent
<220> FEATURE:
<221> NAME/KEY: misc_feature
<222> LOCATION: (5)..(5)
<223> OTHER INFORMATION: Xaa may be G, L or absent
<220> FEATURE:
<221> NAME/KEY: misc_feature
<222> LOCATION: (6)..(12)
<223> OTHER INFORMATION: Xaa may be SGGSGGS or absent
<220> FEATURE:
<221> NAME/KEY: NON_CONS
<222> LOCATION: (12)..(13)
<220> FEATURE:
<221> NAME/KEY: misc_feature
<222> LOCATION: (19)..(19)
<223> OTHER INFORMATION: Xaa may be G, N or absent
<220> FEATURE:
<221> NAME/KEY: misc_feature
<222> LOCATION: (20)..(20)
<223> OTHER INFORMATION: Xaa may be G, E or absent
<220> FEATURE:
<221> NAME/KEY: misc_feature
<222> LOCATION: (21)..(21)
<223> OTHER INFORMATION: Xaa may be S, D or absent
<220> FEATURE:
<221> NAME/KEY: misc_feature
<222> LOCATION: (22)..(22)
<223> OTHER INFORMATION: Xaa may be G, L or absent
<220> FEATURE:
<221> NAME/KEY: misc_feature
<222> LOCATION: (23)..(27)
<223> OTHER INFORMATION: Xaa may be GSGGS or absent

<400> SEQUENCE: 126

Gln Val Asp Xaa Xaa Xaa Xaa Xaa Xaa Xaa Xaa Asn Tyr Tyr Phe
1               5                   10                  15

Lys Ser Xaa Xaa Xaa Xaa Xaa Xaa Xaa Xaa Xaa Val Leu Thr
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa may be A, G or absent
```

```
<220> FEATURE:
<221> NAME/KEY: misc_feature
<222> LOCATION: (5)..(5)
<223> OTHER INFORMATION: Xaa may be G or absent
<220> FEATURE:
<221> NAME/KEY: misc_feature
<222> LOCATION: (6)..(12)
<223> OTHER INFORMATION: Xaa may be SGGSGGS or absent
<220> FEATURE:
<221> NAME/KEY: NON_CONS
<222> LOCATION: (12)..(13)
<220> FEATURE:
<221> NAME/KEY: misc_feature
<222> LOCATION: (19)..(19)
<223> OTHER INFORMATION: Xaa may be L, G or D
<220> FEATURE:
<221> NAME/KEY: misc_feature
<222> LOCATION: (20)..(20)
<223> OTHER INFORMATION: Xaa may be P, G or L
<220> FEATURE:
<221> NAME/KEY: misc_feature
<222> LOCATION: (21)..(27)
<223> OTHER INFORMATION: Xaa may be SGGSGGS or absent

<400> SEQUENCE: 127

Gln Val Asp Xaa Xaa Xaa Xaa Xaa Xaa Xaa Xaa Asn Tyr Tyr Phe
1               5                   10                  15

Lys Ser Xaa Xaa Xaa Xaa Xaa Xaa Xaa Xaa Val Leu Thr
            20                  25              30
```

SCAFFOLD PROTEINS

RELATED APPLICATIONS

This application is a national stage filing under 35 U.S.C. § 371 of international application number PCT/GB2018/051855, filed Jul. 2, 2018, which claims the benefit of Great Britain application number GB 1710973.7, filed Jul. 7, 2017, each of which is herein incorporated by reference in its entirety.

REFERENCE TO A SEQUENCE LISTING SUBMITTED VIA EFS-WEB

This application contains a Sequence Listing which has been submitted in ASCII format via EFS-Web and is hereby incorporated by reference in its entirety. Said ASCII copy, created on Dec. 17, 2021, is named A122470008US00-SUBSEQ-HJD and is 96,132 bytes in size

BACKGROUND TO THE INVENTION

WO 2009/136182 discloses the mutation of prior art scaffold STM using D48L and G50S, which are disclosed as leading to increased expression in the bacterial system (page 22, lines 12 to 13).

WO 2009/136182 as well as WO 2006/131749 have each previously disclosed mutation of the V48 site of wild-type Stefin A, in particular to V48D which is useful for the abolition of domain-swap dimerisation (WO 2006/131749 page 35, line 25).

Simultaneous mutation of E78A and L80R has been disclosed for scaffold SQT in WO 2009/136182, as well as disclosing simultaneous mutation of L82R and T83S in the SQM scaffold (paragraph bridging pages 22 to 23 of WO 2009/136182). These pairs of simultaneous mutations have been disclosed as exhibiting high expression in E. coli.

WO 2009/136182 discloses modified Stefin A scaffold proteins. In particular, the disclosures in this document focus on the "position 4 mutation", which corresponds to the G4 site of Stefin A or the W4 site of STM. In particular, this document teaches the special advantages of a G4R mutant. This document makes no teachings whatsoever regarding alteration of thermal stability of the scaffold protein. Thermal stability is mentioned in only one paragraph in this document, merely as a one of several properties which might be measured in order to assess a scaffold protein's resistance to being deformed by a target peptide (WO 2009/136182 page 13, first paragraph).

WO 2006/131749 discloses the use of Stefin A as a scaffold protein, and discloses several mutations useful for ensuring biological neutrality of the scaffold. This document discloses a thermostability assay (page 32, first paragraph) and shows data on the heat stability of STM (page 35, lines 9 to 12). Thermostability in this document is solely disclosed as a property which can be measured in order to assess the scaffold protein's resistance to being deformed by the target peptide (see paragraph bridging pages 6 to 7 of WO 2006/131749). There is no teaching whatsoever regarding the variation or modulation of the thermal stability in this document.

WO 2014/125290 discloses scaffold proteins derived from plant cystatins. In particular, this document discloses three preferred synthetic proteins as SEQ ID NO: 1, SEQ ID NO: 2 and SEQ ID NO: 3 of WO 2014/125290. This document discloses measurement of the thermal stability of their preferred scaffold by differential scanning calorimetry (page 48, lines 31 to 32 and FIG. 7a). There is no disclosure anywhere in this document of mutations which might be made to affect the thermal stability. Indeed, the inventors do not comment on any way of affecting the thermal stability of their scaffold proteins. They assert that the thermal stability of their preferred scaffold is "high", but attribute this to the compact nature of their scaffold:

"The compact nature of the scaffold, which is more pronounced than seen in other structures of stefins or cystatins seems likely to contribute to its high thermal stability." (WO 2014/125290 page 53, lines 17 to 19).

There is no teaching in this document as to how thermal stability might be modulated or altered. Moreover, the only discussion of mutations in this document is in connection with prior art mutations, or with the need to use trimer insertions or deletions so as not to produce frame shift mutations. The scientific focus of this document is concentrated on designing a consensus sequence derived from plant cystatin proteins—there is no disclosure of manipulating a sequence to influence thermal stability.

SUMMARY OF THE INVENTION

The inventors studied the Stefin A scaffold protein with aims of improving its properties such as its thermal stability. Building on their insights into the protein structure and function, they designed a range of changes and substitutions to improve those properties. This led to various surprising results including unpredicted anomalies where for example it might have been expected for the protein to behave in a certain manner, but for which the objective findings were at odds with predictions (for example the Q42D/E anomaly discussed in detail below). The result of this substantial research and intellectual effort is a comprehensive teaching of how to alter the thermal stability of the Stefin A protein and how those changes in thermal stability deliver benefits to its use as a scaffold protein.

Thus the invention relates to a polypeptide, such as an AFFIMER® polypeptide, comprising an amino acid sequence having at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 1;

characterised in that said polypeptide comprises one or more mutations relative to SEQ ID NO: 1 selected from the group consisting of:

T51L, T51V, M65V, N32G, A59I, L38A, V20I, A40I, L38V, A12I, A12V, I16L, V20L, Q26E, E29M, T31K, N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K) and (T83D, Q86E).

The invention relates to a polypeptide, such as an AFFIMER® polypeptide, comprising an amino acid sequence having at least 80% identity to SEQ ID NO: 1;

characterised in that said polypeptide comprises one or more mutations relative to SEQ ID NO: 1 selected from the group consisting of:

T51L, T51V, M65V, N32G, A59I, L38A, V20I, A40I, L38V, A12I, A12V, I16L, V20L, Q26E, E29M, T31K,

N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K) and (T83D, Q86E).

The invention relates to a polypeptide, such as an AFFIMER® polypeptide, comprising an amino acid sequence having at least 80% identity to amino acid residues 1 to 98 of SEQ ID NO: 1;

characterised in that said polypeptide comprises one or more mutations relative to SEQ ID NO: 1 selected from the group consisting of:

T51L, T51V, M65V, N32G, A59I, L38A, V20I, A40I, L38V, A12I, A12V, I16L, V20L, Q26E, E29M, T31K, N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K) and (T83D, Q86E).

Suitably said one or more mutations relative to SEQ ID NO: 1 is or are selected from the group consisting of:

T51L, T51V, M65V, N32G, A59I, E29M, T34V, T34R, T45I, T45V, T51F, A59L, L67I, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

preferably wherein said polypeptide has a Tm higher than the Tm of SEQ ID NO: 1.

Suitably said one or more mutations relative to SEQ ID NO: 1 is or are selected from the group consisting of:

L38A, V20I, A40I, L38V, A12I, A12V, I16L, V20L, Q26E, T31K, N32D, N32H, T34D, T34P, A40V, Q42D, V48E, V48G, V48A, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

preferably wherein said polypeptide has a Tm lower than the Tm of SEQ ID NO: 1.

Another aspect of the invention provides a polypeptide, such as an AFFIMER® polypeptide, comprising an amino acid sequence represented in the general formula:

n and m are each, independently, an integer from 3 to 20;

Xaa1 is Gly, Ala, Val, Arg, Lys, Asp, or Glu;
Xaa2 is Gly, Ala, Val, Ser or Thr;
Xaa3 is Arg, Lys, Asn, Gln, Ser, Thr;
Xaa4 is Gly, Ala, Val, Ser or Thr;
Xaa5 is Ala, Val, Ile, Leu, Gly or Pro;
Xaa6 is Gly, Ala, Val, Asp or Glu; and
Xaa7 is Ala, Val, Ile, Leu, Arg or Lys;

and wherein at least one of the following amino acid positions is selected from a recited alternative amino residue $A^{12}$ is Ala, or an alternative amino acid residue selected from Val, Ile or Leu, and preferably from Ile or Val;

$I^{16}$ is Ile or an alternative amino acid residue selected from Val or Leu, preferably Leu;

$V^{20}$ is Val or an alternative amino acid residue selected from Ala, Ile or Leu, preferably Ile or Leu;

$Q^{26}$ is Gln or an alternative amino acid residue selected from Asp or Glu, preferably Glu;

$E^{29}$ is Glu, or an alternative amino acid residue selected from Asp or Met, preferably Met;

$K^{30}$ is Lys, or an alternative amino acid residue selected from Arg, His, Glu or Asp, preferably Glu;

$T^{31}$ is Thr, or an alternative amino acid residue selected from Ser, Arg or Lys, preferably Lys;

$N^{32}$ is Asn, or an alternative amino acid residue selected from Gly, Asp, Glu or His, preferably Gly, Asp or His;

$E^{33}$ is Glu, or an alternative amino acid residue selected from Arg, His, Lys or Asp, preferably Lys;

$T^{34}$ is Thr, or an alternative amino acid residue selected from Ser, Ala, Val, Ile, Leu, Arg, Lys, Asp, Glu or Pro, preferably Val, Arg, Asp or Pro;

$L^{38}$ is Leu, or an alternative amino acid residue selected from Gly, Ala or Val, preferably Ala or Val;

$A^{40}$ is Ala, or an alternative amino acid residue selected from Gly, Val, Leu or Ile, preferably Ile or Val;

$Q^{42}$ is Gln, or an alternative amino acid residue selected from Asp, Glu, or Asn, preferably Asp;

$T^{45}$ is Thr, or an alternative amino acid residue selected from Ser, Ala, Val, Ile or Leu, preferably Ile or Val;

$V^{48}$ is Val, or an alternative amino acid residue selected from Gly, Ala, Ile, Leu, Glu or Asp, preferably Gly, Ala or Glu;

$T^{51}$ is Thr, or an alternative amino acid residue selected from Gly, Ala, Val, Ile, Leu, Ser or Phe, preferably Phe, Ala, Val or Leu;

$Y^{54}$ is Tyr, or an alternative amino acid residue selected from Asp or Glu, preferably Asp;

$A^{59}$ is Ala, or an alternative amino acid residue selected from Gly, Val, Ile or Leu, preferably Ile, Leu or Val;

$G^{60}$ is Gly, or an alternative amino acid residue selected from Asn, Gln, Gly or Pro, preferably Asn or Pro;

(SEQ ID NO: 107)
MIP-Xaa1-GLSEAKPA$^{12}$TPEI$^{16}$QEIV$^{20}$DKVKPQ$^{26}$LEE$^{29}$K$^{30}$T$^{31}$N$^{32}$E$^{33}$T$^{34}$YGKL$^{38}$EA$^{40}$VQ$^{42}$

YKT$^{45}$QVV$^{48}$A-(Xaa)n-Xaa2-T$^{51}$NYY$^{54}$IKVRA$^{59}$G$^{60}$D$^{61}$N$^{62}$KYM$^{65}$HL$^{67}$KVF-Xaa3-Xaa4-

Xaa5-(Xaa)m-Xaa6-D-Xaa7-VLT$^{83}$GYQ$^{86}$VDKNKDDELTGF wherein
Xaa, individually for each occurrence, is an amino acid residue;

$D^{61}$ is Asp, or an alternative amino acid residue selected from ΔD61 (absent), Gly, Pro, Glu, Asn or Gln, preferably ΔD61 (absent), Gly, Pro or Asn;

$N^{62}$ is Asn, or an alternative amino acid residue selected from Gln, Lys, Arg, His, Gly or Pro, preferably Lys, Pro or Gly;

$M^{65}$ is Met, or an alternative amino acid residue selected from Ala, Val, Ile, Leu, preferably Val;

$L^{67}$ is Leu, or an alternative amino acid residue selected from Ala, Val or Ile, preferably Ile;

$T^{83}$ is Thr, or an alternative amino acid residue selected from Ser, Asp or Glu, preferably Asp; and $Q^{86}$ is Gln, or an alternative amino acid residue selected from Asn, Glu or Asp, preferably Glu.

In one aspect, the invention relates to a polypeptide as described above,
wherein said polypeptide further comprises at least one heterologous peptide insertion,
wherein said heterologous peptide insertion comprises a heterologous peptide inserted at one of the following positions relative to SEQ ID NO: 1:
a) 47-<heterologous peptide>-55
b) 46-<heterologous peptide>-54
c) 46-<heterologous peptide>-50
d) 48-<heterologous peptide>-50
e) 49-<heterologous peptide>-51
f) 50-<heterologous peptide>-52
g) 66-<heterologous peptide>-85
h) 67-<heterologous peptide>-84
i) 70-<heterologous peptide>-74
j) 72-<heterologous peptide>-74
k) 71-<heterologous peptide>-73
l) 72-<heterologous peptide>-81
m) 73-<heterologous peptide>-80
n) 79-<heterologous peptide>-81
o) 80-<heterologous peptide>-81
p) 82-<heterologous peptide>-83
q) 72-<heterologous peptide>-77
r) 73-<heterologous peptide>-78
s) 74-<heterologous peptide>-79
t) 4-<heterologous peptide>-5

Suitably said polypeptide comprises two heterologous peptide insertions, a first heterologous peptide insertion at any of positions (a) to (f), and a second heterologous peptide insertion at any of positions (g) to (s).

Suitably said polypeptide comprises two heterologous peptide insertions, a first heterologous peptide insertion at any of positions (a) to (f), and a second heterologous peptide insertion at position (t).

Suitably said polypeptide comprises two heterologous peptide insertions, a first heterologous peptide insertion at any of positions (g) to (s), and a second heterologous peptide insertion at position (t).

Suitably said polypeptide comprises three heterologous peptide insertions, a first heterologous peptide insertion at any of positions (a) to (f), and a second heterologous peptide insertion at any of positions (g) to (s), and a third heterologous peptide insertion at position (t).

In one aspect, the invention relates to a polypeptide, such as an AFFIMER® polypeptide, comprising an amino acid sequence having at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 1;
wherein said polypeptide comprises at least one heterologous peptide insertion;
characterised in that said polypeptide comprises one or more mutations relative to SEQ ID NO: 1 selected from the group consisting of:
M65I, T51I, T51L, T51V, M65V, A59V, N32G, A59I, L38A, V20A, V20I, A40I, L38V, G50S, L38F, A12I, A12V, I16L, V20L, Q26E, E29M, T31K, N32D, N32H, T34V, T34R, T34K, T34D, T34P, A40V, Q42E, Q42D, T45I, T45V, V48E, V48D, V48G, V48A, V48L, T51F, T51A, A59L, K63R, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);
wherein said heterologous peptide insertion comprises a heterologous peptide inserted at one of the following positions relative to SEQ ID NO: 1:
d) 48-<heterologous peptide>-50,
e) 49-<heterologous peptide>-51,
f) 50-<heterologous peptide>-52,
q) 72-<heterologous peptide>-77,
r) 73-<heterologous peptide>-78; or
s) 74-<heterologous peptide>-79.

In one aspect, the invention relates to a polypeptide, such as an AFFIMER® polypeptide, comprising an amino acid sequence having at least 80% identity to SEQ ID NO: 1;
wherein said polypeptide comprises at least one heterologous peptide insertion;
characterised in that said polypeptide comprises one or more mutations relative to SEQ ID NO: 1 selected from the group consisting of:
M65I, T51I, T51L, T51V, M65V, A59V, N32G, A59I, L38A, V20A, V20I, A40I, L38V, G50S, L38F, A12I, A12V, I16L, V20L, Q26E, E29M, T31K, N32D, N32H, T34V, T34R, T34K, T34D, T34P, A40V, Q42E, Q42D, T45I, T45V, V48E, V48D, V48G, V48A, V48L, T51F, T51A, A59L, K63R, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);
wherein said heterologous peptide insertion comprises a heterologous peptide inserted at one of the following positions relative to SEQ ID NO: 1:
d) 48-<heterologous peptide>-50,
e) 49-<heterologous peptide>-51,
f) 50-<heterologous peptide>-52,
q) 72-<heterologous peptide>-77,
r) 73-<heterologous peptide>-78; or
s) 74-<heterologous peptide>-79.

In one aspect, the invention relates to a polypeptide, such as an AFFIMER® polypeptide, comprising an amino acid sequence having at least 80% identity to amino acid residues 1 to 98 of SEQ ID NO: 1;
wherein said polypeptide comprises at least one heterologous peptide insertion;
characterised in that said polypeptide comprises one or more mutations relative to SEQ ID NO: 1 selected from the group consisting of:

M65I, T51I, T51L, T51V, M65V, A59V, N32G, A59I, L38A, V20A, V20I, A40I, L38V, G50S, L38F, A12I, A12V, I16L, V20L, Q26E, E29M, T31K, N32D, N32H, T34V, T34R, T34K, T34D, T34P, A40V, Q42E, Q42D, T45I, T45V, V48E, V48D, V48G, V48A, V48L, T51F, T51A, A59L, K63R, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);

wherein said heterologous peptide insertion comprises a heterologous peptide inserted at one of the following positions relative to SEQ ID NO: 1:
d) 48-<heterologous peptide>-50,
e) 49-<heterologous peptide>-51,
f) 50-<heterologous peptide>-52,
q) 72-<heterologous peptide>-77,
r) 73-<heterologous peptide>-78; or
s) 74-<heterologous peptide>-79.

Suitably said polypeptide comprises two heterologous peptide insertions, a first heterologous peptide insertion at any of positions (d) to (f), and a second heterologous peptide insertion at any of positions (q) to (s).

Suitably said one or more mutations relative to SEQ ID NO: 1 is or are selected from the group consisting of:
M65I, T51I, T51L, T51V, M65V, A59V, N32G, A59I, E29M, T34V, T34R, T34K, Q42E, T45I, T45V, T51F, A59L, K63R, L67I, N90T, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

preferably wherein said polypeptide has a Tm higher than the Tm of SEQ ID NO: 1.

Suitably said one or more mutations relative to SEQ ID NO: 1 is or are selected from the group consisting of:
L38A, V20A, V20I, A40I, L38V, G50S, L38F, A12I, A12V, I16L, V20L, Q26E, T31K, N32D, N32H, T34D, T34P, A40V, Q42D, V48E, V48D, V48G, V48A, V48L, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

preferably wherein said polypeptide has a Tm lower than the Tm of SEQ ID NO: 1.

Suitably said one or more mutations relative to SEQ ID NO: 1 is or are selected from the group consisting of:
T51L, T51V, M65V, N32G, A59I, L38A, V20I, A40I, L38V, A12I, A12V, I16L, V20L, Q26E, E29M, T31K, N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K) and (T83D, Q86E).

Suitably said one or more mutations relative to SEQ ID NO: 1 is or are selected from the group consisting of:
T51L, T51V, M65V, N32G, A59I, E29M, T34V, T34R, T45I, T45V, T51F, A59L, L67I, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

preferably wherein said polypeptide has a Tm higher than the Tm of SEQ ID NO: 1.

Suitably said one or more mutations relative to SEQ ID NO: 1 is or are selected from the group consisting of:
L38A, V20I, A40I, L38V, A12I, A12V, I16L, V20L, Q26E, T31K, N32D, N32H, T34D, T34P, A40V, Q42D, V48E, V48G, V48A, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

preferably wherein said polypeptide has a Tm lower than the Tm of SEQ ID NO: 1.

In one aspect, the invention relates to a polypeptide as described above wherein said polypeptide has a Tm higher than the Tm of SEQ ID NO: 1.

In one aspect, the invention relates to a polypeptide as described above wherein said polypeptide has a Tm lower than the Tm of SEQ ID NO: 1.

Suitably said polypeptide further comprises one or more mutations relative to SEQ ID NO: 1 selected from the group consisting of: G4R, G4W, V48D, V48E, G50 S, Y35W, Y43W, Y53W, Y54W, Y64W, F70W, Y85W, F98W, (K71N S72G L73P), or (E78A L80R).

Suitably the polypeptide as described above comprises five or fewer mutations relative to SEQ ID NO: 1.

Suitably said five or fewer mutations are selected from the group consisting of Y35W, N32G, V48D, M65I, Q42E and T51L.

In one aspect, the invention relates to a polypeptide as described above wherein said five or fewer mutations are selected from the group consisting of N32G, V48D, M65I, Q42E and T51L.

In one embodiment, the invention relates to a polypeptide as described above having each of the mutations in one of the following groups:
i) N32G V48D
ii) N32G V48D M65I
iii) N32G V48D M65I T51L
iv) N32G V48D M65I Q42E
v) N32G V48D M65I Q42E T51L.

In one embodiment, the invention relates to a polypeptide as described above having each of the mutations in one of the following groups:
i) N32G V48D
ii) N32G V48D M65I
iii) N32G V48D M65I T51L
iv) N32G V48D M65I Q42E
v) N32G V48D M65I Q42E T51L, and having no further mutations relative to SEQ ID NO: 1.

In one embodiment, the invention relates to a polypeptide as described above having each of the mutations iv) N32G, V48D, M65I and Q42E.

In one embodiment, the invention relates to a polypeptide as described above having each of the mutations iv) N32G, V48D, M65I and Q42E, and having no further mutations relative to SEQ ID NO: 1.

In one embodiment, the invention relates to a polypeptide as described above having each of the mutations in one of the following groups:
a) Y35W N32G V48D M65I Q42E T51L (A59V ΔD61) (E29K K30E E33K)
b) Y35W N32G V48D M65I Q42E T51L (A59V G60N ΔD61 N62G) (E29K K30E E33K).

In one embodiment, the invention relates to a polypeptide as described above having each of the mutations in one of the following groups:
a) Y35W N32G V48D M65I Q42E T51L (A59V ΔD61) (E29K K30E E33K)
b) Y35W N32G V48D M65I Q42E T51L (A59V G60N ΔD61 N62G) (E29K K30E E33K), and having no further mutations relative to SEQ ID NO: 1.

In one embodiment, the invention relates to a polypeptide as described above having each of the mutations b) Y35W N32G V48D M65I Q42E T51L (A59V G60N ΔD61 N62G) (E29K K30E E33K).

In one embodiment, the invention relates to a polypeptide as described above having each of the mutations b) Y35W N32G V48D M65I Q42E T51L (A59V G60N ΔD61 N62G) (E29K K30E E33K), and having no further mutations relative to SEQ ID NO: 1.

Suitably said heterologous peptide is 6 to 36 amino acids in length.

In one aspect, the invention relates to a fusion protein comprising:
a polypeptide as described above; and
one or more additional amino acid sequences selected from the group consisting of: secretion signal sequences, peptide linker sequences, affinity tags, transmembrane domains, cell surface retention sequence, substrate recognition sequences for post-translational modifications, multimerization domains to create multimeric structures of the protein aggregating through protein-protein interactions, half-life extending polypeptide moieties, polypeptide sequences for altering tissue localization and antigen binding site of an antibody, one or more additional polypeptides as described above binding to the same or different targets, and one or more additional AFFIMER® polypeptide sequences binding to the same or different targets.

Suitably said fusion protein comprises one or more half-life extending polypeptide moieties selected from the group consisting of an Fc domain or portion thereof, an albumin protein or portion thereof, an albumin-binding polypeptide moiety, transferrin or portion thereof, a transferrin-binding polypeptide moiety, fibronectin or portion thereof, or a fibronectin-binding polypeptide moiety.

Suitably the Fc domain or a portion thereof retains FcN binding.

Suitably the Fc domain or a portion thereof is from IgA, IgD, IgE, IgG, and IgM or a subclass (isotype) thereof such as IgG1, IgG2, IgG3, IgG4, IgA1 or IgA2.

Suitably the Fc domain or a portion thereof retains effector function selected from C1q binding, complement dependent cytotoxicity (CDC), antibody-dependent cell-mediated cytotoxicity (ADCC); phagocytosis; down regulation of B cell receptor, or a combination thereof.

Suitably the half-life extending polypeptide moiety increases the serum half-life of the protein by at least 5-fold relative to its absence from the protein.

Suitably the polypeptide is an AFFIMER® or an AFFIMER® polypeptide. AFFIMERs®/AFFIMER® polypeptides are described in more detail below.

In one aspect, the invention relates to a nucleic acid comprising nucleotide sequence encoding a polypeptide as described above.

In one aspect, the invention relates to a vector comprising a nucleic acid as described above.

In one aspect, the invention relates to a library comprising a population of polypeptides as described above, wherein at least two individual polypeptides within said population comprise different heterologous peptide insertions.

In one aspect, the invention relates to a library comprising a population of nucleic acids, said nucleic acids comprising nucleotide sequences encoding a population of polypeptides as described above. Suitably each nucleic acid encodes a single polypeptide as described above.

In one aspect, the invention relates to a host cell comprising a polypeptide as described above, a nucleic acid as described above, or a library as described above.

In one aspect, the invention relates to a polypeptide as described above for use in medicine.

In one aspect, the invention relates to a method for identifying a peptide capable of binding a structure of interest, said method comprising:
(i) providing a polypeptide as described above comprising a heterologous peptide insertion;
(ii) contacting said polypeptide with said structure of interest; and
(iii) monitoring the association between the polypeptide and the structure of interest;
wherein association of the polypeptide with the structure of interest identifies the peptide as a candidate peptide capable of binding said structure.

In one aspect, the invention relates to use of a polypeptide as described above as a scaffold protein.

More suitably the invention relates to a polypeptide as described above wherein said heterologous peptide insertion comprises a heterologous peptide inserted at one of the following positions relative to SEQ ID NO: 1:
d) 48-<heterologous peptide>-50
e) 49-<heterologous peptide>-51
f) 50-<heterologous peptide>-52
q) 72-<heterologous peptide>-77
r) 73-<heterologous peptide>-78
s) 74-<heterologous peptide>-79
t) 4-<heterologous peptide>-5.

More suitably said polypeptide comprises two heterologous peptide insertions, a first heterologous peptide insertion at any of positions (d) to (f), and a second heterologous peptide insertion at any of positions (q) to (s).

More suitably said polypeptide comprises two heterologous peptide insertions, a first heterologous peptide insertion at any of positions (d) to (f), and a second heterologous peptide insertion at position (t).

More suitably said polypeptide comprises two heterologous peptide insertions, a first heterologous peptide insertion at any of positions (q) to (s), and a second heterologous peptide insertion at position (t).

More suitably said polypeptide comprises three heterologous peptide insertions, a first heterologous peptide insertion at any of positions (d) to (f), and a second heterologous peptide insertion at any of positions (q) to (s), and a third heterologous peptide insertion at position (t).

Suitably the polypeptide of the invention comprises amino acid sequence corresponding to amino acids 1 to 98 of SEQ ID NO: 1, comprising mutation(s) as described. A small number of mutations described are deletions e.g. the amino acid corresponding to amino acid 61 of SEQ ID NO: 1 may be mutated by substitution or by deletion. If mutated by deletion, the final resulting polypeptide may comprise only 97 amino acids corresponding to SEQ ID NO: 1—in other words when D61 is deleted then ΔD61 corresponds to D61 of SEQ ID NO: 1—the skilled person will interpret such feature accordingly. Most suitably mutations are substitutions.

In a broad aspect, also disclosed is a polypeptide, such as an AFFIMER® polypeptide, comprising an amino acid sequence corresponding to amino acids 1 to 98 of SEQ ID NO: 1, said polypeptide comprising a mutation relative to SEQ ID NO: 1 selected from the group consisting of
  M65I, T51I, T51L, T51V, M65V, A59V, N32G, A59I, L38A, V20A, V20I, A40I, L38V, G50S, L38F, A12I, A12V, I16L, V20L, Q26E, E29M, T31K, N32D, N32H, T34V, T34R, T34K, T34D, T34P, A40V, Q42E, Q42D, T45I, T45V, V48E, V48D, V48G, V48A, V48L, T51F, T51A, A59L, K63R, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);
and further comprising a heterologous peptide insertion. Suitably said heterologous peptide insertion comprises a heterologous peptide inserted at one of the following positions relative to SEQ ID NO: 1:
  d) 48-<heterologous peptide>-50,
  e) 49-<heterologous peptide>-51,
  f) 50-<heterologous peptide>-52,
  q) 72-<heterologous peptide>-77,
  r) 73-<heterologous peptide>-78, or
  s) 74-<heterologous peptide>-79.

An AFFIMER® is an engineered non-antibody binding protein (i.e. a polypeptide affinity reagent). AFFIMER® is a registered trade mark.

As is known in the art, aptamers and AFFIMER® reagents are not the same. AFFIMER® technology has been engineered to overcome many of the problems associated with aptamers or with antibodies and possesses a number of benefits. For example, sensitivity to the assay environment has been improved because AFFIMER® scaffolds are resistant to a wide pH range, making them suitable for a wide range of assay conditions. AFFIMER® molecules are also not sensitive to EDTA (a problem for aptamers that require Mg++ for folding and function). An aptamer is not constrained, whereas an AFFIMER® protein constrains the displayed heterologous peptide.

Suitably the AFFIMER® reagents such as AFFIMER® scaffolds/polypeptides described herein are based on or derived from the human Stefin A protein. This is described in more detail below.

Suitably the polypeptide is a Stefin A polypeptide.

In one aspect the invention relates to a Stefin A polypeptide having a combination of one or more mutations from a set of defined mutations which all share the common technical feature of each being demonstrated to affect the stability such as thermal stability (Tm) of the polypeptide AND a heterologous peptide insertion. To the best of the inventors' knowledge and belief at the filing date these combinations are novel.

A small number of the amino acids at particular positions taught by the inventors may have occurred in the art before (e.g. as a naturally occurring residue in a distantly related Stefin A homologue i.e. without a heterologous peptide insertion and therefore not occurring in the above described novel combination); or in combination with a heterologous peptide insertion e.g. in prior art scaffold STM. Examples of such mutations (substitutions) which may have occurred in the art before include:
  V20A, T34K, L38F, Q42E, V48D, G50S, T51I, A59V, K63R, M65I, and N90T. In one embodiment suitably the polypeptide of the invention does not comprise a mutation selected from this group. Suitably when the polypeptide of the invention has a mutation selected from this group, it also has at least one heterologous peptide insertion, most suitably at one or more of the following positions relative to SEQ ID NO: 1:
  d) 48-<heterologous peptide>-50,
  e) 49-<heterologous peptide>-51,
  f) 50-<heterologous peptide>-52,
  q) 72-<heterologous peptide>-77,
  r) 73-<heterologous peptide>-78, or
  s) 74-<heterologous peptide>-79.

Suitably when the polypeptide of the invention has a mutation selected from this group, it also has at least one further mutation selected from Table A.

TABLE A

| novel mutations for modulating thermal stability of Stefin A polypeptides |
|---|
| A12I, A12V, I16L, V20I, V20L, Q26E, E29M, T31K |
| N32G, N32D, N32H, T34V, T34R, T34D, T34P, L38A |
| L38V, A40I, A40V, Q42D, T45I, T45V, V48E, V48G |
| V48A, T51F, T51V, T51L, T51A, A59L, A59I, M65V |
| L67I |
| (V20I, L38A), (V20L, L38A), (V20I, L38V), (V20L, L38V) |
| (E29K, K30E, E33K), (Y54D, T83D, Q86E) |
| (A59L, G60N, D61G, N62K), (A59V, D61N, N62K) |
| (G60N, D61G, N62K), (G60N, ΔD61, N62G) |
| ΔD61, (A59L, G60N, ΔD61, N62G) |
| (A59V, G60N, D61G, N62K), (A59I, G60N, D61G, N62K) |
| (A59I, G60N, ΔD61, N62G), (A59V, G60N, ΔD61, N62G) |
| (A59V, ΔD61), (G60P, ΔD61, N62P) |
| (G60P, D61P, N62K), (G60P, ΔD61, N62G) |
| (G60P, D61G, N62K), (D61N, N62K) and |
| (T83D, Q86E) |

With reference to increasing the Tm of the Stefin A polypeptide, examples of such mutations (substitutions) which may have occurred in the art before include:
  T34K, Q42E, G50S, T51I, A59V, K63R, M65I, and N90T. In one embodiment suitably the polypeptide of the invention does not comprise a mutation selected from this group. Suitably when the polypeptide of the invention has a mutation selected from this group, it also has at least one heterologous peptide insertion, most suitably at one or more of the following positions relative to SEQ ID NO: 1:
  d) 48-<heterologous peptide>-50,
  e) 49-<heterologous peptide>-51,
  f) 50-<heterologous peptide>-52,
  q) 72-<heterologous peptide>-77,
  r) 73-<heterologous peptide>-78, or
  s) 74-<heterologous peptide>-79.

Suitably when the polypeptide of the invention has a mutation selected from this group, it also has at least one further mutation selected from Table B.

TABLE B

| novel mutations for increasing thermal stability of Stefin A polypeptides |
|---|
| E29M, N32G, T34V, T34R, T451, T45V, T51F, T51V T51L, A59L, A59I, M65V, L67I (E29K, K30E, E33K), (A59L, G60N, D61G, N62K) (A59V, D61N, N62K), (G60N, D61G, N62K) (G60N, ΔD61, N62G), ΔD61 (A59L, G60N, ΔD61, N62G), (A59V, G60N, D61G, N62K) (A59I, G60N, D61G, N62K), (A59I, G60N, ΔD61, N62G) (A59V, G60N, ΔD61, N62G), and (A59V, ΔD61) |

With reference to decreasing the Tm of the Stefin A polypeptide, examples of such mutations (substitutions) which may have occurred in the art before include: V20A, L38F, and V48D. In one embodiment suitably the polypeptide of the invention does not comprise a mutation selected from this group. Suitably when the polypeptide of the invention has a mutation selected from this group, it also has at least one heterologous peptide insertion, most suitably at one or more of the following positions relative to SEQ ID NO: 1:

d) 48-<heterologous peptide>-50,
e) 49-<heterologous peptide>-51,
f) 50-<heterologous peptide>-52,
q) 72-<heterologous peptide>-77,
r) 73-<heterologous peptide>-78, or
s) 74-<heterologous peptide>-79.

Suitably when the polypeptide of the invention has a mutation selected from this group, it also has at least one further mutation selected from Table C.

TABLE C

| novel mutations for decreasing thermal stability of Stefin A polypeptides |
|---|
| A12I, A12V, I16L, V20I, V20L, Q26E, T31K, N32D N32H, T34D, T34P, L38A, L38V, A40I, A40V, Q42D V48E, V48G, V48A, T51A (V20I, L38A), (V20L, L38A), (V20I, L38V), (V20L, L38V) (Y54D, T83D, Q86E), (G60P, ΔD61, N62P) (G60P, D61P, N62K), (G60P, ΔD61, N62G) (G60P, D61G, N62K), (D61N, N62K) and (T83D, Q86E) |

Suitably the polypeptide comprises amino acid sequence corresponding to amino acids 1 to 98 of SEQ ID NO: 1, comprising mutation(s) as described above.

Thus in one aspect the invention relates to a polypeptide, such as an AFFIMER® polypeptide, comprising an amino acid sequence corresponding to amino acids 1 to 98 of SEQ ID NO: 1, wherein said amino acid sequence has at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 1;

characterised in that said polypeptide comprises one or more mutations relative to SEQ ID NO: 1 selected from a group disclosed above.

Suitably the polypeptide comprises at least 80 amino acids; suitably at least 81 amino acids, suitably at least 82 amino acids, suitably at least 83 amino acids, suitably at least 84 amino acids, suitably at least 85 amino acids, suitably at least 86 amino acids, suitably at least 87 amino acids, suitably at least 88 amino acids, suitably at least 89 amino acids, suitably at least 90 amino acids, suitably at least 91 amino acids, suitably at least 92 amino acids, suitably at least 93 amino acids, suitably at least 94 amino acids, suitably at least 95 amino acids, suitably at least 96 amino acids; more suitably at least 97 amino acids; most suitably 98 amino acids (excluding any heterologous peptide insertions). Suitably the polypeptide comprises amino acid sequence corresponding to full length hSteA. Suitably full length hSteA means 98aa, most suitably corresponding to those shown in SEQ ID NO: 1.

Scaffold

As is well known in the art, the term 'scaffold' refers to a protein which can present target peptide(s) to solvent without its own structure being deformed by the target peptide.

Regarding the presentation of peptide to solvent, this can be tested using immunoprecipitation experiments. For example, an indication that a peptide is being presented to solvent may be obtained by its availability to an antibody capable of recognising it. Thus, in order to test the ability of a scaffold protein to present a peptide to solvent, the scaffold comprising the peptide would be expressed and an antibody recognising the peptide would be used to try to immunoprecipitate the scaffold-peptide fusion. If this protein can be immunoprecipitated or captured on the antibody, this shows that the peptide was presented to solvent as is required by a scaffold protein. Another, or an alternative, indication that a peptide is being presented to solvent may be obtained by phosphorylation studies. By incorporating a phosphate acceptor site into the target peptide, and then contacting the scaffold-peptide fusion with the cognate kinase in conditions permissive of phosphorylation, then the presentation of the peptide to solvent can be verified. Phosphorylation of the peptide indicates correct presentation to solvent.

A scaffold protein must be able to accept a peptide insert i.e. a heterologous peptide insertion ('target' peptide) as taught herein. Preferably the peptide insert is 36 amino acids or fewer, preferably 20 amino acids or fewer. Preferably the peptide insert is 12 amino acids or fewer.

Concerning a scaffold protein's resistance to being deformed by the target peptide which it bears, this can be tested using techniques such as circular dichroism. Specifically, a circular dichroism analysis of a scaffold protein without target peptide inserted into it should be substantially the same as the circular dichroism characteristics of the same scaffold protein when bearing a target peptide. This provides a demonstration that the presence of the target peptide in the scaffold protein has not compromised or deformed the structure of the scaffold protein bearing it.

For example, the near UV CD spectra report on the environment of the aromatic side chains. Peaks, positive or negative, in a near UV CD spectrum indicate that the environment around the aromatic residues is fixed. This is interpreted as a protein having a fixed tertiary structure. Incorporating heterologous peptides into insertion site(s) as taught herein suitably results in near UV CD spectra with the same shape as the "empty" scaffolds, indicating that the addition of heterologous peptides has not disrupted the tertiary structure of the scaffold proteins. As will be realised by the person skilled in the art, the spectra may have different magnitudes, e.g. the peaks may be higher and/or the troughs may be lower, but retention of the same shaped spectra is the important factor.

For example, the far UV CD spectra report on gross secondary structure. The alpha-helix, beta-strand and random coil all have distinctly different far UV CD spectra. Incorporating heterologous peptides into insertion site(s) as taught herein suitably results in far UV CD spectra with the same shape as the "empty" scaffolds, indicating that the addition of heterologous peptides has not disrupted the gross secondary structure of the scaffold proteins. As will be realised by the person skilled in the art, the spectra may have different magnitudes, e.g. the peaks may be higher and/or the troughs may be lower, but retention of the same shaped spectra is the important factor.

Suitably a scaffold protein constrains the target peptide. The presence of a constraint effect in a scaffold protein can be demonstrated by comparing the affinity of an entity binding the target peptide when the target peptide is in the scaffold protein with the affinity when the peptide is not in the scaffold protein. A difference in these two affinities indicates that the scaffold protein is constraining the peptide to assume a particular three dimensional conformation. Suitably a scaffold protein constrains a peptide so that it demonstrates an increased binding affinity when present in the context of the scaffold protein. In other words, suitably the scaffold protein decreases the entropic cost of binding and so increases the measured affinity when compared with binding of a free peptide.

A scaffold protein is suitably biologically neutral. By 'biologically neutral' it is meant that known interactions with other proteins have been abolished. Furthermore, any signalling abilities possessed by the protein are preferably removed. Mutations for biological neutrality of Stefin A based scaffolds are known, and preferred examples are discussed herein. Combination of such mutations for biological neutrality with the mutations taught herein for modulation of thermal stability is expressly contemplated.

Suitably the polypeptide of the invention is a scaffold protein.

In another aspect, the invention relates to use of a polypeptide as disclosed herein as a scaffold protein.

Thermal Stability

A key part of the invention is the modulation of thermal stability. Without knowledge of the invention, in principle mutating any residue in the polypeptide of the invention might lead to a change in thermal stability. However, the inventors studied the protein in detail at all levels of its structure and designed particular changes in the protein in order to influence thermal stability. To their surprise, not all of the mutations which the inventors designed produced the expected effects. Thus, there is a large degree of unpredictability associated with making mutations to influence thermal stability in a scaffold protein. As a result of significant intellectual effort and experimentation, the inventors have arrived at a very detailed teaching presented herein regarding which residues may be used to influence thermal stability.

Also included for comparison purposes are various data surprisingly showing residues with no effect or neutral effect on stability such as Tm—those data further illustrate how the invention could not have been arrived at by prediction from the art.

Thermal stability may be assessed by any suitable means known in the art. Most suitably thermal stability is suitably read out or assessed by measuring the Tm. Thus, suitably references to 'thermal stability' may be understood as references to 'Tm'. Unless otherwise apparent from the context, 'improved' thermal stability/Tm means increased thermal stability/Tm. 'Increased' is a relative term—unless otherwise apparent from the context, 'increased' means 'increased relative to wild type Stefin A'. In other words, relative to Stefin A having the wild type amino acid residue at the stated position; most suitably relative to wild type Stefin A having the amino acid sequence of SEQ ID NO: 1.

It should be noted that the majority of the measurements presented herein are relative to hSteA Y35W; the same relative difference to hSteA is a scientific assumption.

In addition to providing an assessment of thermal stability, the Tm is a good proxy for assessing how easy the scaffold protein is to make—scaffolds with higher Tm's are advantageously easier to make. Moreover, an increase in the Tm can show that the protein is "stiffer" and so better suited to accepting of heterologous peptide insertions. Moreover, the Tm is a good indication of stability, for example the shelf life of a protein may be advantageously increased when it is more stable i.e. having a higher Tm. Moreover, increased Tm may provide further advantage(s) such as improved performance in downstream formatting, long-term stability, and/or flexibility in assay design.

Tm of proteins is also known as the denaturation midpoint, and is defined as the temperature at which both the folded and unfolded states are present in equal amounts or populations at equilibrium. Tm is determined in this manner assuming a two state protein folding.

Tm values given herein refer to the 'empty' polypeptide of the invention/scaffold protein i.e. scaffold protein without heterologous peptide insertions (unless otherwise indicated). Insertion of heterologous sequence(s) can, and often does, reduce the thermal stability such as Tm and therefore the most meaningful value is obtained when empty scaffold proteins are compared.

Melting temperature is a particularly useful indicator of protein stability. As used herein, melting temperature means the apparent mid-point of a thermal unfolding transition. The relative proportions of folded and unfolded proteins can be determined by any technique known to the skilled person, including differential scanning calorimetry, UV difference spectroscopy, fluorescence, circular dichroism (CD), or NMR (for example see Pace, C. Nick, and J. Martin Scholtz. "Measuring the conformational stability of a protein." Protein structure: A practical approach 2 (1997): 299-321).

Measurement Techniques

It is possible to use alternative measurement techniques to assess the same property such as Tm. Preferred techniques for measuring Tm include Optim (most suitably Optim 2) and/or differential scanning calorimetry (DSC). Most suitably assessment of thermal stability such as Tm is carried out by differential scanning calorimetry (DSC) using any commercially available instrument, and/or by using an 'Optim 2' High Throughput Protein Stability Instrument (also known as UNit) available from Avacta Analytical (Unit 20, Ash Way Thorp Arch Estate, Wetherby L S23 7FA, UK) and/or from Unchained Labs (6870 Koll Center Parkway, Pleasanton, CA 94566, USA).

In more detail, it will be appreciated by any scientist/person skilled in the art that it is not likely to produce the same absolute value when a property is measured by two different techniques. Having said that, Tm measured by Optim and measured by DSC produces very similar, but sometimes not precisely identical, values. Tm's measured by DSC and Tm's measured by Optim produce the same indication of changes. Therefore, if the Tm of a polypeptide is measured by Optim and the Tm of the same polypeptide is measured by DSC, they may not give precisely the same absolute values, but they will both give the same indication of change e.g. +10° C. Moreover, the ranking of individual polypeptides is the same using either technique. Thus, it must be borne in mind that, in accordance with normal scientific practice, the absolute values quoted may vary slightly depending on the technique used to make the measurement. Unless otherwise stated, values herein are suitably determined by Optim. Advantages of Optim include that it is quick, and that it is reliable using very little input material. One limitation of Optim is that measurements are most reliable when the Tm is below 95° C., suitably below 92° C., most suitably below 90° C. An advantage of DSC is that it works very well at higher temperatures, and may be slightly better for avoiding interference effects. Thus, if it is desired to attempt to determine absolute Tm's, then DSC would be the measurement technique of choice. However, as a practical matter when measuring "deltas" or differences between individual polypeptides then Optim is a very convenient and very reliable and robust technique to use. Unless otherwise stated, values provided herein are determined using Optim. In all circumstances, it is good scientific practice to compare measurements between individual polypeptides which were determined using the same measurement technique. Suitably the Tm is Tm where determined by DSC or Optim. Most suitably, Tm is Tm when determined by Optim.

Most suitably the stability such as Tm is assessed for wild type Stefin A in the same manner as stability such as Tm is assessed for the polypeptides/scaffold proteins bearing mutations as disclosed herein. For reference purposes, the Tm of wild type Stefin A when assessed by DSC (r/t) is 89.0° C.

For comparison purposes, the prior art SQT scaffold protein has a Tm of 64.6° C. when assessed by the same techniques.

Measurement techniques are discussed in more detail below.

Similarly, human SteA is the preferred starting point for the scaffolds before mutating and/or inserting heterologous peptides as described. Advantageously the Y35W mutation is included to give a signal that can be measured to easily monitor thermal stability. Thus many or most of the measurements provided have been made in scaffolds including Y35W. For example, when we show data for N32G increasing the stability by 3 degrees, the measurement was that hSteA Y35W N32G increases the stability by 3 degrees over hSteA Y35W.

It is a reasonable and robust scientific expectation that the effect of a mutation as measured on hSteA Y35W has the same effect on hSteA. This has been carefully validated and we present data to support this: We carried out a DSC experiment on several mutations in both hSteA and hSteA Y35W. We include these data below, giving the difference in stability from hSteA/hSteA Y35W and showing this expectation is scientifically acceptable: Difference in stability from hSteA/hSteA Y35W:

| | |
|---|---|
| N23G | 3.3/2.1 |
| M65I | 7.6/6.6 |
| Q42E | 10/9.6 |
| T51L | 14.4/12.4 |
| A59V dD61 | 13.6/11.6 |
| A59V dD61 G60N N62G | 17.1/13.6 |

Suitably the polypeptide of the invention/scaffold protein has a melting temperature (Tm) of at least 90° C., more preferably at least 91° C., more preferably at least 92° C., more preferably at least 94° C., more preferably at least 95° C., more preferably at least 98° C., and most preferably at least 100° C.

In one aspect, the invention relates to increasing thermal stability of a Stefin A polypeptide such as a Stefin A scaffold protein by use of mutations as taught herein.

In another aspect, the invention relates to reduction of thermal stability of a Stefin A polypeptide such as a Stefin A scaffold protein by use of mutations as taught herein.

Thus in one aspect the invention relates to a method of increasing the thermal stability of a Stefin A polypeptide such as a Stefin A scaffold protein by making one or more mutation(s) in said Stefin A polypeptide such as a Stefin A scaffold protein, which mutation(s) are selected from the group consisting of:

E29M, N32G, T34V, T34R, T34K, Q42E, T45I, T45V, T51F, T51V, T51L, T51I, A59L, A59I, A59V, K63R, M65V, M65I, L67I, N90T, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

more suitably selected from the group consisting of:

E29M, N32G, T34V, T34R, T45I, T45V, T51F, T51V, T51L, A59L, A59I, M65V, L67I, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61).

Thus in one aspect the invention relates to a method of decreasing the thermal stability of a Stefin A polypeptide such as a Stefin A scaffold protein by making one or more mutation(s) in said Stefin A polypeptide such as a Stefin A scaffold protein, which mutation(s) are selected from the group consisting of:

A12I, A12V, I16L, V20A, V20I, V20L, Q26E, T31K, N32D, N32H, T34D, T34P, L38A, L38V, L38F, A40I, A40V, Q42D, V48E, V48D, V48G, V48A, V48L, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

more suitably selected from the group consisting of:

A12I, A12V, I16L, V20I, V20L, Q26E, T31K, N32D, N32H, T34D, T34P, L38A, L38V, A40I, A40V, Q42D, V48E, V48G, V48A, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E).

The invention is remarkable in that the mutations which are taught are not interdependent (unless otherwise stated in the text). In other words, the mutations (or groups of mutations if otherwise mentioned in the text) taught herein to influence thermal stability are independent may be combined in different permutations to achieve the same technical benefit of the invention i.e. to increase (or decrease) thermal stability. Thus, if a particular subset of mutations is desired to be used in a polypeptide according to the invention, then the subset may be chosen from the overall collection of mutations disclosed herein, since advantageously those mutations are not reliant on other parts of the protein in order to deliver their advantageous effects. Thus, if a large change in thermal stability is required, then a person skilled in the art will select a larger number of mutations as disclosed. If an increase in thermal stability is required, then the person skilled in the art may select mutations disclosed herein which increase thermal stability, or may select any subset of those mutations combined in order to deliver the desired level of increase in thermal stability.

Equally, if a reduction of thermal stability is required, then the person skilled in the art may select mutations disclosed herein which reduce thermal stability, or may select any subset of those mutations combined in order to deliver the desired level of reduction of thermal stability.

Each of the mutations disclosed herein as useful in the manipulation or modulation of the thermal stability (such as Tm) of the polypeptide of the invention may be used independently. As explained, in some embodiments the skilled operator may seek to choose each of the mutations useful for increasing the Tm in order to provide a polypeptide with a higher thermal stability (unless otherwise stated, higher/increased or lower/decreased are relative to the thermal stability of the wild type Stefin A, the sequence of which is already provided herein). In another set of embodiments, the skilled operator may choose each of the mutations disclosed to decrease or reduce the thermal stability (e.g. Tm) of the polypeptide such as scaffold protein relative to wild type Stefin A. In another set of embodiments, the skilled operator may select mutations from those which increase thermal stability and from those which decrease thermal stability—such "mixed" embodiments may advantageously allow the skilled operator to arrive at a more precise preselected thermal stability (such as Tm) for the polypeptide/scaffold protein produced in this manner. For example, if a particular thermal stability (such as Tm) is desired, then in selecting which particular mutants to use the skilled person would carry out arithmetic in order to select mutations which might (for example) increase the thermal stability towards the desired value. However, since each mutation contributes a slightly different value to the increase of thermal stability (such as Tm), then it may be necessary to also choose one or mutations from those which decrease thermal stability in order to "balance" the overall desired selected thermal stability value. For example, if the desired thermal stability is 6° higher than wild type Stefin A, it may be possible to select two different mutations which each increase thermal stability by 4°, and one further mutation which decreases thermal stability by 2°, thereby arriving at an overall effect of thermal stability increased relative to wild type Stefin A by 6° (+4, +4, −2). Any such combination of mutations may be used by the skilled operator, expressly including combinations of mutations which are selected from both those which increase Tm and those which decrease Tm relative to wild type Stefin A. This may be important when designing scaffolds incorporating further mutations, for example those mutations useful in achieving biological neutrality. In particular, when it is desired to use a V48 mutation such as V48D, this inhibits domain swap dimerisation and so is extremely useful in proving biological neutrality. However, this mutation also has a destabilising (decreasing thermal stability such as Tm) effect on the polypeptide/scaffold protein. Therefore, in order to affect the thermal stability and arrive at the desired value, it will be important to select mutations in order to "balance" the effect of selecting the V48D biological neutrality mutation. An exemplary polypeptide/scaffold protein designed in this manner might have the following mutations: V48D, N32G, M65I (referred to herein as 3 T2).

Thus the exemplary 3t series scaffolds are examples of "mixed" embodiments. These have the destabilising V48D mutation, plus different numbers of stabilising mutations to 'restore' (i.e. move back towards wild type Tm by increasing Tm from the destabilised lower Tm V48D mutant) and then further increase the Tm. Data demonstrating the Tm of different examples of such mixed embodiments as follows:

hSteA N32G V48D=3t1=85.6° C.
hSteA N32G V48D M65I=3t2=89.2° C.
hSteA N32G V48D M65I T51L=3t3=91.6° C.
hSteA N32G V48D M65I Q42E=3t4=92.4° C.
hSteA N32G V48D Q42E T51L M65I=3t5=94.7° C.

Clearly it will be possible to produce polypeptides/scaffold proteins according to the invention with combined mutations which result in a modest final change in thermal stability e.g. Tm relative to wild type Stefin A. For example, one such embodiment may comprise a polypeptide/scaffold protein having a V48D mutation, which lowers Tm, and also having one or more mutations according to the present invention which raise Tm, so that the final Tm of that polypeptide/scaffold protein might be higher or lower than the Tm of wild type Stefin A depending on the mutations selected. The change in Tm relative to wild type Stefin A is therefore suitably not determinative whether or not a scaffold protein is a scaffold protein of the invention—that will be as defined in the claims—but it is important that a scaffold protein of the invention will comprise at least one mutation as taught herein for affecting Tm such as increasing it or reducing it relative to Stefin A. If those mutation(s) are used in a polypeptide/scaffold protein in combination with other mutations such as the known V48D mutation then the resulting polypeptide/scaffold protein is still regarded as a part of the invention by virtue of including the mutation(s) disclosed herein for influencing thermal stability such as Tm, whether or not the final product has a Tm higher or lower than wild type Stefin A.

The assessment of whether the mutation raises or lowers Tm relative to wild type Stefin A is suitably determined for the mutation (or group of interdependent mutations as appropriate as apparent from the context) in isolation i.e. when made singly (or as a single group of interdependent mutations as appropriate as apparent from the context) and when the polypeptide/scaffold protein so mutated is compared to wild type Stefin A.

Nevertheless, in preferred embodiments of the invention the polypeptide/scaffold protein has a thermal stability increased relative to wild type Stefin A. Thus suitably when the polypeptide/scaffold protein comprises mutations which lower its thermal stability such as Tm relative to wild type Stefin A (e.g. the V48D mutation), suitably said polypeptide/scaffold protein further comprises mutations as disclosed herein sufficient to compensate for the decrease in thermal stability such as Tm caused by that mutation or mutations (e.g. the V48D mutation) and thereby still result in a polypeptide/scaffold protein with increased thermal stability relative to wild type Stefin A.

Thus, suitably the polypeptide/scaffold protein has a Tm increased by at least +1° C. relative to wild type Stefin A, suitably increased by at least +2° C., suitably increased by at least +3° C., suitably increased by at least +4° C., suitably increased by at least +5° C., suitably increased by at least +6° C., suitably increased by at least +7° C., suitably increased by at least +10° C., suitably increased by at least +13° C., suitably increased by at least +14° C., suitably increased by at least +17° C., relative to wild type Stefin A.

Examples of such values for particular mutations or combinations of mutations include:

hSteA N32G M65I+7.6° C.
hSteA N32G M65I Q42E+10.0° C.
hSteA N32G M65I Q42E T51L+14.4° C.

hSteA N32G M65I Q42E T51L A59V dD61+13.6° C.
hSteA N32G M65I Q42E T51L A59V G60N dD61 N62G+17.1° C.

Examples of mixed embodiments (i.e. sequences including a destabilising mutation but with compensating stabilising mutations) may be made. As examples, scaffolds which include V48D are made and their Tm determined—values shown below:

hSteA N32G V48D M65I=3t2; Tm 89.2° C. hSteA N32G V48D M65I T51L=3t3; Tm 91.6° C. hSteA N32G V48D M65I Q42E=3t4; Tm 92.4° C. hSteA N32G V48D Q42E T51L M65I=3t5; Tm 94.7° C. hSteA Y35W V48D N32G Q42E T51L M65I (A59V ΔD61) (E29K K30E E33K)=3r1; Tm 95.1° C. hSteA Y35W V48D N32G Q42E T51L M65I (A59V G60N ΔD61 N62G) (E29K K30E E33K)=3r2; Tm>98.3° C.

Exemplary scaffolds such as 3t1 may be slightly less stable than wild type hSteA and 3t2 is approximately as stable as hSteA (slightly more stable than hSteA) but such scaffolds are still useful. For example 3t1 has very few mutations compared to wild type (only 3 mutations) and so represents an excellent compromise between maintaining sequence close to wild type whilst still designing a useful scaffold with good stability. In 3t1, the destabilising V48D is strongly compensated for by the two additional stabilising mutations, resulting in a very stable scaffold yet still bearing the useful V48D mutation for biological neutrality.

Suitably the polypeptide of the invention comprises D at position 48, such as V48D.

Decreasing Thermal Stability

Equally, in certain peripheral embodiments of the invention the polypeptide/scaffold protein may have a thermal stability decreased relative to wild type Stefin A. Thus suitably when the polypeptide/scaffold protein comprises mutations which raise its thermal stability such as Tm relative to wild type Stefin A (e.g. the N32G mutation), suitably said polypeptide/scaffold protein further comprises mutations as disclosed herein sufficient to compensate for the increase in thermal stability such as Tm caused by that mutation or mutations (e.g. the N32G mutation) and thereby still result in a polypeptide/scaffold protein with decreased thermal stability relative to wild type Stefin A.

For reference, wild type human Stefin A has a Tm of 89.0° C.

Thus in some embodiments, suitably the polypeptide/scaffold protein has a Tm reduced by at least −1° C. relative to wild type Stefin A, suitably reduced by at least −2° C., suitably reduced by at least −3° C., suitably reduced by at least −4° C., suitably reduced by at least −5° C., suitably reduced by at least −6° C., suitably reduced by at least −7° C., suitably reduced by at least −8° C., suitably reduced by at least −9° C., suitably reduced by at least −10° C., suitably reduced by at least −11° C., suitably reduced by at least −12° C., suitably reduced by at least −13° C., suitably reduced by at least −15° C., suitably reduced by at least −16° C., suitably reduced by at least −21° C., relative to wild type Stefin A.

Examples of such values for particular mutations or combinations of mutations include:

hSteA Y35W V20I L38A-16.7° C.
hSteA Y35W V20L L38A-15.3° C.
hSteA Y35W Y54D T83D Q86E-21.1° C.

More suitable examples are:

hSteA N32D V48D Y54D T83D Q86E (Tm approx. 58° C.)
hSteA V48D Y35W V20A L38A (Tm approx. 57° C.)
hSteA V48D Y35W A40I T31K A121 V20I (Tm approx. 50° C.)

The person skilled in the art will be aware that destabilising mutations should be chosen whilst maintaining a scaffold protein which folds correctly for example at room temperature e.g. 18-24° C. Clearly if all the destabilising mutations taught herein are simultaneously introduced into a SteA polypeptide, that polypeptide might have a Tm lower than room temperature and would be of limited practical use. Thus in this embodiment suitably mutations as taught herein are used in combinations resulting in a polypeptide with a Tm no lower than 25° C., suitably no lower than 30° C., suitably no lower than 40° C., suitably no lower than 50° C. Thus in this embodiment suitably mutations as taught herein are used in combinations resulting in a polypeptide with a Tm of 25° C. or more, suitably 30° C. or more, suitably 40° C. or more, suitably 50° C. or more. Thus in this embodiment suitably mutations as taught herein are used in combinations resulting in a polypeptide with a Tm of 25-88° C. or more, suitably 30-88° C. or more, suitably 40-88° C. or more, suitably 50-88° C. or more.

Assessing the correct folding (e.g. structure or conformation) is taught herein, for example using near and far UV CD spectra. Thus if there is any doubt, the skilled worker needs only to make the protein with the mutation combination to be checked, and then assess the correct folding (e.g. structure or conformation), and/or measure the Tm as taught herein.

Most preferred embodiments are those with increased thermal stability relative to wild type Stefin A.

P25 Site

P25 may be mutated. P25 mutants such as P25S can be useful in improving the polypeptide/scaffold protein, for example by making it stiffer. The P25 site is located at a kink in the helix of the Stefin A based scaffold protein. Mutating P25 to another residue (such as P25S) retains the kink in the helix. P25 mutants such as P25S show no significant effect, or no effect on thermal stability.

V48 Site

V48 is important for domain swap dimerisation. Suitably V48 is mutated to prevent or inhibit domain swap dimerisation. Most suitably V48 is V48D.

V48 is also important for Cathepsin binding. Therefore, for superior biological neutrality suitably V48 is mutated. Most suitably V48 is mutated to V48D.

V48G or V48D mutations may be used, most suitably V48D.

N32 Site

Advantageously the N32 site is mutated. For example, it may be mutated to N32G. This has an advantageous effect in increasing thermal stability of the polypeptide/scaffold protein. In addition, this has the advantageous property of removing a glycosylation site from the polypeptide/scaffold protein, thereby helping to ensure biological neutrality.

Other mutations at the N32 site may be used. For example, the N32G mutation prevents glycosylation by removing the residue that would be glycosylated. However, the N is only glycosylated when it is recognised in an NXS/T motif where X is any residue except P. In hSteA the sequence at this site is NET. We can prevent glycosylation by either mutating the N to anything else, or the T to anything but an S. N32G has the advantage of extra thermostability. Suitably T34 is substituted for any amino acid except S. T34E has the property that it does not change the thermostability. Either N32 or T34 mutations will stop glycosylation at N32 by removing the required motif.

N32G has a further benefit in helix-capping. G is found more than twice as often than average at this position. Next most favoured is histidine, closely followed by N. All other mutations are less favoured than N for helix capping. Suitably histidine at 32 (N32H) is not used, as this amino acid residue adds a titratable side chain which may not be desirable.

An additional advantage of the N32G mutation is that this optimises the cap at the end of the helix in this area of the polypeptide/scaffold protein. Thus, although other N32 mutants may be used, N32G delivers particular advantages as noted above.

As a matter of convention, if certain mutations are bracketed together, for example as shown in some of the FIGS. or tables herein, this indicates that those mutations are suitably made together i.e. in combination. For example "(T83D, Q86E)" means "substitution of T83D AND substitution of Q86E" in the same polypeptide. In other words, mutations which are bracketed together are suitably made as a group in a polypeptide/scaffold protein according to the invention. This can be important, for example when a pair of mutations are made in a "charge-swap" arrangement—in this case it is important to mutate a first position to swap the charge, and to make the corresponding opposite charge-swap mutation at the second site thereby preserving the charge-charge interaction between those two residues in the final polypeptide/scaffold protein. For example, the E29K K30E E33K mutations are surface charge mutations and are suitably mutated as a group and so are described as a single option bracketed together: "(E29 K30 E33)" i.e. suitably all three mutations E29K K30E E33K or none of the three mutations are made in an individual polypeptide/scaffold protein according to the invention. An advantage of the (E29K K30E E33K) set of mutations is the formation of favourable Coulombic interactions on the surface of the scaffold.

Reference Sequence

Suitably all sequences herein are discussed with reference to human wild-type Stefin A (Cystatin A) having the sequence Uniprot P01040 (most suitably Uniprot P01040-1). For the avoidance of doubt, this sequence is presented below:

```
SEQ ID NO: 1—Uniprot P01040—wild type human Cystatin A
         10          20          30          40          50
MIPGGLSEAK  PATPEIQEIV  DKVKPQLEEK  TNETYGKLEA  VQYKTQVVAG 60          70          80          90
TNYYIKVRAG  DNKYMHLKVF  KSLPGQNEDL  VLTGYQVDKN  KDDELTGF
```

When particular amino acid residues are referred to herein using numeric addresses, the numbering is taken with reference to the wild type Stefin A (Cystatin A) amino acid sequence (or to the polynucleotide sequence encoding same if referring to nucleic acid). An exemplary nucleic acid encoding wild type Stefin A (Cystatin A) is:

```
SEQ ID NO: 2 (DNA sequence; artificial (not
natural); the amino acid sequence SEQ ID NO: 1
was used to generate a codon-optimised DNA
sequence suitable for expression in E. coli):
ATGATTCCTGGTGGTTTGTCGGAAGCCAAACCGGCTACTCCGGAAATC

CAGGAGATTGTGGACAAAGTCAAACCGCAACTGGAGGAAAAGACCAAT

GAAACCTATGGCAAACTCGAAGCGGTACAGTACAAAACCCAAGTCGTT

GCGGGTACGAACTACTACATCAAAGTACGCGCAGGAGATAACAAGTAT
```

-continued

```
ATGCATCTGAAAGTGTTCAAAAGCTTACCAGGGCAGAATGAGGATCTG

GTTCTTACGGGCTATCAGGTGGATAAGAACAAAGACGATGAACTGACA

GGCTTT
```

Suitably the current version of sequence database(s) are relied upon. Alternatively, the release in force at the date of filing is relied upon. For the avoidance of doubt, UniProt release 2017_02 is relied upon. In more detail, the UniProt consortium European Bioinformatics Institute (EBI), SIB Swiss Institute of Bioinformatics and Protein Information Resource (PIR)'s UniProt Knowledgebase (UniProtKB) Release 2017_02 published 15 Feb. 2017 is relied upon. UniProt (Universal Protein Resource) is a comprehensive catalogue of information on proteins ("UniProt: the universal protein knowledgebase" Nucleic Acids Res. 45: D158-D169 (2017)).

This is to be used as is well understood in the art to locate the residue of interest. This is not always a strict counting exercise—attention must be paid to the context. For example, if the protein of interest is of a slightly different length, then location of the correct residue in that sequence may require the sequences to be aligned and the equivalent or corresponding residue picked. This is well within the ambit of the skilled reader.

Mutating has it normal meaning in the art and may refer to the substitution or truncation or deletion of one or more residues, motifs or domains. Mutation may be effected at the polypeptide level, for example, by synthesis of a polypeptide having the mutated sequence, or may be effected at the nucleotide level, for example, by making a polynucleotide encoding the mutated sequence, which polynucleotide may be subsequently translated to produce the mutated polypeptide. Suitably, the mutations to be used are as set out herein. Unless otherwise apparent from the context, mutations mentioned herein are substitutions. For example 'N32G' means that the residue corresponding to 'N32' in the wild type Stefin A (SEQ ID NO: 1) is substituted with G.

Sequence Variation

The polypeptides described herein may comprise sequence changes relative to the wild type sequence in addition to the key mutations described herein for modulating thermal stability such as Tm. Specifically the polypeptides described herein may comprise additional sequence changes at sites which do not significantly compromise the function or operation of the polypeptides described herein. The sequence changes may be at the polypeptide or the nucleotide level.

Polypeptide function may be easily tested using the methods as set out in the examples section, for example in order to verify that the peptide structure or conformation has not been significantly altered. Thus, provided that the polypeptide retains its structure or conformation which can be easily tested as set out herein, sequence variations may be made in the polypeptide relative to the wild type reference sequence.

For example, a polypeptide may be tested to see if it retains its structure or conformation by assessing the near and far UV CD spectra; these are recorded in a compatible buffer (for example 50 mM sodium phosphate, pH 7.4) at 0.6 mg/mL and 0.2 mg/mL, respectively. Spectra are processed by subtracting a buffer spectrum from the sample spectrum and converting the units to molar ellipticity (for near UV CD spectra) or mean residue ellipticity (far UV CD spectra). Near UV CD spectra should have a maximum between 275 nm-280 nm, and an addition minimum around 295 nm if a single tryptophan is present at position 35. This could be a maximum if a different position is chosen for the tryptophan. Far UV CD spectra should resemble that of a typical beta-sheet protein, having a minimum around 218 nm. If these conditions are met, the polypeptide has retained correct structure or conformation. If there is no near UV CD spectrum, or the far UV CD spectrum has minima at 208 nm and 222 nm, or a minimum at 198 nm, polypeptide has not retained correct structure or conformation and may have been significantly altered.

Polypeptides include variants produced by introducing any type of additional alterations (for example, insertions, deletions, or substitutions of amino acids; changes in glycosylation states; changes that affect refolding or isomerizations, three-dimensional structures, or self-association states), which can be deliberately engineered. The variant may have alterations which produce a silent change and result in a functionally equivalent polypeptide. Deliberate amino acid substitutions may be made on the basis of similarity in polarity, charge, solubility, hydrophobicity, hydrophilicity and the amphipathic nature of the residues as long as the structure or conformation of the polypeptide is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and suitably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In considering what mutations, substitutions or other such changes might be made relative to the wild type sequence, retention of the structure or conformation of the polypeptide is important. Typically conservative amino acid substitutions would be less likely to adversely affect the function.

When engineering the polypeptide to modulate thermal stability as taught herein, one or more of amino acids A12I, A12V, I16L, V20A, V20I, V20L, Q26E, E29M, T31K, N32G, N32D, N32H, T34V, T34R, T34K, T34D, T34P, L38A, L38V, L38F, A40I, A40V, Q42E, Q42D, T45I, T45V, V48E, V48D, V48G, V48A, V48L, G50S, T51F, T51V, T51L, T51I, T51A, A59L, A59I, A59V, K63R, M65V, M65I, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);

should be substituted as taught herein, or if not substituted should suitably correspond to SEQ ID NO: 1. Residues other than as shown in SEQ ID NO: 1 or substitutions other than as taught herein are suitably not used at these positions.

When engineering the polypeptide to increase thermal stability as taught herein, one or more of amino acids E29M, N32G, T34V, T34R, T34K, Q42E, T45I, T45V, T51F, T51V, T51L, T51I, A59L, A59I, A59V, K63R, M65V, M65I, L67I, N90T, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

should be substituted as taught herein, or if not substituted should suitably correspond to SEQ ID NO: 1. Residues other than as shown in SEQ ID NO: 1 or substitutions other than as taught herein are suitably not used at these positions.

When engineering the polypeptide to decrease thermal stability as taught herein, one or more of amino acids A12I, A12V, I16L, V20A, V20I, V20L, Q26E, T31K, N32D, N32H, T34D, T34P, L38A, L38V, L38F, A40I, A40V, Q42D, V48E, V48D, V48G, V48A, V48L, G50S, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

should be substituted as taught herein, or if not substituted should suitably correspond to SEQ ID NO: 1. Residues other than as shown in SEQ ID NO: 1 or substitutions other than as taught herein are suitably not used at these positions.

When engineering the polypeptide to provide aromatic residue(s) for fluorescence/absorbance as taught herein, one or more of amino acids Y35W, Y43W, Y53W, Y54W, Y64W, F70W or Y85W should be substituted as taught herein, or if not substituted should suitably correspond to SEQ ID NO: 1. Residues other than as shown in SEQ ID NO: 1 or substitutions other than as taught herein are suitably not used at these positions.

Suitably the polypeptide of the invention comprises W at position 35, e.g. Y35W.

It should be noted that Y85W displays a clear transition upon unfolding as judged by BCM of intrinsic fluorescence emission spectra and improved absorbance properties compared to hSteA, but no obvious improvement in amplitude of the raw fluorescence emission spectra. For the avoidance of doubt, Y85W may still be used for transitions in unfolding—small improvements are provided. Therefore, this mutation is still useful to observe transitions, but does not increase fluorescence very much, but still works in this setting.

When engineering the polypeptide for biological neutrality as taught herein, one or more amino acids from the following table should be substituted as taught herein, or if not substituted should suitably correspond to SEQ ID NO: 1. Residues other than as shown in SEQ ID NO: 1 or substitutions other than as taught herein are suitably not used at these positions:

| SUBSTITUTION(S) FOR BIOLOGICAL NEUTRALITY | | | |
|---|---|---|---|
| Amino acid (in SEQ ID NO: 1 - wild type Stefin A) | substitution(s) | advantage(s) | notes |
| G4 | R W | increases the accessibility of the recognition (target binding) surface | G4 is also part of the inhibitory sequence motif |
| V48 | D E | abolish domain swap dimerisation | V48 is also part of the inhibitory sequence motif |
| G50 | S | increased expression in a bacterial system | G50 is also part of the inhibitory sequence motif |
| Y35 | W | introduces a fluorophore | |
| Y43 | W | introduces a fluorophore | |
| Y53 | W | introduces a fluorophore | |
| Y54 | W | introduces a fluorophore | |

| SUBSTITUTION(S) FOR BIOLOGICAL NEUTRALITY | | | |
|---|---|---|---|
| Amino acid (in SEQ ID NO: 1 - wild type Stefin A) | substitution(s) | advantage(s) | notes |
| Y64 | W | introduces a fluorophore | |
| F70 | W | introduces a fluorophore | |
| Y85 | W | introduces a fluorophore | |
| F98 | W | introduces a fluorophore | |
| 71KSL | 71NGP | Blocks secondary structure from the loop 4 propagating into the scaffold | |
| 78EDL | 78ADR | | most suitably for research scaffolds; present in prior art SQT scaffold |
| 71KSLPGQNEDL (SEQ ID NO: 108) | 71NGPPGQNADR (SEQ ID NO: 109) | | most suitably for research scaffolds; present in prior art SQT scaffold |

Residues which are less conserved between proteins are more likely to tolerate mutation.

In total, as many as 15 substitutions relative to SEQ ID NO: 1 may be made to increase thermal stability.

In addition, as many as 2 substitutions relative to SEQ ID NO: 1 may be made for biological neutrality.

In addition, as many as 1 substitutions relative to SEQ ID NO: 1 may be made to provide aromatic residue(s) for fluorescence/absorbance.

Therefore, in one embodiment the invention relates to polypeptide(s) having up to 18 substitutions relative to SEQ ID NO: 1.

By way of example, in one embodiment the invention relates to a polypeptide having the following substitutions relative to SEQ ID NO: 1:

1 for fluorescence (e.g. Y35W); 2 for biological neutrality (e.g. N32G, V48D); 15 for Tm (T34, Q42, T45, T51, K63, M65, L67, N90 (these are all single mutations), E29K K30E E33K (charge interactions), A59 G60 D61 N62 (the b-turn).

Additional mutation, most suitably substitution, of one or more residues other than those expressly mentioned above may be made, provided that of the structure or conformation of the polypeptide is retained. Therefore, in one embodiment the invention relates to polypeptide(s) having up to 25 mutations most suitably substitutions relative to SEQ ID NO: 1.

For example (1—novel and Tm increased or decreased):

(SEQ ID NO: 110)

MIPGGLSEAK PX1TPEX2QEIX3 DKVKPX4LEX5X6 X7X8X9X10YGKX11EX12

VX13YKX14QVX15AG X16NYX17IKVRX18X19 X20X21KYX22HX23KVF

KSLPGQNEDL VLX24GYX25VDKN KDDELTGF

X1 where wild type is A and mutations are I, V
X2 where wild type is I and mutations are L
X3 where wild type is V and mutations are I, L
X4 where wild type is Q and mutations are E
X5 where wild type is E and mutations are M
X7 where wild type is T and mutations are K
X8 where wild type is N and mutations are G, D, H
X10 where wild type is T and mutations are V, R, D, P
X11 where wild type is L and mutations are A, V
X12 where wild type is A and mutations are I, V
X13 where wild type is Q and mutations are D
X14 where wild type is T and mutations are I, V
X15 where wild type is V and mutations are E, G, A
X16 where wild type is T and mutations are F, V, L, A
X18 where wild type is A and mutations are L, I
X20 where wild type is D and mutations are A
X22 where wild type is M and mutations are V
X23 where wild type is L and mutations are I
(X3, X11) where wild type is (V, L) and mutations are (I, A), (L, A), (I, V), (L, V)
(X5, X6, X9) where wild type is (E, K, E) and mutations are (K, E, K)
(X17, X24, X25) where wild type is (Y, T, Q) and mutations are (D, D, E)
(X18, X19, X20, X21) where wild type is (A, G, D, N) and mutations are (L, N, G, K), (L, N, Δ, G), (V, N, G, K), (I, N, G, K), (I, N, Δ, G), (V, N, Δ, G)
(X18, X20, X21) where wild type is (A, D, N) and mutations are (V, N, K)
(X18, X20) where wild type is (A, D) and mutations are (V, Δ)
(X19, X20, X21) where wild type is (G, D, N) and mutations are (N, G, K), (N, Δ, G), (P, Δ, P), (P, P, K), (P, Δ, G), (P, G, K)
(X24, X25) where wild type is (T, Q) and mutations are (D, E)
(X20, X21) where wild type is (D, N) and mutations are (N, K)

Therefore, in one embodiment the invention relates to polypeptide(s) having up to 13 mutations most suitably substitutions relative to SEQ ID NO: 1. For example (2—novel and Tm increased):

```
                                                              (SEQ ID NO: 111)
MIPGGLSEAK    PATPEIQEIV    DKVKPQLEX1X2   TX3X4X5YGKLEA   VQYKX6QVVAG

X7NYYIKVRX8X9    X10X11KYX12HX13KVF    KSLPGQNEDL    VLTGYQVDKN    KDDELTGF
```

X1 where wild type is E and mutations are M
X3 where wild type is N and mutations are G
X5 where wild type is T and mutations are V, R
X6 where wild type is T and mutations are I, V
X7 where wild type is T and mutations are F, V, L
X8 where wild type is A and mutations are L, I
X10 where wild type is D and mutations are Δ
X12 where wild type is M and mutations are V
X13 where wild type is L and mutations are I
(X1, X2, X4) where wild type is (E, K, E) and mutations are (K, E, K)
(X8, X9, X10, X11) where wild type is (A, G, D, N) and mutations are (L, N, G, K), (L, N, Δ, G), (V, N, G, K), (I, N, G, K), (I, N, Δ, G), (V, N, Δ, G)
(X8, X10, X11) where wild type is (A, D, N) and mutations are (V, N, K)
(X9, X10, X11) where wild type is (G, D, N) and mutations are (N, G, K), (N, Δ, G)
(X8, X10) where wild type is (A, D) and mutations are (V, Δ)

Therefore, in one embodiment the invention relates to polypeptide(s) having up to 18 mutations most suitably substitutions relative to SEQ ID NO: 1. For example (3—novel and Tm decreased):

```
                                                              (SEQ ID NO: 112)
MIPGGLSEAK    PX1TPEX2QEIX3    DKVKPX4LEEK    X5X6EX7YGKX8EX9

VX10YKTQVX11AG    X12NYX13IKVRAX14    X15X16KYMHLKVF    KSLPGQNEDL

VLX17GYX18VDKN    KDDELTGF
```

X1 where wild type is A and mutations are I, V
X2 where wild type is I and mutations are L
X3 where wild type is V and mutations are I, L
X4 where wild type is Q and mutations are E
X5 where wild type is T and mutations are K
X6 where wild type is N and mutations are D, H
X7 where wild type is T and mutations are D, P
X8 where wild type is L and mutations are A, V
X9 where wild type is A and mutations are I, V
X10 where wild type is Q and mutations are D
X11 where wild type is V and mutations are E, G, A
X12 where wild type is T and mutations are A
(X3, X8) where wild type is (V, L) and mutations are (I, A), (L, A), (I, V), (L, V)
(X13, X17, X18) where wild type is (Y, T, Q) and mutations are (D, D, E)
(X14, X15, X16) where wild type is (G, D, N) and mutations are (P, Δ, P), (P, P, K), (P, Δ, G), (P, G, K)
(X15, X16) where wild type is (D, N) and mutations are (N, K)
(X17, X18) where wild type is (T, Q) and mutations are (D, E)

Therefore, in one embodiment the invention relates to polypeptide(s) having up to 28 mutations most suitably substitutions relative to SEQ ID NO: 1, suitably together with heterologous peptide insertion wherein said heterologous peptide insertion comprises a heterologous peptide inserted at one of the following positions relative to SEQ ID NO: 1:
  d) 48-<heterologous peptide>-50,
  e) 49-<heterologous peptide>-51,
  f) 50-<heterologous peptide>-52,
  q) 72-<heterologous peptide>-77,
  r) 73-<heterologous peptide>-78; or
  s) 74-<heterologous peptide>-79. For example (9—Tm increased or decreased):

X15 where wild type is V and mutations are E, D, G, A, L
X16 where wild type is G and mutations are S
X17 where wild type is T and mutations are F, V, L, I, A
X19 where wild type is A and mutations are L, I, V
X21 where wild type is D and mutations are Δ
X23 where wild type is K and mutations are R
X24 where wild type is M and mutations are V, I
X25 where wild type is L and mutations are I
X28 where wild type is N and mutations are T
(X3, X11) where wild type is (V, L) and mutations are (I, A), (L, A), (I, V), (L, V)
(X5, X6, X9) where wild type is (E, K, E) and mutations are (K, E, K)
(X18, X26, X27) where wild type is (Y, T, Q) and mutations are (D, D, E)
(X19, X20, X21, X22) where wild type is (A, G, D, N) and mutations are (L, N, G, K), (L, N, Δ, G), (V, N, G, K), (I, N, G, K), (I, N, Δ, G), (V, N, Δ, G)
(X19, X21, X22) where wild type is (A, D, N) and mutations are (V, N, K)
(X20, X21, X22) where wild type is (G, D, N) and mutations are (N, G, K), (N, Δ, G), (P, Δ, P), (P, P, K), (P, Δ, G), (P, G, K)
(X19, X21) where wild type is (A, D) and mutations are (V, Δ)
(X21, X22) where wild type is (D, N) and mutations are (N, K)
(X26, X27) where wild type is (T, Q) and mutations are (D, E)

Suitably when considering sequence identity, the amino acids marked as 'X' are not considered; suitably sequence identity is assessed across the amino acid residues specified or defined as above (i.e. the non-X residues).

In case any further guidance is required, to assess sequence identity when the reference sequence has variable residues (e.g. 'X' s) in it, sequence identity is calculated

```
                                                        (SEQ ID NO: 113)
MIPGGLSEAK       PX1TPEX2QEIX3       DKVKPX4LEX5X6       X7X8X9X10YGKX11EX12

VX13YKX14QVX15AX16   X17NYX18IKVRX19X20   X21X22X23YX24HX25KVF

KSLPGQNEDL       VLX26GYX27VDKX28    KDDELTGF
```

X1 where wild type is A and mutations are I, V
X2 where wild type is I and mutations are D
X3 where wild type is V and mutations are A, I, L
X4 where wild type is Q and mutations are E
X5 where wild type is E and mutations are M
X7 where wild type is T and mutations are K
X8 where wild type is N and mutations are G, D, H
X10 where wild type is T and mutations are V. R, K, D, P
X11 where wild type is L and mutations are A, V, F
X12 where wild type is A and mutations are I, V
X13 where wild type is Q and mutations are E, D
X14 where wild type is T and mutations are I, V using the Protein BLAST server from the NIH (blast.ncbi.nlm.nih.gov/Blast.cgi). The Query Sequence is the amino acid reference sequence with all the X's (Xn) removed. The Subject Sequence is the sequence of interest to be compared with the Query Sequence with equivalent residues removed. The analysis is then run and the Ident value taken as the result.

For Example:

The sequence of hSteA containing X1-X25 (reference sequence) is lined up with the sequence of interest—in this example canine SteA (cSteA):

```
hSteA
                                                              (SEQ ID NO: 110)
MIPGGLSEAKPX1TPEX2QEIX3DKVKPX4LEX5X6X7X8X9X10YGKX11EX12VX13YKX14QVX15AGX16

NYX17IKVRX18X19X20X21KYX22HX23KVFKSLPGQNEDLVLX24GYX25VDKNKDDELTGF
```

-continued cSteA
(SEQ ID NO: 3)
MMPGGLTEAKPA TPEV QEIA NEVKPQ LEE K T N E T YQEF EA VE YKT QVV AGI NYY IKVRV G

D N SYI HL KIFKGLPGQNPTLTLT GYQ TDKSKDDELTGF

All Xn are removed, as are the corresponding residues in the sequence of
interest cSteA:

hSteA-Query Sequence
MIPGGLSEAKPTPEQEIDKVKPLEYGKEVYKQVAGNYIKVRKYHKVFKSLPGQNEDLVLGYVDKNKDDELTG

F cSteA-Subject Sequence
MMPGGLTEAKPTPEQEINEVKPLEYQEEVYKQVAGNYIKVRSYHKIFKGLPGQNPTLTLGYTDKSKDDELTG

F

These Query Sequence and Subject Sequence are compared using Protein BLAST. The result is these sequences have 59 of 73 residues identical, giving 81% sequence identity.

Similarly, when a sequence of interest has 'gaps' or truncations e.g. is shorter than the reference sequence such as SEQ ID NO: 110, such gaps or truncations are assessed by the sequence comparison and contribute to a correspondingly lower sequence identity value. In this regard, sequence identity should suitably be assessed across the whole length of SEQ ID NO: 110. By convention, a shorter sequence might be compared to the reference sequence (SEQ ID NO: 110) only across the length of the shorter sequence of interest. However, unless otherwise apparent from the context, discussion of/determination of sequence identity (and sequence identity values mentioned herein) suitably treat truncations as 'gaps'. To give a practical example, if a sequence of interest was only 49 amino acids long and was compared to SEQ ID NO: 110 (which is 98 amino acids long) then the maximum sequence identity score would be 50%, (and any substitutions relative to SEQ ID NO: 110 would further reduce the sequence identity score). Thus a sequence identity score for a polypeptide of interest compared to SEQ ID NO: 110 of 50% implies presence of at least 49 amino acid residues in the polypeptide of interest, 49 of which are identical to their corresponding residues in SEQ ID NO: 110.

Suitably when a residue is not mutated as above, it is 'wild-type' as above. In other words, suitably when a residue is not mutated as above, it is as shown in hSteA (SEQ ID NO: 1).

Sequence Identity

For precision, sequence relationships have been discussed in terms of substitutions relative to SEQ ID NO: 1 (wild type human Stefin A). However it may be desired to consider sequence relationships in terms of sequence identity.

Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example in an otherwise identical pair of sequences, one insertion or deletion will cause the following amino acid residues to be put out of alignment, thus potentially resulting in a large reduction in percent homology (percent identity) when a global alignment (an alignment across the whole sequence) is performed. Consequently, most sequence comparison methods are designed to produce optimal alignments that take into consideration possible insertions and deletions without penalising unduly the overall homology (identity) score. This is achieved by inserting "gaps" in the sequence alignment to try to maximise local homology/identity.

These more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is –12 for a gap and –4 for each extension.

Calculation of maximum percent homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, *Nucleic Acids Research* 12:387). Examples of other software than can perform sequence comparisons include, but are not limited to, the BLAST package, FASTA (Altschul et al., 1990, *J. Mol. Biol.* 215: 403-410) and the GENEWORKS suite of comparison tools.

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62. Once the software has produced an optimal alignment, it is possible to calculate percent homology, preferably percent sequence identity. The software typically does this as part of the sequence comparison and generates a numerical result.

Suitably the polypeptide of the invention has at least 80% sequence identity to SEQ ID NO: 1, more suitably 85%, more suitably 88%, more suitably 90%, more suitably 92%, more suitably 94%, more suitably 95%, more suitably 96%, more suitably 97%, more suitably 98%, more suitably 99% identity to SEQ ID NO: 1.

In one embodiment more suitably the polypeptide of the invention has at least 80% sequence identity to those residues of SEQ ID NO: 1 which are other than those specifically recited as being substituted when defining the polypeptide of the invention under consideration (e.g. in the appended claim(s)), more suitably 85%, more suitably 88%, more suitably 90%, more suitably 92%, more suitably 94%, more suitably 95%, more suitably 96%, more suitably 97%, more suitably 98%, more suitably 99% identity. In other words, in this embodiment, more suitably percent sequence identity is assessed for the sequence of interest compared to SEQ ID NO: 1, whilst excluding residues which are specifically defined (e.g. substitutions) in the particular embodiment of the polypeptide under consideration.

Suitably any heterologous peptide insertions are excluded from percent identity calculations.

In one embodiment suitably the substitutions and any heterologous peptide insertions are as defined, and sequence identity is judged against the remaining 'background' or 'backbone' sequence of the polypeptide compared to the corresponding residues of SEQ ID NO: 1.

In all discussions of sequence identity, it will be noted that SEQ ID NO: 1 is 98 amino acids in length. Therefore each single substitution is equivalent to 1.020408% change in identity if all 98 amino acids are considered. The above values are given to nearest whole percentage point and should be understood accordingly given that it is not possible to substitute partial amino acids within a polypeptide sequence. Clearly when fewer than 98 amino acids are considered (for example when considering sequence identity to those residues of SEQ ID NO: 1 which are other than those specifically recited as being substituted when defining the polypeptide of the invention under consideration) then each single amino acid substitution may correspond to greater than 1.020408% change in identity; the skilled reader can interpret the values accordingly given that it is not possible to substitute partial amino acids within a polypeptide sequence.

In case any further guidance is needed, the table below shows how the percent sequence identity value varies taking into account number of residues compared and number of amino acid substitutions made within that number of residues compared. Any further values outside the examples in the table can be easily calculated by the skilled worker.

Percent Sequence Identity Values

| total amino acids compared | number of substitutions | | | | | | | | |
|---|---|---|---|---|---|---|---|---|---|
| | 1% | 2% | 3% | 4% | 5% | 6% | 7% | 8% | 9% |
| 98 | 98.98 | 97.96 | 96.94 | 95.92 | 94.90 | 93.88 | 92.86 | 91.84 | 90.82 |
| 97 | 98.97 | 97.94 | 96.91 | 95.88 | 94.85 | 93.81 | 92.78 | 91.75 | 90.72 |
| 96 | 98.96 | 97.92 | 96.88 | 95.83 | 94.79 | 93.75 | 92.71 | 91.67 | 90.63 |
| 95 | 98.95 | 97.89 | 96.84 | 95.79 | 94.74 | 93.68 | 92.63 | 91.58 | 90.53 |
| 94 | 98.94 | 97.87 | 96.81 | 95.74 | 94.68 | 93.62 | 92.55 | 91.49 | 90.43 |
| 93 | 98.92 | 97.85 | 96.77 | 95.70 | 94.62 | 93.55 | 92.47 | 91.40 | 90.32 |
| 92 | 98.91 | 97.83 | 96.74 | 95.65 | 94.57 | 93.48 | 92.39 | 91.30 | 90.22 |
| 91 | 98.90 | 97.80 | 96.70 | 95.60 | 94.51 | 93.41 | 92.31 | 91.21 | 90.11 |
| 90 | 98.89 | 97.78 | 96.67 | 95.56 | 94.44 | 93.33 | 92.22 | 91.11 | 90.00 |
| 89 | 98.88 | 97.75 | 96.63 | 95.51 | 94.38 | 93.26 | 92.13 | 91.01 | 89.89 |
| 88 | 98.86 | 97.73 | 96.59 | 95.45 | 94.32 | 93.18 | 92.05 | 90.91 | 89.77 |
| 87 | 98.85 | 97.70 | 96.55 | 95.40 | 94.25 | 93.10 | 91.95 | 90.80 | 89.66 |
| 86 | 98.84 | 97.67 | 96.51 | 95.35 | 94.19 | 93.02 | 91.86 | 90.70 | 89.53 |
| 85 | 98.82 | 97.65 | 96.47 | 95.29 | 94.12 | 92.94 | 91.76 | 90.59 | 89.41 |
| 84 | 98.81 | 97.62 | 96.43 | 95.24 | 94.05 | 92.86 | 91.67 | 90.48 | 89.29 |
| 83 | 98.80 | 97.59 | 96.39 | 95.18 | 93.98 | 92.77 | 91.57 | 90.36 | 89.16 |
| 82 | 98.78 | 97.56 | 96.34 | 95.12 | 93.90 | 92.68 | 91.46 | 90.24 | 89.02 |
| 81 | 98.77 | 97.53 | 96.30 | 95.06 | 93.83 | 92.59 | 91.36 | 90.12 | 88.89 |
| 80 | 98.75 | 97.50 | 96.25 | 95.00 | 93.75 | 92.50 | 91.25 | 90.00 | 88.75 |
| 79 | 98.73 | 97.47 | 96.20 | 94.94 | 93.67 | 92.41 | 91.14 | 89.87 | 88.61 |
| 78 | 98.72 | 97.44 | 96.15 | 94.87 | 93.59 | 92.31 | 91.03 | 89.74 | 88.46 |

Where an amino acid sequence identity value is given for a particular polypeptide, the skilled reader will be aware that this particular polypeptide might also comprise a heterologous peptide insertion, and this must be borne in mind when assessing the sequence identity. Suitably the sequence identity is assessed across the amino acid residues corresponding to those in the wild type Stefin A sequence of SEQ ID NO: 1. In other words, suitably assessment of sequence identity does not include heterologous peptide insertions (or lack of insertions) but is considered across the amino acids corresponding to those present in SEQ ID NO: 1.

In one embodiment more suitably sequence identity is considered across the amino acids corresponding to those present in SEQ ID NO: 1 but excluding any heterologous peptide insertions and excluding any substitutions already defined in the claim under consideration.

Most suitably the percent sequence identity is calculated for amino acid residues excluding those substituted for thermal stability reasons.

For some applications, for example for intended therapeutic applications, it is desirable to minimise the number of mutations in the polypeptide/scaffold protein used. Thus, in some embodiments suitably the polypeptide/scaffold protein comprises five or fewer mutations compared to wild-type human Stefin A, suitably four or fewer, suitably three or fewer, suitably two or fewer mutations. In this context "mutations" refers to point mutations, or insertion or deletion of a small number such as five or fewer amino acids. Insertion of heterologous peptides into the polypeptide/scaffold protein of the invention is discussed separately. Insertion of one or more heterologous peptides is not counted as a "mutation" in this context. Most suitably mutation(s) means substitution(s).

It should be noted that the standard in the art is the SQT scaffold protein as disclosed in WO 2009/136182. This has a low thermal stability/Tm of 64.6° C. Suitably the SQT scaffold is a scaffold having a sequence of SEQ ID NO:24 of WO 2009/136182 (SQT): MIPRGLSEAK PATPEIQEIV DKVKPQLEEK TNETYGKLEA VQYKTQVLAS TNYYIKVRAG DNKYMHLKVF NGPPGQNADR VLTGYQVDKN KDDELTGF (SEQ ID NO: 116).

Thus, embodiments of the invention show significant advantages compared to the prior art SQT scaffold. However, it should be noted that comparative values expressed herein are relative to wild type Stefin A unless otherwise apparent from the context. Thus, it is possible to have a polypeptide/scaffold protein as disclosed herein having a reduced (lower) Tm compared to wild type Stefin A, but which nevertheless offers the advantage of improved (higher) Tm relative to SQT. The values are all expressed relative to wild type Stefin A (unless otherwise apparent from the context) for ease of understanding and consistency, but the advantages of the invention can be obtained in modulating the Tm whether the resulting Tm is higher or lower than that of wild type Stefin A. The Tm desired by the operator of the invention may be higher or lower than that of wild type Stefin A, or of SQT. The key advantage is that the skilled reader is now enabled to alter/modulate the Tm of the polypeptide/scaffold protein as taught herein.

Suitably the scaffold of the invention has a Tm higher than SQT i.e. higher than 64.6° C. Most suitably the scaffold of the invention has a Tm higher than wild type Stefin A i.e. higher than 89.0° C.

It is an advantage of the invention that a polypeptide/scaffold protein which is biologically neutral is provided.

It is an advantage of the invention that a polypeptide/scaffold protein lacking glycosylation sites is provided.

It is an advantage of the invention that polypeptides/scaffold proteins with reduced or ameliorated propensity to dimerise are provided. This is advantageous because dimerisation can change the pharmacokinetics when the scaffold is a drug. This is also advantageous because dimerisation can affect affinity and therefore can affect interaction with the target. This is also advantageous because dimerisation can affect immunogenicity. Dimerisation can also change the effect of certain molecules from agonist to antagonist (or vice versa). In addition, in some cases dimerisation can promote higher-order structure formations and instability over time. Moreover, there are certain advantages in having monomers (i.e. reducing dimerisation), for example monomers are small (e.g. improving tumour penetration).

Clearly if the skilled operator desires dimers, then dimerisation residues can be treated accordingly e.g. retained as wild-type such as V48 to allow/promote domain-swap dimerisation if this is deemed advantageous for particular applications.

Heterologous Peptide Insertions

Suitably the heterologous peptide comprises 36 amino acids or fewer, more suitably 20 amino acids or fewer, more suitably 12 amino acids or fewer.

It is an advantage of the invention that a small increase in thermal stability is observed when heterologous peptide insertions are included in the polypeptide of the invention as taught herein.

Location of Heterologous Peptide Insertions

A heterologous peptide sequence may be inserted between amino acids 46 to 54 inclusive, (for example as described in WO 2006/131749 (describing scaffolds such as 'STM') or for example WO 2009/136182 (describing scaffolds such as 'SQT')), more suitably between amino acids 46 to 50 inclusive, more suitably between amino acids 48 to 50 inclusive. In this context 'between . . . inclusive' means that the noted amino acids may be deleted in favour of the heterologous peptide insertion i.e. that any or all of the amino acid(s) from (e.g.) 46-54 may be deleted and the heterologous peptide insertion added in their place. Therefore an insertion which deletes amino acids 46-54 and replaces them is embraced by the phrase 'between amino acids 46 to 54'. There is no requirement for amino acid 46 and amino acid 54 to be retained—the peptide is inserted between those positions with reference to SEQ ID NO:1 rather than requiring the actual presence of amino acid 46 and amino acid 54 in order to be 'between' them. When all of amino acids 46-54 are deleted his may be represented as "45-<heterologous peptide>-55".

A heterologous peptide sequence may be inserted between amino acids 67 to 84 inclusive. A heterologous peptide sequence may be inserted between amino acids 71 to 73 inclusive. A heterologous peptide sequence may be inserted between amino acids 82 to 83 inclusive. The 'Leu 73' site is an insertion site for heterologous peptides (sometimes referred to as 'target peptides'). This represents a solvent exposed loop of the Stefin A protein, and is therefore amenable to the display of target peptides in a solvent accessible manner. The term 'Leu73 insertion' is used herein to describe insertion of a heterologous peptide close to or suitably at (e.g. within) the L73-L80 loop of human SteA. The term may refer to addition(s) to or insertion(s) at, or replacement of, Leu 80 of human stefin A. More suitably the term refers to addition(s) or insertion(s) at, or replacement of, Leu 73 of human stefin A. In one embodiment, the Leu73 mutation may comprise replacement of the whole loop between L73 and L80 with a heterologous peptide sequence. A heterologous peptide sequence may be inserted between amino acids 73 to 80 inclusive.

For example, insertions may be made like this (using the SQT sequence as an example):

(SEQ ID NO: 117)
MIPRGLSEAK　　PATPEIQEIV　　DKVKPQLEEK　　TNETYGKLEA　　VQYKTQVLA

[heterologous peptide sequence in Loop2]S
TNYYIKVRAG　　DNKYMHLKVF　　NGP

[heterologous peptide sequence in Loop4]
[APGQN]ADR　　VLTGYQVDKN　　KDDELTGF

Suitably the heterologous peptide comprises 3 amino acids or more, more suitably 12 amino acids or more, more suitably 20 amino acids or more, more suitably up to 36 amino acids.

Suitably the heterologous peptide comprises 3 to 36 amino acids, more suitably 3 to 20 amino acids, more suitably 3 to 12 amino acids, more suitably 3 to 9 amino acids, more suitably 6 to 36 amino acids, more suitably 6 to 20 amino acids, more suitably 6 to 12 amino acids, more suitably 6 to 9 amino acids, most suitably 9 amino acids.

Thus suitably, Loop 2 has a heterologous peptide sequence inserted between 49 and 50 (49-<heterologous peptide>-50) and Loop 4 has a heterologous peptide sequence inserted between 73 and 78 as residues 74-77 are replaced (73-<heterologous peptide>-78).

A heterologous peptide sequence may be inserted at the G4 site. A heterologous peptide sequence may be inserted at position 4. A heterologous peptide sequence may be inserted proximal to position 4 i.e. between position 4 and the centre of the polypeptide such as between amino acids 4 to 45 inclusive, or between amino acids 4 to 44 inclusive. Suitably the G4 residue is retained. Most suitably the G4 residue is mutated to G4R. Thus suitably a heterologous peptide sequence may be inserted between amino acids 5 to 45 inclusive, or between amino acids 5 to 44 inclusive. More suitably a heterologous peptide sequence may be inserted between amino acids 4 and 5 inclusive, most suitably immediately after amino acid 4, e.g. insertion at position 5.

Heterologous peptide(s) may be inserted in at least one of the following positions in the protein (see for example WO2014/125290 (describing scaffolds such as 'plant adhirons')): the loop between a first and second strand of β-sheet (sometimes known as LOOP1); and/or the loop between a third and fourth strand of β-sheet (sometimes known as LOOP2). In this context, first, second, third and fourth mean relative to the protein sequence, i.e. from the N- to C-terminus of the protein. Suitably heterologous peptides are inserted at both of these positions, i.e. at LOOP1 and LOOP2.

Loop Nomenclature

The secondary structure of the polypeptide/scaffold protein may be modelled using open source software, most suitably using "PPopen" available from the Technical University of Munich, Germany. The numbering of structures such as loops in the polypeptide/scaffold protein of the invention adheres to the systematic naming given using the PPopen software.

It should be noted that prior art documents have used an informal nomenclature. Therefore, disclosures in prior art documents such as WO 2006/131749 and/or WO 2009/136182 and/or WO2014/125290 might mention the informal name "loop 1", which would actually relate to "loop 2" using the systematic naming via PPopen software. The table below sets out the nomenclature of the different structural parts of the protein, and this will be adhered to throughout the text unless otherwise indicated.

Unless otherwise apparent from the context, the following loop nomenclature is adhered to. Amino acid residue numbers are as in, or corresponding to, SEQ ID NO: 1:

| Name | Amino Acid address (SEQ ID NO: 1) |
|---|---|
| N-terminus | 1-13 |
| Helix 1 | 14-30 |
| Loop 1 | 31-37 |
| Strand 1 | 38-48 |
| Loop 2 | 49-51 |
| Strand 2 | 52-59 |
| Loop 3 | 60-62 |
| Strand 3 | 63-70 |
| Loop 4 | 71-78 |
| Strand 4 | 79-85 |
| C-terminus | 86-98 (not inc. GH6 tag) |

As used here, the word "loop" means "connecting regular secondary structure" (i.e. alpha/beta).

Occasionally informal nomenclature is used to relate to particular embodiments of the invention. For example, a preferred scaffold may be referred to as "3 T" or "3 R". The particular makeup of preferred embodiments of the invention is always disclosed with specific reference to mutated residues as set out in the text.

Suitably a population of scaffold polypeptides is created, each with a different heterologous peptide sequence (most suitably one per scaffold polypeptide) ie. a library.

'Heterologous' has its natural meaning i.e. the inserted polypeptide has an amino acid sequence which is heterologous to the stefin A sequence used e.g. the sequence derived from or corresponding to SEQ ID NO: 1. Therefore heterologous may mean from another species, and/or may mean from a polypeptide other than human wild type stefin A (SEQ ID NO: 1). Most suitably the heterologous polypeptide insertion comprises artificial amino acid sequence, most suitably artificial amino acid sequence designed by the operator.

Test heterologous peptide insertions may be used, for example GGS repeats such a nonameric peptide comprising GGSGGSGGS (SEQ ID NO: 92) may be used. This is a particularly demanding peptide because it is entropically very difficult to close. Therefore, by inserting this as a heterologous peptide into a polypeptide/scaffold protein of the invention it is demonstrated that the scaffold performs very well in displaying such a soluble and entropically difficult to close loop. The capacity to display such a loop is a very strong indicator of the stability of the polypeptide/scaffold protein of the invention.

Especially Suitable Sites for Heterologous Peptide Insertion

It should be noted that the most preferred sites for heterologous peptide insertion in the polypeptides/scaffold proteins of the invention are themselves different to the sites disclosed for insertion in prior art disclosures of Stefin A based polypeptides/scaffold proteins.

Single Insertions—Loop 2
48-<heterologous peptide>-50
49-<heterologous peptide>-51
50-<heterologous peptide>-52
Single Insertions—Loop 4
72-<heterologous peptide>-77
73-<heterologous peptide>-78
74-<heterologous peptide>-79

For the avoidance of doubt, "48-<heterologous peptide>-50" means between the amino acid corresponding to position 48 of SEQ ID NO: 1 and the amino acid corresponding to position 50 of SEQ ID NO: 1, and so on. Similarly "72-<heterologous peptide>-77" means between the amino acid corresponding to position 72 of SEQ ID NO: 1 and the amino acid corresponding to position 77 of SEQ ID NO: 1 (with the intervening amino acids being deleted (i.e. replaced by the heterologous peptide insertion), and so on.

Combinations—Double Insertions

Combinations of two insertions, one into Loop 2 and one onto Loop 4, may be made as disclosed in FIG. 1.

Further Combinations

In addition to the specific example insertions mentioned above, single insertions or double insertions may be combined with an additional insertion at the N-terminus of the protein e.g. at or proximal to the G4 site as disclosed above—thereby making double insertions (G4 site+loop 2 or G4 site+loop 4) or triple insertions (G4 site+loop 2+loop 4) as desired.

Most suitably a heterologous peptide is inserted between residues D48 and G50, deleting residue A49 (referred to as "48-<heterologous peptide>-50").

Most suitably a heterologous peptide is inserted between residues L73 and E78, deleting residues P74, G75, Q76 and N77 (referred to as "73-<heterologous peptide>-78").

Most suitably a double insertion is made by inserting a first heterologous peptide at 48-<first heterologous peptide>-50 and a second heterologous peptide at 73-<second heterologous peptide>-78.

First and second heterologous peptides are suitably different from each other.

First and second and third heterologous peptides are suitably different from each other.

Exemplary sequences showing exemplary insertions are below (X=any amino acid; in these examples the heterologous peptide insertions are 9 amino acids long):

(SEQ ID NO: 19)
exemplary scaffold 3r2
MIPGGLSEAKPATPEIQEIVDKVKPQLEKETGKTWGKLEAVEYKTQVD48XXXXXXXXXG50LNYYIKVRVN-

GKYIHLKVFKSL73XXXXXXXXXE78DLVLTGYQVDKNKDDELTGF (SEQ ID NO: 23)
exemplary scaffold 3t4
MIPGGLSEAKPATPEIQEIVDKVKPQLEEKTGETYGKLEAVEYKTQVD48XXXXXXXXXG50TNYYIKVRAGD

NKYIHLKVFKSL73XXXXXXXXXE78DLVLTGYQVDKNKDDELTGF

The specific preferred insertion points taught herein deliver certain additional advantages. These advantages are attributable to the choice of insertion site, and therefore could be advantageously employed on polypeptides/scaffold proteins having mutations different from those disclosed herein. In other words, the disclosure of the specific insertion sites made in this document is a discrete disclosure of an advantageous property provided by a technical feature. Therefore, in one aspect the invention may relate to a polypeptide/scaffold protein such as a Stefin A based polypeptide/scaffold protein having a heterologous peptide (or heterologous peptides) inserted at the specific position (or positions) as disclosed herein. For example, Single insertions—Loop 2: 48-<heterologous peptide>-50; 49-<heterologous peptide>-51; 50-<heterologous peptide>-52; Single insertions—Loop 4-72-<heterologous peptide>-77; 73-<heterologous peptide>-78; 74-<heterologous peptide>-79; Combinations—double insertions—combinations of two insertions, one into Loop 2 and one onto Loop 4, may be made as disclosed in FIG. 1.

Affinity Maturation

Affinity maturation may be carried out by any suitable method known in the art. For example, a "mini-library" may be constructed keeping one heterologous peptide from a binder of interest constant whilst only varying the second or further heterologous peptide insertion(s).

Another approach is to alanine scan the heterologous peptide insertions in order to identify the amino acid(s) which are most important for interaction with the target.

An alternative approach is to carry out "slippy PCR" and to rescreen the resulting variants of the heterologous peptide insertion(s) against the target.

In the wild-type Stefin A, it is understood that one of its binding partners (Cathepsin) binds via all three loops on the relevant surface of the Stefin A molecule. Therefore, another approach to affinity maturation is to introduce heterologous peptide into the third position (the region comprising the G4 residue of Stefin A) at the N-terminal end of the protein and to rescreen the scaffold proteins carrying that set of heterologous peptides against the target.

As described herein, 'd' means 'deletion of'—for example 'dD61' means 'deletion of D61'—this is usually shown as 'ΔD61' (i.e. delta D61), as is common in the art. The residue numbering always follows human wild type SteA i.e. SEQ ID NO: 1.

In other words, when a deletion mutation is made in a polypeptide/scaffold protein according to the invention, then the numbering according to the human wild-type Stefin A protein is still adhered to. For example, if amino acid 61 is deleted, the numbering of that particular embodiment of a polypeptide/scaffold protein of the invention would go from amino acid 60 directly to amino acid 62—in other words, the amino acid numbering is retained compared to the human wild-type Stefin A reference sequence rather than adjusting to consecutively number each of the amino acids present in the particular preferred embodiment of the polypeptide/scaffold protein of the invention. This is conventional and easily understood by the person skilled in the art as is normal in the field of molecular biology.

It should be noted that multiple insertion sites for heterologous peptides are disclosed. Thus, the polypeptide/scaffold protein may comprise a single heterologous peptide insertion, may comprise two heterologous peptide insertions at two different insertion sites (i.e. a single insertion at a first and a second site totalling two heterologous peptide insertions in total), or may comprise three heterologous peptide insertions at three different insertion sites (i.e. a single insertion at a first, second and third site totalling three heterologous peptide insertions in total). Libraries comprising polypeptides/scaffold proteins may comprise a single heterologous peptide insertion per polypeptide/scaffold protein, may comprise two heterologous peptide insertions per polypeptide/scaffold protein, or may comprise three heterologous peptide insertions per polypeptide/scaffold protein.

Embodiments of the invention resulting in a decreased thermostability find application in settings where it is desired to remove functionality of the polypeptide/scaffold protein by thermal treatment. One example is reducing the Tm of an AFFIMER® protein designed to inhibit an enzyme such that allows the enzyme to function by heating it to a set temperature (e.g. a hot-start polymerase). For example, AFFIMER® reagents such as a polypeptide/scaffold protein comprising a heterologous peptide insertion as described herein may be used to inhibit thermostable nucleic acid polymerase. These find application in PCR reaction mixtures. For example, it may be useful to produce an AFFIMER® reagent e.g. a polypeptide/scaffold protein according to the invention which inhibits the exonuclease function of thermostable nucleic acid polymerase. This is especially useful when primers are premixed into a PCR reaction mixture and then stored until used. If the exonuclease function of the thermostable nucleic acid polymerase is not inhibited, then that exonuclease function can degrade the primers in the reaction mixture. However, by including a polypeptide/scaffold protein according to the invention capable of inhibiting the exonuclease function of that polymerase into the reaction mixture, this drawback in prior art reaction mixtures can be avoided. In this scenario, it is important that the polypeptide/scaffold protein can be de-functionalised (such as denatured) in order to allow the PCR reaction to proceed.

Thus, suitably the polypeptide/scaffold protein used in this application has a decreased thermal stability so that it is degraded (such as denatured) during a first thermal cycle of the PCR reaction and thereby the inhibition of the exonuclease function of the thermostable polymerase is removed allowing the reaction to proceed.

Another example is an affinity ligand that could be co-eluted with the target protein but then removed (or its function removed) by a heating step where the AFFIMER® protein is designed to have a lower Tm than the target protein.

Fluorescence

In can be useful to exchange aromatic amino acids in the protein such as phenylalanine for alternative aromatic amino acids displaying fluorescence and/or absorbance at 280 nm properties. For example, phenylalanine may be mutated to tyrosine (which has weak fluorescence properties) or may be mutated to tryptophan (which has strong fluorescence properties). There are eight possible sites for these mutations within wild-type Stefin A. These have been tested by the inventors. The mutations and their usefulness in these applications are indicated in the table below.

| Aromatic residue variants of human stefin A | | | |
| --- | --- | --- | --- |
| Variant | Improved absorbance | Improved transition in intrinsic fluorescence properties upon unfolding[1] | Stability (Tm, °C.)[2] |
| Y35W | Yes | Best | 75 |
| Y43W | Yes | Best | 68 |
| Y53W | Yes | Best | 66 |
| Y54W | Yes | Good | 71 |
| Y64W | Yes | Good | 74 |
| F70W | Yes | Good | 73 |
| Y85W | Yes | Good | 75 |
| F98W | Yes | No | N/A |
| F70Y | Marginal | No | N/A |
| F98Y | Marginal | No | N/A |

[1]As judged by Optim thermal ramps.
[2]Measured using intrinsic fluorescence during Optim thermal ramp.

From this it can be concluded that certain of the above mutations are useful for absorbance at 280 nm, for example in determining protein concentrations. Moreover, certain mutations may be useful to introduce fluorescence which is helpful in monitoring changes in conformation of the protein such as protein unfolding.

More suitably the polypeptide of the invention comprises a substitution relative to SEQ ID NO: 1 selected from the group consisting of Y35W, Y43W, Y53W, Y54W, Y64W, F70W or Y85W. These all have good fluorescence properties.

Suitably the polypeptide of the invention comprises a substitution relative to SEQ ID NO: 1 selected from the group consisting of Y35W, Y43W and Y53W. These have the best fluorescence properties.

According to the above table, the most preferred mutation in a polypeptide/scaffold protein according to the invention would be Y35W. This has the advantages of being the least destabilising of the mutations and also offering the best spectra for analysis.

It should be noted that each tryptophan introduced into the polypeptide/scaffold protein of the invention is to some degree destabilising. This would be advantageous when considering embodiments of the invention resulting in reduced thermal stability. Alternatively, the reduced stability effect of these mutations may be ameliorated by making other mutations to increase the thermal stability as is taught throughout this application in detail. Therefore, in some embodiments the polypeptide/scaffold protein of the invention may comprise both stabilising and destabilising mutations depending on the aims or priorities for that particular polypeptide/scaffold protein.

It is an advantage of the N32G mutation that a particularly strong increase in thermal stability is delivered, for example an approximately 3° C. increase.

It is an advantage of the preferred M65I mutation that an especially strong increase in thermal stability is delivered of +6° C.

It is noted that the description of each mutation described herein as increasing the thermal stability of the polypeptide/scaffold protein of the invention is itself novel.

It should be noted that Cystatin C is only distantly related to the sequence of Cystatin A (Stefin A). Cystatin C is naturally a dimer, is a longer protein and has a low sequence identity level compared to Stefin A. The Cystatin fold is similar between Cystatin A and Cystatin C, but these proteins share only one region of homology corresponding to amino acids 49 to 95 of Cystatin C which correspond to amino acid positions 16 to 60 of Cystatin A. Over this region of relatedness, only 13/47 amino acids are identical corresponding to a sequence identity of 28%.

Subsets of Mutations

Mutation(s) from one group may be chosen to increase packing of the hydrophobic core.

Mutation(s) from one group may be chosen to increase charge interactions on the surface of the polypeptide/scaffold protein.

Mutation(s) from one group may be chosen to increase the geometry of a particular turn in the polypeptide structure. By "increase" we mean to make the turn energetically more favourable, for example energetically more stable. An example of one such mutation is deletion of D61 (ΔD61).

Mutation(s) from one group may be chosen to increase stability whilst still operating within the constraints of the three-dimensional structure for example at the end of β turns. More specifically, mutations may be carefully chosen to preserve the I—I+4 hydrogen bonding arrangements at the end of certain β turns.

Mutation(s) from one group may be chosen to improve stability whilst advantageously changing the type of turn in the three-dimensional structure of the protein. For example, mutations may be made to change from a Type-1 to a Type-2 β turn if desired.

It should be noted that there is a comprehensive teaching in this application of the mutations which are useful in providing the disclosed technical features and advantages. For example, with reference to mutation at position Q42, mutating from E to D is widely regarded as a conservative substitution since this effectively drops only a single methylene group from the side chain of the amino acid. However, as can be seen from the data included in this application, a Q42E mutation provides an increase in thermal stability of +3° C., whereas a Q42D mutation provides a decrease in thermal stability of −3° C. Therefore, a seemingly conservative substitution providing a seemingly tiny change to the structure of the amino acid residue at this position can provide a dramatic difference of 6° C. between the Tm's of the two polypeptide/scaffold protein variants. Therefore, the data in this application support unity of invention between each of the different mutations disclosed since they have been carefully chosen, designed and tested as well as demonstrated to each provide the same single special technical effect. Moreover, the claims of this application are limited to only variants known and proven to have and to deliver that known special technical effect. For this reason, the diverse mutations described in the appended claims do indeed relate only to a single invention and meet the requirements of unity.

In all instances, mentions of "increase" or "decrease" of stability, for example as reflected by increases or decreases in the Tm of particular polypeptides/scaffold proteins, are quoted relative to human Stefin A i.e. the properties of the wild-type human Stefin A polypeptide having the amino acid sequence as shown in SEQ ID NO: 1. Similarly, all mutations are described with reference to the same wild-type human Stefin A sequence SEQ ID NO: 1.

The following groups of mutations are especially advantageous for the following reasons.

Solvent Exposed
- Mutations at these positions improve the network of charges on the protein's surface, helping to make it more stable. It can be easier to make charge changing amino acid substitutions on the surface of the Stefin A protein, which is advantageous. In addition, mutating residues on the protein surface can allow more freedom in the choice of substitutions. In addition, it is an advantage that the corresponding structural changes can be more predictable when altering residues on the protein surface compared to other locations.

One or more substitutions of solvent exposed residues may be selected from the group consisting of:
(E29K K30E E33K), N32G, N90T, K63R, T34V, T34K and T34R.

It is to be noted that throughout the text where a group of mutations is bracketed together (e.g. "(E29K K30E E33K)"), suitably those mutations are made together i.e. simultaneously as a group/as a single option from the list given.

In particular, N32G offers improved stability of the helix.
In particular, K63R extends chain resulting in increased hydrophobic moiety, repositioning of charged atom.

Partially Buried
- Mutating these residues advantageously adds extra hydrophobic mass/area to the core of the protein. This increases the amount of hydrophobic interactions in the core of the protein. This has the advantage of improving the stability of the protein.
- With regard to "Aliphatic chain extension" mutations, those advantageously add larger side chains, which again advantageously add extra hydrophobic mass to the core of the protein.

One or more substitutions of partially buried residues may be selected from the group consisting of:
Q42E, T51I, T51V, T51L and T51F.

Additional advantageous properties shared by particular subgroups of substitutions are set out below:
Aliphatic chain extension
T51I, T51L, T51F
Amphipathic to aliphatic
T51I, T51V, T51L
Amphipathic to aromatic
T51F
Amine to acid
Q42E
With reference to the Q42E mutation, this advantageously keeps the chain length of the amino acid residue the same, and advantageously enables a change in chemistry to be isolated from the change to the overall size of the amino acid side chain.

Hydrophobic Core (Tertiary Structure)
These mutations increase burial of hydrophobic moieties, and therefore have the advantage of increasing stability in this manner.

One or more substitutions of hydrophobic core (tertiary structure) residues may be selected from the group consisting of:
T45V, T45I, A59V, A59I, A59L, M65V and M65I.

Additional advantageous properties shared by particular subgroups of substitutions are set out below:
Chain extension
T45I, A59V, A59I, A59L
Amphipathic to aliphatic
T45V, T45I
Beta-branching
M65V, M65I, A59V, A59I
With regard to "chain extension" mutations, these add additional hydrophobic contacts and therefore help to increase the stability further. This is especially true of longer and/or branched side chains in the amino acids which are introduced. Moreover, certain mutations remove polar groups from the amino acid residues and result in completely hydrophobic residue whereas the wild-type might have been amphipathic.

Without wishing to be bound by theory, it is believed that the gain in stability is due to the relative instability of exposed hydrophobic moieties in an unfolded state compared to the buried hydrophobic sidechains in the folded state. Therefore, provided a good packing occurs in the core of the folded state, the more hydrophobic parts the more stable the native state will be relative to the unfolded state—which is what we measure with Tm (a proxy for Gibbs free energy of folding (DG)). Thus the stability gain comes from maximising the amount of hydrophobics that are buried by packing with other hydrophobics efficiently.

With regard to both partially buried and hydrophobic core (tertiary structure) groups of mutations, these share the common property of advantage of tending to have more contacts within the protein structure. The effect of targeting these residues is that potentially larger effects on protein stability can be gained by a smaller number of substitutions compared to targeting other parts of the protein. Therefore, these groups of mutations together form a superset of substitutions all sharing the same single special technical feature.

Secondary Structure
It should be noted that deletion of amino acid 61 converts the 5 amino acid patch from residue 59 to 63 into a sequence consistent with a canonical β turn motif. This 4 amino acid motif created by the deletion of amino acid 61 presents a canonical β turn motif. This innovative approach taken by the inventors takes advantage of the existing residues in the wild-type protein to make considerable changes to the stability whilst enabling minimal mutation of the starting polypeptide. An advantage delivered by the group of mutations is the advantage of stabilising turns in the protein (and/or stabilising the helix in the case of N32G). In either case, targeting these residues delivers the advantage of promoting stable hydrogen bonding throughout the affected region of the protein, and thereby advantageously increasing stability.

One or more substitutions of secondary structure residues may be selected from the group consisting of:
N32G, $^{59}$AN-GK, $^{59}$IN-GK, $^{59}$VN-GK, $^{59}$LN-GK, $^{59}$AG-NK, $^{59}$VG-NK, A59V, A59I, A59L, T34K and T34R.

It is to be noted that throughout the text where a group of mutations is presented as a pair (e.g. "$^{59}$AN-GK"), suitably those mutations are made together i.e. simultaneously as a pair/as a single option from the list given.

Additional advantageous properties shared by particular subgroups of substitutions are set out below:

C-terminal helix cap
N32G, T34K, T34R
Turns
A59V, A59I, A59L, $^{59}$AN-GK, $^{59}$IN-GK, $^{59}$VN-GK, $^{59}$LN-GK, $^{59}$AG-NK, $^{59}$VG-NK
Type 1' (type 1 prime)
$^{59}$AN-GK, $^{59}$IN-GK, $^{59}$VN-GK, $^{59}$LN-GK
Type II' (type 2 prime)
$^{59}$AG-NK, $^{59}$VG-NK
Increased strand propensity
T45V, T45I, M65V, M65I
Charge—Charge Interactions
These mutations deliver the technical advantage of improving charge interactions and thereby increasing stability.

One or more substitutions of charge-charge interaction residues may be selected from the group consisting of:
Q42E, (E29K K30E E33K), T34K and T34R.

Additional advantageous properties shared by particular subgroups of substitutions are set out below:
Surface
(E29K K30E E33K), T34K, T34R
Partially buried
Q42E
Acidic to basic and vice versa (E29K K30E E33K)

Amine to acid

Q42E

Polar to basic

T34R, T34K

In the particular case of Q42E, this improves the surface charge network. Without wishing to be bound by theory, Q42E adds charge and is believed to enables a salt bridge (most likely to a lysine residue) which is otherwise too far away in three-dimensional space of the protein to form such an interaction. A salt bridge is typically considered to be a charge-charge interaction between atoms less than or equal to 4 Å apart. Thus it is believed that this mutation promotes formation of a salt bridge from Q42E to a Lys.

Location

It is advantageous that the overwhelming majority of substitutions taught herein are on the reverse face of the Stefin A based polypeptide/scaffold protein, i.e. the non-binding end of the protein. This is a surprise to the inventors. The expectation would be that the mutations would be scattered throughout the sequence of the polypeptide. However, the teachings presented are that by targeting the reverse face of the protein, significant gains in stability can be made whilst leaving the binding end of the protein unmutated or only minimally mutated.

One or more substitutions of residues in particular locations may be selected from the group consisting of:

T51, A59, M65, N32, Q42, N90, K63, $^{59}$AN-GK, $^{59}$IN-GK, $^{59}$VN-GK, $^{59}$LN-GK, $^{59}$AG-NK, $^{59}$VG-NK and T34.

When it is desired to restrict the mutations to a particular location within the polypeptide, this may be advantageously accomplished by selecting mutation(s) from one of the individual groups set out below.

Obverse face (binding end)

T51.

Reverse face (non-binding end)

A59, M65, N32, Q42, N90, K63, $^{59}$AN-GK, $^{59}$IN-GK, $^{59}$VN-GK, $^{59}$LN-GK, $^{59}$AG-NK, $^{59}$VG-NK and T34.

In this regard, it should be noted that in the comprehensive analysis conducted by the inventors that every residue in the hydrophobic core of the protein was individually studied. It is surprising to the inventors that the most useful stability enhancing mutations are concentrated in the reverse face region of the protein.

Post Translational Modification

An additional advantage of certain of these mutations is to promote chemical stability of the molecule. For example, methionine residues can be oxidised, whereas valine/isoleucine residues cannot. Therefore, the mutations taught by the inventors have the additional advantage of avoiding oxidation at this point in the protein, which is undesirable, and so advantageously deliver a molecule which is resistant to changes which might otherwise be brought about by oxidation.

One or more substitutions of post-translational modification residues may be selected from the group consisting of:

N32G, M65V, M65I, T34V, T34K, and T34R.

When it is desired to eliminate a particular type of post-translational modification, this may be advantageously accomplished by selecting mutation(s) from one of the individual groups set out below:

Potential glycosylation

N32G, T34V, T34K, T34R

Potential oxidation

M65V, M65I

It should be further noted that the N32G mutant also removes the risk of deamidation. Degradation of N residues by deamidation can be a problem—this mutation advantageously removes such a problem. The same applies to Q42E, since Q residues are also prone to deamidation.

Potential deamidation

N32G, Q42E

Different Between hSteA and SQT

It should be noted that N90T may be part of the turn at this region of the protein, and therefore delivers a further advantage of stabilising that turn.

Exemplary Scaffolds

Exemplary Scaffolds for Research Applications named 3r(esearch) scaffolds:

3r1—hSteA Y35W N32G V48D M65I Q42E T51L (A59V ΔD61) (E29K K30E E33K)

3r2—hSteA Y35W N32G V48D M65I Q42E T51L (A59V G60N ΔD61 N62G) (E29K K30E E33K)

Exemplary Scaffolds for Therapeutic Applications named 3t(herapeutic) scaffolds:

3t1—hSteA N32G V48D

3t2—hSteA N32G V48D M651

3t3—hSteA N32G V48D M65I T51L

3t4—hSteA N32G V48D M65I Q42E

3t5—hSteA N32G V48D M65I Q42E T51L

Having regard to the standard/conventional nomenclature used herein, the sequences of the full scaffold proteins are disclosed with reference to SEQ ID NO: 1 and the stated mutations. However, for illustration purposes, the following are representative examples of preferred scaffold protein sequences:

```
3r1 with 2 heterologous peptide insertions. In this example n = 9: SEQ ID NO: 18
MIPGGLSEAKPATPEIQEIVDKVKPQLEKETGKTWGKLEAVEYKTQVD(Xn)GLNYYIKVRVGNKYIHLKVFKS L(Xn)EDLVLTGYQVDKNKDDELTGF 3r2 with 2 heterologous peptide insertions. In this example n = 9: SEQ ID NO: 19
MIPGGLSEAKPATPEIQEIVDKVKPQLEKETGKTWGKLEAVEYKTQVD(Xn)GLNYYIKVRVNGKYIHLKVFKS L(Xn)EDLVLTGYQVDKNKDDELTGF 3t1 with 2 heterologous peptide insertions. In this example n = 9: SEQ ID NO: 20
MIPGGLSEAKPATPEIQEIVDKVKPQLEEKTGETYGKLEAVQYKTQVD(Xn)GTNYYIKVRAGDNKYMHLKVF KSL(Xn)EDLVLTGYQVDKNKDDELTGF 3t2 with 2 heterologous peptide insertions. In this example n = 9: SEQ ID NO: 21
MIPGGLSEAKPATPEIQEIVDKVKPQLEEKTGETYGKLEAVQYKTQVD(Xn)GTNYYIKVRAGDNKYIHLKVFK SL(Xn)EDLVLTGYQVDKNKDDELTGF 3t3 with 2 heterologous peptide insertions. In this example n = 9: SEQ ID NO: 22
MIPGGLSEAKPATPEIQEIVDKVKPQLEEKTGETYGKLEAVQYKTQVD(Xn)GLNYYIKVRAGDNKYIHLKVFK SL(Xn)EDLVLTGYQVDKNKDDELTGF 3t4 with 2 heterologous peptide insertions. In this example n = 9: SEQ ID NO: 23
MIPGGLSEAKPATPEIQEIVDKVKPQLEEKTGETYGKLEAVEYKTQVD(Xn)GTNYYIKVRAGDNKYIHLKVFK SL(Xn)EDLVLTGYQVDKNKDDELTGF 3t5 with 2 heterologous peptide insertions. In this example n = 9: SEQ ID NO: 24
MIPGGLSEAKPATPEIQEIVDKVKPQLEEKTGETYGKLEAVEYKTQVD(Xn)GLNYYIKVRAGDNKYIHLKVFKS L(Xn)EDLVLTGYQVDKNKDDELTGF
``` wherein X is any amino acid,
and wherein n is an integer number from 0 to 36.
Most suitably n is 9.

Cystatin A or Cystatin B

Human Stefin A belongs to family 1 of the cystatin superfamily. Cystatin As and Cystatin Bs are different. Cystatin Bs typically have a near neutral pI and have a cysteine residue near the C-terminus. It is believed that all cystatin Bs have this cysteine and all Cystatin Bs form disulfide bonded dimers, whereas Cystatin As have a more acidic pI and no Cystatin As have this C-Terminal cysteine.

Nucleic Acids, Promoters, Libraries, Host Cells

Manufacture/production of recombinant polypeptides and/or nucleic acids according to the present invention is well known to the person skilled in the art and requires only routine knowledge such as how to synthesise polypeptide or polynucleotide, and/or how to express a polynucleotide to produce a polypeptide in the laboratory or a scaled-up commercial bioreactor. Numerous companies around the world offer such routine production services and require only an indication of the sequence(s) to be produced.

Host cells, vectors for expression of polypeptide(s) according to the invention, promoters for use in such systems and the codon optimisation (if any) of the nucleic acid(s) encoding them are all well known to the person skilled in the art. Choice of particular vectors such as phage, phagemids, plasmids, or of promoters or host cells or other such 'tools' for production of the polypeptides or libraries described herein is a matter for the skilled person working the invention. Similarly, PCR or cloning strategies, ligations, transformation/electroporation techniques are all routine and do not form part of the invention but are determined by the operator.

In case further guidance is needed, general molecular biological techniques are well known in the art, for example as in (2000 Current Protocols in Molecular Biology F. M. Ausubel et al, Eds. ISBN: 978-0-471-50338-5 published by John Wiley & Sons Ltd, Oldlands Way, Bognor Regis, West Sussex, PO22 9NQ, UK).

Exemplary Cell Strains

TG1 (Lucigen, catalogue number 60502-2)
ER2738 (New England Biolabs, catalogue number E4104)

Exemplary Phage Strain

M13KO7 (New England Biolabs, catalogue number N0315)

Exemplary Phagemid Vector pUC119 (Clontech, catalogue number 3319), which contains the lac promoter Exemplary Promoter lac promoter (see above)

The polypeptide/scaffold protein of the invention may further comprise a tag, such as for purification e.g. a 6 his tag, MBP (maltose binding protein) tag, or any other suitable sequence to aid purification.

The polypeptide/scaffold protein of the invention may further comprise a linker, such as a glycine linker, for joining to another polypeptide.

The polypeptide/scaffold protein of the invention may further comprise a detection sequence, such as for detection by an antibody, e.g. a myc tag or flag tag or any other suitable sequence to facilitate detection.

The polypeptide/scaffold protein of the invention may be labelled, such as with a fluorescent label joined to the polypeptide/scaffold protein.

The polypeptide/scaffold protein of the invention may be joined to a carrier protein such as a transport protein to facilitate entry into cells.

The polypeptide/scaffold protein of the invention may be joined to a targeting protein such as an antibody or fragment thereof, or an aptamer, or AFFIMER® reagent, so as to direct the polypeptide/scaffold protein to a particular location such as to attach it to a target cell or any other entity to which the targeting protein is capable of binding.

The polypeptide/scaffold protein of the invention may be attached to a substrate or structure for example a bead, or nanosphere, or an electrode (for example as part of an array of electrodes), or a membrane (such as nitrocellulose membrane), or a reaction vessel such as an ELISA plate or microcentrifuge tube or any other such article.

Suitably the polypeptide/scaffold protein of the invention may be immobilised.

Joining of the polypeptide/scaffold protein to other moieties may be by any suitable means known in the art, for example by covalent joining, by disulfide bridging, by preparation as a single polypeptide (fusion protein), by conjugation to suitable amino acid residue(s) such as cysteine residue(s), joining to the N- or C-terminus of the polypeptide or any other suitable means known in the art.

Making Polypeptide(s)

Also disclosed is a method of making a polypeptide having an altered stability such as an increased thermal stability or a decreased thermal stability compared to SEQ ID NO: 1, said method comprising synthesising a polypeptide comprising one or more substitution(s) relative to SEQ ID NO: 1 selected from the group consisting of:

A12I,A12V,I16L,V20A,V20I,V20L,Q26E,E29M,
T31K,N32G,N32D,N32H,T34V,T34R,T34K,T34D,
T34P,L38A,L38V,L38F,A40I,A40V,Q42E,Q42D,
T45I,T45V,V48E,V48D,V48G,V48A,V48L,G50S,
T51F,T51V,T51L,T51I,T51A,A59L,A59I,A59V,
K63R,M65V,M65I,L67I,N90T,(V20I,L38A),
(V20L,L38A),(V20I,L38V),(V20L,L38V),
(E29K,K30E,E33K),(Y54D,T83D,Q86E),
(A59L,G60N,D61G,N62K),(A59V,D61N,N62K),
(G60N,D61G,N62K),(G60N,ΔD61,N62G),
ΔD61,(A59L,G60N,ΔD61,N62G),
(A59V,G60N,D61G,N62K),(A59I,G60N,D61G,N62K),
(A59I,G60N,ΔD61,N62G),(A59V,G60N,ΔD61,N62G),
(A59V,ΔD61),(G60P,ΔD61,N62P),
(G60P,D61P,N62K),(G60P,ΔD61,N62G),
(G60P,D61G,N62K),(D61N,N62K), and
(T83D,Q86E); more suitably the substitution(s) are selected from the group consisting of:
A12I,A12V,I16L,V20I,V20L,Q26E,E29M,T31K
N32G,N32D,N32H,T34V,T34R,T34D,T34P,L38A
L38V,A40I,A40V,Q42D,T45I,T45V,V48E,V48G
V48A,T51F,T51V,T51L,T51A,A59L,A59I,M65V
L67I
(V20I,L38A),(V20L,L38A),(V20I,L38V),(V20L,L38V)
(E29K,K30E,E33K),(Y54D,T83D,Q86E)
(A59L,G60N,D61G,N62K),(A59V,D61N,N62K)
(G60N,D61G,N62K),(G60N,ΔD61,N62G)
ΔD61,(A59L,G60N,ΔD61,N62G)
(A59V,G60N,D61G,N62K),(A59I,G60N,D61G,N62K)
(A59I,G60N,ΔD61,N62G),(A59V,G60N,ΔD61,N62G)
(A59V,ΔD61),(G60P,ΔD61,N62P)
(G60P,D61P,N62K),(G60P,ΔD61,N62G)
(G60P,D61G,N62K),(D61N,N62K) and
(T83D,Q86E).

Also disclosed is a method of making a polypeptide having an altered stability such as an increased thermal stability compared to SEQ ID NO: 1, said method comprising synthesising a polypeptide comprising one or more substitution(s) relative to SEQ ID NO: 1 selected from the group consisting of:

E29M,N32G,T34V,T34R,T34K,Q42E,T45I,T45V
G50S,T51F,T51V,T51L,T51I,A59L,A59I,A59V
K63R,M65V,M65I,L67I,N90T
(E29K,K30E,E33K),(A59L,G60N,D61G,N62K)
(A59V,D61N,N62K),(G60N,D61G,N62K)
(G60N,ΔD61,N62G),ΔD61
(A59L,G60N,ΔD61,N62G),(A59V,G60N,D61G,N62K)
(A59I,G60N,D61G,N62K),(A59I,G60N,ΔD61,N62G)
(A59V,G60N,ΔD61,N62G), and (A59V,ΔD61); more suitably the substitution(s) are selected from the group consisting of:
E29M,N32G,T34V,T34R,T45I,T45V,T51F,T51V
T51L,A59L,A59I,M65V,L67I
(E29K,K30E,E33K),(A59L,G60N,D61G,N62K)
(A59V,D61N,N62K),(G60N,D61G,N62K)
(G60N,ΔD61,N62G),ΔD61
(A59L,G60N,ΔD61,N62G),(A59V,G60N,D61G,N62K)
(A59I,G60N,D61G,N62K),(A59I,G60N,ΔD61,N62G)
(A59V,G60N,ΔD61,N62G), and (A59V,ΔD61).

Also disclosed is a method of making a polypeptide having an altered stability such as a decreased thermal stability compared to SEQ ID NO: 1, said method comprising synthesising a polypeptide comprising one or more substitution(s) relative to SEQ ID NO: 1 selected from the group consisting of:

A12I,A12V,I16L,V20A,V20I,V20L,Q26E,T31K
N32D,N32H,T34D,T34P,L38A,L38V,L38F,A40I
A40V,Q42D,V48E,V48D,V48G,V48A,V48L,T51A
(V20I,L38A),(V20L,L38A),(V20I,L38V),(V20L,L38V)
(Y54D,T83D,Q86E),(G60P,ΔD61,N62P)
(G60P,D61P,N62K),(G60P,ΔD61,N62G)
(G60P,D61G,N62K),(D61N,N62K) and
(T83D,Q86E); more suitably the substitution(s) are selected from the group consisting of:
A12I,A12V,I16L,V20I,V20L,Q26E,T31K,N32D
N32H,T34D,T34P,L38A,L38V,A40I,A40V,Q42D
V48E,V48G,V48A,T51A
(V20I,L38A),(V20L,L38A),(V20I,L38V),(V20L,L38V)
(Y54D,T83D,Q86E),(G60P,ΔD61,N62P)
(G60P,D61P,N62K),(G60P,ΔD61,N62G)
(G60P,D61G,N62K),(D61N,N62K) and
(T83D,Q86E).

Suitably the step of synthesising comprises preparing a nucleic acid encoding said polypeptide and arranging for translation of said nucleic acid to produce the polypeptide. Suitably the nucleic acid may be comprised by a phage genome, such as one or more members of a phage display library.

Additional Mutations

There may be an additional advantage to making one or more further mutations selected from the group consisting of:

G4R,E18Q,P25S,N32Q,T34E,T34Q,G36E,M65F
M65L,E78A, (K91E,D92K), (K91P,D93G), NPDG

It should be noted that this group of mutations share the property of each contributing a small effect on the thermal stability. Care must be taken in measuring these if measured individually, as the experimental error in the measurements might give an indication of low effect, or even of no effect or a small reversal of effect (e.g. rather than showing as +0.5° C. the effect might show as zero or as −0.2° C. when the experimental error on individual measurements is within +/−0.7 C of ° C. change). This is the case with all scientific measurements when experimental error approaches or exceeds the magnitude of the effect being measured.

Regarding the NPDG mutation beginning at amino acid 90 ('90NPDG'), this increases the statistical likelihood of forming a Type 1 turn at this point in the protein, and thereby increases stability via this mechanism.

Small Effect—Increase in Thermal Stability
G4R+0.05° C.
E18Q+0.57° C.
P25S+0.01° C.
N32Q+0.37° C.
T34Q+0.29° C.
G36E+0.18° C.
M65F+0.19° C.
E78A+0.50° C.
(K91E, D92K)+0.56° C.
(K91P, D93G)+0.22° C.
90NPDG+0.7° C.
(N90 K91P D92 D93G)+0.22° C.
Small Effect—Decrease in Thermal Stability
T34E−0.39° C.
M65L−0.23° C.
PK Effects In certain embodiments, the polypeptide, such as an AFFIMER® polypeptide, comprises a polypeptide portion, such as an AFFIMER® polypeptide portion, that binds a target moiety, preferably a protein, more preferably a human protein, as a monomer with a dissociation constant ($K_D$) of about 1 µM or less, about 100 nM or less, about 40 nM or less, about 20 nM or less, about 10 nM or less, about 1 nM or less, or about 0.1 nM or less.

In certain embodiments, the polypeptide, such as an AFFIMER® polypeptide, comprises a polypeptide portion, such as an AFFIMER® polypeptide portion, that binds a target moiety, preferably a protein, more preferably a human protein, as a monomer with an off-rate constant ($k_{off}$), such as measured by Biacore, of about $10^{-3}$ s$^{-1}$ (i.e., unit of 1/second) or slower; of about $10^{-4}$ s$^{-1}$ or slower or even of about $10^{-5}$ s$^{-1}$ or slower.

In certain embodiments, the polypeptide, such as an AFFIMER® polypeptide, comprises a polypeptide portion, such as an AFFIMER® polypeptide portion, that binds a target moiety, preferably a protein, more preferably a human protein, with an on-rate constant ($k_{on}$), such as measured by Biacore, of at least about $10^3$ M$^{-1}$ s$^{-1}$ or faster; at least about $10^4$ M$^{-1}$ s$^{-1}$ or faster; at least about $10^5$ M$^{-1}$ s$^{-1}$ or faster; or even at least about $10^6$ M$^{-1}$ s$^{-1}$ or faster.

In certain embodiments, the polypeptide, such as an AFFIMER® polypeptide, comprises a polypeptide portion, such as an AFFIMER® polypeptide portion, that binds a target moiety having a cognate binding partner, preferably a protein, more preferably a human protein, as a monomer with an IC50 in a competitive binding assay with cognate binding partner of 1 µM or less, about 100 nM or less, about 40 nM or less, about 20 nM or less, about 10 nM or less, about 1 nM or less, or about 0.1 nM or less.

Advantages

It is an advantage of the invention that a scaffold with excellent expression properties is provided.

It is an advantage of the invention that a scaffold with modest or reduced immunogenicity (low immunogenicity) is provided.

It is an advantage of the invention that the polypeptides/scaffold proteins described do not suffer from problems of aggregation/precipitation. In more detail, the scaffolds of the invention are observed not to aggregate/precipitate before they unfold, thus when the scaffold of the invention has an increased Tm relative to hSteA, that scaffold also advantageously possesses an increased resistance to aggregation/precipitation.

It is an advantage of the polypeptides/scaffold proteins described that they accept heterologous peptide insertions.

It is an advantage of the polypeptides/scaffold proteins of the invention that heterologous peptide insertions are properly displayed.

It is an advantage of the invention that the polypeptides/scaffold proteins described are not negatively affected regarding stability/protease resistance by the mutations which are introduced. In other words, the polypeptides/scaffold proteins of the invention advantageously retain their stability and/or protease resistance. This is another advantageous property of the particular mutations taught herein.

FURTHER EMBODIMENTS

Also disclosed is use of a scaffold as described above in research applications such as screening for peptide(s) capable of binding a particular target, and/or screening for peptide(s) having particular activity/activities.

Also disclosed is use of a scaffold as described above in medical applications such as targeting compound(s) to particular cells or locations within the body, and/or use in inhibiting or promoting particular metabolic activities.

Also disclosed are compositions such as pharmaceutical compositions comprising polypeptide(s)/scaffold protein(s) as described above.

Also disclosed is a composition comprising one or more polypeptide(s)/scaffold protein(s) as described above together with a pharmaceutically acceptable carrier, diluent or excipient.

Also disclosed is use of a polypeptide/scaffold protein as described above as a diagnostic, a therapeutic, a biomarker, an agent to specifically detect a biomarker, a rational drug design template, a target or reagent for drug discovery, an antibody substitute, an aptamer, an AFFIMER® reagent, or a research tool.

Also disclosed is use of a polypeptide as described above as a scaffold protein.

In one embodiment described is a polypeptide, such as an AFFIMER® polypeptide, comprising an amino acid sequence having at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 3 (canine wild type SteA);

characterised in that said polypeptide comprises one or more mutations relative to SEQ ID NO: 3 selected from the group consisting of:

T51L, T51V, M65V, N32G, A59I, L38A, V20I, A40I, L38V, A12I, A12V, I16L, V20L, Q26E, E29M, T31K, N32D, N32H, T34V, T34R, T34D, T34P, A40V, Q42D, T45I, T45V, V48E, V48G, V48A, T51F, T51A, A59L, L67I, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P,

N62K), (G60P, ΔD61, N62G), (G60P, D61G, N62K), (D61N, N62K) and (T83D, Q86E).

Suitably said one or more mutations relative to SEQ ID NO: 1 is or are selected from the group consisting of:
T51L, T51V, M65V, N32G, A59I, E29M, T34V, T34R, T45I, T45V, T51F, A59L, L67I, (E29K, K30E, E33K), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), and (A59V, ΔD61);

preferably wherein said polypeptide has a Tm higher than the Tm of SEQ ID NO: 3; more preferably higher than the Tm of SEQ ID NO: 1. In another embodiment suitably said one or more mutations relative to SEQ ID NO: 1 is or are selected from the group consisting of:
L38A, V20I, A40I, L38V, A12I, A12V, I16L, V20L, Q26E, T31K, N32D, N32H, T34D, T34P, A40V, Q42D, V48E, V48G, V48A, T51A, (V20I, L38A), (V20L, L38A), (V20I, L38V), (V20L, L38V), (Y54D, T83D, Q86E), (G60P, ΔD61, N62P), (G60P, D61P, N62K), (G60P, ΔD61, N62G), (G60P, D61G, N62K), (D61N, N62K) and (T83D, Q86E);

preferably wherein said polypeptide has a Tm lower than the Tm of SEQ ID NO: 3, more preferably lower than the Tm of SEQ ID NO: 1.

In another embodiment described is a polypeptide, such as an AFFIMER® polypeptide, comprising an amino acid sequence having at least 80% identity to amino acid residues 1 to 11, 13 to 15, 17 to 19, 21 to 25, 27 to 28, 35 to 37, 39, 41, 43 to 44, 46 to 47, 49 to 50, 52 to 53, 55 to 58, 63 to 64, 66, 68 to 82, 84 to 85, and 87 to 98 of SEQ ID NO: 3;
wherein said polypeptide comprises at least one heterologous peptide insertion;
characterised in that said polypeptide comprises one or more mutations relative to SEQ ID NO: 1 selected from the group consisting of:
M65I, T51I, T51L, T51V, M65V, A59V, N32G, A59I, L38A, V20A, V20I, A40I, L38V, G50S, L38F, A12I, A12V, I16L, V20L, Q26E, E29M, T31K, N32D, N32H, T34V, T34R, T34K, T34D, T34P, A40V, Q42E, Q42D, T45I, T45V, V48E, V48D, V48G, V48A, V48L, T51F, T51A, A59L, K63R, L67I, N90T, (V20I, L38A), (V20L, L38A), (V20I, L38V), (V20L, L38V), (E29K, K30E, E33K), (Y54D, T83D, Q86E), (A59L, G60N, D61G, N62K), (A59V, D61N, N62K), (G60N, D61G, N62K), (G60N, ΔD61, N62G), ΔD61, (A59L, G60N, ΔD61, N62G), (A59V, G60N, D61G, N62K), (A59I, G60N, D61G, N62K), (A59I, G60N, ΔD61, N62G), (A59V, G60N, ΔD61, N62G), (A59V, ΔD61), (G60P, ΔD61, N62P), (G60P, D61P, N62K), (G60P, ΔD61, N62G), (G60P, D61G, N62K), (D61N, N62K), and (T83D, Q86E);
wherein said heterologous peptide insertion comprises a heterologous peptide inserted at one of the following positions relative to SEQ ID NO: 1:
d) 48-<heterologous peptide>-50,
e) 49-<heterologous peptide>-51,
f) 50-<heterologous peptide>-52,
q) 72-<heterologous peptide>-77,
r) 73-<heterologous peptide>-78; or
s) 74-<heterologous peptide>-79.

BRIEF DESCRIPTION OF THE DRAWINGS

FIG. 12 shows a table of output of an iQue assay for binders to Her2.

DESCRIPTION OF EXEMPLARY EMBODIMENTS

I. Definitions

Figure 1:
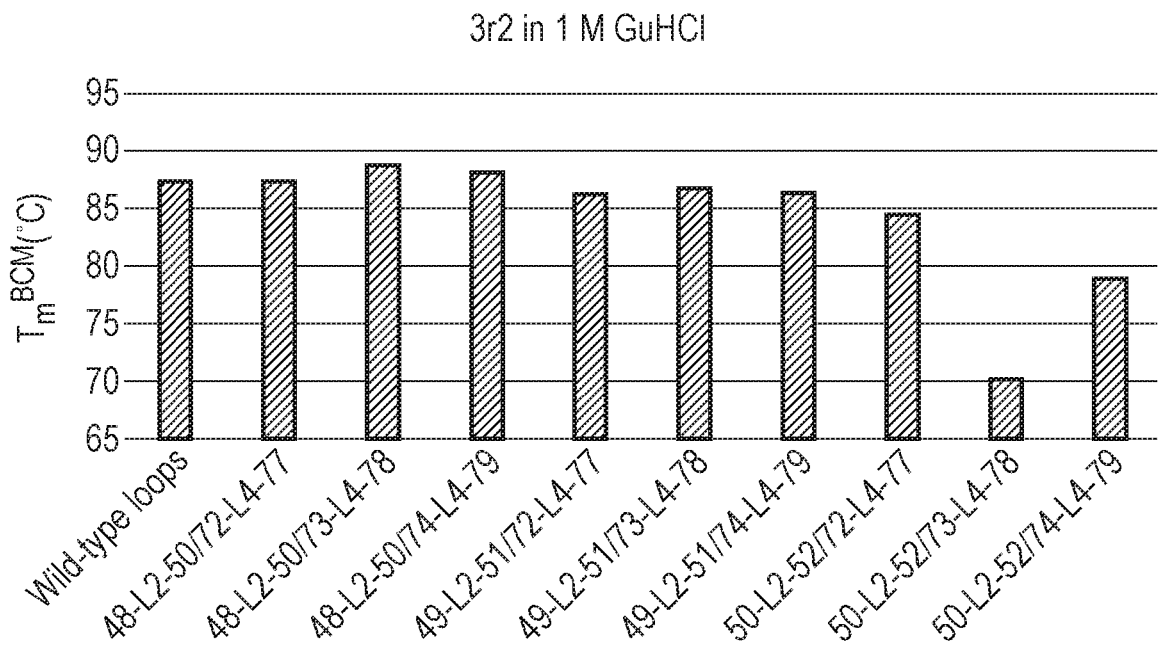
FIG. 1 shows a bar chart of results from experiments testing thermal stability (Tm) of polypeptides with heterologous peptide insertions.
Figure 2:
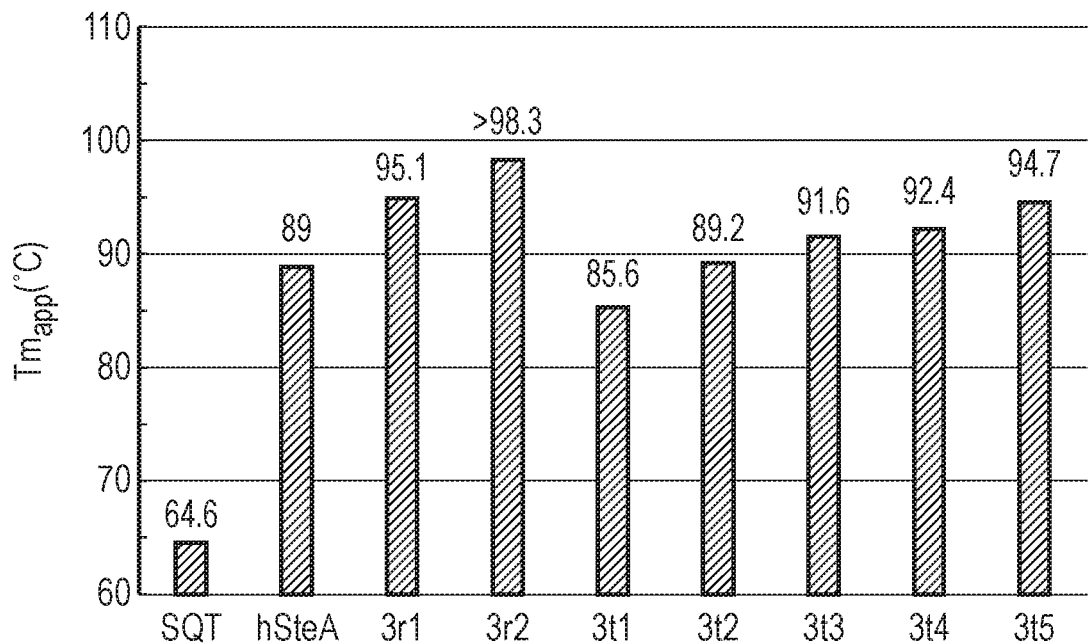
FIG. 2 shows a bar chart of Tm as a measure of thermal stability.
Figure 3:
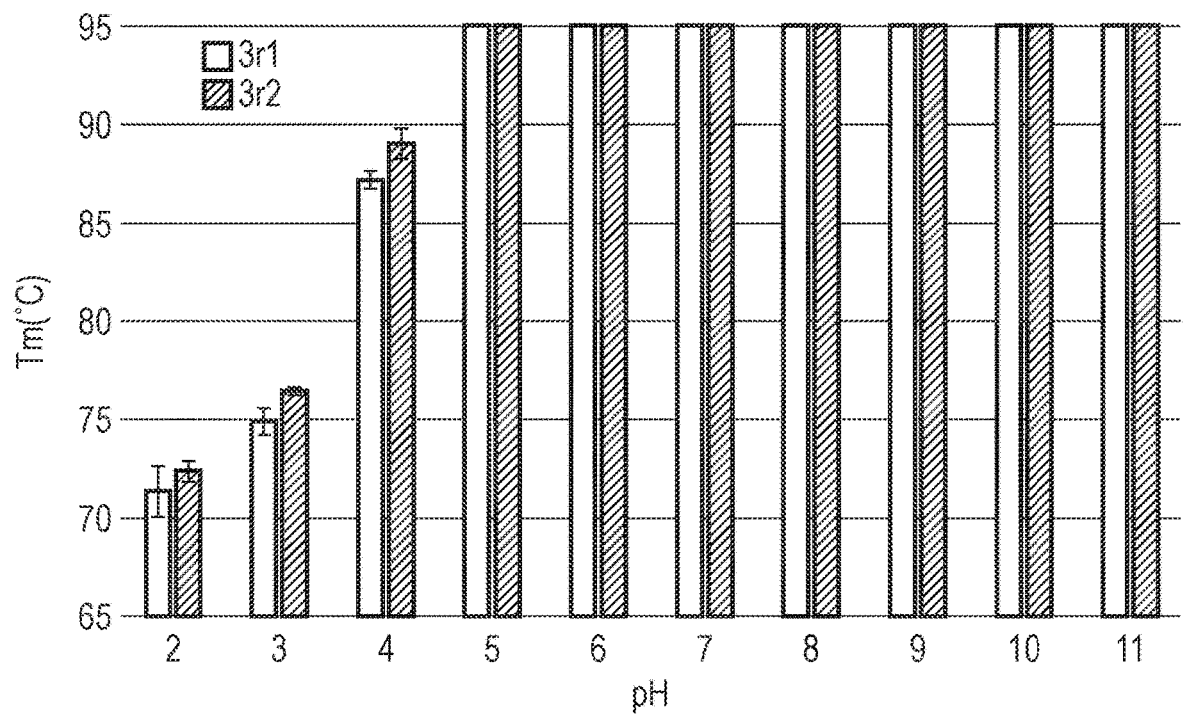
FIG. 3 shows a bar chart of Tm measured at different pH values.
Figure 4A:
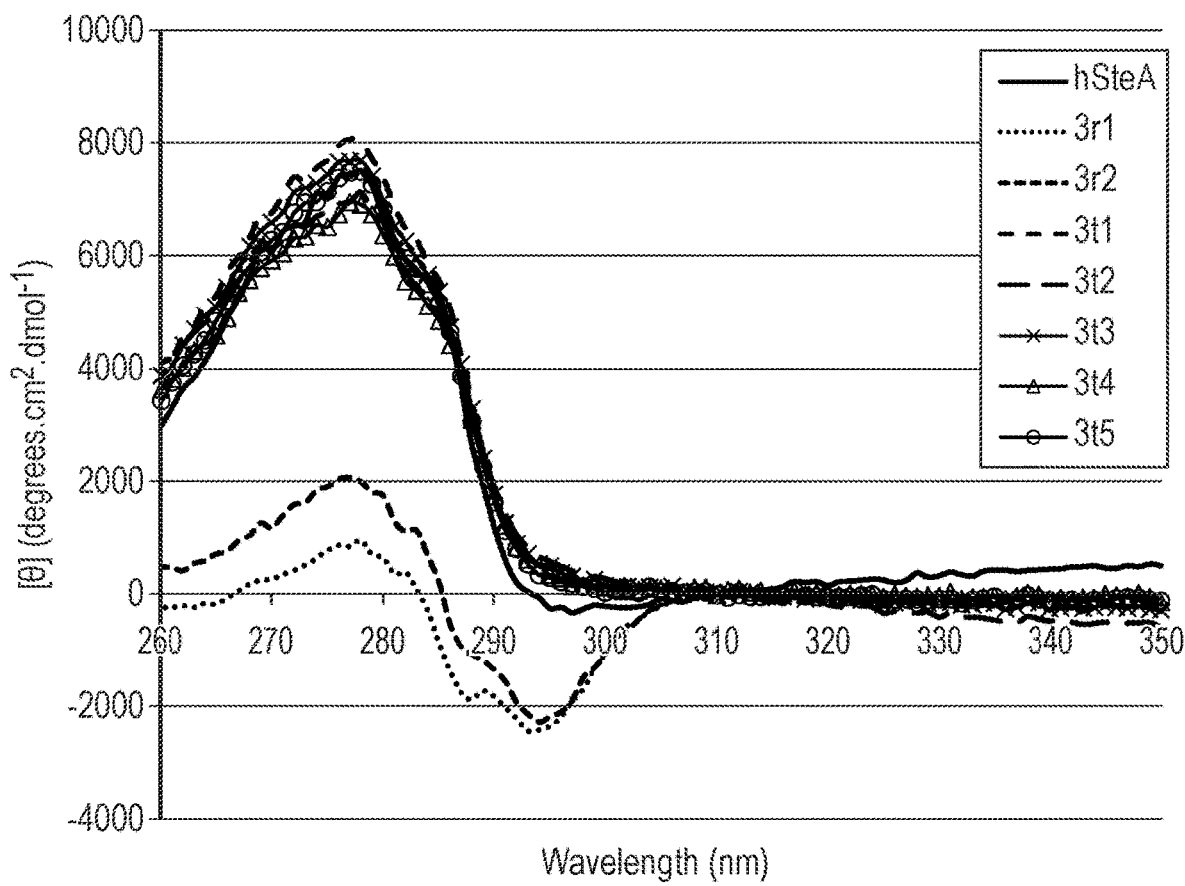
FIGS. 4a and 4b show graphs of circular dichroism (CD) spectroscopy data for various polypeptides with heterologous peptide insertions.
Figure 4B:
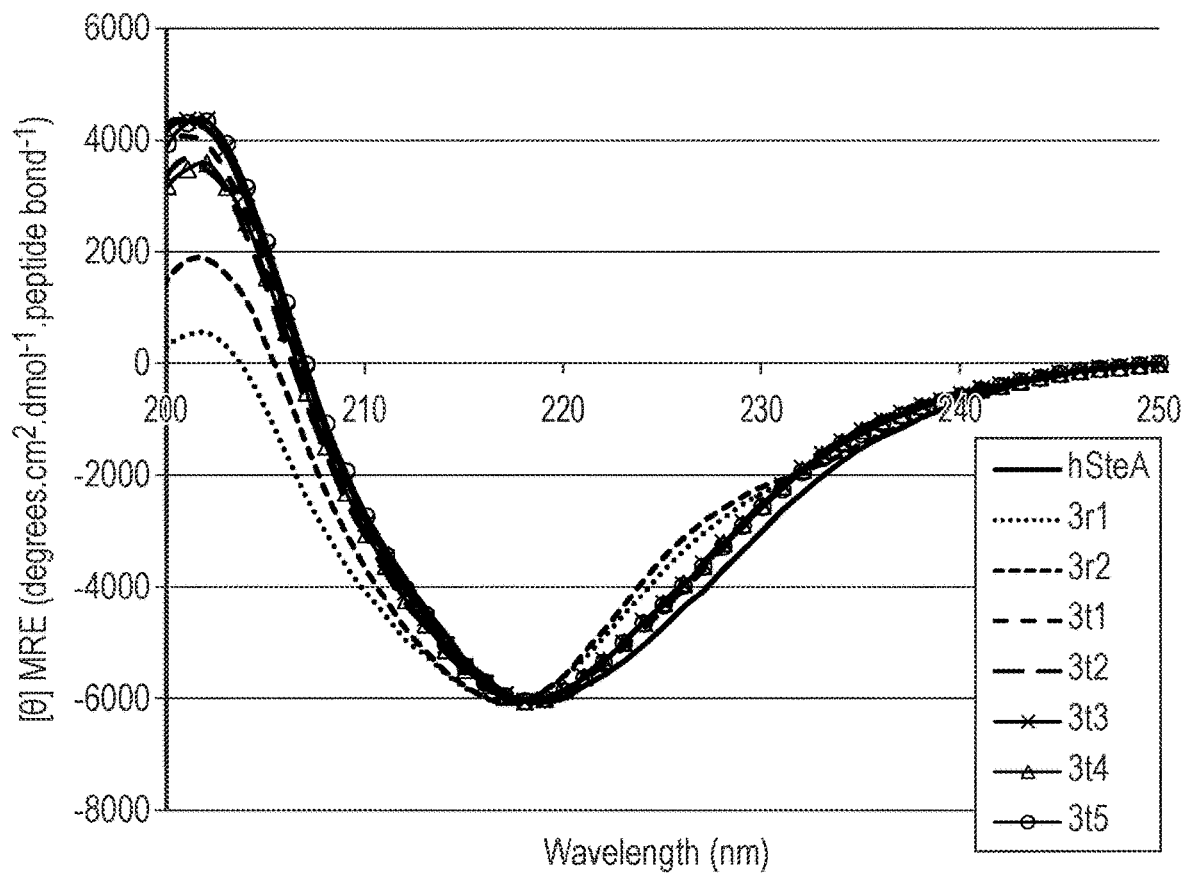
Figure 5:
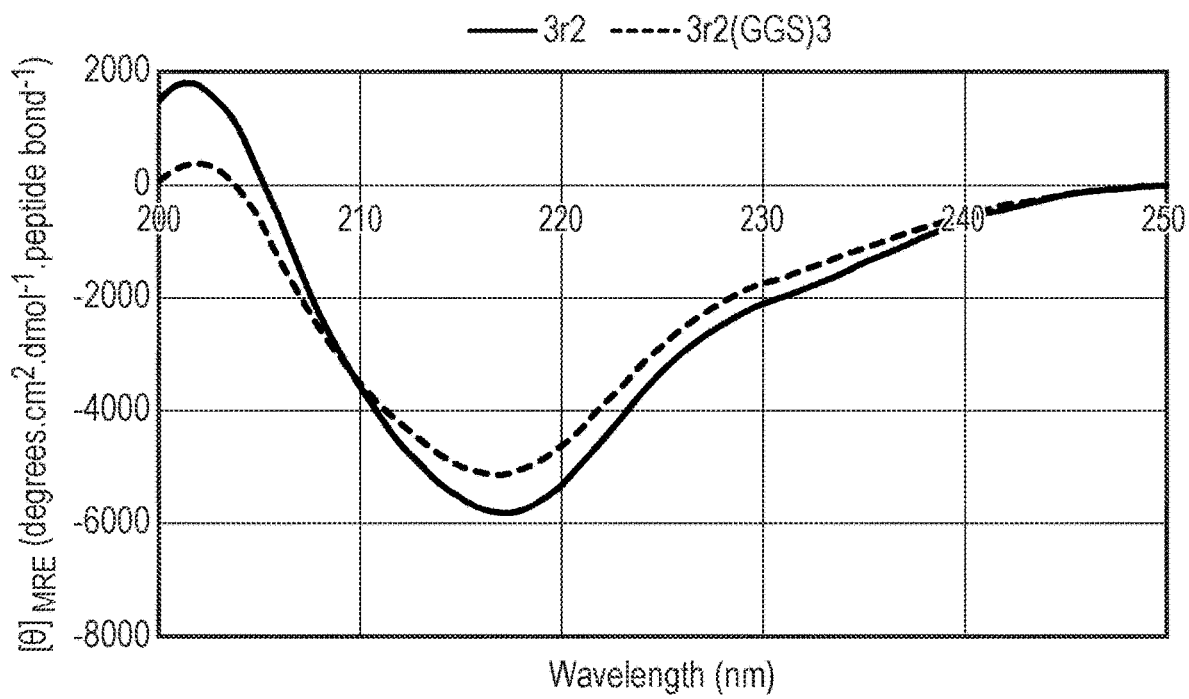
FIG. 5 shows a graph of far ultraviolet (UV) CD spectra of the 3r2 polypeptide (solid line) and the 3r2(GGS)$_3$ polypeptide (dashed line) showing mean residue ellipticity ($[\theta]_{MRE}$).
Figure 6:
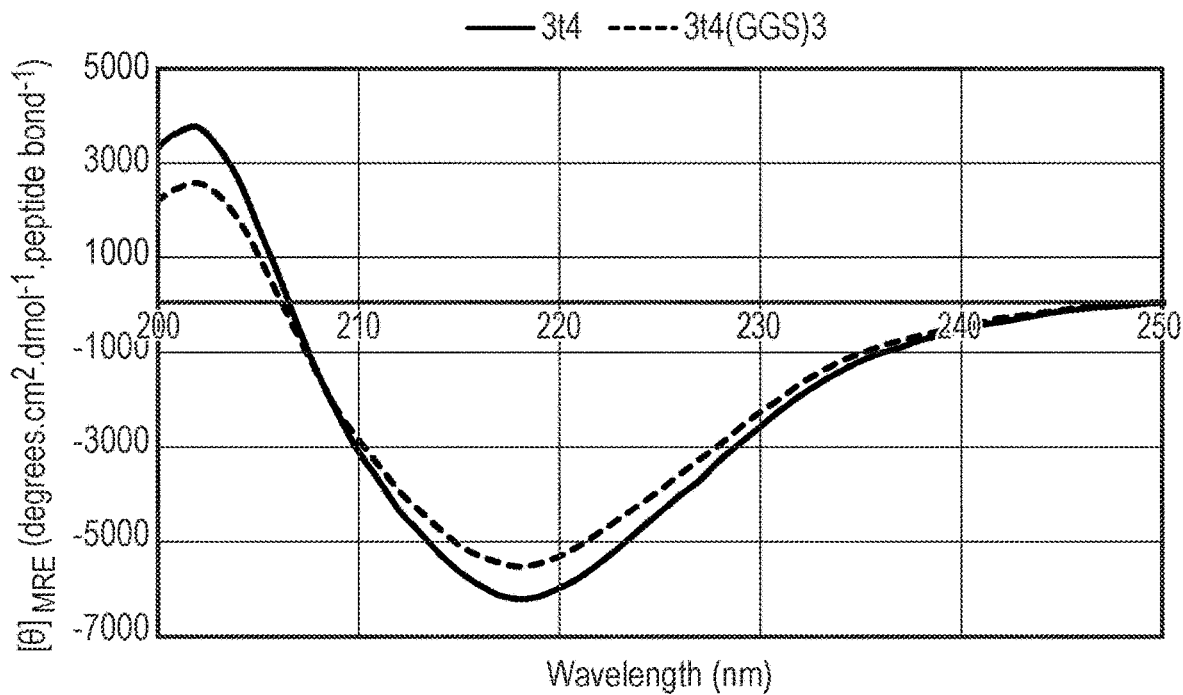
FIG. 6 shows a graph of far UV CD spectra of the 3t4 polypeptide (solid line) and the 3t4(GGS)$_3$ polypeptide (dashed line) showing mean residue ellipticity ($[\theta]_{MRE}$).
Figure 7:
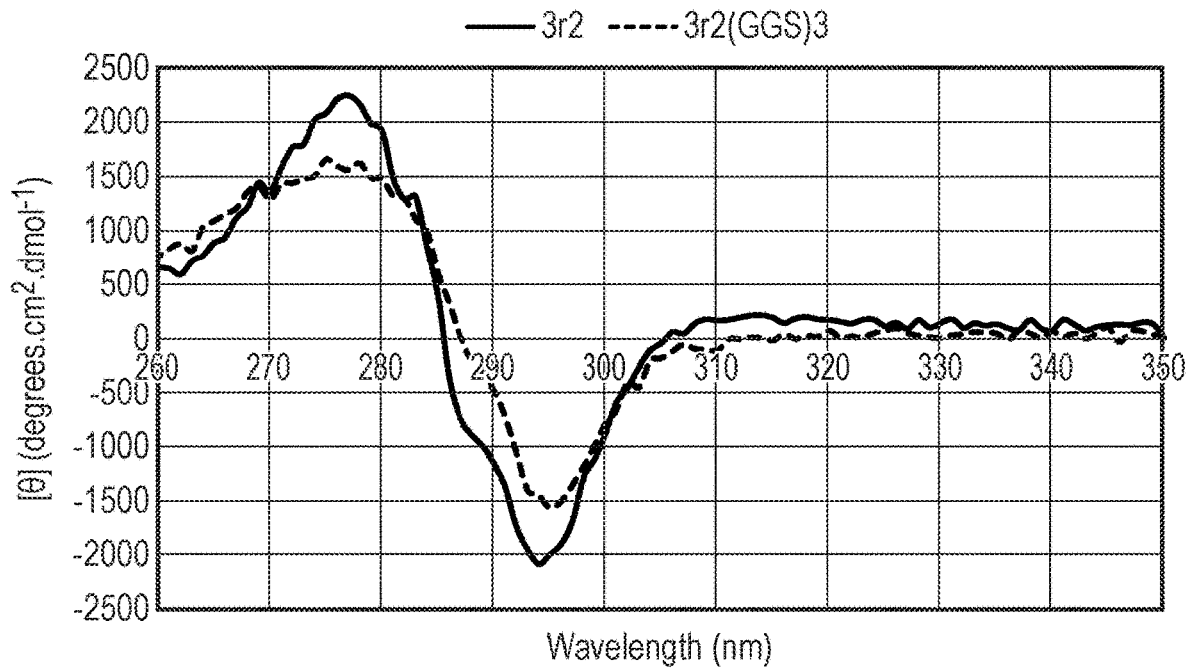
FIG. 7 shows a graph of near UV CD spectra of the 3r2 (solid line) polypeptide and the 3r2(GGS)$_3$ polypeptide (dashed line) showing molar ellipticity ($[\theta]$).
Figure 8:
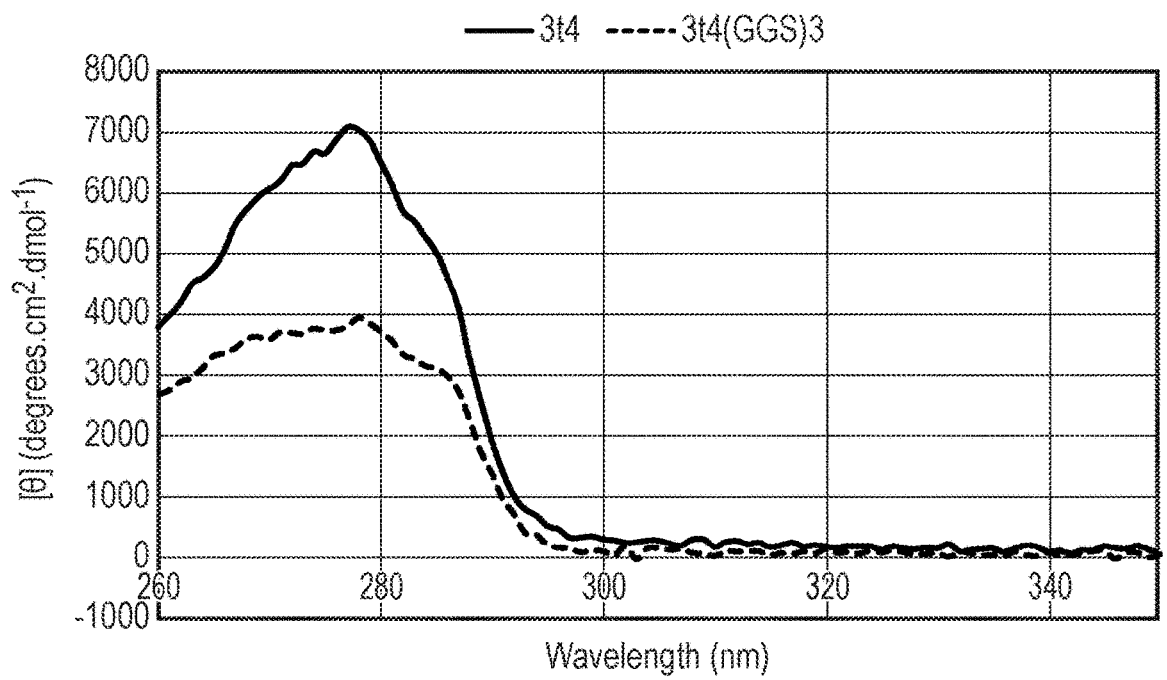
FIG. 8 shows a graph of near UV CD spectra of the 3t4 polypeptide (solid line) and the 3t4(GGS)$_3$ polypeptide (dashed line) showing molar ellipticity ($[\theta]$).
Figure 9:
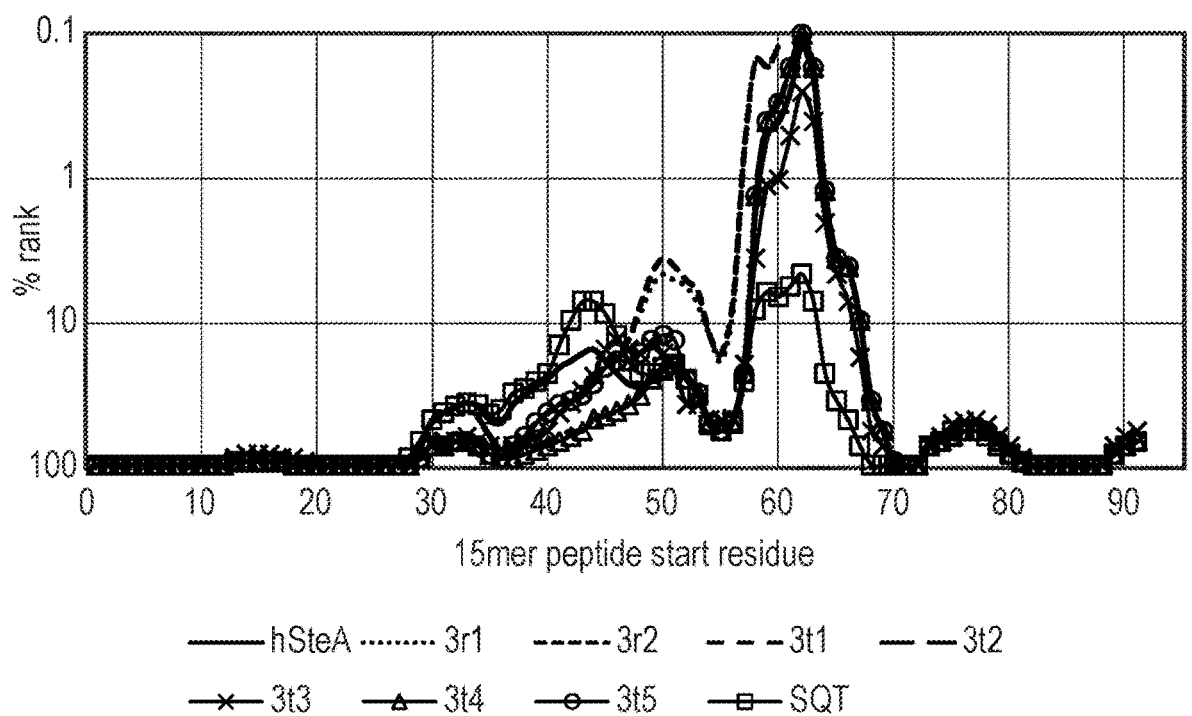
FIG. 9 shows a graph of the % rank of predicted affinity of various polypeptides with heterologous peptide insertions.

To facilitate an understanding of the present invention, a number of terms and phrases are defined below.

The term "AFFIMER®" (or "AFFIMER® Polypeptide") refers to small, highly stable proteins that are a recombinantly engineered variants of Stefin Polypeptides. AFFIMER® proteins display peptide loops (typically two) and an N-terminal sequence that can all be randomised to bind to desired target proteins with high affinity and specificity, in a similar manner to monoclonal antibodies. Stabilisation of the peptide loop(s) by the Stefin protein scaffold constrains the possible conformations that the peptides can take, increasing the binding affinity and specificity compared to libraries of free peptides. These engineered non-antibody binding proteins are designed to mimic the molecular recognition characteristics of monoclonal antibodies in different applications. Variations to other parts of the Stefin polypeptide sequence can be carried out, with such variations improving the properties of these affinity reagents, such as increase stability, make them robust across a range of temperatures and pH and the like.

An "Encoded AFFIMER®" refers to a nucleic acid construct which, when expressed by cells in a patient's body through a gene delivery process, produces an intended AFFIMER® polypeptide in vivo.

An "AFFIMER®-Linked Conjugate" refers to an AFFIMER® polypeptide having one or more moieties conjugated thereto through a chemical conjugation other than through the formation of a continuous peptide bond through the C-terminus or N-terminus of the polypeptide portion of the AFFIMER® polypeptide containing AFFIMER® Polypeptide sequence. An AFFIMER®-linked Conjugate may be an "AFFIMER®-Drug Conjugate", which refers to an AFFIMER® polypeptide including one or more pharmacologically active moieties conjugated thereto. An AFFIMER®-linked Conjugate may also be an "AFFIMER®-Tag Conjugate", which refers to an AFFIMER® polypeptide including one or more detectable moieties (i.e., detectable labels) conjugated thereto.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included within the definition are, for example, polypeptides containing one or more analogues of an amino acid (including, for example, unnatural amino acids), as well as other modifications known in the art.

The terms "amino acid residue" and "amino acid" are used interchangeably and means, in the context of a polypeptide, an amino acid that is participating in one or more peptide bonds of the polypeptide. In general, the abbreviations used herein for designating the amino acids are based on recommendations of the IUPAC-IUB Commission on Biochemical Nomenclature (see Biochemistry (1972) 11:1726-1732). For instance, Met, lie, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH2)COOH portion, as defined by K. D. Kopple, "Peptides and Amino Acids", W. A. Benjamin Inc., New York and Amsterdam, 1966, pages 2 and 33.

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogues which have been identified as constituents of peptidoglycan bacterial cell walls.

Amino acid residues having "basic sidechains" include Arg, Lys and His. Amino acid residues having "acidic sidechains" include Glu and Asp. Amino acid residues having "neutral polar sidechains" include Ser, Thr, Asn, Gln, Cys and Tyr. Amino acid residues having "neutral non-polar sidechains" include Gly, Ala, Val, lie, Leu, Met, Pro, Trp and Phe. Amino acid residues having "non-polar aliphatic sidechains" include Gly, Ala, Val, Ile and Leu. Amino acid residues having "hydrophobic sidechains" include Ala, Val, lie, Leu, Met, Phe, Tyr and Trp. Amino acid residues having "small hydrophobic sidechains" include Ala and Val. Amino acid residues having "aromatic sidechains" include Tyr, Trp and Phe.

The term amino acid residue further includes analogues, derivatives and congeners of any specific amino acid referred to herein, as for instance, the subject polypeptides such as AFFIMER®s (particularly if generated by chemical synthesis) can include an amino acid analogue such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-100 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the invention do not abrogate the binding of the polypeptide, soluble protein, or antibody containing the amino acid sequence, to the target binding site. Methods of identifying amino acid conservative substitutions which do not eliminate binding are well-known in the art.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "fusion protein" or "fusion polypeptide" as used herein refers to a hybrid protein expressed by a nucleic acid molecule comprising nucleotide sequences of at least two genes.

The term "linker" or "linker region" as used herein refers to a linker inserted between a first polypeptide (e.g., copies of an AFFIMER®) and a second polypeptide (e.g., another AFFIMER®, an Fc domain, a ligand binding domain, etc). In some embodiments, the linker is a peptide linker. Linkers should not adversely affect the expression, secretion, or bioactivity of the polypeptides. Preferably, linkers are not antigenic and do not elicit an immune response.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogues, or any substrate that can be incorporated into a polymer by DNA or RNA polymerase.

As used herein, the term "nucleic acid molecule encoding", "DNA sequence encoding," and "DNA encoding" refer to the order or sequence of nucleotides along a strand of deoxyribonucleic acid deoxyribonucleotides. The order of these deoxyribonucleotides determines the order of amino acids along the polypeptide (protein) chain. Thus, a nucleic acid sequence encoding the amino acid sequence.

When used in reference to nucleotide sequences, "sequence" as used herein, the term grammatical and other forms may comprise DNA or RNA, and may be single or double stranded. Nucleic acid sequences may be mutated. Nucleic acid sequence may have any length, for example 2 to 100,000 or more nucleotides (or any integral value above or between) a nucleic acid, for example a length of from about 100 to about 10,000, or from about 200 nucleotides to about 500 nucleotides.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

As used herein, the term "transfection" refers to an exogenous nucleic acid into a eukaryotic cell. Transfection can be achieved by various means known in the art, including calcium phosphate-DNA co-precipitation, DEAE-dextran-mediated transfection, polybrene-mediated transfection, electroporation, microinjection, liposome fusion, lipofection, protoplast fusion, retroviral infection, and biolistics technology (biolistics).

The term "carrier" as used herein is an isolated nucleic acid comprising the isolated nucleic acid can be used to deliver a composition to the interior of the cell. It is known in the art a number of carriers including, but not limited to the linear polynucleotides, polynucleotides associated with ionic or amphiphilic compounds, plasmids, and viruses. Thus, the term "vector" includes an autonomously replicating plasmid or virus. The term should also be construed to include facilitate transfer of nucleic acid into cells of the non-plasmid and non-viral compounds, for example, polylysine compounds, liposomes, and the like. Examples of viral vectors include, but are not limited to adenoviral vectors, adeno-associated virus vectors, retroviral vectors and the like.

As used herein, the term "expression vector" refers to a vector comprising a recombinant polynucleotide comprising expression control sequence and a nucleotide sequence to be expressed operably linked. The expression vector comprises sufficient cis-acting elements (cis-acting elements) used for expression; other elements for expression can be supplied by the host cell or in vitro expression system. Expression vectors include all those known in the art, such as cosmids, plasmids (e.g., naked or contained in liposomes) and viruses (e.g., lentivirus, retroviruses, adenoviruses and adeno-associated viruses).

As used herein, the term "operably linked" refers to functional linkage between the regulatory sequence and a heterologous nucleic acid sequence is connected to a connection results in the expression of the latter. For example, when the first nucleic acid sequence and a second nucleic acid sequence is a functional relationship between the first nucleic acid sequence and the second nucleic acid sequence is operably linked. For example, if the promoter affects the transcription or expression of the coding sequence, the promoter is operably linked to a coding sequence. Typically, DNA sequencing operably linked are contiguous, and to join two protein coding regions in the same reading frame as necessary.

As used herein, the term "promoter" is defined as a promoter DNA sequence recognized by the synthetic machinery required for the synthesis machinery of the cell specific transcription of a polynucleotide sequence or introduced.

The term "constitutive expression" as used herein refers to all expressed under physiological conditions.

The term "inducible expression" as used herein refers to expression under certain conditions, such as activation (or inactivation) of an intracellular signalling pathway or the contacting of the cells harbouring the expression construct with a small molecule that regulates the expression (or degree of expression) of a gene operably linked to an inducible promoter sensitive to the concentration of the small molecule.

The term "electroporation" refers to the use of a transmembrane electric field pulse to induce microscopic pathways (pores) in a bio-membrane; their presence allows biomolecules such as plasmids or other oligonucleotide to pass from one side of the cellular membrane to the other.

Suitably polypeptides of the invention comprise the amino acid sequences as described herein. Suitably polypeptides of the invention consist essentially of the amino acid sequences as described herein. Suitably polypeptides of the invention consist of the amino acid sequences as described herein.

II. Fusions Proteins—General

In some embodiments, the AFFIMER® polypeptides may further comprise one or more additional polypeptide sequences at one or both ends of the AFFIMER® sequence which modulate biological activity of the AFFIMER® polypeptide. For example, the additions may modulate one or more properties or activities of modified AFFIMER® such as affinity, e.g., for binding to and inhibiting a target molecule, modulate the circulating half-life, modulate the therapeutic half-life, modulate the stability of the AFFIMER® polypeptide, modulate cleavage by proteases, modulate dose, modulate release or bio-availability, facilitate purification, decrease deamidation, improve shelf-life, or improve or alter a particular route of administration. Similarly, AFFIMER® polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection, purification or other traits of the polypeptide.

Accordingly, in certain aspects of the invention the AFFIMER® polypeptide is a fusion protein having at least one AFFIMER® polypeptide sequence and one or more heterologous polypeptide sequences ("fusion domain" herein). A fusion domain may be selected so as to confer a desired property, such as secretion from a cell or retention on the cell surface (i.e., for Encoded AFFIMER®s), to serve as substrate or other recognition sequences for post-translational modifications, to create multimeric structures aggregating through protein-protein interactions, to alter (often to extend) serum half-life, or to alter tissue localization or tissue exclusion and other ADME properties—merely as examples.

For example, some fusion domains are particularly useful for isolation and/or purification of the fusion proteins, such as by affinity chromatography. Well known examples of such fusion domains that facilitate expression or purification include, merely to illustrate, affinity tags such as polyhistidine (i.e., a Hiss tag), Strep II tag, streptavidin-binding peptide (SBP) tag, calmodulin-binding peptide (CBP), glutathione S-transferase (GST), maltose-binding protein (MBP), S-tag, HA tag, c-Myc tag, thioredoxin, protein A and protein G.

In order for the AFFIMER® polypeptide to be secreted, it will generally contain a signal sequence that directs the transport of the protein to the lumen of the endoplasmic reticulum and ultimately to be secreted (or retained on the cell surface if a transmembrane domain or other cell surface retention signal). Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence.

In some embodiments, the signal peptide is about 5 to about 40 amino acids in length (such as about 5 to about 7, about 7 to about 10, about 10 to about 15, about 15 to about 20, about 20 to about 25, or about 25 to about 30, about 30 to about 35, or about 35 to about 40 amino acids in length).

In some embodiments, the signal peptide is a native signal peptide from a human protein. In other embodiments, the signal peptide is a non-native signal peptide. For example, in some embodiments, the non-native signal peptide is a mutant native signal peptide from the corresponding native secreted human protein, and can include one or more (such as 2, 3, 4, 5, 6, 7, 8, 9, or 10 or more) substitutions insertions or deletions.

In some embodiments, the signal peptide is a signal peptide or mutant thereof from an immunoglobulin (such as IgG heavy chain or IgG-kappa light chain), a cytokine (such as interleukin-2 (IL-2), or CD33), a serum albumin protein (e.g. HSA or albumin), a human azurocidin preprotein signal sequence, a luciferase, a trypsinogen (e.g. chymotrypsinogen or trypsinogen) or other signal peptide able to efficiently secrete a protein from a cell. Exemplary signal peptides include, but are not limited to:

| Native Protein | Signal Sequence | |
|---|---|---|
| HSA | MKWVTFISLLFLFSSAYS | SEQ ID NO: 25 |
| Ig kappa light chain | MDMRAPAGIFGFLLVLFPGYRS | SEQ ID NO: 26 |
| Human azurocidin preprotein | MTRLTVLALLAGLLASSRA | SEQ ID NO: 27 |
| IgG heavy chain | MELGLSWIFLLAILKGVQC | SEQ ID NO: 28 |
| IgG heavy chain | MELGLRWVFLVAILEGVQC | SEQ ID NO: 29 |

-continued

| Native Protein | Signal Sequence |
|---|---|
| IgG heavy chain | MKHLWFFLLLVAAPRWVLS SEQ ID NO: 30 |
| IgG heavy chain | MDWTWRILFLVAAATGAHS SEQ ID NO: 31 |
| IgG heavy chain | MDWTWRFLFVVAAATGVQS SEQ ID NO: 32 |
| IgG heavy chain | MEFGLSWLFLVAILKGVQC SEQ ID NO: 33 |
| IgG heavy chain | MEFGLSWVFLVALFRGVQC SEQ ID NO: 34 |
| IgG heavy chain | MDLLHKNMKHLWFFLLLVAAPRWVLS SEQ ID NO: 35 |
| IgG Kappa light | MDMRVPAQLLGLLLLWLSGARC SEQ ID NO: 36 |
| IgG Kappa light | MKYLLPTAAAGLLLLAAQPAMA SEQ ID NO: 37 |
| Gaussia luciferase | MGVKVLFALICIAVAEA SEQ ID NO: 38 |
| Human albumin | MKWVTFISLLFLFSSAYS SEQ ID NO: 39 |
| Human chymotrypsinogen | MAFLWLLSCWALLGTTFG SEQ ID NO: 40 |
| Human interleukin-2 | MQLLSCIALILALV SEQ ID NO: 41 |
| Human trypsinogen-2 | MNLLLILTFVAAAVA SEQ ID NO: 42 |
| Human CD33 | MPLLLLLPLLWAGALA SEQ ID NO: 43 |
| Prolactin | MDSKGSSQKGSRLLLLLVVSNLLLCQGVVS SEQ ID NO: 44 |
| Human tPA | MDAMKRGLCCVLLLCGAVFVSPS SEQ ID NO: 45 |
| Synthetic/Consensus | MLLLLLLLLLLALALA SEQ ID NO: 46 |
| Synthetic/Consensus | MWWRLWWLLLLLLLLWPMVWA SEQ ID NO: 47 |

In some embodiments of a secreted AFFIMER® polypeptide, the recombinant polypeptide comprises a signal peptide when expressed, and the signal peptide (or a portion thereof) is cleaved from the AFFIMER® polypeptide upon secretion.

The subject fusion proteins may also include one or more linkers separating heterologous protein sequences or domains. As used herein, the term "linker" refers to a linker amino acid sequence inserted between a first polypeptide (e.g., an AFFIMER®) and a second polypeptide (e.g., a second AFFIMER®, an Fc region, a receptor trap, albumin, etc). Empirical linkers designed by researchers are generally classified into 3 categories according to their structures: flexible linkers, rigid linkers, and in vivo cleavable linkers. Besides the basic role in linking the functional domains together (as in flexible and rigid linkers) or releasing free functional domain in vivo (as in in vivo cleavable linkers), linkers may offer many other advantages for the production of fusion proteins, such as improving biological activity, increasing expression yield, and achieving desirable pharmacokinetic profiles. Linkers should not adversely affect the expression, secretion, or bioactivity of the fusion protein. Linkers should not be antigenic and should not elicit an immune response.

Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. In some embodiments, the linker may comprise a cleavage site. In some embodiments, the linker may comprise an enzyme cleavage site, so that the second polypeptide may be separated from the first polypeptide.

In certain preferred embodiments, the linker can be characterized as flexible. Flexible linkers are usually applied when the joined domains require a certain degree of movement or interaction. They are generally composed of small, non-polar (e.g. Gly) or polar (e.g. Ser or Thr) amino acids. See, for example, Argos P. (1990) "An investigation of oligopeptides linking domains in protein tertiary structures and possible candidates for general gene fusion" J Mol Biol. 211:943-958. The small size of these amino acids provides flexibility and allows for mobility of the connecting functional domains. The incorporation of Ser or Thr can maintain the stability of the linker in aqueous solutions by forming hydrogen bonds with the water molecules, and therefore reduces the unfavorable interaction between the linker and the protein moieties. The most commonly used flexible linkers have sequences consisting primarily of stretches of Gly and Ser residues ("GS" linker). An example of the most widely used flexible linker has the sequence of (Gly-Gly- Gly-Gly-Ser)n (SEQ ID NO: 48). By adjusting the copy number "n", the length of this GS linker can be optimized to achieve appropriate separation of the functional domains, or to maintain necessary inter-domain interactions, and is preferably 1, 2, 3, 4, 5, 6, 7, 8, 9, or 10. Besides the GS linkers, many other flexible linkers have been designed for recombinant fusion proteins. As These flexible linkers are also rich in small or polar amino acids such as Gly and Ser, but can contain additional amino acids such as Thr and Ala to maintain flexibility, as well as polar amino acids such as Lys and Glu to improve solubility.

In certain preferred embodiments, the linker can be characterized as rigid. While flexible linkers have the advantage to connect the functional domains passively and permitting certain degree of movements, the lack of rigidity of these linkers can be a limitation in certain fusion protein embodiments, such as in expression yield or biological activity. The ineffectiveness of flexible linkers in these instances was attributed to an inefficient separation of the protein domains or insufficient reduction of their interference with each other. Under these situations, rigid linkers have been successfully applied to keep a fixed distance between the domains and to maintain their independent functions.

Many natural linkers exhibited α-helical structures. The α-helical structure was rigid and stable, with intra-segment hydrogen bonds and a closely packed backbone. Therefore, the stiff α-helical linkers can act as rigid spacers between protein domains. George et al. (2002) "An analysis of protein domain linkers: their classification and role in protein folding" Protein Eng. 15(11):871-9. In general, rigid linkers exhibit relatively stiff structures by adopting α-helical structures or by containing multiple Pro residues. Under many circumstances, they separate the functional domains more efficiently than the flexible linkers. The length of the linkers can be easily adjusted by changing the copy number to achieve an optimal distance between domains. As a result, rigid linkers are chosen when the spatial separation of the domains is critical to preserve the stability or bioactivity of the fusion proteins. In this regard, alpha helix-forming linkers with the sequence of (EAAAK)n (SEQ ID NO: 54) (where n is preferably 1, 2, 3, 4, 5, 6, 7, 8, 9, or 10) have been applied to the construction of many recombinant fusion proteins. Another type of rigid linkers has a Pro-rich sequence, (XP)n (SEQ ID NO: 118), with X designating any amino acid, preferably Ala, Lys, or Glu and n is preferably 1, 2, 3, 4, 5, 6, 7, 8, 9, or 10.

Merely to illustrate, exemplary linkers include:

```
Flexible
                                        SEQ ID NO: 48
(GGGGS)n (i.e., n = 1-6)

Flexible
                                        SEQ ID NO: 49
(Gly)8

Flexible
                                        SEQ ID NO: 50
(Gly)6

Flexible
                                        SEQ ID NO: 51
KESGSVSSEQLAQFRSLD Flexible
                                        SEQ ID NO: 52
EGKSSGSGSESKST Flexible
                                        SEQ ID NO: 53
GSAGSAAGSGEF Rigid
                                        SEQ ID NO: 54
(EAAAK)n (i.e., n = 1-6)

Rigid
                                        SEQ ID NO: 55
A(EAAAK)4ALEA(EAAAK)4A Rigid
                                        SEQ ID NO: 56
PAPAP Rigid
                                        SEQ ID NO: 57
AEAAAKEAAAKA Rigid
                                        SEQ ID NO: 58
(Ala-Pro)n (10 to 34 aa)
```

Other linkers that may be used in the subject fusion proteins include, but are not limited to, SerGly, GGSG (SEQ ID NO: 59), GSGS (SEQ ID NO: 60), GGGS(SEQ ID NO: 61), S(GGS)n (SEQ ID NO: 62) where n is 1-7, GRA, poly(Gly), poly(Ala), GGGSGGG (SEQ ID NO: 63), ESGGGGVT (SEQ ID NO: 64), LESGGGGVT (SEQ ID NO: 65), GRAQVT (SEQ ID NO: 66), WRAQVT (SEQ ID NO: 67), and ARGRAQVT (SEQ ID NO: 68). The hinge regions of the Fc fusions described below may also be considered linkers.

Various elements can be employed to anchor proteins on the plasma membrane of cells. For example, the transmembrane domains (TM) of type-I (oriented with the N-terminus outside the cell) and type-II (oriented with the N-terminus in the cytosol) integral membrane proteins can be used to target chimeric proteins to the plasma membrane. Proteins can also be attached to the cell surface by fusion of a GPI (glycophosphatidylinositol lipid) signal to the 3' end of genes. Cleavage of the short carboxy-terminal peptide allows attachment of a glycolipid to the newly exposed C-terminus through an amide linkage. See Udenfriend et al. (1995) "How Glycosylphosphatidylinositol Anchored Membrane Proteins are Made" Annu Rev Biochem 64:563-591.

In certain embodiments, the fusion protein includes a transmembrane polypeptide sequence (a transmembrane domain). The distinguishing features of appropriate transmembrane polypeptides comprise the ability to be expressed at the surface of the cell on which the AFFIMER® polypeptide is to be displayed. In certain embodiments, that may be an immune cell, in particular lymphocyte cells or Natural killer (NK) cells, and once there to interact with a tumor cell expressing a cell surface feature which the AFFIMER® polypeptide on the immune cell surface binds so as to direct cellular response of the immune cell against a predefined target tumour cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine.

In certain other embodiments, the AFFIMER® polypeptide is a fusion protein including, in addition to an AFFIMER® polypeptide, a sequence that signals for the posttranslational addition of a glycosylphosphatidylinositol (GPI) anchor. GPI anchors are glycolipid structures that are added post-translationally to the C-terminus of many eukaryotic proteins. This modification to the AFFIMER® polypeptide will cause it to be anchored (attached) on the extracellular surface of the cell membrane of the cell in which the AFFIMER® polypeptide is re-expressed as a recombinant protein (i.e., an Encoded AFFIMER® as described below). In these embodiments, the GPI anchor domain is C-terminal to the AFFIMER® polypeptide sequence, and preferably occurs at the C-terminus of the fusion protein.

In one embodiment, the GPI anchor domain is a polypeptide that signals for the posttranslational addition of a GPI anchor when the fusion protein of which it is a part is expressed in a eukaryotic system. The GPI anchor signal sequence consists of a set of small amino acids at the site of anchor addition (the ω site) followed by a hydrophilic spacer and ending in a hydrophobic stretch (Low, (1989) FASEB J. 3:1600-1608). Cleavage of this signal sequence occurs in the ER before the addition of an anchor with conserved central components but with variable peripheral moieties (Homans et al., Nature, 333:269-272 (1988)). The C-terminus of a GPI-anchored protein is linked through a phosphoethanolamine bridge to the highly conserved core glycan, mannose(α1-2)mannose(α1-6)mannose(α1-4)glucosamine(α1-6)myo-inositol. A phospholipid tail attaches the GPI anchor to the cell membrane.

Exemplary GPI anchor domains that can be used in the subject AFFIMER®-containing fusion proteins include:

```
                                        SEQ ID NO: 69
SGTTSGTTRLLSGHTCFTLTGLLGTLVTMGLLT

SEQ ID NO: 70
SGTSPGLSAGATVGIMIGVLVGVALI

SEQ ID NO: 71
SAPVLSAVATVGITIGVLARVALI

SEQ ID NO: 72
SSPDLSAGTAVSIMIGVLAGMALI

SEQ ID NO: 73
TLGGNSASYTFVSLLFSAVTLLLLC

SEQ ID NO: 70
SGTSPGLSAGATVGIMIGVLVGVALI
```

GPI anchor attachment can be achieved by expression of the AFFIMER® fusion protein containing the GPI anchor domain in a eukaryotic system capable of carrying out GPI posttranslational modifications. As with the transmembrane domain fusion proteins, human cells, including lymphocytes and other cells involved in initiating or promoting an antitumor are so capable and can be engineered to express and Encoded AFFIMER® including a GPI anchor domain in order retain the expressed AFFIMER® containing fusion on the surface of the engineered cell.

Still other modifications that can be made to the AFFIMER® polypeptide sequence itself or to a flanking polypeptide moiety provided as part of a fusion protein is one or more sequences that are sites for post-translational modifications by enzymes. These can include, but are not limited to, glycosylation, acetylation, acylation, lipid-modification, palmitoylation, palmitate addition, phosphorylation, glycolipid-linkage modification, and the like.

a. Engineering PK and ADME Properties

In certain embodiment, the AFFIMER® polypeptide may not have a half-life and/or PK profile that is optimal for the route of administration, such as parenteral therapeutic dosing. The term "half-life" refers to the amount of time it takes for a substance, such as an AFFIMER® polypeptide of the present invention, to lose half of its pharmacologic or physiologic activity or concentration. Biological half-life can be affected by elimination, excretion, degradation (e.g., enzymatic) of the substance, or absorption and concentration in certain organs or tissues of the body. In some embodiments, biological half-life can be assessed by determining the time it takes for the blood plasma concentration of the substance to reach half its steady state level ("plasma half-life"). To address this shortcoming, there are a variety of general strategies for prolongation of half-life that have been used in the case of other protein therapeutics, including the incorporation of half-life extending moieties as part of the AFFIMER® polypeptide.

The term "half-life extending moiety" refers to a pharmaceutically acceptable moiety, domain, or molecule covalently linked ("conjugated" or "fused") to the AFFIMER® polypeptide to form the AFFIMER® polypeptides described herein, optionally via a non-naturally encoded amino acid, directly or via a linker, that prevents or mitigates in vivo proteolytic degradation or other activity-diminishing modification of the AFFIMER® polypeptide, increases half-life, and/or improves or alters other pharmacokinetic or biophysical properties including but not limited to increasing the rate of absorption, reducing toxicity, improving solubility, reducing protein aggregation, increasing biological activity and/or target selectivity of the modified AFFIMER® polypeptide, increasing manufacturability, and/or reducing immunogenicity of the modified AFFIMER® polypeptide, compared to a comparator such as an unconjugated form of the modified AFFIMER® polypeptide. The term "half-life extending moiety" includes non-proteinaceous, half-life extending moieties, such as a water soluble polymer such as polyethylene glycol (PEG) or discrete PEG, hydroxyethyl starch (HES), a lipid, a branched or unbranched acyl group, a branched or unbranched C8-C30 acyl group, a branched or unbranched alkyl group, and a branched or unbranched C8-C30 alkyl group; and proteinaceous half-life extending moieties, such as serum albumin, transferrin, adnectins (e.g., albumin-binding or pharmacokinetics extending (PKE) adnectins), Fc domain, and unstructured polypeptide, such as XTEN and PAS polypeptide (e.g. conformationally disordered polypeptide sequences composed of the amino acids Pro, Ala, and/or Ser), and a fragment of any of the foregoing.

In certain embodiments, the half-life extending moiety extends the half-life of the resulting AFFIMER® polypeptide circulating in mammalian blood serum compared to the half-life of the protein that is not so conjugated to the moiety (such as relative to the AFFIMER® polypeptide alone). In some embodiments, half-life is extended by greater than about 1.2-fold, 1.5-fold, 2.0-fold, 3.0-fold, 4.0-fold, 5.0-fold, or 6.0-fold. In some embodiments, half-life is extended by more than 6 hours, more than 12 hours, more than 24 hours, more than 48 hours, more than 72 hours, more than 96 hours or more than 1 week after in vivo administration compared to the protein without the half-life extending moiety.

As means for further exemplification, half-life extending moieties that can be used in the generation of AFFIMER® polypeptides of the invention include:

Genetic fusion of the pharmacologically active AFFIMER® sequence to a naturally long-half-life protein or protein domain (e.g., Fc fusion, transferrin [Tf]

fusion, or albumin fusion. See, for example, Beck et al. (2011) "Therapeutic Fc-fusion proteins and peptides as successful alternatives to antibodies. MAbs. 3:1-2; Czajkowsky et al. (2012) "Fc-fusion proteins: new developments and future perspectives. EMBO Mol Med. 4:1015-28; Huang et al. (2009) "Receptor-Fc fusion therapeutics, traps, and Mimetibody technology" Curr Opin Biotechnol. 2009; 20:692-9; Keefe et al. (2013) "Transferrin fusion protein therapies: acetylcholine receptor-transferrin fusion protein as a model. In: Schmidt S, editor. Fusion protein technologies for biopharmaceuticals: applications and challenges. Hoboken: Wiley; p. 345-56; Weimer et al. (2013) "Recombinant albumin fusion proteins. In: Schmidt S, editor. Fusion protein technologies for biopharmaceuticals: applications and challenges. Hoboken: Wiley; 2013. p. 297-323; Walker et al. (2013) "Albumin-binding fusion proteins in the development of novel long-acting therapeutics. In: Schmidt S, editor. Fusion protein technologies for biopharmaceuticals: applications and challenges. Hoboken: Wiley; 2013. p. 325-43.

Genetic fusion of the pharmacologically active AFFIMER® sequence to an inert polypeptide, e.g., XTEN (also known as recombinant PEG or "rPEG"), a homoamino acid polymer (HAP; HAPylation), a proline-alanine-serine polymer (PAS; PASylation), or an elastin-like peptide (ELP; ELPylation). See, for example, Schellenberger et al. (2009) "A recombinant polypeptide extends the in vivo half-life of peptides and proteins in a tunable manner. Nat Biotechnol. 2009; 27:1186-90; Schlapschy et al. Fusion of a recombinant antibody fragment with a homo-amino-acid polymer: effects on biophysical properties and prolonged plasma half-life. Protein Eng Des Sel. 2007; 20:273-84; Schlapschy (2013) PASylation: a biological alternative to PEGylation for extending the plasma half-life of pharmaceutically active proteins. Protein Eng Des Sel. 26:489-501. Floss et al. (2012) "Elastin-like polypeptides revolutionize recombinant protein expression and their biomedical application. Trends Biotechnol. 28:37-45. Floss et al. "ELP-fusion technology for biopharmaceuticals. In: Schmidt S, editor. Fusion protein technologies for biopharmaceuticals: application and challenges. Hoboken: Wiley; 2013. p. 372-98.

Increasing the hydrodynamic radius by chemical conjugation of the pharmacologically active peptide or protein to repeat chemical moieties, e.g., to PEG (PEGylation) or hyaluronic acid. See, for example, Caliceti et al. (2003) "Pharmacokinetic and biodistribution properties of poly(ethylene glycol)-protein conjugates" Adv Drug Delivery Rev. 55:1261-77; Jevsevar et al. (2010) PEGylation of therapeutic proteins. Biotechnol J 5:113-28; Kontermann (2009) "Strategies to extend plasma half-lives of recombinant antibodies" BioDrugs. 23:93-109; Kang et al. (2009) "Emerging PEGylated drugs" Expert Opin Emerg Drugs. 14:363-80; and Mero et al. (2013) "Conjugation of hyaluronan to proteins" Carb Polymers. 92:2163-70.

Significantly increasing the negative charge of fusing the pharmacologically active peptide or protein by polysialylation; or, alternatively, (b) fusing a negatively charged, highly sialylated peptide (e.g., carboxy-terminal peptide [CTP; of chorionic gonadotropin (CG) b-chain]), known to extend the half-life of natural proteins such as human CG b-subunit, to the biological drug candidate. See, for example, Gregoriadis et al. (2005) "Improving the therapeutic efficacy of peptides and proteins: a role for polysialic acids" Int J Pharm. 2005; 300:125-30; Duijkers et al. "Single dose pharmacokinetics and effects on follicular growth and serum hormones of a long-acting recombinant FSH preparation (FSHCTP) in healthy pituitary-suppressed females" (2002) Hum Reprod. 17:1987-93; and Fares et al. "Design of a long-acting follitropin agonist by fusing the C-terminal sequence of the chorionic gonadotropin beta subunit to the follitropin beta subunit" (1992) Proc Natl Acad Sci USA. 89:4304-8.35; and Fares "Half-life extension through O-glycosylation.

Binding non-covalently, via attachment of a peptide or protein-binding domain to the bioactive protein, to normally long-half-life proteins such as HSA, human IgG, transferrin or fibronectin. See, for example, Andersen et al. (2011) "Extending half-life by indirect targeting of the neonatal Fc receptor (FcRn) using a minimal albumin binding domain" J Biol Chem. 286: 5234-41; O'Connor-Semmes et al. (2014) "GSK2374697, a novel albumin-binding domain antibody (albudAb), extends systemic exposure of exten-din-4: first study in humans-PK/PD and safety" Clin Pharmacol Ther. 2014; 96:704-12. Sockolosky et al. (2014) "Fusion of a short peptide that binds immunoglobulin G to a recombinant protein substantially increases its plasma half-life in mice" PLoS One. 2014; 9:e102566.

Classical genetic fusions to long-lived serum proteins offer an alternative method of half-life extension distinct from chemical conjugation to PEG or lipids. Two major proteins have traditionally been used as fusion partners: antibody Fc domains and human serum albumin (HSA). Fc fusions involve the fusion of peptides, proteins or receptor exodomains to the Fc portion of an antibody. Both Fc and albumin fusions achieve extended half-lives not only by increasing the size of the peptide drug, but both also take advantage of the body's natural recycling mechanism: the neonatal Fc receptor, FcRn. The pH-dependent binding of these proteins to FcRn prevents degradation of the fusion protein in the endosome. Fusions based on these proteins can have half-lives in the range of 3-16 days, much longer than typical PEGylated or lipidated peptides. Fusion to antibody Fc domains can improve the solubility and stability of the peptide or protein drug. An example of a peptide Fc fusion is dulaglutide, a GLP-1 receptor agonist currently in late-stage clinical trials. Human serum albumin, the same protein exploited by the fatty acylated peptides is the other popular fusion partner. Albiglutide is a GLP-1 receptor agonist based on this platform. A major difference between Fc and albumin is the dimeric nature of Fc versus the monomeric structure of HSA leading to presentation of a fused peptide as a dimer or a monomer depending on the choice of fusion partner. The dimeric nature of an AFFIMER®-Fc fusion can produce an avidity effect if the AFFIMER® target, such as cell surface protein on a target cell, is spaced closely enough together or are themselves dimers or higher order multimers. This may be desirable or not depending on the target.

(i) Fc Fusions

In some embodiments, the AFFIMER® polypeptide may be part of a fusion protein with an immunoglobulin Fc domain ("Fc domain"), or a fragment or variant thereof, such as a functional Fc region. In this context, an Fc fusion ("Fc-fusion"), such as an AFFIMER® polypeptide created as an AFFIMER®-Fc fusion protein, is a polypeptide comprising one or more AFFIMER® sequences covalently linked through a peptide backbone (directly or indirectly) to an Fc region of an immunoglobulin. An Fc-fusion may comprise, for example, the Fc region of an antibody (which facilitates effector functions and pharmacokinetics) and an AFFIMER® sequence as part of the same polypeptide. An immunoglobulin Fc region may also be linked indirectly to one or more AFFIMER®s. Various linkers are known in the art and can optionally be used to link an Fc to a polypeptide including an AFFIMER® sequence to generate an Fc-fusion. In certain embodiments, Fc-fusions can be dimerized to form Fc-fusion homodimers, or using non-identical Fc domains, to form Fc-fusion heterodimers.

There are several reasons for choosing the Fc region of human antibodies for use in generating the subject AFFIMER® polypeptides as AFFIMER® fusion proteins. The principle rationale is to produce a stable protein, large enough to demonstrate a similar pharmacokinetic profile compared with those of antibodies, and to take advantage of the properties imparted by the Fc region; this includes the salvage neonatal FcRn receptor pathway involving FcRn-mediated recycling of the fusion protein to the cell surface post endocytosis, avoiding lysosomal degradation and resulting in release back into the bloodstream, thus contributing to an extended serum half-life. Another obvious advantage is the Fc domain's binding to Protein A, which can simplify downstream processing during production of the AFFIMER® polypeptide and permit generation of highly pure preparation of the AFFIMER® polypeptide.

In general, an Fc domain will include the constant region of an antibody excluding the first constant region immunoglobulin domain. Thus, Fc domain refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ2. Although the boundaries of the Fc domain may vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, NIH, Bethesda, Md. (1991)). Fc may refer to this region in isolation, or this region in the context of a whole antibody, antibody fragment, or Fc fusion protein. Polymorphisms have been observed at a number of different Fc positions and are also included as Fc domains as used herein.

In certain embodiments, the Fc As used herein, a "functional Fc region" refers to an Fc domain or fragment thereof which retains the ability to bind FcRn. A functional Fc region binds to FcRn, but does not possess effector function. The ability of the Fc region or fragment thereof to bind to FcRn can be determined by standard binding assays known in the art. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions can be assessed using various assays known in the art for evaluating such antibody effector functions.

In an exemplary embodiment, the Fc domain is derived from an IgG1 subclass, however, other subclasses (e.g., IgG2, IgG3, and IgG4) may also be used. An exemplary sequence of a human IgG1 immunoglobulin Fc domain which can be used is:

```
                                              (SEQ ID NO: 4)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGK
```

In some embodiments, the Fc region used in the fusion protein may comprise the hinge region of an Fc molecule. An exemplary hinge region comprises the core hinge residues spanning positions 1-16 (i.e., DKTHTCPPCPAPELLG (SEQ ID NO: 76)) of the exemplary human IgG1 immunoglobulin Fc domain sequence provided above. In certain embodiments, the AFFIMER®-containing fusion protein may adopt a multimeric structure (e.g., dimer) owing, in part, to the cysteine residues at positions 6 and 9 within the hinge region of the exemplary human IgG1 immunoglobulin Fc domain sequence provided above. In other embodiments, the hinge region as used herein, may further include residues derived from the CH1 and CH2 regions that flank the core hinge sequence of the exemplary human IgG1 immunoglobulin Fc domain sequence provided above. In yet other embodiments, the hinge sequence may comprise or consist of GSTHTCPPCPAPELLG (SEQ ID NO: 77) or EPKSCDKTHTCPPCPAPELLG (SEQ ID NO: 78).

In some embodiments, the hinge sequence may include one or more substitutions that confer desirable pharmacokinetic, biophysical, and/or biological properties. Some exemplary hinge sequences include:

```
                              SEQ ID NO: 79
    EPKSCDKTHTCPPCPAPELLGGPS

SEQ ID NO: 80
    EPKSSDKTHTCPPCPAPELLGGPS;

SEQ ID NO: 81
    EPKSSDKTHTCPPCPAPELLGGSS;

SEQ ID NO: 82
    EPKSSGSTHTCPPCPAPELLGGSS;

SEQ ID NO: 83
    DKTHTCPPCPAPELLGGPS
    and

SEQ ID NO: 84
    DKTHTCPPCPAPELLGGSS.
```

In one embodiment, the residue P at position 18 of the exemplary human IgG1 immunoglobulin Fc domain sequence provided above may be replaced with S to ablate Fc effector function; this replacement is exemplified in hinges having the sequences EPKSSDKTHTCPPCPA-PELLGGSS (SEQ ID NO: 81), EPKSSGSTHTCPPCPA-PELLGGSS (SEQ ID NO: 82), and DKTHTCPPCPA-PELLGGSS (SEQ ID NO: 84). In another embodiment, the residues DK at positions 1-2 of the exemplary human IgG1 immunoglobulin Fc domain sequence provided above may be replaced with GS to remove a potential clip site; this replacement is exemplified in the sequence EPKSSGSTH-TCPPCPAPELLGGSS (SEQ ID NO: 82). In another embodiment, the C at the position 103 of the heavy chain constant region of human IgG1 (i.e., domains CH1-CH3), may be replaced with S to prevent improper cysteine bond formation in the absence of a light chain; this replacement is exemplified by EPKSSDKTHTCPPCPAPELLGGPS (SEQ ID NO: 80), EPKSSDKTHTCPPCPAPELLGGSS (SEQ ID NO: 81), and EPKSSGSTHTCPPCPAPELLGGSS (SEQ ID NO: 82).

In some embodiments, the Fc is a mammalian Fc such as a human Fc, including Fc domains derived from IgG1, IgG2, IgG3 or IgG4. The Fc region may possess at least about 80%, 85%, 90%, 95%, 96%, 97%, 98%, or 99% sequence identity with a native Fc region and/or with an Fc region of a parent polypeptide. In some embodiments, the Fc region may have at least about 90% sequence identity with a native Fc region and/or with an Fc region of a parent polypeptide.

In some embodiments, the Fc domain comprises an amino acid sequence selected from the examples provided by SEQ ID Nos. 4-16. It should be understood that the C-terminal lysine of an Fc domain is an optional component of a fusion protein comprising an Fc domain. In some embodiments, the Fc domain comprises an amino acid sequence selected from SEQ ID NOs: 4-16, except that the C-terminal lysine thereof is omitted.

| | |
|---|---|
| hIgG1a_191 [A subtype] (SEQ ID NO: 4) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1a_189 [hIgG1a_191 sans "GK" on C term; A subtype] (SEQ ID NO: 5) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSP |
| hIgG1a_191b [A/F subtype] (SEQ ID NO: 6) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDEMTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1f_1.1_191 [Contains 5 point mutations to alter ADCC function, F subtype] (SEQ ID NO: 7) | DKTHTCPPCPAPEAEGAPSVFLFPPKPKDTLMISRTPEVTCVVVDVSHE DPEVKFNWYVDGVEVHNAKTKPREEQYNSTYRVVSVLTVLHQDWLNGKE YKCKVSNKALPSSIEKTISKAKGQPREPQVYTLPPSREEMTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1f_1.1_186 [Contains 5 point mutations to alter ADCC function and C225S (Edlemen numbering); F subtype] (SEQ ID NO: 8) | EPKSSDKTHTCPPCPAPEAEGAPSVFLFPPKPKDTLMISRTPEVTCVVV DVSHEDPEVKFNWYVDGVEVHNAKTKPREEQYNSTYRVVSVLTVLHQDW LNGKEYKCKVSNKALPSSIEKTISKAKGQPREPQVYTLPPSREEMTKNQ VSLTCLVKGFYPSDIAVEWESNGQPENNYKTTPPVLDSDGSFFLYSKLT VDKSRWQQGNVFSCSVMHEALHNHYTQKSLSLSPGK |
| hIgG1a_(N297G)_191 [A subtype] (SEQ ID NO: 9) | DKTHTCPPCPAPELLGGPSVFLFPPKPKDTLMISRTPEVTCVVVDVSHE DPEVKFNWYVDGVEVHNAKTKPREEQYGSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1a_190 [hIgG1a_190 sans "K" on C term; A subtype] (SEQ ID NO: 10) | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPG |
| hIgG1a_(N297Q)_191 [A subtype] (SEQ ID NO: 11) | DKTHTCPPCPAPELLGGPSVFLFPPKPKDTLMISRTPEVTCVVVDVSHE DPEVKFNWYVDGVEVHNAKTKPREEQYQSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1a_(N297S)_191 [A subtype] (SEQ ID NO: 12) | DKTHTCPPCPAPELLGGPSVFLFPPKPKDTLMISRTPEVTCVVVDVSHE DPEVKFNWYVDGVEVHNAKTKPREEQYSSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1a_(N297A)_191 [A subtype] (SEQ ID NO: 13) | DKTHTCPPCPAPELLGGPSVFLFPPKPKDTLMISRTPEVTCVVVDVSHE DPEVKFNWYVDGVEVHNAKTKPREEQYASTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |
| hIgG1a_(N297H)_191 [A subtype] (SEQ ID NO: 14) | DKTHTCPPCPAPELLGGPSVFLFPPKPKDTLMISRTPEVTCVVVDVSHE DPEVKFNWYVDGVEVHNAKTKPREEQYHSTYRVVSVLTVLHQDWLNGKE YKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSR WQQGNVFSCSVMHEALHNHYTQKSLSLSPGK |

```
h1gG4                    DKRVESKYGPPCPSCPAPEFLGGPSVFLFPPKPKDTLMISRTPEVTCVV
(SEQ ID NO: 15)          VDVSQEDPEVQFNWYVDGVEVHNAKTKPREEQFNSTYRVVSVLTVLHQD
                         WLNGKEYKCKVSNKGLPSSIEKTISKAKGQPREPQVYTLPPSQEEMTKN
                         QVSLTCLVKGFYPSDIAVEWESNGQPENNYKTTPPVLDSDGSFFLYSRL
                         TVDKSRWQEGNVFSCSVMHEALHNHYTQKSLSLSLGK h1gG4_(S241P)            DKRVESKYGPPCPPCPAPEFLGGPSVFLFPPKPKDTLMISRTPEVTCVV
(SEQ ID NO: 16)          VDVSQEDPEVQFNWYVDGVEVHNAKTKPREEQFNSTYRVVSVLTVLHQD
                         WLNGKEYKCKVSNKGLPSSIEKTISKAKGQPREPQVYTLPPSQEEMTKN
                         QVSLTCLVKGFYPSDIAVEWESNGQPENNYKTTPPVLDSDGSFFLYSRL
                         TVDKSRWQEGNVFSCSVMHEALHNHYTQKSLSLSLGK
```

The AFFIMER® sequence can be placed at either the N-terminal or C-terminal end of the Fc domain, and may be attached directly or the fusion protein may have other polypeptide sequences intervening between the Fc domain and the AFFIMER® polypeptide sequence.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins.

In certain embodiments, the fusion protein includes an Fc domain sequence for which the resulting AFFIMER® polypeptide has no (or reduced) ADCC and/or complement activation or effector functionality. For example, the Fc domain may comprise a naturally disabled constant region of IgG2 or IgG4 isotype or a mutated IgG1 constant region. Examples of suitable modifications are described in EP0307434. One example comprises the substitutions of alanine residues at positions 235 and 237 (EU index numbering).

In other embodiments, the fusion protein includes an Fc domain sequence for which the resulting AFFIMER® polypeptide will retain some or all Fc functionality for example will be capable of one or both of ADCC and CDC activity, as for example if the fusion protein comprises the Fc domain from human IgG1 or IgG3. Levels of effector function can be varied according to known techniques, for example by mutations in the CH2 domain, for example wherein the IgG1 CH2 domain has one or more mutations at positions selected from 239 and 332 and 330, for example the mutations are selected from S239D and I332E and A330L such that the antibody has enhanced effector function, and/or for example altering the glycosylation profile of the antigen-binding protein of the invention such that there is a reduction in fucosylation of the Fc region.

(ii) Albumin Fusion

In other embodiments, the AFFIMER® polypeptide is a fusion protein comprising, in addition to at least one AFFIMER® sequence, an albumin sequence or an albumin fragment. In other embodiments, the AFFIMER® polypeptide is conjugated to the albumin sequence or an albumin fragment through chemical linkage other than incorporation into the polypeptide sequence including the AFFIMER®. In some embodiments, the albumin, albumin variant, or albumin fragment is human serum albumin (HSA), a human serum albumin variant, or a human serum albumin fragment. Albumin serum proteins comparable to HSA are found in, for example, cynomolgus monkeys, cows, dogs, rabbits and rats. Of the non-human species, bovine serum albumin (BSA) is the most structurally similar to HSA. See, e.g., Kosa et al., (2007) J Pharm Sci. 96(11):3117-24. The present disclosure contemplates the use of albumin from non-human species, including, but not limited to, albumin sequence derived from cyno serum albumin or bovine serum albumin.

Mature HSA, a 585 amino acid polypeptide (approx. 67 kDa) having a serum half-life of about 20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulfide bridges. In certain preferred embodiments, the AFFIMER® polypeptide can be an albumin fusion protein including one or more AFFIMER® polypeptide sequences and the sequence for mature human serum albumin (SEQ ID NO: 17) or a variant or fragment thereof which maintains the PK and/or biodistribution properties of mature albumin to the extent desired in the fusion protein.

```
                                               (SEQ ID NO: 17)
DAKHSEVAHRFKDLGEENFKALVLIAFAQYLQQCPFEDHVKLVNEVTEF

AKTCVADESAENCDKSLHTLFGDKLCTVATLRETYGEMADCCAKQEPER

NECFLQHKDDNPNLPRLVRPEVDVMCTAFHDNEETFLKKYLYEIARRHP

YFYAPELLFFAKRYKAAFTECCQAADKAACLLPKLDELRDEGKASSAKQ

RLKCASLQKFGERAFKAWAVARLSQRFPKAEFAEVSKLVTDLTKVHTEC

CHGDLLECADDRADLAKYICENQDSISSKLKECCEKPLLEKSHCIAEVE

NDEMPADLPSLAADFVESKDVCKNYAEAKDVFLGMFLYEYARRHPDYSV

VLLLRLAKTYETTLEKCCAAADPHECYAKVFDEFKPLVEEPQNLIKQNC

ELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSA

LEVDETYVPKEFNAETFTFHADICTLSEKERQIKKQTALVELVKHKPKA

TKEQLKAVMDDFAAFVEKCCKADDKETCFAEEGKKLVAASQAALGL
```

The albumin sequence can be set off from the AFFIMER® polypeptide sequence or other flanking sequences in the AFFIMER® polypeptide by use of linker sequences as described above.

While unless otherwise indicated, reference herein to "albumin" or to "mature albumin" is meant to refer to HSA. However, it is noted that full-length HSA has a signal peptide of 18 amino acids (MKWVTFISLLFLFSSAYS (SEQ ID NO: 25)) followed by a pro-domain of 6 amino acids (RGVFRR (SEQ ID NO: 119)); this 24 amino acid residue peptide may be referred to as the pre-pro domain. The AFFIMER®-HSA fusion proteins can be expressed and secreted using the HSA pre-pro-domain in the recombinant proteins coding sequence. Alternatively, the AFFIMER®-

HSA fusion can be expressed and secreted through inclusion of other secretion signal sequences, such as described above.

In alternative embodiments, rather than provided as part of a fusion protein with the AFFIMER® polypeptide, the serum albumin polypeptide can be covalently coupled to the AFFIMER®-containing polypeptide through a bond other than a backbone amide bond, such as cross-linked through chemical conjugation between amino acid sidechains on each of the albumin polypeptide and the AFFIMER®-containing polypeptide.

(iii) Albumin Binding Domain

In certain embodiments, the AFFIMER® polypeptide can include a serum-binding moiety—either as part of a fusion protein (if also a polypeptide) with the AFFIMER® polypeptide sequence or chemically conjugated through a site other than being part of a contiguous polypeptide chain.

In certain embodiments, the serum-binding polypeptide is an albumin binding moiety. Albumin contains multiple hydrophobic binding pockets and naturally serves as a transporter of a variety of different ligands such as fatty acids and steroids as well as different drugs. Furthermore, the surface of albumin is negatively charged making it highly water-soluble.

The term "albumin binding moiety" as used herein refers to any chemical group capable of binding to albumin, i.e. has albumin binding affinity. Albumin binds to endogenous ligands such as fatty acids; however, it also interacts with exogenous ligands such as warfarin, penicillin and diazepam. As the binding of these drugs to albumin is reversible the albumin-drug complex serves as a drug reservoir that can enhance the drug biodistribution and bioavailability. Incorporation of components that mimic endogenous albumin-binding ligands, such as fatty acids, has been used to potentiate albumin association and increase drug efficacy.

In certain embodiments, a chemical modification method that can be applied in the generation of the subject AFFIMER® polypeptides to increase protein half-life is lipidation, which involves the covalent binding of fatty acids to peptide side chains. Originally conceived of and developed as a method for extending the half-life of insulin, lipidation shares the same basic mechanism of half-life extension as PEGylation, namely increasing the hydrodynamic radius to reduce renal filtration. However, the lipid moiety is itself relatively small and the effect is mediated indirectly through the non-covalent binding of the lipid moiety to circulating albumin. One consequence of lipidation is that it reduces the water-solubility of the peptide but engineering of the linker between the peptide and the fatty acid can modulate this, for example by the use of glutamate or mini PEGs within the linker. Linker engineering and variation of the lipid moiety can affect self-aggregation which can contribute to increased half-life by slowing down biodistribution, independent of albumin. See, for example, Jonassen et al. (2012) Pharm Res. 29(8):2104-14.

Other examples of albumin binding moieties for use in the generation of certain AFFIMER® polypeptides include albumin-binding (PKE2) adnectins (See WO2011140086 "Serum Albumin Binding Molecules", WO2015143199 "Serum albumin-binding Fibronectin Type III Domains" and WO2017053617 "Fast-off rate serum albumin binding fibronectin type iii domains"), the albumin binding domain 3 (ABD3) of protein G of *Streptococcus* strain G148, and the albumin binding domain antibody GSK2374697 ("AlbudAb") or albumin binding nanobody portion of ATN-103 (Ozoralizumab).

(iv) PEGylation, XTEN, PAS and Other Polymers

A wide variety of macromolecular polymers and other molecules can be linked to the AFFIMER® containing polypeptides of the present disclosure to modulate biological properties of the resulting AFFIMER® polypeptide, and/or provide new biological properties to the AFFIMER® polypeptide. These macromolecular polymers can be linked to the AFFIMER® containing polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

For this purpose, various methods including pegylation, polysialylation, HESylation, glycosylation, or recombinant PEG analogue fused to flexible and hydrophilic amino acid chain (500 to 600 amino acids) have been developed (See Chapman, (2002) Adv Drug Deliv Rev. 54. 531-545; Schlapschy et al., (2007) Prot Eng Des Sel. 20, 273-283; Contermann (2011) Curr Op Biotechnol. 22, 868-876; Jevsevar et al., (2012) Methods Mol Biol. 901, 233-246).

Examples of polymers include but are not limited to polyalkyl ethers and alkoxy-capped analogues thereof (e.g., polyoxyethylene glycol, polyoxyethylene/propylene glycol, and methoxy or ethoxy-capped analogues thereof, especially polyoxyethylene glycol, the latter is also known as polyethylene glycol or PEG); discrete PEG (dPEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogues thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyamino-acids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The polymer selected may be water soluble so that the AFFIMER® polypeptide to which it is attached does not precipitate in an aqueous environment, such as a physiological environment. The water-soluble polymer may be any structural form including but not limited to linear, forked or branched. Typically, the water soluble polymer is a poly (alkylene glycol), such as poly(ethylene glycol) (PEG), but other water soluble polymers can also be employed. By way of example, PEG is used to describe certain embodiments of this disclosure. For therapeutic use of the AFFIMER® polypeptide, the polymer may be pharmaceutically acceptable.

The term "PEG" is used broadly to encompass any polyethylene glycol molecule, without regard to size or to modification at an end of the PEG, and can be represented as linked to the AFFIMER® containing polypeptide by the formula:

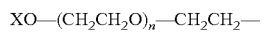

or

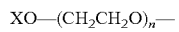

where n is 2 to 10,000 and X is H or a terminal modification, including but not limited to, a C1-4 alkyl, a protecting group, or a terminal functional group. In some cases, a PEG used in the polypeptides of the disclosure terminates on one end with hydroxy or methoxy, i.e., X is H or CH3 ("methoxy PEG").

It is noted that the other end of the PEG, which is shown in the above formulas by a terminal "—" may attach to the AFFIMER® containing polypeptide via a naturally-occurring or non-naturally encoded amino acid. For instance, the attachment may be through an amide, carbamate or urea linkage to an amine group (including but not limited to, the epsilon amine of lysine or the N-terminus) of the polypeptide. Alternatively, the polymer is linked by a maleimide linkage to a thiol group (including but not limited to, the thiol group of cysteine)—which in the case of attachment to the AFFIMER® polypeptide sequence per se requires altering a residue in the AFFIMER® sequence to a cysteine.

The number of water soluble polymers linked to the AFFIMER®-containing polypeptide (i.e., the extent of PEGylation or glycosylation) can be adjusted to provide an altered (including but not limited to, increased or decreased) pharmacologic, pharmacokinetic or pharmacodynamic characteristic such as in vivo half-life in the resulting AFFIMER® polypeptide. In some embodiments, the half-life of the resulting AFFIMER® polypeptide is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

Another variation of polymer system useful to modify the PK or other biological properties of the resulting AFFIMER® polypeptide are the use of unstructured, hydrophilic amino acid polymers that are functional analogues of PEG, particularly as part of a fusion protein with the AFFIMER® polypeptide sequence. The inherent biodegradability of the polypeptide platform makes it attractive as a potentially more benign alternative to PEG. Another advantage is the precise molecular structure of the recombinant molecule in contrast to the polydispersity of PEG. Unlike HSA and Fc peptide fusions, in which the three-dimensional folding of the fusion partner needs to be maintained, the recombinant fusions to unstructured partners can, in many cases, be subjected to higher temperatures or harsh conditions such as HPLC purification.

One of the more advanced of this class of polypeptides is termed XTEN (Amunix) and is 864 amino acids long and comprised of six amino acids (A, E, G, P, S and T). See Schellenberger et al. "A recombinant polypeptide extends the in vivo half-life of peptides and proteins in a tuneable manner" 2009 Nat Biotechnol. 27(12):1186-90. Enabled by the biodegradable nature of the polymer, this is much larger than the 40 kDa PEGs typically used and confers a concomitantly greater half-life extension. The fusion of XTEN to the AFFIMER® containing polypeptide should result in half-life extension of the final AFFIMER® polypeptide by 60- to 130-fold over the unmodified polypeptide.

A second polymer based on similar conceptual considerations is PAS (XL-Protein GmbH). Schlapschy et al. "PASYlation: a biological alternative to PEGylation for extending the plasma half-life of pharmaceutically active proteins" 2013 Protein Eng Des Sel. 26(8):489-501. A random coil polymer comprised of an even more restricted set of only three small uncharged amino acids, proline, alanine and serine. AS with Fc, HAS and XTEN, the PAS modification can be genetically encoded with the AFFIMER® polypeptide sequence to produce an inline fusion protein when expressed.

b. Multi-Specific Fusion Proteins

In certain embodiments, the AFFIMER® polypeptide is a multi-specific and/or multivalent polypeptide including, for example, a first AFFIMER® polypeptide that binds to a first target and at least one additional binding domain that binds to a second target that is difference from the first target—which may be a different molecule altogether (bispecific) or the same molecule type at the same site (multivalent) or the same molecule but at a different site (biparatopic or multi-paratopic). The additional binding domain may be a polypeptide sequence selected from amongst, to illustrate, a second AFFIMER® polypeptide sequence (which may be the same or different than the first AFFIMER® polypeptide sequence), an antibody or fragment thereof or other antigen binding polypeptide, a ligand binding portion of a receptor (such as a receptor trap polypeptide), a receptor-binding ligand (such as a cytokine, growth factor or the like), engineered T-cell receptor, an enzyme or catalytic fragment thereof, or other polypeptide sequence that confers some In certain embodiments, the AFFIMER® polypeptide includes one or more antigen binding sites from an antibody. The resulting AFFIMER® polypeptide can be a single chain including both the AFFIMER® sequence and the sequence for the antibody antigen binding site (such as in the case of an scFV), or can be a multimeric protein complex such as in antibody assembled with heavy and/or light chains to which the sequence of the AFFIMER® has also been fused.

In some embodiments with respect to a multi-specific AFFIMER® polypeptide comprising a full-length immunoglobulin, the fusion of the AFFIMER® polypeptide sequence to the antibody will preserve the Fc function of the Fc region of the immunoglobulin. For instance, in certain embodiments, the AFFIMER® polypeptide will be capable of binding, via its Fc portion, to the Fc receptor of Fc receptor-positive cells. In some further embodiments, the AFFIMER® polypeptide may activate the Fc receptor-positive cell by binding to the Fc receptor-positive cell, thereby initiating or increasing the expression of cytokines and/or co-stimulatory antigens. Furthermore, the AFFIMER® polypeptide may transfer at least a second activation signal required for physiological activation of the T cell to the T cell via the co-stimulatory antigens and/or cytokines.

In some embodiments, resulted from the binding of its Fc portion to other cells that express Fc receptors present on the surface of effector cells from the immune system, such as immune cells, hepatocytes, and endothelial cells, the AFFIMER® polypeptide may possess antibody-dependent cellular cytotoxicity (ADCC) function, a mechanism of cell-mediated immune defence whereby an effector cell of the immune system actively lyses a target cell, whose membrane-surface antigen has been bound by an antibody, and therefore, trigger tumor cell death via ADCC. In some further embodiments, the AFFIMER® polypeptide is capable of demonstrating ADCC function.

As described above, apart from the Fc-mediated cytotoxicity, the Fc portion may contribute to maintaining the serum levels of the AFFIMER® polypeptide, critical for its stability and persistence in the body. For example, when the Fc portion binds to Fc receptors on endothelial cells and on phagocytes, the AFFIMER® polypeptide may become internalized and recycled back to the blood stream, enhancing its half-life within the body.

Exemplary targets of the additional AFFIMER® polypeptides include, but are not limited to, another immune checkpoint protein, and immune co-stimulatory receptor (particularly if the additional AFFIMER®(s) can agonize the co-stimulatory receptor), a receptor, a cytokine, a growth factor, or a tumor-associated antigen, mere to illustrate.

c. Conjugates

The subject AFFIMER® polypeptides may also include one or more Functional Moieties intended to impart detectability or additional pharmacologic activity to the AFFIMER® polypeptide. Functional Moieties for detection are those which can be employed to detect association of the AFFIMER® polypeptide with a cell or tissue (such as a tumour cell) in vivo. Functional Moieties with pharmacologic activity are those agents which are meant to be delivered to the tissue expressing the target of the AFFIMER® polypeptide and in doing so have a pharmacologic consequence to the targeted tissues or cells.

The present disclosure provides AFFIMER® polypeptides including conjugates of substances having a wide variety of functional groups, substituents or moieties, with those Functional Moieties including but not limited to a label; a dye; an immunoadhesion molecule; a radionuclide; a cytotoxic compound; a drug; an affinity label; a photoaffinity label; a reactive compound; a resin; a second protein or polypeptide or polypeptide analogue; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labelled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance.

(i) Labels and Detectable Moieties

Where the moiety is a detectable label, it can be a fluorescent label, radioactive label, enzymatic label or any other label known to the skilled person. In certain embodiments, the Functional Moiety is a detectable label that can be included as part of a conjugate to form certain AFFIMER® polypeptides suitable for medical imaging. By "medical imaging" is meant any technique used to visualise an internal region of the human or animal body, for the purposes of diagnosis, research or therapeutic treatment. For instance, the AFFIMER® polypeptide can be detected (and quantitated) by radio-scintigraphy, magnetic resonance imaging (MRI), computed tomography (CT scan), nuclear imaging, positron emission comprising a metal tomography (PET) contrast agent, optical imaging (such as fluorescence imaging including near-infrared fluorescence (NIRF) imaging), bioluminescence imaging, or combinations thereof. The Functional Moiety is optionally a contrast agent for X-ray imaging. Agents useful in enhancing such techniques are those materials that enable visualization of a particular locus, organ or disease site within the body, and/or that lead to some improvement in the quality of the images generated by the imaging techniques, providing improved or easier interpretation of those images. Such agents are referred to herein as contrast agents, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging).

In certain preferred embodiments, the detectable label includes a chelate moiety for chelating a metal, e.g., a chelator for a radiometal or paramagnetic ion. In certain preferred embodiments, the detectable label is a chelator for a radionuclide useful for radiotherapy or imaging procedures. Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: 43K, 47Sc, 51Cr, 57Co, 58Co, 59Fe, 64Cu, 67Ga, 67Cu, 68Ga, 71Ge, 75Br, 76Br, 77Br, 77As, 81Rb, 90Y, 97Ru, 99mTc, 100Pd, 101Rh, 103Pb, 105Rh, 109Pd, 111Ag, 111In, 113In, 119Sb 121Sn, 123I, 125I, 127Cs, 128Ba, 129Cs, 131I, 131Cs, 143Pr, 153Sm, 161Tb, 166Ho, 169Eu, 177Lu, 186Re, 188Re, 189Re, 191O s, 193Pt, 194Ir, 197Hg, 199Au, 203Pb, 211At, 212Pb, 212Bi and 213Bi. Conditions under which a chelator will coordinate a metal are described, for example, by Gansow et al., U.S. Pat. Nos. 4,831,175, 4,454,106 and 4,472,509. Examples of chelators includes, merely to illustrate, 1,4,7-triazacyclononane-N,N', N"-triacetic acid (NOTA) 1,4,7,10-tetraazacyclododecane-N,N',N",N'"-tetraacetic acid (DOTA) 1,4,8,11-tetraazacyclotetradecane-N,N',N",N'"-tetraacetic acid (TETA).

Other detectable isotopes that can be incorporated directly into the amino acid residues of the AFFIMER® polypeptide or which otherwise do not require a chelator, include 3H, 14C, 32P, 35S and 36Cl.

Paramagnetic ions, useful for diagnostic procedures, may also be administered. Examples of paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), or combinations of these paramagnetic ions.

Examples of fluorescent labels include, but are not restricted to, organic dyes (e.g. cyanine, fluorescein, rhodamine, Alexa Fluors, Dylight fluors, ATTO Dyes, BODIPY Dyes, etc.), biological fluorophores (e.g. green fluorescent protein (GFP), R-Phycoerythrin, etc.), and quantum dots.

Non-limiting fluorescent compound that may be used in the present invention include, Cy5, Cy5.5 (also known as Cy5++), Cy2, fluorescein isothiocyanate (FITC), tetramethylrhodamine isothiocyanate (TRITC), phycoerythrin, Cy7, fluorescein (FAM), Cy3, Cy3.5 (also known as Cy3++), Texas Red, LightCycler-Red 640, LightCycler Red 705, tetramethylrhodamine (TMR), rhodamine, rhodamine derivative (ROX), hexachlorofluorescein (HEX), rhodamine 6G (R6G), the rhodamine derivative JA133, Alexa Fluorescent Dyes (such as Alexa Fluor 488, Alexa Fluor 546, Alexa Fluor 633, Alexa Fluor 555, and Alexa Fluor 647), 4',6-diamidino-2-phenylindole (DAPI), Propidium iodide, AMCA, Spectrum Green, Spectrum Orange, Spectrum Aqua, Lissamine, and fluorescent transition metal complexes, such as europium. Fluorescent compound that can be used also include fluorescent proteins, such as GFP (green fluorescent protein), enhanced GFP (EGFP), blue fluorescent protein and derivatives (BFP, EBFP, EBFP2, Azurite, mKalama1), cyan fluorescent protein and derivatives (CFP, ECFP, Cerulean, CyPet) and yellow fluorescent protein and derivatives (YFP, Citrine, Venus, YPet). WO2008142571, WO2009056282, WO9922026.

Examples of enzymatic labels include, but are not restricted to, horseradish peroxidase (HRP), alkaline phosphatase (AP), glucose oxidase and ▯-galactosidase.

Another well-known label is biotin. Biotin labels are typically composed of the biotinyl group, a spacer arm and a reactive group that is responsible for attachment to target functional groups on proteins. Biotin can be useful for attaching the labelled protein to other moieties which comprise an avidin moiety.

(ii) AFFIMER®-Drug Conjugates

In certain embodiments, the AFFIMER® polypeptide includes one or more therapeutic agents, e.g., to form an AFFIMER®-drug conjugate. As used herein, the term "therapeutic agent" refers to a substance that may be used in the cure, mitigation, treatment, or prevention of disease in a human or another animal. Such therapeutic agents include substances recognized in the official United States Pharmacopeia, official Homeopathic Pharmacopeia of the United States, official National Formulary, or any supplement thereof, and include but are not limited to small molecules, nucleotides, oligopeptides, polypeptides, etc. Therapeutic agents that may be attached to AFFIMER®-containing polypeptides include, but are not limited to, cytotoxic agents, anti-metabolites, alkylating agents, antibiotics, growth factor, cytokines, anti-angiogenic agents, anti-mitotic agents, toxins, apoptotic agents or the like, such as DNA alkylating agents, topoisomerase inhibitors, endoplasmic reticulum stress inducing agents, platinum compounds, antimetabolites, vincalkaloids, taxanes, epothilones, enzyme inhibitors, receptor antagonists, therapeutic antibodies, tyrosine kinase inhibitors, radiosensitizers, and chemotherapeutic combination therapies, such as illustrations.

Non-limiting examples of DNA alkylating agents are nitrogen mustards, such as Mechlorethamine, Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Camptothecin derivatives including CPT-11 (irinotecan), SN-38, APC, NPC, camptothecin, topotecan, exatecan mesylate, 9-nitrocamptothecin, 9-aminocamptothecin, lurtotecan, rubitecan, silatecan, gimatecan, diflomotecan, exatecan, BN-80927, DX-8951f, and MAG-CPT as described in Pommier Y. (2006) Nat. Rev. Cancer 6(10): 789-802 and U.S. Patent Publication No. 200510250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11 (8): 1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-]25, Crow et al. (1994) J. Med. Chem. 37(19):31913194, and Crespi et al. (1986) Biochem. Biophys. Res. Commun. 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamides, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e] Perimidines, and Anthracenyl-amino Acid Conjugates as described in Denny and Baguley (2003) Curr. Top. Med. Chem. 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Anthracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Non-limiting examples of platinum-based compound include Carboplatin, Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201: 1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogues and derivative thereof such as 5'-deoxy-5-fluorouridine (doxifluridine), 1-tetrahydrofuranyl-5-fluorouracil (ftorafur), Capecitabine (Xeloda), S—I (MBMS-247616, consisting of tegafur and two modulators, a 5-chloro-2,4-dihydroxypyridine and potassium oxonate), raltitrexed (tomudex), no latrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifamib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of therapeutic antibodies include, but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab). U.S. Pat. Nos. 5,776,427 and 7,601,355.

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Chemotherapeutic agents that can be attached to the present AFFIMER®-containing polypeptides may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

Examples of specific therapeutic agents that can be linked, ligated, or associated with the AFFIMER®-containing polypeptides of the invention are flomoxef; fortimicin(s); gentamicin(s); glucosulfone solasulfone; gramicidin S; gramicidin(s); grepafloxacin; guamecycline; hetacillin; isepamicin; josamycin; kanamycin(s); flomoxef; fortimicin(s); gentamicin(s); glucosulfone solasulfone; gramicidin S; gramicidin(s); grepafloxacin; guamecycline; hetacillin; isepamicin; josamycin; kanamycin(s); bacitracin; bambermycin(s); biapenem; brodimoprim; butirosin; capreomycin; carbenicillin; carbomycin; carumonam; cefadroxil; cefamandole; cefatrizine; cefbuperazone; cefclidine; cefdinir; cefditoren; cefepime; cefetamet; cefixime; cefinenoxime; cefinnox; cladribine; apalcillin; apicycline; apramycin; arbekacin; aspoxicillin; azidamfenicol; aztreonam; cefodizime; cefonicid; cefoperazone; ceforamide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilyanilinoethanol; 4,4'-sulfinyldianiline; 4-sulfanilamidosalicylic acid; butorphanol; nalbuphine. streptozocin; doxorubicin; daunorubicin; plicamycin; idarubicin; mitomycin C; pentostatin; mitoxantrone; cytarabine; fludarabine phosphate; butorphanol; nalbuphine. streptozocin; doxorubicin; daunorubicin; plicamycin; idarubicin; mitomycin C; pentostatin; mitoxantrone; cytarabine; fludarabine phosphate; acediasulfone; acetosulfone; amikacin; amphotericin B; ampicillin; atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; floxuridine; dirithromycin; doxycycline; enoxacin; enviomycin; epicillin; erythromycin; leucomycin(s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin; 6-azauridine; 6-diazo-5-oxo-L-norleucine; aclacinomycin(s); ancitabine; anthramycin; azacitidine; azaserine; bleomycin(s); ethyl biscoumacetate; ethylidene dicoumarol; iloprost; lamifiban; taprostene; tioclomarol; tirofiban; amiprilose; bucillamine; gusperimus; gentisic acid; glucamethacin; glycol salicylate; meclofenamic acid; mefenamic acid; mesalamine; niflumic acid; olsalazine; oxaceprol; S-enosylmethionine; salicylic acid; salsalate; sulfasalazine; tolfenamic acid; carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; Tomudex (N-[[5-[[(1,4-Dihydro-2-methyl-4-oxo-6-quinazolinyl)methyl]methylamino]-2-thienyl]carbonyl]-L-glutamic acid), trimetrexate, tubercidin, ubenimex, vindesine, zorubicin; argatroban; coumetarol or dicoumarol.

In certain embodiments, the AFFIMER® polypeptide includes a conjugated cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, Phytolacca americana proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating to antibodies and other proteins may be employed in generating the conjugates of the present invention, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating peptide, polypeptide and organic and inorganic moieties to antibodies and other proteins are conventional and very well known in the art and readily adapted for generating those versions of the subject AFFIMER® polypeptides.

Where the conjugated moiety is a peptide or polypeptide, that moiety can be chemically cross-linked to the AFFIMER®-containing polypeptide, or can be included as part of a fusion protein with the AFFIMER®-containing polypeptide. And illustrative example would be a diphtheria toxin-AFFIMER® fusion protein. In the case of non-peptide entities, the addition to the AFFIMER®-containing polypeptide will generally be by way of chemical conjugation to the AFFIMER®-containing polypeptide—such as through a functional group on an amino acid side chain or the carboxyl group at the C-terminal or amino group at the N-terminal end of the polypeptide. In certain embodiment, whether as a fusion protein or chemically cross-linked moiety, the conjugated moiety will include one or more sites that can be cleaved by an enzyme or are otherwise sensitive to an environmental condition (such as pH) that permits the conjugated moiety to be released from the AFFIMER®-containing polypeptide, such as in the tumour or other diseased tissue (or tissue to be protected if the conjugated moiety functions to protect healthy tissue).

III. Expression Methods and Systems

Recombinant AFFIMER®-containing proteins described herein can be produced by any suitable method known in the art. Such methods range from direct protein synthesis methods to constructing a DNA sequence encoding polypeptide sequences and expressing those sequences in a suitable host. For those recombinant AFFIMER® polypeptides including further modifications, such as a chemical modifications or conjugation, the recombinant AFFIMER® polypeptide can be further manipulated chemically or enzymatically after isolation form the host cell or chemical synthesis.

The present invention includes recombinant methods and nucleic acids for recombinantly expressing the recombinant AFFIMER® polypeptides of the present invention comprising (i) introducing into a host cell a polynucleotide encoding the amino acid sequence of said AFFIMER® polypeptide, for example, wherein the polynucleotide is in a vector and/or is operably linked to a promoter; (ii) culturing the host cell (e.g., eukaryotic or prokaryotic) under condition favorable to expression of the polynucleotide and, (iii) optionally, isolating the AFFIMER® polypeptide from the host cell and/or medium in which the host cell is grown. See e.g., WO 04/041862, WO 2006/122786, WO 2008/020079, WO 2008/142164 or WO 2009/068627.

In some embodiments, a DNA sequence encoding a recombinant AFFIMER® polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once a nucleic acid sequence encoding a recombinant AFFIMER® polypeptide of the invention has been obtained, the vector for the production of the recombinant AFFIMER® polypeptide may be produced by recombinant DNA technology using techniques well known in the art. Methods which are well known to those skilled in the art can be used to construct expression vectors containing the recombinant AFFIMER® polypeptide coding sequences and appropriate transcriptional and translational control signals. These methods include, for example, in vitro recombinant DNA techniques, synthetic techniques, and in vivo genetic recombination. (See, for example, the techniques described in Sambrook et al, 1990, MOLECULAR CLONING, A LABORATORY MANUAL, 2d Ed., Cold Spring Harbor Laboratory, Cold Spring Harbor, N.Y. and Ausubel et al. eds., 1998, CURRENT PROTOCOLS IN MOLECULAR BIOLOGY, John Wiley & Sons, NY).

An expression vector comprising the nucleotide sequence of a recombinant AFFIMER® polypeptide can be transferred to a host cell by conventional techniques (e.g., electroporation, liposomal transfection, and calcium phosphate precipitation) and the transfected cells are then cultured by conventional techniques to produce the recombinant AFFIMER® polypeptide of the invention. In specific embodiments, the expression of the recombinant AFFIMER® polypeptide is regulated by a constitutive, an inducible or a tissue, specific promoter.

The expression vector may include an origin of replication, such as may be selected based upon the type of host cell being used for expression. By way of example, the origin of replication from the plasmid pBR322 (Product No. 303-3 s, New England Biolabs, Beverly, Mass.) is useful for most Gram-negative bacteria while various origins from SV40, polyoma, adenovirus, vesicular stomatitis virus (VSV) or papillomaviruses (such as HPV or BPV) are useful for cloning vectors in mammalian cells. Generally, the origin of replication component is not needed for mammalian expression vectors (for example, the SV40 origin is often used because it contains the early promoter).

The vector may include one or more selectable marker genes, e.g., genetic elements that encode a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells. Other selection genes may be used to amplify the gene which will be expressed. Amplification is a process where genes which are in greater demand for the production of a protein critical for growth are reiterated in tandem within the chromosomes of successive generations of recombinant cells. Examples of selectable markers for mammalian cells include dihydrofolate reductase (DHFR) and thymidine kinase. The mammalian cell transformants are placed under selection pressure which only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes the recombinant AFFIMER® polypeptide. As a result, increased quantities of the recombinant AFFIMER® polypeptide are synthesized from the amplified DNA.

The vector may also include one or more ribosome binding site, which will be transcribed into the mRNA including the coding sequence for the recombinant AFFIMER® polypeptide. For example, such a site is characterized by a Shine-Dalgarno sequence (prokaryotes) or a Kozak sequence (eukaryotes). The element is typically located 3' to the promoter and 5' to the coding sequence of the polypeptide to be expressed. The Shine-Dalgarno sequence is varied but is typically a polypurine (having a high A-G content). Many Shine-Dalgarno sequences have been identified, each of which can be readily synthesized using methods set forth above and used in a prokaryotic vector.

The expression vectors will typically contain a promoter that is recognized by the host organism and operably linked to a nucleic acid molecule encoding the recombinant AFFIMER® polypeptide. Either a native or heterologous promoter may be used depending the host cell used for expression and the yield desired.

Promoters for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, and they can be ligated to a desired nucleic acid sequence(s), using linkers or adapters as desired to supply restriction sites.

Promoters for use with yeast hosts are also known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be used for expressing the selective binding agents of the invention include, but are not limited to: the SV40 early promoter region (Bernoist and Chambon, Nature, 290:304-310, 1981); the CMV promoter; the promoter contained in the 3' long terminal repeat of Rous sarcoma virus (Yamamoto et al. (1980), Cell 22: 787-97); the herpes thymidine kinase promoter (Wagner et al. (1981), Proc. Natl. Acad. Sci. U.S.A. 78: 1444-5); the regulatory sequences of the metallothionine gene (Brinster et al, Nature, 296; 39-42, 1982); prokaryotic expression vectors such as the beta-lactamase promoter (Villa-Kamaroff, et al., Proc. Natl. Acad. Sci. U.S.A., 75; 3727-3731, 1978); or the tac promoter (DeBoer, et al. (1983), Proc. Natl. Acad. Sci. U.S.A., 80: 21-5). Also of interest are the following animal transcriptional control regions, which exhibit tissue specificity and have been utilized in transgenic animals: the elastase I gene control region which is active in pancreatic acinar cells (Swift et al. (1984), Cell 38: 639-46; Ornitz et al. (1986), Cold Spring Harbor Symp. Quant. Biol. 50: 399-409; MacDonald (1987), Hepatology 7: 425-515); the insulin gene control region which is active in pancreatic beta cells (Hanahan (1985), Nature 315: 115-22); the immunoglobulin gene control region which is active in lymphoid cells (Grosschedl et al. (1984), Cell 38; 647-58; Adames et al. (1985), Nature 318; 533-8; Alexander et al. (1987), Mol. Cell. Biol. 7: 1436-44); the mouse mammary tumor virus control region which is active in testicular, breast, lymphoid and mast cells (Leder et al. (1986), Cell 45: 485-95), albumin gene control region which is active in liver (Pinkert et al. (1987), Genes and Devel. 1: 268-76); the alphafetoprotein gene control region which is active in liver (Krumlauf et al. (1985), Mol. Cell. Biol. 5: 1639-48; Hammer et al. (1987), Science, 235: 53-8); the alpha 1-antitrypsin gene control region which is active in the liver (Kelsey et al. (1987), Genes and Devel. 1: 161-71); the beta-globin gene control region which is active in myeloid cells (Mogram et al., Nature, 315 338-340, 1985; Kollias et al. (1986), Cell 46: 89-94); the myelin basic protein gene control region which is active in oligodendrocyte cells in the brain (Readhead et al. (1987), Cell, 48: 703-12); the myosin light chain-2 gene control region which is active in skeletal muscle (Sani (1985), Nature, 314: 283-6); and the gonadotropic releasing hormone gene control region which is active in the hypothalamus (Mason et al. (1986), Science 234: 1372-8).

An enhancer sequence may be inserted into the vector to increase transcription in eukaryotic host cells. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters.

While an enhancer may be spliced into the vector at a position 5' or 3' to the polypeptide coding region, it is typically located at a site 5' from the promoter.

Vectors for expressing nucleic acids include those which are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (Blue- BacII; Invitrogen), pDSR-alpha (PCT Publication No. WO90/14363) and pFastBacDual (Gibco/BRL, Grand Island, N.Y.).

Additional possible vectors include, but are not limited to, cosmids, plasmids or modified viruses, but the vector system must be compatible with the selected host cell. Such vectors include, but are not limited to plasmids such as Bluescript® plasmid derivatives (a high copy number ColEl-based phagemid, Stratagene Cloning Systems Inc., La Jolla Calif.), PCR cloning plasmids designed for cloning Taq-amplified PCR products (e.g., TOPO™. TA Cloning® Kit, PCR2.1 plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques Eukaryotic and prokaryotic host cells, including mammalian cells as hosts for expression of the recombinant AFFIMER® polypeptide disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells.

Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Physcomitrella patens* and *Neurospora crassa*. *Pichia* sp., any *Saccharomyces* sp., *Hansenula polymorpha*, any *Kluyveromyces* sp., *Candida albicans*, any *Aspergillus* sp., *Trichoderma reesei*, *Chrysosporium lucknowense*, any *Fusarium* sp., *Yarrowia lipolytica*, and *Neurospora crassa*.

A variety of host-expression vector systems may be utilized to express the recombinant AFFIMER® polypeptide of the invention. Such host-expression systems represent vehicles by which the coding sequences of the recombinant AFFIMER® polypeptide may be produced and subsequently purified, but also represent cells which may, when transformed or transfected with the appropriate nucleotide coding sequences, express the recombinant AFFIMER® polypeptide of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing AFFIMER® polypeptide coding sequences; yeast (e.g., *Saccharomyces pichia*) transformed with recombinant yeast expression vectors containing AFFIMER® polypeptide coding sequences; insect cell systems infected with recombinant virus expression vectors (e.g., baculovirus) containing the AFFIMER® polypeptide coding sequences; plant cell systems infected with recombinant virus expression vectors (e.g., cauliflower mosaic virus (CµMV) and tobacco mosaic virus (TMV)) or transformed with recombinant plasmid expression vectors (e.g., Ti plasmid) containing AFFIMER® polypeptide coding sequences; or mammalian cell systems (e.g., COS, CHO, BHK, 293, 293T, 3T3 cells, lymphotic cells (see U.S. Pat. No. 5,807, 715), Per C.6 cells (rat retinal cells developed by Crucell)) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the recombinant AFFIMER® polypeptide being expressed. For example, when a large quantity of such a protein is to be produced, for the generation of pharmaceutical compositions of the recombinant AFFIMER® polypeptide, vectors which direct the expression of high levels of fusion protein products that are readily purified may be desirable. Such vectors include, but are not limited, to the *E. coli* expression vector pUR278 (Ruther et al. (1983) "Easy Identification Of cDNA Clones," EMBO J. 2:1791-1794), in which the AFFIMER® polypeptide coding sequence may be ligated individually into the vector in frame with the lac Z coding region so that a fusion protein is produced; pIN vectors (Inouye et al. (1985) "Up-Promoter Mutations In The Lpp Gene Of *Escherichia coli*," Nucleic Acids Res. 13:3101-3110; Van Heeke et al. (1989) "Expression Of Human Asparagine Synthetase In *Escherichia coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The AFFIMER® polypeptide coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the AFFIMER® polypeptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts. (see e.g., see Logan et al. (1984) "Adenovirus Tripartite Leader Sequence Enhances Translation Of mRNAs Late After Infection," Proc. Natl. Acad. Sci. (U.S.A.) 81:3655-3659). Specific initiation signals may also be required for efficient translation of inserted AFFIMER® polypeptide coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the recombinant AFFIMER® polypeptides of the invention. Such engineered cell lines may be particularly useful in screening and evaluation of compounds that interact directly or indirectly with the recombinant AFFIMER® polypeptides.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11:223-232), hypoxanthine-guanine phosphoribosyltransferase (Szybalska et al. (1962) "Genetics Of Human Cess Line. IV. DNA-Mediated Heritable Transformation Of A Biochemical Trait," Proc. Natl. Acad. Sci. (U.S.A.) 48:2026-2034), and adenine phosphoribosyltransferase (Lowy et al. (1980) "Isolation Of Transforming DNA: Cloning The Hamster Aprt Gene," Cell 22:817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. (U.S.A.) 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. (U.S.A.) 78:1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. (U.S.A.) 78:2072-2076); neo, which confers resistance to the aminoglycoside G-418 (Tachibana et al. (1991) "Altered Reactivity Of Immunoglobulin Produced By Human-Human Hybridoma Cells Transfected By pSV2-Neo Gene," Cytotechnology 6(3):219-226; Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human gene therapy," Ann. Rev. Biochem. 62:191-217). Methods commonly known in the art of recombinant DNA technology which can be used are described in Ausubel et al. (eds.), 1993, CURRENT PROTOCOLS IN MOLECULAR BIOLOGY, John Wiley & Sons, NY; Kriegler, 1990, GENE TRANSFER AND EXPRESSION, A LABORATORY MANUAL, Stockton Press, NY; and in Chapters 12 and 13, Dracopoli et al. (eds), 1994, CURRENT PROTOCOLS IN HUMAN GENETICS, John Wiley & Sons, NY; Colbere-Garapin et al. (1981) "A New Dominant Hybrid Selective Marker For Higher Eukaryotic Cells," J. Mol. Biol. 150:1-14; and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156).

The expression levels of a recombinant AFFIMER® polypeptide can be increased by vector amplification (for a review, see Bebbington and Hentschel, "The Use Of Vectors Based On Gene Amplification For The Expression Of Cloned Genes In Mammalian Cells," in DNA CLONING, Vol. 3. (Academic Press, New York, 1987)). When a marker in the vector system expressing a recombinant AFFIMER® polypeptide is amplifiable, increase in the level of inhibitor present in culture of host cell will increase the number of copies of the marker gene. Since the amplified region is associated with the nucleotide sequence of the recombinant AFFIMER® polypeptide, production of the recombinant AFFIMER® polypeptide will also increase (Crouse et al. (1983) "Expression And Amplification Of Engineered Mouse Dihydrofolate Reductase Minigenes," Mol. Cell. Biol. 3:257-266).

Where the AFFIMER® polypeptide is an AFFIMER® antibody fusion or other multiprotein complex, the host cell may be co-transfected with two expression vectors, for instance the first vector encoding a heavy chain and the second vector encoding a light chain derived polypeptide, one or both of which includes an AFFIMER® polypeptide coding sequence. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot (1986) "Expression And Amplification Of Engineered Mouse Dihydrofolate Reductase Minigenes," Nature 322:562-565; Kohler (1980) "Immunoglobulin Chain Loss In Hybridoma Lines," Proc. Natl. Acad. Sci. (U.S.A.) 77:2197-2199). The coding sequences for the heavy and light chains may comprise cDNA or genomic DNA.

In general, glycoproteins produced in a particular cell line or transgenic animal will have a glycosylation pattern that is characteristic for glycoproteins produced in the cell line or transgenic animal. Therefore, the particular glycosylation pattern of the recombinant AFFIMER® polypeptide will depend on the particular cell line or transgenic animal used to produce the protein. In certain embodiments of AFFIMER®/antibody fusions, a glycosylation pattern comprising only non-fucosylated N-glycans may be advantageous, because in the case of antibodies this has been shown to typically exhibit more potent efficacy than fucosylated counterparts both in vitro and in vivo (See for example, Shinkawa et al., J. Biol. Chem. 278: 3466-3473 (2003); U.S. Pat. Nos. 6,946,292 and 7,214,775).

Further, expression of an AFFIMER® polypeptide from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0216846, 0256055, and 0323997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell. Such host cells containing the binder or polynucleotide or vector as discussed herein as well as expression methods, as discussed herein, for making the binder using such a host cell are part of the present invention.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

The recombinant AFFIMER® polypeptides produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, recombinant AFFIMER® polypeptides produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

IV. Encoded AFFIMER®s for In Vivo Delivery

An alternative approach to the delivery of therapeutic AFFIMER® polypeptides would be to leave the production of the therapeutic polypeptide to the body itself. A multitude of clinical studies have illustrated the utility of in vivo gene transfer into cells using a variety of different delivery systems. In vivo gene transfer seeks to administer to patients the "Encoded AFFIMER®" nucleotide sequence, rather than the AFFIMER® polypeptide. This allows the patient's body to produce the therapeutic AFFIMER® polypeptide of interest for a prolonged period of time, and secrete it either systemically or locally, depending on the production site. Gene-based Encoded AFFIMER®s can present a labor- and cost-effective alternative to the conventional production, purification and administration of the polypeptide version of the AFFIMER® polypeptide. A number of antibody expression platforms have been pursued in vivo to which delivery of Encoded AFFIMER®s can be adapted: these include viral vectors, naked DNA and RNA. Encoded AFFIMER® gene transfer can not only enable cost-savings by reducing the cost of goods and of production, but may also be able to reduce the frequency of drug administration. Overall, a prolonged in vivo production of the therapeutic AFFIMER® polypeptide by expression of the Encoded AFFIMER® can contribute to (i) a broader therapeutic or prophylactic application of AFFIMER® polypeptides in price-sensitive conditions, (ii) an improved accessibility to therapy in both developed and developing countries, and (iii) more effective and affordable treatment modalities. In addition to in vivo gene transfer, cells can be harvested from the host (or a donor), engineered with Encoded AFFIMER® sequences to produce AFFIMER® polypeptides and re-administered to patients.

Intramuscular antibody gene administration has been most widely evaluated (reviewed in Deal et al. (2015) "Engineering humoral immunity as prophylaxis or therapy" Curr Opin Immunol. 35:113-22), and also carries the highest clinical translatability and application when applied to Encoded AFFIMER®s. Indeed, the inherent anatomical, cellular and physiological properties of skeletal muscle make it a stable environment for long-term Encoded AFFIMER® expression and systemic circulation. Skeletal muscle is easily accessible, allowing multiple or repeated administrations. The abundant blood vascular supply provides an efficient transport system for secreted therapeutic AFFIMER® polypeptides into the circulation. The syncytial nature of muscle fibers allows dispersal of nucleotides from a limited site of penetration to a large number of neighboring nuclei within the fiber. Skeletal muscle fibers are also terminally differentiated cells, and nuclei within the fibers are post-mitotic. Consequently, integration in the host genome is not a prerequisite to attain prolonged mAb expression. The liver is another site often used for pre-clinical antibody gene transfer, and is typically transfected via i.v. injection, and can also be a site of gene transfer for Encoded AFFIMER®s either for local delivery of AFFIMER® polypeptides (such as in the treatment of liver cancer and/or metaplasias) or for the generation of AFFIMER® polypeptides that are secreted into the vascular for systemic circulation. This organ has various physiological functions, including the synthesis of plasma proteins. This organ can be particularly well suited for in vivo Encoded AFFIMER® expression.

The tumor presents another site for Encoded AFFIMER® transfer, targeted either via i.v. or direct injection/electroporation. Indeed, intratumoral Encoded AFFIMER® expression can allow for a local production of the therapeutic AFFIMER® polypeptides, waiving the need for high systemic AFFIMER® polypeptide levels that might otherwise be required to penetrate and impact solid tumors. A similar rationale applies for the brain, which is frequently targeted in the context of antibody gene transfer to avoid the difficulties with blood-brain barrier trafficking and would likewise be a target for delivery of Encoded AFFIMER®s. See, for example, Beckman et al. (2015) "Antibody constructs in cancer therapy: protein engineering strategies to improve exposure in solid tumors" Cancer 109(2):170-9; Dronca et al. (2015) "Immunomodulatory antibody therapy of cancer: the closer, the better" Clin Cancer Res. 21(5):944-6; and Neves et al. (2016) "Antibody approaches to treat brain diseases" Trends Biotechnol. 34(1):36-48.

The success of gene therapy has largely been driven by improvements in nonviral and viral gene transfer vectors. An array of physical and chemical nonviral methods have been used to transfer DNA and mRNA to mammalian cells and a substantial number of these have been developed as clinical stage technologies for gene therapy, both ex vivo and in vivo, and are readily adapted for delivery of the Encoded AFFIMER®s of the present invention. To illustrate, cationic liposome technology can be employed, which is based on the ability of amphipathic lipids, possessing a positively charged head group and a hydrophobic lipid tail, to bind to negatively charged DNA or RNA and form particles that generally enter cells by endocytosis. Some cationic liposomes also contain a neutral co-lipid, thought to enhance liposome uptake by mammalian cells. See, for example, Felgner et al. (1987) Lipofection: a highly efficient, lipid-mediated DNA-transfection procedure. MNAS 84:7413-7417; San et al. (1983) "Safety and short term toxicity of a novel cationic lipid formulation for human gene therapy" Hum. Gene Ther. 4:781-788; Xu et al. (1996) "Mechanism of DNA release from cationic liposome/DNA complexes used in cell transfection" Biochemistry 35:5616-5623; and Legendre et al. (1992) "Delivery of plasmid DNA into mammalian cell lines using pH-sensitive liposomes: comparison with cationic liposomes" Pharm. Res. 9, 1235-1242.

Similarly, other polycations, such as poly-I-lysine and polyethylene-imine, can be used to deliver Encoded AFFIMER®s. These polycations complex with nucleic acids via charge interaction and aid in the condensation of DNA or RNA into nanoparticles, which are then substrates for endosome-mediated uptake. Several of these cationic nucleic acid complex technologies have been developed as potential clinical products, including complexes with plasmid DNA, oligodeoxynucleotides, and various forms of synthetic RNA. Modified (and unmodified or "naked") DNA and RNA have also been shown to mediate successful gene transfer in a number of circumstances and can also be used as systems for delivery of Encoded AFFIMER®s. These include the use of plasmid DNA by direct intramuscular injection, the use of intratumoral injection of plasmid DNA. See, for example, Rodrigo et al. (2012) "De novo automated design of small RNA circuits for engineering synthetic riboregulation in living cells" PNAS 109:15271-15276; Oishi et al. (2005) "Smart polyion complex micelles for targeted intracellular delivery of PEGylated antisense oligonucleotides containing acid-labile linkages" Chembiochem. 6:718-725; Bhatt et al. (2015) "Microbeads mediated oral plasmid DNA delivery using polymethacrylate vectors: an effectual groundwork for colorectal cancer" Drug Deliv. 22:849-861; Ulmer et al. (1994) Protective immunity by intramuscular injection of low doses of influenza virus DNA vaccines" Vaccine 12: 1541-1544; and Heinzerling et al. (2005) "Intratumoral injection of DNA encoding human interleukin 12 into patients with metastatic melanoma: clinical efficacy" Hum. Gene Ther. 16:35-48.

Viral vectors are currently used as a delivery vehicle in the vast majority of pre-clinical and clinical gene therapy trials and in the first to be approved directed gene therapy. See Gene Therapy Clinical Trials Worldwide 2017 (abedia.com/wiley/). The main driver thereto is their exceptional gene delivery efficiency, which reflects a natural evolutionary development; viral vector systems are attractive for gene delivery, because viruses have evolved the ability to cross through cellular membranes by infection, thereby delivering nucleic acids such as Encoded AFFIMER®s to target cells. Pioneered by adenoviral systems, the field of viral vector-mediated antibody gene transfer made significant strides in the past decades. The myriad of successfully evaluated administration routes, pre-clinical models and disease indications puts the capabilities of antibody gene transfer at full display through which the skilled artisan would readily be able to identify and adapt antibody gene transfer systems and techniques for in vivo delivery of Encoded AFFIMER® constructs. Muscle has emerged as the administration site of choice for prolonged mAb expression and would similarly be a suitable target tissue for prolonged AFFIMER® polypeptide expression. In the context of vectored intratumoral Encoded AFFIMER® gene transfer, oncolytic viruses have a distinct advantage, as they can specifically target tumor cells, boost AFFIMER® polypeptide expression, and amplify therapeutic responses—such as to a checkpoint inhibitory or a costimulatory agonist AFFIMER® polypeptide.

In vivo gene transfer of Encoded AFFIMER®s can also be accomplished by use of nonviral vectors, such as expression plasmids. Nonviral vectors are easily produced and do not seem to induce specific immune responses. Muscle tissue is most often used as target tissue for transfection, because muscle tissue is well vascularized and easily accessible, and myocytes are long-lived cells. Intramuscular injection of naked plasmid DNA results in transfection of a certain percentage of myocytes. Using this approach, plasmid DNA encoding cytokines and cytokine/IgG1 chimeric proteins has been introduced in vivo and has positively influenced (autoimmune) disease outcome.

In some instances, in order to increase transfection efficiency via so-called intravascular delivery in which increased gene delivery and expression levels are achieved by inducing a short-lived transient high pressure in the veins. Special blood-pressure cuffs that may facilitate localized uptake by temporarily increasing vascular pressure and can be adapted for use in human patients for this type of gene delivery. See, for example, Zhang et al. (2001) "Efficient expression of naked DNA delivered intraarterially to limb muscles of nonhuman primates" Hum. Gene Ther., 12:427-438

Increased efficiency can also be gained through other techniques, such as in which delivery of the nucleic acid is improved by use of chemical carriers—cationic polymers or lipids- or via a physical approach-gene gun delivery or electroporation. See Tranchant et al. (2004) "Physicochemical optimisation of plasmid delivery by cationic lipids" J. Gene Med., 6 (Suppl. 1):S24-S35; and Niidome et al. (2002) "Gene therapy progress and prospects: nonviral vectors" Gene Ther., 9:1647-1652. Electroporation is especially regarded as an interesting technique for nonviral gene delivery. Somiari, et al. (2000) "Theory and in vivo application of electroporative gene delivery" Mol. Ther. 2:178-187; and Jaroszeski et al. (1999) "In vivo gene delivery by electroporation" Adv. Drug Delivery Rev., 35:131-137. With electroporation, pulsed electrical currents are applied to a local tissue area to enhance cell permeability, resulting in gene transfer across the membrane. Research has shown that in vivo gene delivery can be at least 10-100 times more efficient with electroporation than without. See, for example, Aihara et al. (1998) "Gene transfer into muscle by electroporation in vivo" Nat. Biotechnol. 16:867-870; Mir, et al.

(1999) "High-efficiency gene transfer into skeletal muscle mediated by electric pulses" PNAS 96:4262-4267; Rizzuto, et al. (1999) "Efficient and regulated erythropoietin production by naked DNA injection and muscle electroporation" PNAS 96: 6417-6422; and Mathiesen (1999) "Electropermeabilization of skeletal muscle enhances gene transfer in vivo" Gene Ther., 6:508-514.

Encoded AFFIMER®s can be delivered by a wide range of gene delivery system commonly used for gene therapy including viral, non-viral, or physical. See, for example, Rosenberg et al., Science, 242:1575-1578, 1988, and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGraw-Hill, New York, (1996), Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions. The routes of delivery include, for example, systemic administration and administration in situ.

An effective Encoded AFFIMER® gene transfer approach must be directed to the specific tissues/cells where it is needed, and the resulting transgene expression should be at a level that is appropriate to the specific application. Promoters are a major cis-acting element within the vector genome design that can dictate the overall strength of expression as well as cell-specificity,

TABLE 1

Exemplary Ubiquitous and Cell-specific Promoters.

| Promoter | Specificity | Relative Strength | Size (bps) | Reference(s) |
| --- | --- | --- | --- | --- |
| CMV | Ubiquitous | +++ | 750-800 | Xu et al. Gene Ther. 2001 8: 1323-1332; Gray et al., Hum Gene Ther. 2011 22: 1143-1153 |
| CBA (including derivatives: CAG, CBh, etc.) | Ubiquitous | +++ | 248-1,600 | Klein et al. Exp Neurol. 2002 176(1): 66-74; Ohlfest et al. Blood. 2005 105: 2691-2698; and Gray et al. Hum Gene Ther. 2011 22: 1143-1153. |
| EF-1α | Ubiquitous | ++ | 2,500 | Gill et al. Gene Ther. 2001 8(20):1539-1546; Xu et al. Gene Ther. 2001 8: 1323-1332; and Gilham et al. J Gene Med. 2010 12(2): 129-136. |
| PGK | Ubiquitous | ++ | 426 | Gilham et al. J Gene Med. 2010 12(2): 129-136. |
| UBC | Ubiquitous | + | 403 | Gill et al. Gene Ther. 2001 8(20): 1539-1546; Qin et al. PLoS One. 2010 5(5): e10611. |
| GUSB (hGBp) | Ubiquitous | + | 378 | Husain et al. Gene Ther. 2009 16: 927-932. |
| UCOE (Promoter of HNRPA2B1-CBX3) | Ubiquitous | ++ | 600-2,500 | Antoniou et al. Hum Gene Ther. 2013 24(4): 363-374. |
| hAAT | Liver | ++ | 347-1,500 | Van Linthout et al. Hum Gene Ther. 2002 13(7): 829-840; Cunningham et al. Mol Ther. 2008 16(6): 1081-1088 |
| TBG | Liver | ++ | 400 | Yan et al. Gene. 2012 506(2): 289-294. |
| Desmin | Skeletal muscle | +++ | 1,700 | Talbot et al. Mol Ther. 2010 18: 601-608. |
| MCK | Skeletal muscle | ++ | 595-1,089 | Talbot et al. Mol Ther. 2010 18: 601-608; Wang et al. Gene Ther. 2008 15: 1489-1499; Katwal et al. Gene Ther. 2013 20(9): 930-938. |
| C5-12 | Skeletal, cardiac, and diaphragm | ++ | 312 | Wang et al. Gene Ther. 2008 15: 1489-1499 |
| NSE | Neuron | +++ | 300-2,200 | Xu et al. Gene Ther. 2001 8: 1323-1332 |
| Synapsin | Neuron | + | 470 | Kügler et al. Virology. 2003 311: 89-95; Hioki et al. Gene Ther. 2007 14: 872-882; Kuroda et al. J Gene Med. 2008 10: 1163-1175. |
| PDGF | Neuron | +++ | 1,400 | Patterna et al. Gene Ther. 2000 7(15): 1304-1311; Hioki et al. Gene Ther. 2007 14: 872-882 |
| MecP2 | Neuron | + | 229 | Rastegar et al. LoS One. 2009 4:e6810; Gray et al., Hum Gene Ther. 2011 22: 1143-1153 |
| CaMKII | Neuron | ++ | 364-2,300 | Hioki et al. Gene Ther. 2007 14: 872-882; Kuroda et al. J Gene Med. 2008 10: 1163-1175 |
| mGluR2 | Neuron | + | 1,400 | Brené et al. Eur .1 Neurosci. 2000 12: 1525-1533; Kuroda et al. J Gene Med. 2008 10: 1163-1175 |
| NFL | Neuron | + | 650 | Xu et al. Gene Ther. 2001 8: 1323-1332 |
| NFH | Neuron | + | 920 | Xu et al. Gene Ther. 2001 8: 1323-1332 |
| nβ2 | Neuron | + | 650 | Xu et al. Gene Ther. 2001 8: 1323-1332 |

TABLE 1-continued

Exemplary Ubiquitous and Cell-specific Promoters.

| Promoter | Specificity | Relative Strength | Size (bps) | Reference(s) |
|---|---|---|---|---|
| PPE | Neuron | + | 2700 | Xu et al. Gene Ther. 2001 8: 1323-1332 |
| Enk | Neuron | + | 412 | Xu et al. Gene Ther. 2001 8: 1323-1332 |
| EAAT2 | Neuron and astrocyte | ++ | 966 | Su et al. Proc Natl Acad Sci U S A. 2003 100:1955-1960; Kuroda et al. J Gene Med. 2008 10: 1163-1175 |
| GFAP | Astrocyte | ++ | 681-2,200 | Brenner et al. J Neurosci. 1994 14: 1030-1037; Xu et al. Gene Ther. 2001 8: 1323-1332; Lee et al. Glia. 2008 56: 481-493; Dirren et al. Hum Gene Ther. 2014 25: 109-120 |
| MBP | Oligodendrocytes | ++ | 1,900 | Chen et al. Gene Ther. 1998 5(1): 50-58 |

In some cases, ubiquitous expression of the Encoded AFFIMER® construct in all cell types is desired. Constitutive promoters such as the human elongation factor 1α-subunit (EF1α), immediate-early cytomegalovirus (CMV), chicken β-actin (CBA) and its derivative CAG, the β glucuronidase (GUSB), or ubiquitin C (UBC) can be used to promote expression of the Encoded AFFIMER® Construct in most tissues. Generally, CBA and CAG promote the larger expression among the constitutive promoters; however, their size of ~1.7 kbs in comparison to CMV (~0.8 kbs) or EF1α (~1.2 kbs) may limit use in vectors with packaging constraints such as AAV, particularly where AFFIMER® polypeptide produced by expression of the Encoded AFFIMER® construct is large. The GUSB or UBC promoters can provide ubiquitous gene expression with a smaller size of 378 bps and 403 bps, respectively, but they are considerably weaker than the CMV or CBA promoter. Thus, modifications to constitutive promoters in order to reduce the size without affecting its expression have been pursued and examples such as the CBh (~800 bps) and the miniCBA (~800 bps) can promote expression comparable and even higher in selected tissues (Gray et al., Hum Gene Ther. 2011 22:1143-1153).

When expression of the Encoded AFFIMER® construct should be restricted to certain cell types within an organ, promoters can be used to mediate this specificity. For example, within the nervous system promoters have been used to restrict expression to neurons, astrocytes, or oligodendrocytes. In neurons, the neuron-specific enolase (NSE) promoter drives stronger expression than ubiquitous promoters. Additionally, the platelet-derived growth factor B-chain (PDGF-β), the synapsin (Syn), and the methyl-CpG binding protein 2 (MeCP2) promoters can drive neuron-specific expression at lower levels than NSE. In astrocytes, the 680 bps-long shortened version [gfaABC(1)D] of the glial fibrillary acidic protein (GFAP, 2.2 kbs) promoter can confer higher levels of expression with the same astrocyte-specificity as the GFAP promoter. Targeting oligodendrocytes can also be accomplished by the selection of the myelin basic protein (MBP) promoter, whose expression is restricted to this glial cell; however, its size of 1.9 kbs and low expression levels limit its use.

In the case of expressing the Encoded AFFIMER® constructs in skeletal muscle cells, exemplary promoters based on muscle creatine kinase (MCK) and desmin (1.7 kbs) have showed a high rate of specificity (with minimal expression in the liver if desired). The promoter of the α-myosin heavy chain (α-MHC; 1.2 kbs) has shown significant cardiac specificity in comparison with other muscle promoters (Lee et al., 2011 J Cardiol. 57(1):115-22). In hematopoietic stem cells the synthetic MND promoter (Li et al., 2010 J Neurosci Methods. 189(1):56-64) and the promoter contained in the 2AUCOE (ubiquitous chromatin opening element) have shown to drive a higher transgene expression in all cell lineages when compared to the EF1α and CMV promoters, respectively (Zhang et al., 2007 Blood. 110(5):1448-57; Koldej 2013 Hum Gene Ther Clin Dev. 24(2):77-85; Dighe et al., 2014 PLoS One. 9(8):e104805). Conversely, using promoters to restrict expression to only liver hepatocytes after vector-mediated gene transfer has been shown to reduce transgene-specific immune responses in systems where that is a risk, and to even induce immune tolerance to the expressed protein (Zhang et al., 2012 Hum Gene Ther. 23(5):460-72), which for certain AFFIMER® polypeptides may be beneficial. The al-antitrypsin (hAAT; 347 bps) and the thyroxine binding globulin (TBG; ~400 bps) promoters drive gene expression restricted to the liver with minimal invasion to other tissues (Yan et al., 2012 Gene. 506(2):289-94; Cunningham et al., 2008 Mol Ther. 16(6):1081-8).

In certain embodiments, a mechanism to control the duration and amount of in vivo Encoded AFFIMER® expression will typically be desired. There are a variety of inducible promoters which can be adapted for use with viral vectored- and plasmid DNA-based Encoded AFFIMER® gene transfer. See Fang et al. (2007) "An antibody delivery system for regulated expression of therapeutic levels of monoclonal antibodies in vivo" Mol Ther. 5(6):1153-9; and Perez et al. (2004) "Regulatable systemic production of monoclonal antibodies by in vivo muscle electroporation" Genet Vaccines Ther. 2(1):2. An exemplary a regulatable mechanism currently under clinical evaluation is an ecdysone-based gene switch activated by a small molecule ligand. Cai et al. (2016) "Plasma pharmacokinetics of veledimex, a small-molecule activator ligand for a proprietary gene therapy promoter system, in healthy subjects" Clin Pharmacol Drug Dev. 2016.

In certain embodiments of the Encoded AFFIMER® constructs, viral post-transcriptional regulatory elements (PREs) may be used; these cis-acting elements are required for nuclear export of intronless viral RNA (Huang and Yen, 1994 J Virol. 68(5):3193-9; and 1995 Mol Cell Biol. 15(7):3864-9). Examples include HPRE (Hepatitis B Virus PRE, 533 bps) and WPRE (Woodchuck Hepatitis Virus PRE, 600 bps), which can increase the level of transgene expression by almost 10-fold in certain instances (Donello et al., 1998 J Virol. 72(6):5085-92). To further illustrate, using lentiviral and AAV vectors, WPRE was found to increase CMV promoter driven transgene expression, as well as increase PPE, PDGF and NSE promoter-driven transgene expression. Another effect of the WPRE can be to protect Encoded AFFIMER® constructs transgenes from silencing (Paterna et al., 2000 Gene Ther. 7(15):1304-11; Xia et al., 2007 Stem Cells Dev. 2007 February; 16(1):167-76).

The polyadenylation of a transcribed Encoded AFFIMER® transcript can also be important for nuclear export, translation, and mRNA stability. Therefore, in certain embodiments, the Encoded AFFIMER® construct will include a polyadenylation signal sequence. A variety of studies are available that have determined the effects of different polyA signals on gene expression and mRNA stability. Exemplary polyadenylation signal sequences include SV40 late or bovine growth hormone polyA (bGHpA) signal sequences, as well as minimal synthetic polyA (SPA) signal (Levitt et al., 1989 Genes Dev. 3(7): 1019-25; Yew et al., 1997 Hum Gene Ther. 1997 8(5):575-84). The efficiency of polyadenylation is increased by the SV40 late polyA signal upstream enhancer (USE) placed upstream of other polyA signals (Schek et al., 1992 Mol Cell Biol. 12(12):5386-93). In certain embodiments, merely to illustrate, the Encoded AFFIMER® construct will include an SV40 late+2×USE polyA signal.

(platelet-derived growth factor-β) promoter (merely as examples). Altogether, the CMV enhancer increases transgene expression under different cell-specific promoters and different cell types making it a broadly applicable tool to increase transgene expression levels. In muscle, for example, in AAV expression systems transgene expression using the CMV enhancer with a muscle-specific promoter can increase expression levels of the protein encoded by the transgene, so would be particularly useful in the current invention for expressing AFFIMER® polypeptides from Encoded AFFIMER® constructs introduced into muscle cells of a patient.

The subject Encoded AFFIMER® constructs may also include one or more intronic sequences. The presence of an intron or intervening sequence in mRNA was first described, in vitro, to be important for mRNA processing and increased transgene expression (Huang and Gorman, 1990 Mol Cell Biol. 10(4):1805-10; Niwa et al., 1990 Genes Dev. 4(9): 1552-9). The intron(s) can be placed within the coding sequence for the AFFIMER® polypeptide and/or can be placed between the promoter and transgene. A variety of introns (Table 3) placed between the promoter and transgene were compared, in mice using AAV2, for liver transgene expression (Wu et al., 2008). The MVM (minute virus of

TABLE 2

Exemplary Polyadenylation Signals

| PolyA Signal and USE | Relative Strength | Size (bps) | Source | Reference(s) |
|---|---|---|---|---|
| hGH | + | 624 | Human growth hormone | Ostedgaard et al. Proc Natl Acad Sci U S A. 2005 102(8): 2952-2957 |
| SV40 late | +++ | 135 | Simian virus 40 | Choi et al. Mol Brain. 2014 7:17 |
| SPA (synthetic polyA) | + | 49 | Rabbit β-globin | Levitt et al. Genes Dev. 3(7): 1019-1025; Yew et al. Hum Gene Ther. 1997 8(5): 575-584; Ostedgaard et al. Proc Natl Acad Sci USA. 2005 102(8): 2952-2957; Choi et al. Mol Brain. 2014 7:17 |
| bGH | ++ | 250 | Bovine growth hormone | Yew et al. Hum Gene Ther. 1997 8(5): 575-584; Xu et al. Gene Ther. 2001 8: 1323-1332; Wu et al. Mol Ther. 2008 16(2): 280-289; Gray et al., Hum Gene Ther. 2011 22: 1143-1153; Choi et al. Mol Brain. 2014 7:17 |
| SV40 late 2xUSE | ++ | 100 | Simian virus 40 | Schambach et al. Mol Ther. 2007 15(6):1167-1173; Choi et al. Mol Brain. 2014 7:17 |
| HIV-1 USE | + | 35 | Human immunodeficiency virus 1 | Schambach et al. Mol Ther. 2007 15(6): 1167-1173 |
| GHV USE | + | 39 | Ground squirrel hepatitis virus | Schambach et al. Mol Ther. 2007 15(6): 1167-1173 |
| Adenovirus (L3) USE | + | 21 | Adenovirus | Schambach et al. Mol Ther. 2007 15(6): 1167-1173 |
| hTHGB USE | + | 21 | Human prothrombin | Schambach et al. Mol Ther. 2007 15(6): 1167-1173 |
| hC2 USE | + | 53 | Human C2 complement gene | Schambach et al. Mol Ther. 2007 15(6): 1167-1173 |

In certain embodiments, it may be desirable for the Encoded AFFIMER® construct to include one or more regulatory enhancers, i.e., in addition to any promoter sequences. The CMV enhancer is upstream of the CMV promoter at −598 to −68 (Boshart et al., 1985 Cell. 41(2): 521-30) (~600 bps) and contains transcription binding sites. In certain embodiments, a CMV enhancer can be included in the construct to increase tissue-specific promoter-driven transgene expression, such as using the ANF (atrial natriuretic factor) promoter, the CC10 (club cell 10) promoter, SP—C(surfactant protein C) promoter, or the PDGF-β mice) intron increased transgene expression more than any other intron tested and more than 80-fold over no intron (Wu et al., 2008). However, in cultured neurons using AAV expression cassettes, transgene expression was less under a CaMPKII promoter with a chimeric intron (human β-globin donor and immunoglobulin heavy chain acceptor) between the transgene and polyA signal compared to a WPRE (Choi et al., 2014). Together, an intron can be a valuable element to include in an expression cassette to increase transgene expression.

TABLE 3

Exemplary Introns

| Itron | Relative Strength | Size (bps) | Source | Reference(s) |
|---|---|---|---|---|
| MVM | +++ | 67-97 | Minute virus of mice | Wu et al. Mol Ther. 2008 16(2): 280-289 |
| FIX truncated intron 1 | + | 300 | Human factor IX | Wu et al. Mol Ther. 2008 16(2): 280-289; Kurachi et al. J Biol Chem. 1995 270(10): 5276-5281 |
| β-globin SD / immunoglobin heavy chain SA | + | 250 | Human, pZac2.1 | Wu et al. Mol Ther. 2008 16(2): 280-289; Choi et al. Mol Brain. 2014; 7:17 |
| Adenovirus SD#/ immunoglobulin SA* | ++ | 500 | pAdβ | Wong et al. Chromosoma. 1985 92(2): 124-135; Yew et al. Hum Gene Ther. 19978(5): 575-584 |
| SV40 late SD#/SA* (195/16S) | + | 180 | pCMVB | Yew et al. Hum Gene Ther. 1997 8(5):575-584 |
| Hybrid adenovirus SD#/ IgG SA* | +++ | 230 | Adenovirus | Choi et al. Mol Brain. 2014; 7:17; Huang et al. Mol Cell Biol. 1990 10(4): 1805-1810 |

In the case of episomal vectors, the subject Encoded AFFIMER® constructs may also include one or more origins of replication, minichromosome maintenance elements (MME) and/or nuclear localization elements. Episomal vectors of the invention comprise a portion of a virus genomic DNA that encodes an origin of replication (ori), which is required for such vectors to be self-replicating and, thus, to persist in a host cell over several generations. In addition, an episomal vector of the invention also may contain one or more genes encoding viral proteins that are required for replication, i.e., replicator protein (s). Optionally, the replicator protein(s) which help initiate replication may be expressed in trans on another DNA molecule, such as on another vector or on the host genomic DNA, in the host cell containing a self-replicating episomal expression vector of this invention. Preferred self-replicating episomal LCR-containing expression vectors of the invention do not contain viral sequences that are not required for long-term stable maintenance in a eukaryotic host cell such as regions of a viral genome DNA encoding core or capsid proteins that would produce infectious viral particles or viral oncogenic sequences which may be present in the full-length viral genomic DNA molecule. The term "stable maintenance" herein, refers to the ability of a self-replicating episomal expression vector of this invention to persist or be maintained in non-dividing cells or in progeny cells of dividing cells in the absence of continuous selection without a significant loss (e.g., >50%) in copy number of the vector for two and preferably five or more generations. The most preferred vectors will be maintained over 10-15 or more cell generations. In contrast, "transient" or "short-term" persistence of a plasmid in a host cell refers to the inability of a vector to replicate and segregate in a host cell in a stable manner; that is, the vector will be lost after one or two generations, or will undergo a loss of >51% of its copy number between successive generations.

Several representative self-replicating, LCR-containing, episomal vectors useful in the context of the present invention are described further below. The self-replicating function may alternatively be provided by one or more mammalian sequences such as described by Wohlgeuth et al., 1996, Gene Therapy 3:503; Vos et al., 1995, Jour. Cell. Biol., Supp. 21A, 433; and Sun et al., 1994, Nature Genetics 8:33, optionally in combination with one or more sequence which may be required for nuclear retention. The advantage of using mammalian, especially human sequences for providing the self-replicating function is that no extraneous activation factors are required which could have toxic or oncogenic properties. It will be understood by one of skill in the art that the invention is not limited to any one origin of replication or any one episomal vector, but encompasses the combination of the tissue-restricted control of an LCR in an episomal vector. See also WO1998007876 "Self-replicating episomal expression vectors conferring tissue-specific gene expression" and U.S. Pat. No. 7,790,446 "Vectors, cell lines and their use in obtaining extended episomal maintenance replication of hybrid plasmids and expression of gene products"

Epstein-Barr Virus-Based Self-Replicating Episomal Expression Vectors. The latent origin oriP from Epstein-Barr Virus (EBV) is described in Yates et. al., Proc. Natl. Acad. Sci. USA 81:3806-3810 (1984); Yates et al., Nature 313: 812-815 (1985); Krysan et al., Mol. Cell. Biol. 9:1026-1033 (1989); James et al. Gene 86: 233-239 (1990), Peterson and Legerski, Gene 107:279-284 (1991); and Pan et al., Som. Cell Molec. Genet. 18:163-177 (1992)). An EBV-based episomal vector useful according to the invention can contain the oriP region of EBV which is carried on a 2.61 kb fragment of EBV and the EBNA-1 gene which is carried on a 2.18 kb fragment of EBV. The EBNA-1 protein, which is the only viral gene product required to support in trans episomal replication of vectors containing oriP, may be provided on the same episomal expression vector containing oriP. It is also understood, that as with any protein such as EBNA-1 known to be required to support replication of viral plasmid in trans, the gene also may be expressed on another DNA molecule, such as a different DNA vector.

Papilloma Virus-Based, Self-Replicating, Episomal Expression Vectors. The episomal expression vectors of the invention also may be based on replication functions of the papilloma family of virus, including but not limited to Bovine Papilloma Virus (BPV) and Human Papilloma Viruses (HPVs). BPV and HPVs persist as stably maintained plasmids in mammalian cells. —S trans-acting factors encoded by BPV and HPVs, namely E1 and E2, have also been identified which are necessary and sufficient for mediate replication in many cell types via minimal origin of replication (Ustav et al., EMBO J. 10: 449-457 (1991); Ustav et al., EMBO J. 10:4231-4329, (1991); Ustav et al., Proc. Natl. Acad. Sci. USA 90: 898-902 (1993)).

An episomal vector useful according to the invention is the BPV-I vector system described in Piirsoo et al., EMBO J., 15:1 (1996) and in WO 94/12629. The BPV-1 vector system described in Piirsoo et al. comprises a plasmid harboring the BPV-1 origin of replication (minimal origin plus extrachro osomal maintenance element) and optionally the E1 and E2 genes. The BPV-I EI and E2 genes are required for stable maintenance of a BPV episomal vector. These factors ensure that the plasmid is replicated to a stable copy number of up to thirty copies per cell independent of cell cycle status. The gene construct therefore persists stably in both dividing and non-dividing cells. This allows the maintenance of the gene construct in cells such as hemopoietic stem cells and more committed precursor cells.

The BPV origin of replication has been located at the 3' end of the upstream regulatory region within a 60 base pair (bp) DNA fragment (nucleotides (nt) 7914-7927) which includes binding sites for the EI and E2 replication factors. The minimal origin of replication of HPV has also been characterized and located in the URR fragment (nt 7022-7927) of HPV (see, for example, Chiang et al., Proc. Natl. Acad. Sci. USA 89:5799-5803 (1992)). As used herein, "E1" refers to the protein encoded by nucleotides (nt) 849-2663 of BPV subtype 1 or by nt 832-2779 of HPV of subtype 11, to equivalent E1 proteins of other papilloma viruses, or to functional fragments or mutants of a papilloma virus E1 protein, i.e., fragments or mutants of E1 which possess the replicating properties of E1.

As used herein, "E2H refers to the protein encoded by nt 2594-3837 of BPV subtype 1 or by nt 2723-3823 of HPV subtype 11, to equivalent E2 proteins of other papilloma viruses, or to functional fragments or mutants of a papilloma virus E2 protein, i.e., fragments or mutants of E2 which possess the replicating properties of E2. "Minichromosomal maintenance element" (MME) refers to the extrachromosomal maintenance element of the papilloma viral genome to which viral or human proteins essential for papilloma viral replication bind, which region is essential for stable episomal maintenance of the papilloma viral MO in a host cell, as described in Piirsoo et al. (supra). Preferably, the MME is a sequence containing multiple binding sites for the transcriptional activator E2. The MME in BPV is herein defined as the region of BPV located within the upstream regulatory region which includes a minimum of about six sequential E2 binding sites, and which gives optimum stable maintenance with about ten sequential E2 binding sites. E2 binding site 9 is a preferred sequence for this site, as described hereinbelow, wherein the sequential sites are separated by a spacer of about 4-10 nucleotides, and optimally 6 nucleotides. E1 and E2 can be provided to the plasmid either in cis or in trans, also as described in WO 94/12629 and in Piirsoo et al. (supra).

"E2 binding site" refers to the minimum sequence of papillomavirus double-stranded DNA to which the E2 protein binds. An E2 binding site may include the sequence 5*ACCGTTGCCGGT 3' (SEQ ID NO: 120), which is high affinity E2 binding site 9 of the BPV-1 URR; alternatively, an E2 binding site may include permutations of binding site 9, which permutations are found within the URR, and fall within the generic E2 binding sequence 5' ACCN6GGT 3' (SEQ ID NO: 121). One or more transcriptional activator E2 binding sites are, in most papillomaviruses, located in the upstream regulatory region, as in BPV and HPV. A vector which also is useful according to the invention may include a region of BPV between 6959-7945/1-470 on the BPV genetic map (as described in WO 94/12629), which region includes an origin of replication, a first promoter operatively associated with a gene of interest, the BPV E1 gene operatively associated with a second promoter to drive transcription of the E1 gene; and the BPV E2 gene operatively associated with a third promoter to drive transcription of the E2 gene.

E1 and E2 from BPV will replicate vectors containing the BPV origin or the origin of many HPV subtypes (Chiang et al., supra). E1 and E2 from HPV will replicate vectors via the BPV origin and via the origin of many HPV subtypes (Chiang et al., supra). As with all vectors of the invention, the BPV-based episomal expression vectors of the invention must persist through 2-5 or more divisions of the host cell.

See also U.S. Pat. No. 7,790,446 and Abroi et al. (2004) "Analysis of chromatin attachment and partitioning functions of bovine papillomavirus type 1 E2 protein. Journal of Virology 78:2100-13 which have shown that the BPV1 E2 protein dependent MME and EBV EBNA1 dependent FR segregation/partitioning activities function independently from replication of the plasmids. The stable-maintenance function of EBNA1/FR and E2/MME can be used to ensure long-time episomal maintenance for cellular replication origins.

Papovavirus-Based, Self-Replicating, Episomal Expression Vectors. The vectors of the invention also may be derived from a human papovavirus BK genomic DNA molecule. For example, the BK viral genome can be digested with restriction enzymes EcoRI and BamHI to produce a 5 kilobase (kb) fragment that contains the BK viral origin of replication sequences that can confer stable maintenance on vectors (see, for example, De Benedetti and Rhoads, Nucleic Acids Res. 19:1925 (1991), as can a 3.2 kb fragment of the BK virus (Cooper and Miron, Human Gene Therapy 4:557 (1993)).

The Encoded AFFIMER® constructs of the present invention can be provided as circular or linear nucleic acids. The circular and linear nucleic acids are capable of directing expression of the AFFIMER® polypeptide coding sequence in an appropriate subject cell. The one or more nucleic acid systems for expressing an AFFIMER® polypeptide may be chimeric, meaning that at least one of its components is heterologous with respect to at least one of its other components.

Viral Vectors

Exemplary viral gene therapy system that are readily adapted for use in the present invention include plasmid, adenovirus, adeno-associated virus (AAV), retrovirus, lentivirus, herpes simplex virus, vaccinia virus, poxvirus, reovirus, measles virus, Semliki Forest virus, and the like. Preferred viral vectors are based on non-cytopathic eukaryotic viruses in which non-essential genes have been replaced with the nucleic acid construct carrying the nucleic acid sequences encoding the epitopes and targeting sequences of interest.

To further illustrate, encoded AFFIMER®s can be delivered in vivo using adenoviruses and adeno-associated (AAV) viruses, which are double-stranded DNA viruses that have already been approved for human use in gene therapy.

Adenovirus Vectors

One illustrative method for in vivo delivery of one or more nucleic acid sequences involves the use of an adenovirus ("AdV") expression vector. AdVs are non-enveloped, double-stranded DNA viruses that neither integrate in the host genome nor replicate during cell division. AdV-mediated antibody gene transfer has shown therapeutic efficacy in a variety of different disease models advancing towards the clinic. Systemic mAb expression has mostly been pursued, via s.c. and especially i.v. and intramuscular AdV injection. See Wold et al. (2013) "Adenovirus vectors for gene therapy, vaccination and cancer gene therapy" Curr Gene Ther.

13(6):421-33; and Deal et al. "Engineering humoral immunity as prophylaxis or therapy" 2015 Curr Opin Immunol. 35:113-22. Other routes of delivery have focused on more local mAb production, such as via intranasal, intratracheal or intrapleural administration of the encoding AdV. The use of AdVs as oncolytic vectors is a popular approach particularly for generation of encoded antibodies at the site of tumors. Foreign genes delivered by current adenoviral gene delivery system are episomal, and therefore, have low genotoxicity to host cells. Therefore, gene therapy using adenoviral gene delivery systems may be considerably safe. The present invention specifically contemplates the delivery of AFFIMER® polypeptides by expression of Encoded AFFIMER® constructs delivered in the form of an adenoviral vector and delivery system.

Adenovirus has been usually employed as a gene delivery vector because of its mid-sized genome, ease of manipulation, high titer, wide target-cell range and high infectivity. Both ends of the viral genome contains 100-200 bp ITRs (inverted terminal repeats), which are cis elements necessary for viral DNA replication and packaging. The E1 region (E1A and E1B) of genome encodes proteins responsible for the regulation of transcription of the viral genome and a few cellular genes. The E2 region (E2A and E2B) encodes proteins responsible for viral DNA replication. Of adenoviral vectors developed so far, the replication incompetent adenovirus having the deleted E1 region is usually used and represent one exemplary choice of AdV for generating the Encoded AFFIMER® constructs of the present invention. The deleted E3 region in adenoviral vectors may provide an insertion site for transgenes (Thimmappaya, B. et al., Cell, 31:543-551(1982); and Riordan, J. R. et al., Science, 245: 1066-1073(1989)).

An "adenovirus expression vector" is meant to include those constructs containing adenovirus sequences sufficient to (a) support packaging of the construct and (b) to express a polynucleotide that encodes a polypeptide including an AFFIMER® polypeptide (the Encoded AFFIMER® sequence). In certain embodiments, the sequence for an Encoded AFFIMER® may be inserted into the DA promoter region. According to an exemplary embodiment, the recombinant adenovirus comprises deleted E1B and E3 region and the nucleotide sequence for an encoded AFFIMER® is inserted into the deleted E1B and E3 region.

Adeno-Associated Virus Vectors (AAV)

AAVs (or "rAAV" for recombinant AAV) are non-enveloped small, single-stranded DNA viruses capable of infecting both dividing and non-dividing cells. Similar to AdV, AAV-based vectors remain in an episomal state in the nucleus and display a limited risk of integration. In contrast to the generally limited durability of AdV-mediated gene transfer, transgene expression can persist for years following intramuscular recombinant AAV (rAAV) vector delivery.

Alipogene tiparvovec (Glybera™), an rAAV encoding the human lipoprotein lipase gene, was approved in 2012 as the first gene therapy product in Europe. Since then, various rAAV-based gene therapy products are currently under clinical evaluation. In the context of antibody gene transfer, a variety of reports have demonstrated in vivo production of an anti-human immune deficiency virus (HIV) mAb in mice following intramuscular injection of the mAb-encoding rAAV. The rAAV vector's potential for combination therapy has also been demonstrated, i.e. by expressing two mAbs. Similar to AdV, intramuscular and i.v. rAAV administration have been most often pursued. Reviewed in Deal et al. "Engineering humoral immunity as prophylaxis or therapy" 2015 Curr Opin Immunol. 35:113-22. A variety of additional delivery sites have also been demonstrated to achieve more local therapeutic effects, including intracranial, intranasal, intravitreal, intrathecal, intrapleural, and intraperitoneal routes. With the utility of rAAV demonstrated for antibody gene transfer, the present invention also specifically contemplates the use of rAAV systems for the delivery of Encoded AFFIMER® sequences in vivo and the production of AFFIMER® polypeptides in the body of a patient as a consequence to expression of the rAAV construct.

One important feature to AAV is that these gene transfer viruses are capable of infecting non-dividing cells and various types of cells, making them useful in constructing the Encoded AFFIMER® delivery system of this invention. The detailed descriptions for use and preparation of exemplary AAV vectors are found in, for example, U.S. Pat. Nos. 5,139,941 and 4,797,368, as well as LaFace et al, Viology, 162:483486 (1988), Zhou et al., Exp. Hematol. (NY), 21:928-933 (1993), Walsh et al, J. Clin. Invest., 94:1440-1448(1994) and Flotte et al., Gene Therapy, 2:29-37(1995). AAV is a good choice of delivery vehicles due to its safety, i.e., genetically engineered (recombinant) does not integrate into the host genome. Likewise, AAV is not pathogenic and not associated with any disease. The removal of viral coding sequences minimizes immune reactions to viral gene expression, and therefore, recombinant AAV does not evoke an inflammatory response.

Typically, a recombinant AAV virus is made by co-transfecting a plasmid containing the gene of interest (i.e., the coding sequence for an AFFIMER® polypeptide) flanked by the two AAV terminal repeats (McLaughlin et al., J. Virol., 62:1963-1973(1988); Samulski et al., J. Virol., 63:3822-3828(1989)) and an expression plasmid containing the wild type AAV coding sequences without the terminal repeats (McCarty et al., J. Virol., 65:2936-2945(1991)). Typically, viral vectors containing an Encoded AFFIMER® construct are assembled from polynucleotides encoding the AFFIMER® containing polypeptide, suitable regulatory elements and elements necessary for expression of the encoded AFFIMER® which mediate cell transduction. In one embodiment, adeno-associated viral (AAV) vectors are employed. In a more specific embodiment, the AAV vector is an AAV1, AAV6, or AAV8.

The AAV expression vector which harbors the Encoded AFFIMER® sequence bounded by AAV ITRs, can be constructed by directly inserting the selected sequence(s) into an AAV genome which has had the major AAV open reading frames ("ORFs") excised therefrom.

For eukaryotic cells, expression control sequences typically include a promoter, an enhancer, such as one derived from an immunoglobulin gene, SV40, cytomegalovirus, etc. (see above), and a polyadenylation sequence which may include splice donor and acceptor sites. The polyadenylation sequence generally is inserted following the transgene sequences and before the 3' ITR sequence.

Selection of these and other common vector and regulatory elements are conventional, and many such sequences are available. See, e.g., Sambrook et al., and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the Retrovirus Vectors Non-cytopathic viruses useful in the context of delivery of Encoded AFFIMER® constructs include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known to those of skill in the art.

In order to construct a retroviral vector, the AFFIMER® polypeptide coding sequence is inserted into the viral genome in the place of certain viral sequences to produce a replication-defective virus. To produce virions, a packaging cell line containing the gag, pol and env genes but without the LTR (long terminal repeat) and psi (Ψ) components is constructed (Mann et al., Cell, 33:153-159(1983)). When a recombinant plasmid containing the cytokine gene, LTR and psi is introduced into this cell line, the psi sequence allows the RNA transcript of the recombinant plasmid to be packaged into viral particles, which are then secreted into the culture media (Nicolas and Rubinstein "Retroviral vectors," In: Vectors: A survey of molecular cloning vectors and their uses, Rodriguez and Denhardt (eds.), Stoneham: Butterworth, 494-513(1988)). The media containing the recombinant retroviruses is then collected, optionally concentrated and used for gene delivery system.

Successful gene transfer using such second-generation retroviral vectors has been reported. Kasahara et al. (Science, 266:1373-1376(1994)) prepared variants of Moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

In certain embodiments, the retrovirus is a "gammaretroviruses", which refers to a genus of the retroviridae family. Exemplary gammaretroviruses include mouse stem cell virus, murine leukemia virus, feline leukemia virus, feline sarcoma virus, and avian reticuloendotheliosis viruses.

In certain preferred embodiments, the retroviral vector for use in the present invention is a lentiviral vector, which refers to a genus of retroviruses that are capable of infecting dividing and non-dividing cells and typically produce high viral titers. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

Another class of widely used retroviral vectors that can be used for the delivery and expression of an Encoded AFFIMER® include those based upon murine leukemia virus (MuLV), gibbon ape leukemia virus (GaLV) and combinations thereof (see, e.g., Buchscher et al., J. Virol. 66:2731-2739, 1992; Johann et al., J. Virol. 66: 1635-1640, 1992; Sommerfelt et al., Virol. 176:58-59, 1990; Wilson et al., J. Virol. 63:2374-2378, 1989; Miller et al., J. Virol. 65:2220-2224, 1991; and PCT/US94/05700).

Still other retroviral vectors that can be also be used in the present invention include, e.g., vectors based on human foamy virus (HFV) or other viruses in the Spumavirus genera. Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, which provide a description of methods for efficiently introducing nucleic acids into human cells using such retroviral vectors. Other retroviral vectors include, for example, mouse mammary tumor virus vectors (e.g., Shackleford et al., Proc. Natl. Acad. Sci. U.S.A. 85:9655-9659, 1998), lentiviruses, and the like.

Additional retroviral viral delivery systems that can be readily adapted for delivery of a transgene encoding an AFFIMER® polypeptide include, merely to illustrate Published PCT Applications WO/2010/045002, WO/2010/148203, WO/2011/126864, WO/2012/058673, WO/2014/066700, WO/2015/021077, WO/2015/148683, WO/2017/040815—the specifications and FIGS. of each of which are incorporated by reference herein.

In certain embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, Biotherapy 6:291-302; Clowes, et ai, 1994, J. Clin. Invest. 93:644-651; Kiem, et al., 1994, Blood 83: 1467-1473; Salmons and Gunzberg, 1993, Human Gene Therapy 4: 129-141; Miller, et al., 1993, Meth. Enzymol. 217:581-599; and Grossman and Wilson, 1993, Curr. Opin. in Genetics and Devel. 3: 110-114.

In certain embodiments, the retrovirus is a recombinant replication competent retrovirus comprising: a nucleic acid sequence encoding a retroviral GAG protein; a nucleic acid sequence encoding a retroviral POL protein; a nucleic acid sequence encoding a retroviral envelope; an oncoretroviral polynucleotide sequence comprising Long-Terminal Repeat (LTR) sequences at the 5' and 3' end of the oncoretroviral polynucleotide sequence; a cassette comprising an internal ribosome entry site (IRES) operably linked to a coding sequence for an AFFIMER® polypeptide wherein the cassette is positioned 5' to the U3 region of the 3' LTR and 3' to the sequence encoding the retroviral envelope; and cis-acting sequences for reverse transcription, packaging and integration in a target cell.

In certain embodiments, the retrovirus is a recombinant replication competent retrovirus comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, the promoter being suitable for expression in a mammalian cell, a gag nucleic acid domain, a pol nucleic acid domain and an env nucleic acid domain; a cassette comprising an Encoded AFFIMER® sequence, wherein the cassette is positioned 5' to the 3' LTR and is operably linked and 3' to the env nucleic acid domain encoding the retroviral envelope; and cis-acting sequences necessary for reverse transcription, packaging and integration in a target cell.

In certain preferred embodiments of the recombinant replication competent retrovirus, the envelope is chosen from one of amphotropic, polytropic, xenotropic, 10A1, GALV, Baboon endogenous virus, RD114, rhabdovirus, alphavirus, measles or influenza virus envelopes.

In certain preferred embodiments of the recombinant replication competent retrovirus, the retroviral polynucleotide sequence is engineered from a virus selected from the group consisting of murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV).

In certain preferred embodiments of the recombinant replication competent retrovirus, retrovirus is a gammaretrovirus.

In certain preferred embodiments of the recombinant replication competent retrovirus, there is a second cassette comprising a coding sequence for a second therapeutic protein, such as another checkpoint inhibitor polypeptide, a co-stimulatory polypeptide and/or a immunostimulatory cytokine (merely as examples), e.g., downstream of the cassette. In certain instances, the second cassette can include an internal ribosome entry site (IRES) or a minipromoter or a polIII promoter operably linked to the coding sequence for the second therapeutic protein.

In certain preferred embodiments of the recombinant replication competent retrovirus, it is a nonlytic, amphotropic retroviral replicating vector which, preferably, selectively infects and replicates in the cells of the tumor microenvironment.

Other Viral Vectors as Expression Constructs

In the context of vectored intratumoral Encoded AFFIMER® gene transfer, oncolytic viruses have a distinct advantage, as they can specifically target tumor cells, boost therapeutic AFFIMER® polypeptide expression, and amplify antitumor therapeutic responses. Oncolytic viruses, which overlap with certain viral systems described above, promote anti-tumor responses through selective tumor cell killing and induction of systemic anti-tumor immunity. The mechanisms of action are not fully elucidated but are likely to depend on viral replication within transformed cells, induction of primary cell death, interaction with tumor cell anti-viral elements and initiation of innate and adaptive anti-tumor immunity. Reviewed in Kaufman et al. 2015 "Oncolytic viruses: a new class of immunotherapy drugs" Nat Rev Drug Discov. 14(9):642-62. Many of the oncolytic viruses that are currently in the clinic have a natural tropism for cell surface proteins that are aberrantly expressed by cancer cells. To date, AdV, poxviruses, coxsackieviruses, poliovirus, measles virus, Newcastle disease virus, reovirus, and others have entered into early-phase clinical trials. In 2015, the FDA and EMA approved talimogene laherparepvec (T-VEC, Imlygic™), an oncolytic herpes virus armed with the gene for granulocyte-macrophage colony-stimulating factor (GM-CSF). The self-perpetuating nature of oncolytic viruses makes them an appealing platform for Encoded AFFIMER® gene transfer of the present invention, as transgene products can be amplified along with viral replication, thereby maximizing therapeutic effect. Liu et al. 2008 "Oncolytic adenoviruses for cancer gene therapy" Methods Mol Biol. 433:243-58.

In the case of AFFIMER® polypeptides that are large fusion proteins, i.e., which comprise other protein domains beyond a single AFFIMER® domain, local intratumoral expression can present an appealing strategy to overcome poor penetration in solid tumors if and where that might be an issue. Beckman et al. (2007) "Antibody constructs in cancer therapy: protein engineering strategies to improve exposure in solid tumors" Cancer 109(2):170-9; and Dronca et al. 2015 "Immunomodulatory antibody therapy of cancer: the closer, the better" Clin Cancer Res. 21(5):944-6. Likewise, intratumoral delivery of the Encoded AFFIMER® construct and concomitant local expression of the AFFIMER® polypeptide can create a better therapeutic index where dose-limiting toxicities might otherwise prevent reaching the effective intratumoral concentration for efficacy when the AFFIMER® polypeptide is delivered (or expressed) systemically.

In the case of the immuno-oncology active AFFIMER® polypeptides of the present invention, such as checkpoint inhibitors or costimulatory agonists, the immunomodulatory nature of these AFFIMER®s are very relevant to the use of oncolytic viruses. Indeed, for oncolytic virus therapy, it is desirable to override immune checkpoint inhibitor networks and thereby create a pro-inflammatory environment within the cancer. Numerous clinical trials are currently underway to evaluate the combination of oncolytic viruses and conventional immunomodulatory mAb administration. Kaufman et al. 2015 "Oncolytic viruses: a new class of immunotherapy drugs" Nat Rev Drug Discov. 14(9):642-62; and Lichty et al. 2014 "Going viral with cancer immunotherapy" Nat Rev Cancer. 14(8):559-67. However, systemic treatment with checkpoint-blocking mAbs can lead to severe immune-related adverse effects, highlighting the opportunity for local therapies, e.g. via Encoded AFFIMER®-armed oncolytic viruses. Different studies have pursued this approach and can be readily adapted for use with the subject Encoded AFFIMER®s. Dias et al. armed a replication-deficient and -competent oncolytic AdV with an anti-human CTLA-4 mAb. Dias et al. 2012 "Targeted cancer immunotherapy with oncolytic adenovirus coding for a fully human monoclonal antibody specific for CTLA-4" Gene Ther. 19(10):988-98. Another system recently described (and that can be adapted for use with the Encoded AFFIMER®s of the present invention) involved armed oncolytic vaccinia viruses with anti-murine programmed cell death protein 1 (PD-1) Fab, scFv or full-length mAb. Reflecting virus replication, mAb levels in the tumor peaked 3-5 days after intratumoral injection at 9 or 30 µg/ml, depending on the tumor model. Serum mAb levels followed the same trend, albeit threefold or more lower, although mAb detection was lost after 5 days. Intratumorally expressed mAbs lasted longer compared to intratumoral injection of anti-PD-1 mAb protein, with follow-up limited to 11 days after injection. Fab and scFv expression were not reported. Anti-tumor responses of the virus armed with either the anti-PD-1 scFv or mAb were superior to the unarmed virus and as effective as the combination of the unarmed virus and systemic anti-PD-1 mAb protein injections. Kleinpeter et al. 2016 "Vectorization in an oncolytic vaccinia virus of an antibody, a Fab and a scFv against programmed cell death-1 (PD-1) allows their intratumoral delivery and an improved tumor-growth inhibition"

Oncoimmunology. 5(10):e1220467 (online). Also recently, intratumoral administration of a combination of an oncolytic AdV and a helper-dependent AdV, armed with an anti-PD-L1 mini-antibody (a scFv CH2-CH3 fusion protein), improved the anti-tumor effect of chimeric antigen receptor (CAR) T cell therapy in mice. The benefits of locally produced anti-PD-L1 mini-antibody could not be achieved by anti-PD-L1 IgG infusion plus CAR T-cells and co-administration of an unarmed AdV. Tanoue et al 2017 "Armed oncolytic adenovirus expressing PD-L1 mini-body enhances anti-tumor effects of chimeric antigen receptor T-cells in solid tumors" Cancer Res. 77(8):2040-51. The use of that system, particularly in combination with CAR-T cell therapy, is also contemplated for use in delivering an Encoded AFFIMER® to a target tumor.

Other viral vectors may be employed as a gene delivery system in the present invention. Vectors derived from viruses such as vaccinia virus (Puhlmann M. et al., Human Gene Therapy, 10:649-657(1999); Ridgeway, "Mammalian expression vectors," In: Vectors: A survey of molecular cloning vectors and their uses. Rodriguez and Denhardt, eds. Stoneham: Butterworth, 467-492(1988); Baichwal and Sugden, "Vectors for gene transfer derived from animal DNA viruses: Transient and stable expression of transferred genes," In: Kucherlapati R, ed. Gene transfer. New York: Plenum Press, 117-148(1986) and Coupar et al., Gene, 68:1-10(1988)), lentivirus (Wang G. et al., J. Clin. Invest., 104(11):R55-62(1999)), herpes simplex virus (Chamber R., et al., Proc. Natl. Acad. Sci USA, 92:1411-1415(1995)), poxvirus (GCE, NJL, Krupa M, Esteban M., The poxvirus vectors MVA and NYVAC as gene delivery systems for vaccination against infectious diseases and cancer Curr Gene Ther 8(2):97-120(2008)), reovirus, measles virus, Semliki Forest virus, and polioviruses may be used in the present delivery systems for transferring the gene of interest into cells. They offer several attractive features for various mammalian cells. Also included are hepatitis B viruses.

b. Non-Viral Vectors

In 1990, Wolff et al. showed how injection of naked plasmid DNA (pDNA) into the skeletal muscle of mice led to the local expression of the encoded protein, kick-starting the field of DNA-based therapeutics. See Wolff et al. 1990 "Direct gene transfer into mouse muscle in vivo" Science. 247(4949 Pt 1):1465-8. The use of "pDNA" for delivering Encoded AFFIMER®s of the present invention waives the need for a virus as biological vector, and presents an appealing platform for Encoded AFFIMER® gene transfer. Compared to viral vectors, pDNA is considered low-immunogenic (allowing e.g. repeated dosing), is cheaper to produce, ship, and store, and has a much longer shelf-life. After entry in the nucleus, pDNA remains in a non-replicating non-integrating episomal state, and is lost during the breakdown of the nuclear envelope at mitosis. pDNA has no defined restrictions regarding the size of the transgene compared to viral vectors, and its modular nature allows for straightforward molecular cloning, making them easy to manipulate and design for therapeutic use. Hardee et al. 2017 "Advances in non-viral DNA vectors for gene therapy" Genes. 8(2):65. Plasmids are used in about 17% of the ongoing or completed gene therapy clinical trials, and showed to be well-tolerated and safe.

The method of DNA administration can greatly impact transgene expression. In vivo DNA-mediated Encoded AFFIMER® gene transfer can utilize such physical methods of transfection used for antibody gene transfer, such as electroporation or hydrodynamic injection. Electroporation presents the propagation of electrical fields within tissues, which induces a transient increase in cell membrane permeability. Electrotransfer of DNA is a multistep process, involving (i) electrophoretic migration of DNA towards the plasma membrane, (ii) DNA accumulation and interaction with the plasma membrane, and (iii) intracellular trafficking of the DNA to the nucleus, after which gene expression can commence. Heller L C. 2015 "Gene electrotransfer clinical trials" Adv Genet. 89:235-62. Intramuscular, intratumoral and intradermal administration have been evaluated in clinical trials and are also suitable target tissues for electroporation of Encoded AFFIMER® constructs.

Hydrodynamic-based transfection utilizes the i.v. injection of high volumes of pDNA, driving DNA molecules out of the blood circulation and into tissue. Other potentially less invasive physical delivery methods include sonoporation and magnetofection. DNA uptake can also be improved by complexing the molecules with chemical delivery vehicles (e.g. cationic lipids or polymers and lipid nanoparticles). Such techniques can also be applied to in vivo DNA-mediated Encoded AFFIMER® gene transfer.

In addition to the choice of delivery method, Encoded AFFIMER® transgene expression can be improved by modifying the make-up of pDNA constructs. See, for example, Hardee et al. 2017 "Advances in non-viral DNA vectors for gene therapy" Genes 8(2):65; and Simcikova et al. 2015 "Towards effective non-viral gene delivery vector" Biotechnol Genet Eng Rev. 31(1-2):82-107. Conventional pDNA consists of a transcription unit and bacterial backbone. The transcription unit carries the Encoded AFFIMER® sequence along with regulatory elements. The bacterial backbone includes elements like an antibiotic resistance gene, an origin of replication, unmethylated CpG motifs, and potentially cryptic expression signals. Some of these sequences are required for the production of plasmid DNA. However, in general, for therapeutic Encoded AFFIMER® gene therapy the presence of a bacterial backbone will likely be counterproductive. However, there are a variety of different types of available minimal vectors that can be selected, including minicircle DNA (mcDNA) which already been used for antibody gene transfer and can be readily adapted for Encoded AFFIMER® gene transfer. Minicircles are plasmid molecules devoid of bacterial sequences, generated via a process of recombination, restriction and/or purification. Simcikova et al. 2015 supra. Elimination of the bacterial backbone has shown higher transfection efficiency and prolonged transgene expression in a variety of tissues.

Also provided herein is a linear nucleic acid, or linear expression cassette ("LEC"), that is capable of being efficiently delivered to a subject via electroporation and expressing the Encoded AFFIMER® sequence included therein. The LEC may be any linear DNA devoid of any phosphate backbone. The LEC may contain a promoter, an intron, a stop codon, and/or a polyadenylation signal. The expression of the Encoded AFFIMER® coding sequence may be controlled by the promoter.

Plasmid Vectors

In certain embodiments, the subject Encoded AFFIMER®s constructs are delivered as plasmid vectors. Plasmid vectors have been extensively described in the art and are well known to those of skill in the art. See e.g. Sambrook et al., 1989, cited above. In the last few years, plasmid vectors have been used as DNA vaccines for delivering antigen-encoding genes to cells in vivo. They are particularly advantageous for this because they reduced safety concerns relative to other vectors. These plasmids, however, having a promoter compatible with the host cell, can express a peptide epitope encoded by nucleic acid within the plasmid. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

To expand the application and efficiency of using plasmid DNA to deliver an Encoded AFFIMER® construct to tissue in vivo, different approaches can be pursued based on principles producing higher mAb expression or overall efficacy in prior art reports. A first strategy simply relies on giving multiple or repeated pDNA doses. Kitaguchi et al. 2005 "Immune deficiency enhances expression of recombinant human antibody in mice after nonviral in vivo gene transfer" Int J Mol Med 16(4):683-8; and Yamazaki et al. 2011 "Passive immune-prophylaxis against influenza virus infection by the expression of neutralizing anti-hemagglutinin monoclonal antibodies from plasmids" Jpn J Infect Dis. 64(1):40-9. Another approach relates to the use of a delivery adjuvant. pDNA electrotransfer can be enhanced by pretreating the muscle with hyaluronidase, an enzyme that transiently breaks down hyaluronic acid, decreasing the viscosity of the extracellular matrix and facilitating DNA diffusion. Yamazaki et al. 2011, supra; and McMahon et al. 2001 "Optimisation of electrotransfer of plasmid into skeletal muscle by pretreatment with hyaluronidase: increased expression with reduced muscle damage" Gene Ther. 8(16): 1264-70. For antibody gene transfer, this led to an increase in mAb expression by approximately 3.5-fold, achieving plasma peak titers of 3.5 µg/ml with 30 µg pDNA, and would can be adapted by one skilled in the art for Encoded AFFIMER® gene transfer. Still another strategy focuses on antibody or cassette engineering. Following codon-, RNA- and leader sequence-optimization, peak serum mAb or Fab titers have been attained with intramuscular electrotransfer of 'optimized' pDNA. See, for example, Flingai et al. 2015 "Protection against dengue disease by synthetic nucleic acid antibody prophylaxis/immunotherapy" Sci Rep. 5:12616.

The purpose of the plasmid is the efficient delivery of nucleic acid sequences to and expression of therapeutic AFFIMER® polypeptides in a cell or tissue. In particular, the purpose of the plasmid may be to achieve high copy number, avoid potential causes of plasmid instability and provide a means for plasmid selection. As for expression, the nucleic acid cassette contains the necessary elements for expression of the Encoded AFFIMER® within the cassette. Expression includes the efficient transcription of an inserted gene, nucleic acid sequence, or nucleic acid cassette with the plasmid. Thus, in one aspect, a plasmid is provided for expression of Encoded AFFIMER® construct which includes an expression cassette comprising the coding sequence for the AFFIMER® polypeptide; also referred to as a transcription unit. When a plasmid is placed in an environment suitable for epitope expression, the transcriptional unit will express the AFFIMER® polypeptide and anything else encoded in the construct. The transcription unit includes a transcriptional control sequence, which is transcriptionally linked with a cellular immune response element coding sequence. Transcriptional control sequence may include promoter/enhancer sequences such as cytomegalovirus (CMV) promoter/enhancer sequences, such as described above. However, those skilled in the art will recognize that a variety of other promoter sequences suitable for expression in mammalian cells, including human patient cells, are known and can similarly be used in the constructs disclosed herein. The level of expression of the AFFIMER® polypeptide will depend on the associated promoter and the presence and activation of an associated enhancer element.

In certain embodiments, the Encoded AFFIMER® sequence (encoding the desired AFFIMER® polypeptide) can be cloned into an expression plasmid which contains the regulatory elements for transcription, translation, RNA stability and replication (i.e., including a transcriptional control sequence). Such expression plasmids are well known in the art and one of ordinary skill would be capable of designing an appropriate expression construct for producing a recombinant AFFIMER® polypeptide in vivo.

Minicircle

Minicircle (mcDNA)-based antibody gene transfer can also be adapted for delivery of Encoded AFFIMER®s to tissues in vivo. Under certain circumstances, plasmid DNA used for non-viral gene delivery can cause unacceptable inflammatory responses. Where this happens, immunotoxic responses are largely due to the presence of unmethylated CpG motifs and their associated stimulatory sequences on plasmids following bacterial propagation of plasmid DNA. Simple methylation of DNA in vitro may be enough to reduce an inflammatory response, but can result in reduced gene expression. The removal of CpG islands by cloning out, or elimination of non-essential sequences has been a successful technique for reducing inflammatory responses. Yew et al. 2000 "Reduced inflammatory response to plasmid DNA vectors by elimination and inhibition of immunostimulatory CpG motifs" Mol Ther 1(3), 255-62.

Since bacterial DNA contains on average 4 times more CpG islands than mammalian DNA, a good solution is to eliminate entirely the bacterial control regions, such as the origin of replication and antibiotic resistance genes, from gene delivery vectors during the process of plasmid production. Thus, the "parent" plasmid is recombined into a "minicircle" which generally comprises the gene to be delivered (in this case, the Encoded AFFIMER® coding sequence) and suitable control regions for its expression, and a miniplasmid which generally comprises the remainder of the parent plasmid.

Removal of bacterial sequences needs to be efficient, using the smallest possible excision site, whilst creating supercoiled DNA minicircles which consist solely of gene expression elements under appropriate—preferably mammalian—control regions. Some techniques for minicircle production use bacterial phage lamda (λ) integrase mediated recombination to produce minicircle DNA. See, for example, Darquet, et al. 1997 Gene Ther 4(12): 1341-9; Darquet et al. 1999 Gene Ther 6(2): 209-18; and Kreiss, et al. 1998 Appl Micbiol Biotechnol 49(5):560-7).

Therefore, embodiments of nucleic acid constructs described herein may be processed in the form of minicircle DNA. Minicircle DNA pertains to small (2-4 kb) circular plasmid derivatives that have been freed from all prokaryotic vector parts. Since minicircle DNA vectors contain no bacterial DNA sequences, they are less likely to be perceived as foreign and destroyed. As a result, these vectors can be expressed for longer periods of time compared to certain conventional plasmids. The smaller size of minicircles also extends their cloning capacity and facilitates their delivery into cells. Kits for producing minicircle DNA are known in the art and are commercially available (System Biosciences, Inc., Palo Alto, Calif.). Information on minicircle DNA is provided in Dietz et al., Vector Engineering and Delivery Molecular Therapy (2013); 21 8, 1526-1535 and Hou et al., Molecular Therapy—Methods & Clinical Development, Article number: 14062 (2015) doi:10.1038/mtm.2014.62. More information on Minicircles is provided in Chen Z Y, He C Y, Ehrhardt A, Kay M A. Mol Ther. 2003 September; 8(3):495-500 and Minicircle DNA vectors achieve sustained expression reflected by active chromatin and transcriptional level. Gracey Maniar L E, Maniar J M, Chen Z Y, Lu J, Fire A Z, Kay M A. Mol Ther. 2013 January; 21(1):131-8

As a nonlimiting example, a minicircle DNA vector may be produced as follows. An expression cassette, which comprises the Encoded AFFIMER® coding sequence along with regulatory elements for its expression, is flanked by attachment sites for a recombinase. A sequence encoding the recombinase is located outside of the expression cassette and includes elements for inducible expression (such as, for example, an inducible promoter). Upon induction of recombinase expression, the vector DNA is recombined, resulting in two distinct circular DNA molecules. One of the circular DNA molecules is relatively small, forming a minicircle that comprises the expression cassette for the Encoded AFFIMER®; this minicircle DNA vector is devoid of any bacterial DNA sequences. The second circular DNA sequence contains the remaining vector sequence, including the bacterial sequences and the sequence encoding the recombinase. The minicircle DNA containing the Encoded AFFIMER® sequence can then be separately isolated and purified. In certain embodiments, a minicircle DNA vector may be produced using plasmids similar to pBAD.Φ.C31.hFIX and pBAD.Φ.C31.RHB. See, e.g., Chen et al. (2003) Mol. Ther. 8:495-500.

Exemplary recombinases that may be used for creating a minicircle DNA vector include, but are not limited to, *Streptomyces* bacteriophage Φ31 integrase, Cre recombinase, and the λ integrase/DNA topoisomerase IV complex. Each of these recombinases catalyzes recombination between distinct sites. For example, Φ31 integrase catalyzes recombination between corresponding attP and attB sites, Cre recombinase catalyzes recombination between loxP sites, and the λ integrase/DNA topoisomerase IV complex catalyzes recombination between bacteriophage λ attP and attB sites. In certain embodiments, such as, for example, with Φ31 integrase or with λ integrase in the absence of the λ is protein, the recombinase mediates an irreversible reaction to yield a unique population of circular products and thus high yields. In other embodiments, such as, for example, with Cre recombinase or with λ integrase in the presence of the λ is protein, the recombinase mediates a reversible reaction to yield a mixture of circular products and thus lower yields. The reversible reaction by Cre recombinase can be manipulated by employing mutant loxP71 and loxP66 sites, which recombine with high efficiency to yield a functionally impaired P71/66 site on the minicircle molecule and a wild-type loxP site on the minicircle molecule, thereby shifting the equilibrium towards the production of the minicircle DNA product.

Published US Application 20170342424 also describes a system making use of a parent plasmid which is exposed to an enzyme which causes recombination at recombination sites, thereby forming a (i) minicircle including the Encoded AFFIMER® sequence and (ii) a miniplasmid comprising the remainder of the parent plasmid. One recombination site is modified at the 5' end such that its reaction with the enzyme is less efficient than the wild type site, and the other recombination site is modified at the 3' end such that its reaction with the enzyme is less efficient than the wild type site, and the other recombination site is modified at the 3' end such that its reaction with the enzyme is less efficient than the wild type site, both modified sites being located in the minicircle after recombination. This favors the formation of minicircle.

c. RNA-Mediated Encoded AFFIMER® Gene Transfer

Exemplary nucleic acids or polynucleotides for the encoded AFFIMER® polypeptides of the present invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, a-LNA having an a-L-ribo configuration (a diastereomer of LNA), 2'-amino-LNA having a 2'-amino functionalization, and 2'-amino-a-LNA having a 2'-amino functionalization), ethylene nucleic acids (ENA), cyclohexenyl nucleic acids (CeNA) or hybrids or combinations thereof.

mRNA presents an emerging platform for antibody gene transfer that can be adapted by those skilled in the art for delivery of Encoded AFFIMER® constructs of the present invention. Although current results differ considerably, in certain instances the mRNA constructs appear to be able to rival viral vectors in terms of generated serum mAb titers. Levels were in therapeutically relevant ranges within hours after mRNA administration, a marked shift in speed compared to DNA. The use of lipid nanoparticles (LNP) for mRNA transfection, rather than the physical methods typically required for DNA, can provide significant advantages in certain embodiments towards application range.

In their 1990 study, Wolff et al. (1990, supra) found that, in addition to pDNA, intramuscular injection of in vitro transcribed (IVT) mRNA also led to local expression of the encoded protein. mRNA was not pursued as actively as DNA at that time because of its low stability. Progress over the past years allowed mRNA to catch up with DNA and viral vectors as a tool for gene transfer. Reviewed in Sahin et al. (2014) "mRNA-based therapeutics: developing a new class of drugs" Nat Rev Drug Discov. 13(10):759-80. Conceptually, there are several differences with these expression platforms. mRNA does not need to enter into the nucleus to be functional. Once it reaches the cytoplasm, mRNA is translated instantly. mRNA-based therapeutics are expressed more transiently compared to DNA- or viral vector-mediated gene transfer, and do not pose the risk of insertional mutagenesis in the host genome. mRNA production is relatively simple and inexpensive. In terms of administration, mRNA uptake can be enhanced using electroporation. Broderick et al. 2017 "Enhanced delivery of DNA or RNA vaccines by electroporation" Methods Mol Biol. 2017; 1499:193-200. Most focus, however, has gone to non-physical transfection methods. Indeed, a variety of mRNA complexing formulations have been developed, including lipid nanoparticles (LNP), which have proven to be safe and very efficient mRNA carriers for administration in a variety of tissues and i.v. Pardi et al. 2015 "Expression kinetics of nucleoside-modified mRNA delivered in lipid nanoparticles to mice by various routes" J Control Release 217:345-51. In line with this progress, IVT mRNA has reached the stage of clinical evaluation.

Beissert et al. WO2017162266 "RNA Replicon for Versatile and Efficient Gene Expression" describes agents and methods suitable for efficient expression of AFFIMER®s of the present invention, such as suitable for immunotherapeutic treatment for the prevention and therapy of tumors. For instance, the AFFIMER® polypeptide coding sequence can be provided as an RNA replicon comprising a 5' replication recognition sequence such as from an alphavirus 5' replication recognition sequence. In certain embodiments, the RNA replicon comprises a (modified) 5' replication recognition sequence and an open reading frame encoding the AFFIMER® polypeptide, in particular located downstream from the 5' replication recognition sequence such as that the 5' replication recognition sequence and the open reading frame do not overlap, e.g. the 5' replication recognition sequence does not contain a functional initiation codon and preferably does not contain any initiation codon. Most preferably, the initiation codon of the open reading frame encoding the AFFIMER® polypeptide is in the 5'-3' direction of the RNA replicon.

In certain embodiments, to prevent immune activation, modified nucleosides can be incorporated into the in vitro-transcribed mRNA. In certain embodiments, the IVT RNA can be 5' capped, such an m7G5'ppp5'G2'—O-Met-capped IVT. Efficient translation of the modified mRNA can be ensured by removing double-stranded RNA. Moreover, the 5' and 3' UTRs and the poly(A) tail can be optimized for improved intracellular stability and translational efficiency. See, for example, Stadler et al. (2017) Nature Medicine 23:815-817 and Kariko et al. WO/2017/036889 "Method for Reducing Immunogenicity of RNA".

In certain embodiments, the mRNA that encodes the AFFIMER® polypeptide may include at least one chemical modification described herein. As a non-limiting example, the chemical modification may be 1-methylpseudouridine, 5-methylcytosine or 1-methylpseudouridine and 5-methylcytosine. In one embodiment, linear polynucleotides encoding one or more AFFIMER® polypeptides of the present invention which are made using only in vitro transcription (IVT) enzymatic synthesis methods are referred to as "IVT polynucleotides." Methods of making IVT polynucleotides are known in the art and are described in PCT Application WO2013/151666, the contents of which are incorporated herein by reference in their entirety.

In another embodiment, the polynucleotides that encode the AFFIMER® polypeptide of the present invention have portions or regions which differ in size and/or chemical modification pattern, chemical modification position, chemical modification percent or chemical modification population and combinations of the foregoing are known as "chimeric polynucleotides." A "chimera" according to the present invention is an entity having two or more incongruous or heterogeneous parts or regions. As used herein a "part" or "region" of a polynucleotide is defined as any portion of the polynucleotide which is less than the entire length of the polynucleotide. Such constructs are taught in for example PCT Application WO2015/034928.

In yet another embodiment, the polynucleotides of the present invention that are circular are known as "circular polynucleotides" or "circP." As used herein, "circular polynucleotides" or "circP" means a single stranded circular polynucleotide which acts substantially like, and has the properties of, an RNA. The term "circular" is also meant to encompass any secondary or tertiary configuration of the circP. Such constructs are taught in for example PCT Application WO2015/034925 and WO2015/034928, the contents of each of which are incorporated herein by reference in their entirety.

Exemplary mRNA (and other polynucleotides) that can be used to encode AFFIMER® polypeptides of the present invention include those which can be adapted from the specifications and FIGS. of, for example, PCT Publications WO2017/049275, WO2016/118724, WO2016/118725, WO2016/011226, WO2015/196128, WO/2015/196130, WO/2015/196118, WO/2015/089511, with WO2015/105926 (the later titled "Polynucleotides for the In Vivo Production Of Antibodies"), each of which is incorporated by reference herein. Electroporation, as described below, is one exemplary method for introducing mRNA or other polynucleotides into a cell.

Lipid-containing nanoparticle compositions have proven effective as transport vehicles into cells and/or intracellular compartments for a variety of RNAs (and related polynucleotides described herein). These compositions generally include one or more "cationic" and/or ionizable lipids, phospholipids including polyunsaturated lipids, structural lipids (e.g., sterols), and lipids containing polyethylene glycol (PEG lipids). Cationic and/or ionizable lipids include, for example, amine-containing lipids that can be readily protonated.

d. Delivery of Encoded AFFIMER® Constructs into Target Cells

The introduction into host cell of the gene delivery system can be performed through various methods known to those skilled in the art.

Where the present gene delivery system is constructed on the basis of viral vector construction, delivery can be performed as conventional infection methods known in the art.

Physical methods to enhance delivery both viral and non-viral Encoded AFFIMER® constructs include electroporation (Neumann, E. et al., EMBO J., 1:841 (1982); and Tur-Kaspa et al., Mol. Cell Biol., 6:716-718(1986)), gene bombardment (Yang et al., Proc. Natl. Acad. Sci., 87:9568-9572 (1990) where DNA is loaded onto (e.g., gold) particles and forced to achieve penetration of the DNA into the cells, sonoporation, magnetofection, hydrodynamic delivery and the like, all of which are known to those of skill in the art.

Electroporation

In the past several years, there has been a great advance in the plasmid DNA delivery technology that is utilized for in vivo production of proteins. This included codon optimization for expression in human cells, RNA optimization to improve mRNA stability as well as more efficient translation at the ribosomal level, the addition of specific leader sequences to enhance translation efficiency, the creation of synthetic inserts to further enhance production in vivo and the use of improved adaptive electroporation (EP) delivery protocols to improve in vivo delivery. EP assists in the delivery of plasmid DNA by generating an electrical field that allows the DNA to pass into the cell more efficiently. In vivo electroporation is a gene delivery technique that has been used successfully for efficient delivery of plasmid DNA to many different tissues. Kim et al. "Gene therapy using plasmid DNA-encoded anti-HER2 antibody for cancers that overexpress HER2" (2016) Cancer Gene Ther. 23(10): 341-347 teaches a vector and electroporation system for intramuscular injection and in vivo electroporation of the plasmids that results in high and sustained antibody expression in sera; the plasmid and electroporation system of Kim et al. can be readily adapted for the in vivo delivery of a plasmid for expressing an encoded AFFIMER® of the present invention.

Accordingly, in certain particular embodiments of the present disclosure, the Encoded AFFIMER® construct is introduced into target cells via electroporation.

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a pre-set current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analogue closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the pre-set current. The feedback mechanism may maintain the constant current continuously and instantaneously during the delivery of the pulse of energy.

Examples of electroporation devices and electroporation methods that may facilitate delivery of the Encoded AFFIMER® constructs of the present invention, include those described in U.S. Pat. Nos. 7,245,963; 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

In certain embodiments, the electroporation is carried using a minimally invasive electroporation device ("MID"). The device may comprise a hollow needle, DNA cassette, and fluid delivery means, wherein the device is adapted to actuate the fluid delivery means in use so as to concurrently (for example, automatically) inject the Encoded AFFIMER® nucleic acid construct into body tissue during insertion of the needle into the body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the Encoded AFFIMER® nucleic acid construct into tissue without the use of a needle. The MID may inject the Encoded AFFIMER® nucleic acid construct as a small stream or jet with such force that the nucleic acid pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired Encoded AFFIMER® nucleic acid construct in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the nucleic acid into the tissue. For example, if the tissue to be treated is a mucosa, skin or muscle, the agent is projected towards the mucosal or skin surface with sufficient force to cause the agent to penetrate through the stratum corneum and into dermal layers, or into underlying tissue and muscle, respectively. Needle-free injectors are well suited to deliver Encoded AFFIMER® nucleic acid construct to all types of tissues, including into tumors (intratumoral delivery).

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering the Encoded AFFIMER® nucleic acid construct to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the Encoded AFFIMER® nucleic acid construct and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Plymouth Meeting, Pa.) device and system, which is a modular electrode system, that facilitates the introduction of a macromolecule, such as an Encoded AFFIMER® nucleic acid construct, into cells of a selected tissue in a body. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The nucleic acid is then delivered via the hypodermic needle into the selected tissue. The programmable constant-current pulse controller is activated and constant-current electrical pulse is applied to the plurality of needle electrodes. The applied constant-current electrical pulse facilitates the introduction of the nucleic acid into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described Encoded AFFIMER® nucleic acid construct herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin and other epithelial tissues, liver tissue and muscle tissue, merely as examples.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached the target tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a pre-set needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprise means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Use of in vivo electroporation enhances plasmid DNA uptake in tumor tissue, resulting in expression within the tumor, and delivers plasmids to muscle tissue, resulting in systemic expression of secreted proteins, such as cytokines (see, e.g., U.S. Pat. No. 8,026,223). Additional exemplary techniques, vectors and devices for electroporating AFFIMER® polypeptide transgenes into cells in vivo include PCT Publications WO/2017/106795, WO/2016/161201, WO/2016/154473, WO/2016/112359 and WO/2014/066655.

Typically, the electric fields needed for in vivo cell electroporation are generally similar in magnitude to the fields required for cells in vitro. In one embodiment, the magnitude of the electric field ranges from approximately, 10 V/cm to about 1500 V/cm, preferably from about 300 V/cm to 1500 V/cm and preferably from about 1000 V/cm to 1500 V/cm. Alternatively, lower field strengths (from about 10 V/cm to 100 V/cm, and more preferably from about 25 V/cm to 75 V/cm) the pulse length is long. For example, when the nominal electric field is about 25-75 V/cm, if is preferred that the pulse length is about 10 msec.

The pulse length can be about 10 s to about 100 ms. There can be any desired number of pulses, typically one to 100 pulses per second. The delay between pulse sets can be any desired time, such as one second. The waveform, electric field strength and pulse duration may also depend upon the type of cells and the type of molecules that are to enter the cells via electroporation.

Also encompassed are electroporation devices incorporating electrochemical impedance spectroscopy ("EIS"). Such devices provide real-time information on in vivo, in particular, intratumoral electroporation efficiency, allowing for the optimization of conditions. Examples of electroporation devices incorporating EIS can be found, e.g., in WO2016/161201, which is hereby incorporated by reference.

Uptake of the Encoded AFFIMER® nucleic acid constructs of the present invention may also be enhanced by plasma electroporation also termed avalanche transfection. Briefly, microsecond discharges create cavitation microbubbles at electrode surface. The mechanical force created by the collapsing microbubbles combined with the magnetic field serve to increase transport efficiency across the cell membrane as compared with the diffusion mediated transport associated with conventional electroporation. The technique of plasma electroporation is described in U.S. Pat. Nos. 7,923,251 and 8,283,171. This technique may also be employed in vivo for the transformation of cells. Chaiberg, et al (2006) Investigative Ophthalmology & Visual Science 47:4083-4090; Chaiberg, et al United States Patent No 8, 101 169 Issued Jan. 24, 2012.

Other alternative electroporation technologies are also contemplated. In vivo nucleic acid delivery can also be performed using cold plasma. Plasma is one of the four fundamental states of matter, the others being solid, liquid, and gas. Plasma is an electrically neutral medium of unbound positive and negative particles (i.e. the overall charge of a plasma is roughly zero). A plasma can be created by heating a gas or subjecting it to a strong electromagnetic field, applied with a laser or microwave generator. This decreases or increases the number of electrons, creating positive or negative charged particles called ions (Luo, et al. (1998) Phys. Plasma 5:2868-2870) and is accompanied by the dissociation of molecular bonds, if present.

Cold plasmas (i.e., non-thermal plasmas) are produced by the delivery of pulsed high voltage signals to a suitable electrode. Cold plasma devices may take the form of a gas jet device or a dielectric barrier discharge (DBD) device. Cold temperature plasmas have attracted a great deal of enthusiasm and interest by virtue of their provision of plasmas at relatively low gas temperatures. The provision of plasmas at such a temperature is of interest to a variety of applications, including wound healing, anti-bacterial processes, various other medical therapies and sterilization. As noted earlier, cold plasmas (i.e., non-thermal plasmas) are produced by the delivery of pulsed high voltage signals to a suitable electrode. Cold plasma devices may take the form of a gas jet device, a dielectric barrier discharge (DBD) device or multi-frequency harmonic-rich power supply.

Dielectric barrier discharge device, relies on a different process to generate the cold plasma. A dielectric barrier discharge (DBD) device contains at least one conductive electrode covered by a dielectric layer. The electrical return path is formed by the ground that can be provided by the target substrate undergoing the cold plasma treatment or by providing an in-built ground for the electrode. Energy for the dielectric barrier discharge device can be provided by a high voltage power supply, such as that mentioned above. More generally, energy is input to the dielectric barrier discharge device in the form of pulsed DC electrical voltage to form the plasma discharge. By virtue of the dielectric layer, the discharge is separated from the conductive electrode and electrode etching and gas heating is reduced. The pulsed DC electrical voltage can be varied in amplitude and frequency to achieve varying regimes of operation. Any device incorporating such a principle of cold plasma generation (e.g., a DBD electrode device) falls within the scope of various embodiments of the present invention.

Cold plasma has been employed to transfect cells with foreign nucleic acids. In particular, transfection of tumor cells (see, e.g., Connolly, et al. (2012) Human Vaccines & Immune-therapeutics 8: 1729-1733; and Connolly et al (2015) Bioelectrochemistry 103: 15-21).

In certain illustrative embodiments, the transgene construct encoding the AFFIMER® polypeptide of the present invention is delivered using an electroporation device comprising: an applicator; a plurality of electrodes extending from the applicator, the electrodes being associated with a cover area; a power supply in electrical communication with the electrodes, the power supply configured to generate one or more electroporating signals to cells within the cover area; and a guide member coupled to the electrodes, wherein the guide member is configured to adjust the cover area of the electrodes. At least a portion of the electrodes can be positioned within the applicator in a conical arrangement. The one or more electroporating signals may be each associated with an electric field. The device may further comprise a potentiometer coupled to the power supply and electrodes. The potentiometer may be configured to maintain the electric field substantially within a predetermined range.

The one or more electroporating signals may be each associated with an electric field. The device may further comprise a potentiometer coupled to the power supply and the electrodes. The potentiometer may be configured to maintain the electric field within a predetermined range so as to substantially prevent permanent damage in the cells within the cover area and/or substantially minimize pain. For instance, potentiometer may be configured to maintain the electric field to about 1300 V/cm.

The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

In certain embodiments, the present invention provides a method for treating a subject having a tumor, the method comprising: injecting the tumor with an effective dose of plasmid coding for a AFFIMER® polypeptide; and administering electroporation therapy to the tumor. In certain embodiments, the electroporation therapy further comprises the administration of at least one voltage pulse of about 200 V/cm to about 1500 V/cm over a pulse width of about 100 microseconds to about 20 milliseconds.

In certain embodiments, the plasmid (or a second electroporated plasmid) further encodes at least one immunostimulatory cytokine, such as selected from the group encoding IL-12, IL-15, and a combination of IL-12 and IL-15.

Transfection Enhancing Formulations

Encoded AFFIMER® nucleic acid constructs can also be encapsulated in liposomes, preferably cationic liposomes (Wong, T. K. et al., Gene, 10:87 (1980); Nicolau and Sene, Biochim. Biophys. Acta, 721:185-190 (1982); and Nicolau et al., Methods Enzymol., 149:157-176 (1987)) or polymersomes (synthetic liposomes) which can interact with the cell membrane and fuse or undergo endocytosis to effect nucleic acid transfer into the cell. The DNA also can be formed into complexes with polymers (polyplexes) or with dendrimers which can directly release their load into the cytoplasm of a cell.

Illustrative carriers useful in this regard include microparticles of poly(lactide-co-glycolide), polyacrylate, latex, starch, cellulose, dextran and the like. Other illustrative carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active agent contained within a sustained release formulation depends upon the site of implantation, the rate and expected duration of release and the nature of the condition to be treated or prevented.

Biodegradable microspheres (e.g., polylactate polyglycolate) may be employed as carriers for compositions. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S.

Pat. No. 5,928,647, which can have the added benefit when used intratumorally to deliver the coding sequence for an AFFIMER®

Biodegradable polymeric nanoparticles facilitate non-viral nucleic acid transfer to cells. Small (approximately 200 nm), positively charged (approximately 10 mV) particles are formed by the self-assembly of cationic, hydrolytically degradable poly(beta-amino esters) and plasmid DNA.

Polynucleotides may also be administered to cells by direct microinjection, temporary cell permeabilizations (e.g., co-administration of repressor and/or activator with a cell permeabilizing agent), fusion to membrane translocating peptides, and the like.

Lipid-mediated nucleic acid delivery and expression of foreign nucleic acids, including mRNA, in vitro and in vivo has been very successful. Lipid based non-viral formulations provide an alternative to viral gene therapies. Current in vivo lipid delivery methods use subcutaneous, intradermal, intratumoral, or intracranial injection. Advances in lipid formulations have improved the efficiency of gene transfer in vivo (see PCT Application WO 98/07408). For instance, a lipid formulation composed of an equimolar ratio of I,2-bis(oleoyloxy)-3-(trimethyl ammonio)propane (DOTAP) and cholesterol can significantly enhances systemic in vivo gene transfer. The DOTAP:cholesterol lipid formulation forms unique structure termed a "sandwich liposome". This formulation is reported to "sandwich" DNA between an invaginated bi-layer or 'vase' structure. Beneficial characteristics of these lipid structures include a positive p, colloidal stabilization by cholesterol, two-dimensional nucleic acid packing and increased serum stability.

Cationic liposome technology is based on the ability of amphipathic lipids, possessing a positively charged head group and a hydrophobic lipid tail, to bind to negatively charged DNA or RNA and form particles that generally enter cells by endocytosis. Some cationic liposomes also contain a neutral co-lipid, thought to enhance liposome uptake by mammalian cells. Similarly, other polycations, such as poly-L-lysine and polyethylene-imine, complex with nucleic acids via charge interaction and aid in the condensation of DNA or RNA into nanoparticles, which are then substrates for endosome-mediated uptake. Several of these cationic-nucleic acid complex technologies have been developed as potential clinical products, including complexes with plasmid DNA (pDNA), oligodeoxynucleotides, and various forms of synthetic RNA, and be used as part of the delivery system for the Encoded AFFIMER® nucleic acid constructs of the present invention.

The Encoded AFFIMER® nucleic acid constructs disclosed herein may be associated with polycationic molecules that serve to enhance uptake into cells. Complexing the nucleic acid construct with polycationic molecules also helps in packaging the construct such their size is reduced, which is believed to assist with cellular uptake. Once in the endosome, the complex dissociates due to the lower pH, and the polycationic molecules can disrupt the endosome's membrane to facilitate DNA escape into the cytoplasm before it can be degraded. Preliminary data shows that the nucleic acid construct embodiments had enhanced uptake into SCs over DCs when complexed with the polycationic molecules polylysine or polyethyleneimine.

One example of polycationic molecules useful for comuplexing with nucleic acid constructs includes cell penetrating peptides (CPP), examples include polylysine (described above), polyarginine and Tat peptides. Cell penetrating peptides (CPP) are small peptides which can bind to DNA and, once released, penetrate cell membranes to facilitate escape of the DNA from the endosome to the cytoplasm. Another example of a CPP pertains to a 27 residue chimeric peptide, termed MPG, was shown some time ago to bind ss- and ds-oligonucleotides in a stable manner, resulting in a non-covalent complex that protected the nucleic acids from degradation by DNase and effectively delivered oligonucleotides to cells in vitro (Mahapatro A, et al., J Nanobiotechnol, 2011, 9:55). The complex formed small particles of approximately 150 nm to 1 um when different peptide:DNA ratios were examined, and the 10:1 and 5:1 ratios (150 nm and 1 um respectively). Another CPP pertains to a modified tetrapeptide [tetralysine containing guanidinocarbonylpyrrole (GCP) groups (TL-GCP)], which was reported to bind with high affinity to a 6.2 kb plasmid DNA resulting in a positive charged aggregate of 700-900 nm Li et al., Agnew Chem Int Ed Enl 2015; 54(10):2941-4). RNA can also be complexed by such polycationic molecules for in vivo delivery.

Other examples of polycationic molecules that may be complexed with the nucleic acid constructs described herein include polycationic polymers commercially available as JETPRIME® and In Vivo JET (Polypus-transfection, S.A., Illkirch, France).

In certain embodiments, the present invention contemplates a method of delivering an mRNA (or other polynucleotide)f encoding a AFFIMER® polypeptide to a patient's cells by administering a nanoparticle composition comprising (i) a lipid component comprising a compound of formula (I), a phospholipid, a structural lipid, and a PEG lipid; and (ii) an mRNA (or other polynucleotide)f, said administering comprising contacting said mammalian cell with said nanoparticle composition, whereby said mRNA (or other polynucleotide)f is delivered to said cell.

In exemplary embodiments, the PEG lipid is selected from the group consisting of a PEG-modified phosphatidylethanolamine, a PEG-modified phosphatide acid, a PEG-modified ceramide, a PEG-modified dialkylamine, a PEG-modified diacylglycerol and a PEG-modified dialkylglycerol. In exemplary embodiments, the structural lipid is selected from the group consisting of cholesterol, fecosterol, sitosterol, ergosterol, campesterol, stigmasterol, brassicasterol, tomatidine, ursolic acid, and alpha-tocopherol. In certain preferred embodiments, the structural lipid is cholesterol.

In exemplary embodiments, the phospholipid includes a moiety selected from the group consisting of phosphatidyl choline, phosphatidyl ethanolamine, phosphatidyl glycerol, phosphatidyl serine, phosphatidic acid, 2-lysophosphatidyl choline, and a sphingomyelin. In certain embodiments, the phospholipid includes one or more fatty acid moieties selected from the group consisting of lauric acid, myristic acid, myristoleic acid, palmitic acid, palmitoleic acid, stearic acid, oleic acid, linoleic acid, alpha-linolenic acid, erucic acid, arachidic acid, arachidonic acid, phytanoic acid, eicosapentaenoic acid, behenic acid, docosapentaenoic acid, and docosahexaenoic acid. In certain preferred embodiments, the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-0-octadecenyl-sn-glycero-3-phosphocholine (1 8:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine,1,2-dioleoyl-sn-glycero-3-phosphoethanolamine (DOPE), 1,2-diphytanoyl-sn-glycero-3-phosphoethanolamine (ME 1 6.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin In certain preferred embodiments, the phospholipid is DOPE or DSPC.

To further illustrate, the phospholipid can be DOPE and said the component can comprise about 35 mol % to about 45 mol % said compound, about 10 mol % to about 20 mol % DOPE, about 38.5 mol % to about 48.5 mol % structural lipid, and about 1 0.5 mol % PEG lipid. The lipid component can be about 40 mol % said compound, about 15 mol % phospholipid, about 43.5 mol % structural lipid, and about 1 0.5 mol % PEG lipid.

In certain embodiments, the wt/wt ratio of lipid component to AFFIMER® polypeptide encoding mRNA (or other polynucleotide) is from about 5:1 to about 50:1 and more preferably about 10:1 to about 40:1

In certain embodiments, the mean size of said nanoparticle composition is from about 50 nm to about 150 nm, and even more preferably is from about 80 nm to about 120 nm.

In certain embodiments, the polydispersity index of said nanoparticle composition is from about 0 to about 0.18, more preferably from about 0.13 to about 0.17.

In certain embodiments, the nanoparticle composition has a zeta potential of about −10 to about +20 mV.

In certain embodiments, the nanoparticle composition further comprises a cationic and/or ionizable lipid selected from the group consisting of 3-(didodecylamino)-N1,N1,4-tridodecyl-1-piperazineethanamine (KL1 0), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-1 9-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), and (2R)-2-({8-[(3P)-cholest-5-en-3-yloxy]octyl}oxy)-N,N-dimethyl-3-[(9Z,1 2Z)-octadeca-9,12-dien-1-yl oxy]propan-1-amine (Octyl-CLinDMA (2R)).

The invention is now described by way of example. These examples are illustrative and are not intended to be construed as limiting the invention, which is defined by the scope of the claims.

Some data in these examples has been produced with scaffolds having a C-Terminal G6H tag (i.e. GHHHHHH (SEQ ID NO: 104) as an addition at the C-terminal end of the polypeptide). This is standard in the art for ease of manipulation/detection to carry out the experiments shown, for example by using standard 'off-the-shelf' electra vector System® cloning vectors from ATUM, Newark, California, USA. Especially suitably are the pMOTHER and pDAUGHTER plasmids, or vectors derived from them. Of course a skilled operator may easily use a parallel cloning system based on the same principles, or a different system based on operator choices.

V. Pharmaceutical Compositions

The present invention also provides pharmaceutical compositions comprising an AFFIMER® polypeptide described herein and a pharmaceutically acceptable vehicle. In some embodiments, the pharmaceutical compositions find use in immunotherapy. In some embodiments, the pharmaceutical compositions find use in immuno-oncology. In some embodiments, the compositions find use in inhibiting tumor growth. In some embodiments, the pharmaceutical compositions find use in inhibiting tumor growth in a subject (e.g., a human patient). In some embodiments, the compositions find use in treating cancer. In some embodiments, the pharmaceutical compositions find use in treating cancer in a subject (e.g., a human patient).

Formulations are prepared for storage and use by combining a purified AFFIMER® polypeptide of the present invention with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition.

In some embodiments, an AFFIMER® polypeptide described herein is lyophilized and/or stored in a lyophilized form. In some embodiments, a formulation comprising an AFFIMER® polypeptide described herein is lyophilized.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (Remington: The Science and Practice of Pharmacy, 22.sup.nd Edition, 2012, Pharmaceutical Press, London).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The AFFIMER® polypeptides described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22nd Edition, 2012, Pharmaceutical Press, London.

In certain embodiments, pharmaceutical formulations include an AFFIMER® polypeptide of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations comprising AFFIMER® polypeptides described herein can be produced. Suitable examples of sustained-release preparations include semi-permeable matrices of solid hydrophobic polymers containing an AFFIMER® polypeptide, where the matrices are in the form of shaped articles (e.g., films or microcapsules). Examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

EXAMPLES

Example 1—Mutations can be Combined Independently to Modulate Stability

The following mutations were made relative to SEQ ID NO: 1:

| Mutations | Stability (change in Tm compared to SEQ ID NO: 1) |
|---|---|
| hSteA Y35W T51L N32G | +9.9° C. |
| hSteA Y35W Q42E M65I | +10.8° C. |
| hSteA Y35W Q42E M65I E29K K30E E33K | +14.8° C. |

| Mutations | Stability (change in Tm compared to SEQ ID NO: 1) |
|---|---|
| hSteA Y35W $^{59}$AG-NK N32G | +8.6° C. |
| hSteA Y35W N32G M65I | +11.8° C. |

These all also increased the Tm of hSteA Y35W.

This shows that the order of mutation does not matter. In other words, this demonstrates that the mutations taught herein to modulate stability (e.g. Tm) can be made independently or combined independently.

It is an advantage of the invention that particular mutations taught herein to modulate stability do not depend on each other to achieve their individual effects.

Example 2: Heterologous Peptide Insertions test heterologous peptide GGSGGSGGS (SEQ ID NO: 92) inserted in to L2 and L4
3 different positions for each loop (9 combinations)
Thermal stability measured on Optim 2
3r2 measured in absence of denaturant but the stabilities were over range
3r2 measured again in presence of 1 M GuHCl to bringing Tm within range
3t4 measured in presence of SYPRO Orange as no intrinsic tryptophan fluorescence in this polypeptide
In summary various options illustrated are shown below:

```
SQT (SEQ ID NO: 24 of WO 2009/136182)
                                               (SEQ ID NO: 122)
MIPRGLSEAKPATPEIQEIVDKVKPQLEEKTNETYGKLEAVQYKTQV

L[ A||ST]NYYIKVRAGDNKYMHLKVFNG[P| PGQN |ADR]VLTG

YQVDKNKDDELTGF

3r2 (SEQ ID NO: 19)
                                               (SEQ ID NO: 123)
MIPGGLSEAKPATPEIQEIVDKVKPQLEKETGKTWGKLEAVEYKTQV

D[A| G |L]NYYIKVRVN-GKYIHLKVFKS[L| PGQN |EDL]VLT

GYQVDKNKDDELTGF

3t4 (SEQ ID NO: 23)
                                               (SEQ ID NO: 124)
MIPGGLSEAKPATPEIQEIVDKVKPQLEEKTGETYGKLEAVEYKTQV

D[A| G |T]NYYIKVRAGDNKYIHLKVFKS[L| PGQN |EDL]VLT

GYQVDKNKDDELTGF

3r2 /t4
                                               (SEQ ID NO: 125)
 . . . QVD[A|GGSGGSGGS|L]NYY . . . FKS[L|GGSGGSG

GS|EDL]VLT . . . 0

3r2 /t4
                                               (SEQ ID NO: 126)
 . . . QVD[|GGSGGSGGS|GL]NYY . . . FKS[|GGSGGSGG

S|NEDL]VLT . . . −1

3r2 /t4
                                               (SEQ ID NO: 127)
 . . . QVD[AG|GGSGGSGGS|]NYY . . . FKS[LP|GGSGGS

GGS|DL]VLT . . . +1
```

Results are shown in FIG. 1.

This demonstrates that inserting heterologous peptides into loops 3r2 advantageously does not adversely affect stability.

For L2 Tm, 48-L2-50>49-L2-51>50-L2-52

For L4 Tm, 73-L4-78 is usually most stable, except in combination with 50-L2-52 where it is by far the least stable The most stable combination is 48-L2-50 with 73-L4-78

3t4 did not give good data, even in the presence of SYPRO, except for one variant which was clearly much less stable than the rest. This is the same combination as for 3r2.

Thus, most suitably the insertions/loops for both 3r2 and 3t4 should be as follows:

L2 inserted between residues D48 and G50, deleting residue A49

L4 inserted between residues L73 and E78, deleting residues P74, G75, Q76 and N77 (using hSteA numbering)

Example 3: Exemplary Scaffold Proteins

Exemplary scaffold proteins are demonstrated.

In this experiment, Tm is measured by DSC (r/t) and Optim 2 (3r).

Exemplary Scaffolds for Research Applications

3r1—hSteA Y35W N32G V48D M65I Q42E T51L (A59V ΔD61) (E29K K30E E33K) (SEQ ID NO: 18)
3r2—hSteA Y35W N32G V48D M65I Q42E T51L (A59V G60N ΔD61 N62G) (E29K K30E E33K) (SEQ ID NO: 19)

Exemplary Scaffolds for Therapeutic Applications

SEQ ID NO: 20 3t1—hSteA N32G V48D
SEQ ID NO: 21 3t2—hSteA N32G V48D M65I

SEQ ID NO: 22 3t3—hSteA N32G V48D M65I T51L

SEQ ID NO: 23 3t4—hSteA N32G V48D M65I Q42E

SEQ ID NO: 24 3t5—hSteA N32G V48D M65I Q42E T51L

FIG. 2 shows data for Tm as a measure of thermal stability.

FIG. 3 shows Tm measured at different pH values.

FIG. 4 shows CD spectra.

We generated DSC data for exemplary scaffolds as above and observed the following Tm values:

3t1=85.6° C.

3t2=89.2° C.

3t3=91.6° C.

3t4=92.4° C.

3t5=94.7° C.

Thus we demonstrate that exemplary scaffold proteins show improved stability.

Example 4: Structural Integrity of Scaffold Proteins

Scaffold proteins of the invention advantageously maintain their structural integrity when complete with target peptide insertions. To demonstrate this, we measured the near and far UV CD spectra for the 3r2 and 3t4 scaffolds with heterologous peptide insertions. In this example, the heterologous peptide insertions are 9mer insertions having the sequence (GGS)3 i.e. GGSGGSGGS (SEQ ID NO: 92).

The near UV CD spectra report on the environment of the aromatic side chains. Peaks, positive or negative, in a near UV CD spectrum indicate that the environment around the aromatic residues is fixed. This is interpreted as a protein having a fixed tertiary structure. Adding the heterologous peptide (GGS)3 (SEQ ID NO: 92) to loops 2 and 4 results in near UV CD spectra with the same shape as the "empty" scaffolds, albeit with different magnitudes, indicating that the addition of heterologous peptides has not disrupted the tertiary structure of the scaffold proteins.

The far UV CD spectra report on gross secondary structure. The alpha-helix, beta-strand and random coil all have distinctly different far UV CD spectra. Adding the heterologous peptide (GGS)3 (SEQ ID NO: 92) to loops 2 and 4 results in far UV CD spectra with the same shape as the "empty" scaffolds, albeit with different magnitudes, indicating that the addition of heterologous peptides has not disrupted the gross secondary structure of the scaffold proteins.

Referring to FIG. 5, far UV CD spectra of 3r2 (solid line) and 3r2 $(GGS)_3$ (dashed line) showing mean residue ellipticity ($[\theta]_{MRE}$). 3r2 is an "empty" scaffold, whose loops do not contain heterologous peptides. 3r2$(GGS)_3$ contains the heterologous peptide sequence GGSGGSGGS (SEQ ID NO: 92) in place of A49 (loop 2) (i.e. 48-<heterologous peptide>-50) and in place of P74-G75-Q76-N77 (loop 4) (i.e. 73-<heterologous peptide>-78).

Referring to FIG. 6: Far UV CD spectra of 3t4 (solid line) and 3t4$(GGS)_3$ (dashed line) showing mean residue ellipticity ($[\theta]_{MRE}$). 3t4 is an "empty" scaffold, whose loops do not contain heterologous peptides. 3t4$(GGS)_3$ contains the heterologous peptide sequence GGSGGSGGS (SEQ ID NO: 92) in place of A49 (loop 2) and in place of P74-G75-Q76-N77 (loop 4).

Referring to FIG. 7: Near UV CD spectra of 3r2 (solid line) and 3r2$(GGS)_3$ (dashed line) showing molar ellipticity ([θ]). 3r2 is an "empty" scaffold, whose loops do not contain heterologous peptides. 3r2$(GGS)_3$ contains the heterologous peptide sequence GGSGGSGGS (SEQ ID NO: 92) in place of A49 (loop 2) and in place of P74-G75-Q76-N77 (loop 4).

Referring to FIG. 8: Near UV CD spectra of 3t4 (solid line) and 3t4$(GGS)_3$ (dashed line) showing molar ellipticity ([θ]). 3t4 is an "empty" scaffold, whose loops do not contain heterologous peptides. 3t4$(GGS)_3$ contains the heterologous peptide sequence GGSGGSGGS (SEQ ID NO: 92) in place of A49 (loop 2) and in place of P74-G75-Q76-N77 (loop 4).

Thus it can be seen that over the wavelengths measured, the shape of the spectra for the scaffolds bearing heterologous peptide insertions are essentially no different from the scaffolds without insertions. This shows the structure has been maintained with heterologous peptide insertions. This is shown for different exemplary scaffolds of the invention.

Example 5: Immunogenicity

The immunogenicity of polypeptides according to the present invention was modelled. % rank is the % rank of predicted affinity compared with a set of 200000 random natural human peptides, e.g. a value of 1% means the 15mer peptide is predicted to bind as strongly as the top 1% of the 200000 random peptides. Any rank below 10% (i.e. 10%-100%) is not considered immunogenic. These calculations were carried out using the NetMHCIIpan (v3.1) server. Forty-one MHC alleles were tested in total for each sequence. This plot shows the result for one allele (the DRB1 1502 allele) as a representative example.

Referring to FIG. 9, it can concluded that the mutations taught herein produce only small movements up or down on immunogenicity. The plots are largely similar to hSteA. No large immunogenic region has been introduced. No large changes/deviations from wild type have been introduced.

Example 6: Serum Stability

Stability such as serum stability was tested.

Figure 10A:
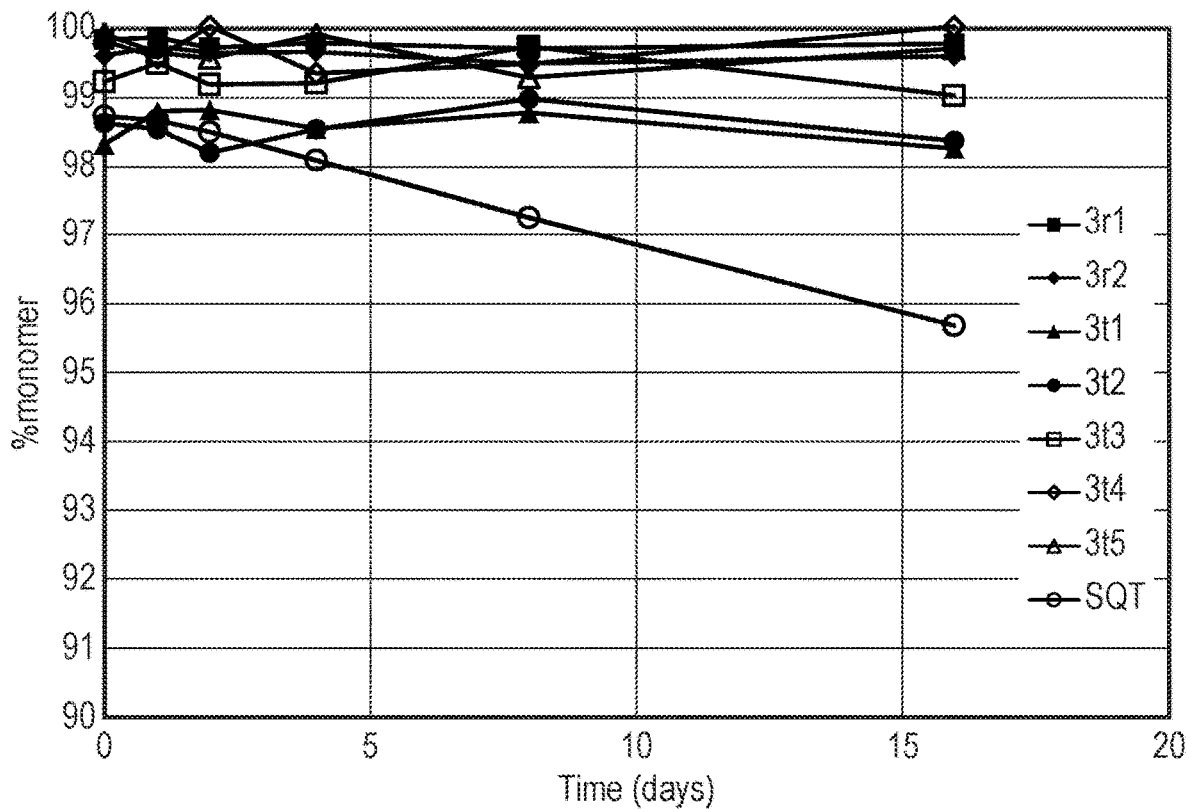
FIGS. 10a and 10b show graphs of % monomer (FIG. 10a) and % dimer (FIG. 10b) formation as a measure of serum stability of various polypeptides with heterologous peptide inserts.
Figure 10B:
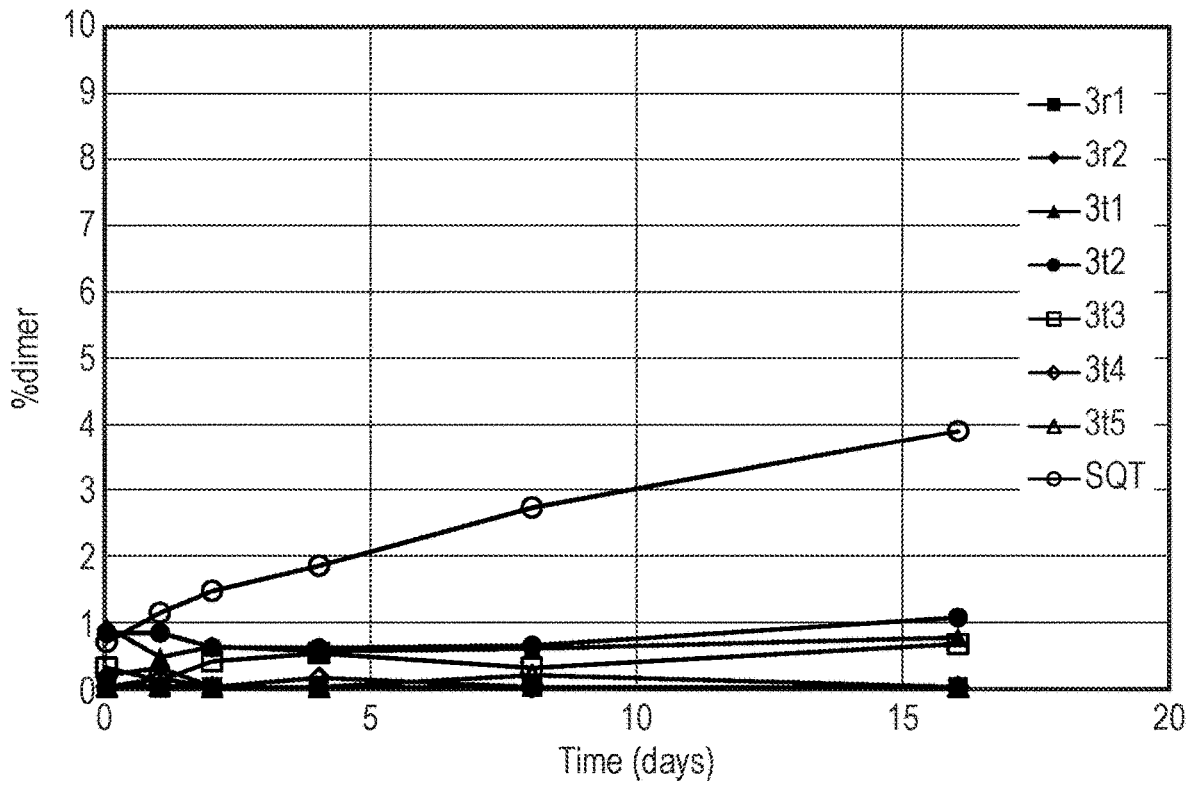

Each protein was incubated in human serum (Sigma) at 37° C. for up to 16 days. Samples were withdrawn at days 0, 1, 2, 4, 8 and 16 and kept frozen until measurement. All samples were analysed using the Wes simple western system (Protein Simple) to detect the presence of monomer and any other species present. Detection was via an anti-(His6) monoclonal. Over the course of this experiment, SQT showed a steady decrease in the area of the monomer peak (FIG. 10a), whereas the other proteins remained steady. The decrease in the amount of SQT monomer was matched by an increase in SQT dimer (FIG. 10b). This is expected as SQT has V48L and so is still able to dimerise.

There was no evidence of any material appearing at lower molecular weights, for example from protease digestion.

The same results were seen in buffer (rather than serum).

Thus it is demonstrated that polypeptides according to the present invention are stable and do not significantly degrade in human serum over the time course shown, or indeed in standard storage buffer.

Example 7: Biological Neutrality (Papain Binding)

Figure 11:
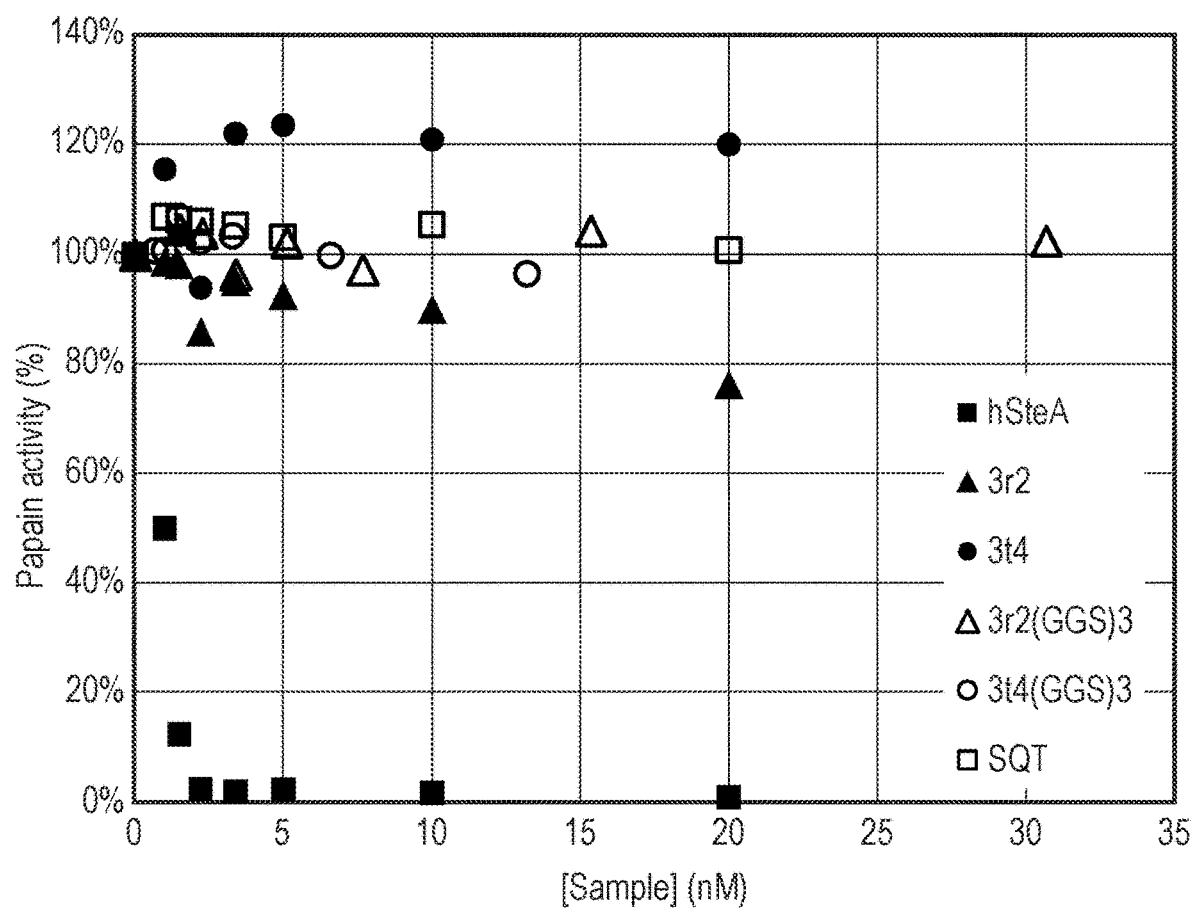
FIG. 11 shows a plot of papain activity (%) of various polypeptides with heterologous peptide inserts.

Human stefin A is an inhibitor of the cysteine protease papain. Human stefin A, SQT and variants of hSteA referred to as 3r2 and 3t4 were tested in a papain activity assay. 3r2 and 3t4 were also tested with heterologous peptides (GGSGGSGGS) (SEQ ID NO: 92) inserted between residues 48-50 and 73-78 (hSteA residue numbering). Activated papain was incubated with a dilution series of each variant before substrate (N-Carbobenzyloxy-Phe-Arg-7-amido-4-methylcoumarin) was added. The fluorescence of each reaction was measured (excitation at 380 nm, emission at 460 nm) for 5 minutes after substrate emission. Data are presented in FIG. 11. Although hSteA is a potent inhibitor of papain, none of the variants tested show significant inhibition of papain for the concentrations tested. This demonstrates that biological neutrality has been achieved in exemplary scaffold proteins of the invention.

Example 8: Exemplary Library Build

1. Vector Preparation
a. SapI Digest
Reaction mixture:
  60 μL SapI (10 U/μL)
  7.5 μL MfeI-HF (20 U/μL)
  150 μg vector (contains a truncated gene III; library will be scaffold-linker-gene III)
  150 μL CutSmart buffer (10×)
  add H20 to 1500 μL
Incubate at 37° C. for 1 h (500 μL aliquots).
Check success of digest on agarose gel.
b. Phenol/Chloroform Extraction
Add one volume of phenol/chloroform (Sigma; 77617) to one volume of your sample (larger volumes are easier to handle; 500 μL are ideal) in a 1.5 mL tube, make sure the tube is fully closed and mix thoroughly by inverting.
Spin sample at 13,000×g for 5 min (at room temperature).
Transfer the upper layer carefully into a fresh tube (initially 400 μL, then the rest).
Add one volume of chloroform (Sigma; C0549) to the sample, make sure the tube is fully closed and mix thoroughly by inverting.
Spin sample at 13,000×g for 5 min (at room temperature).
Transfer the upper layer carefully into a fresh 2 mL tube (initially 400 μL, then the rest).
The DNA is now extracted.
c. Ethanol Precipitation
Add 0.1× volume of 3 M Sodium Acetate (pH 5.2; ThermoFisher; R1181), 1 μL glycogen (Roche; 10901393001) and 2.5× volume of pre-chilled (−20° C.) absolute ethanol to the phenol/chloroform extracted sample; mix thoroughly by inverting.
Incubate the samples at −80° C. for at least 2 h (overnight would be better).
Spin precipitated DNA in a pre-cooled centrifuge at 16,000×g/4° C. for 15 min.
Remove supernatant by pipetting and wash pellet by adding 400 μL pre-chilled 70% (v/v) ethanol opposite of the pellet.
Spin again at 16,000×g/4° C. for 5 min.
Remove as much ethanol as possible by carefully pipetting.
Leave tubes open for pellets to dry at room temperature.
Resuspend DNA in molecular grade water (typically 100 μL).
d. Purification with Chromaspin TE-1000 Columns
Further purification of digested vector DNA via Chromaspin TE-1000 columns in order to remove digestion fragments smaller than 300 bp. Purified vector DNA will be in the flow through. This is not a concentration step. 70-100 μL DNA can be applied with a maximum concentration of 1 mg/mL.
Mix the slurry of the columns by inverting (Takara Clontech; 636079).
Snap off the end of the column and place it in a collection tube.
Remove the lid of the column and place it together with the collection tube in a 15 mL falcon tube.
Spin at 700×g/4° C. for 5 min.
Transfer the column into a new collection tube and back into a 15 mL falcon tube.
Apply the sample by carefully pipetting it on top of the slurry.
Spin at 700×g/4° C. for 5 min.
The purified vector DNA is now in the flow through and can be transferred into a 1.5 mL tube for storage at −20° C.

2. Insert Preparation
a. SapI Digest
Reaction mixture:
15 μg library DNA (biotinylated)
  75 μL CutSmart buffer (10×)
  30 μL SapI (10 U/μL)
  add H₂O to 750 μL
Split in 3×250 μL aliquots.
Incubate at 37° C. for 1 h (Eppendorf Thermomixer) and subsequently heat inactivate at 65° C./20 min (heat block).
b. Beads Purification I (Streptavidin Beads)
Prepare washing buffer (2×):
  10 mM Tris-HCl (pH 7.5)
  1 mM EDTA
  2 M NaCl
Mix 50 μL M280 streptavidin beads (LifeTechnologies 11205D) with 1 mL washing buffer (1×). Mix by vortexing for ≥5 s.
Immobilise beads on a magnetic rack for 1 min.
Remove supernatant and add again 1 mL of washing buffer (1×).

Immobilise beads on a magnetic rack for 1 min.
Remove supernatant and resuspend beads in 250 µL washing buffer (2×).
Add 250 µL digest to washed beads and incubate on a roller mixer at room temperature for 15 min.
Immobilise beads on a magnetic rack for 2-3 min.
Transfer supernatant into a new tube (contains digested library insert).

c. Beads Purification II (AMPure Beads)

Transfer supernatant into a new tube (contains digested library insert).
Add 600 µL AMPure beads to 250 µL digested and streptavidin-purified insert. Incubate on a roller mixer for 10 min.
Immobilise beads on a magnet for 2-3 min. Discard supernatant.
Wash beads with 1.1 mL 70% (v/v) ethanol.
Immobilise beads on a magnet for 2-3 min. Discard supernatant.
Wash beads again with 1.1 mL 70% (v/v) ethanol.
Immobilise beads on a magnet for 2-3 min. Discard supernatant.
Air-dry the beads for 10 min.
Resuspend beads in 50 µL water for 2 min.
Immobilise beads on a magnet for 2-3 min and transfer supernatant into a new tube.
Resuspend beads again in 50 µL water for 2 min.
Immobilise beads on a magnet for 2-3 min and transfer supernatant into the same tube as the previous one.
Check success of digest and purification on an analytical agarose gel.

3. Test Ligations and Initial QC a. Ligations

Testing Different Vector:Insert Ratios
Ligation mixture (include negative control without insert):
100 ng digested vector
X ng digested library insert (X varies with ligation ratio)
0.5 µL T4 DNA ligase (2000 U/µL)
2 µL T4 DNA ligase buffer (10×)
Ad H$_2$O to 20 µL
Incubate ligation mixture at room temperature for 30 min. Inactivate ligase at 65° C. for 10 min.

b. Electroporations

Place electroporation cuvettes (2 mm) in their bags, 1.5 mL Eppendorf tubes and sterile water on ice to pre-chill.
Place aliquots of electrocompetent TG1 cells on ice to thaw.
Add 60 µL ice-cold sterile water to 60 µL TG1 cells.
Aliquot 2 µL ligation mixture into pre-chilled 1.5 mL tubes.
Add 25 µL of diluted TG1 cells to each tube and mix by flicking.
Transfer cell/DNA mixture into pre-chilled cuvette, place cuvette into electroporator and pulse cells (25 µF/200 ohm/2500 V).
Add immediately 975 µL Recovery Medium, pipette up and down 3× and transfer cell suspension into new 1.5 mL tubes.
Incubate cells at 37° C./1000 rpm for 1 h.
Dilute cells $10^{-2}$ and $10^{-3}$ in 2YT and plate 50 µL on 2YT agar plates supplemented with 25 µg/mL chloramphenicol and 2% glucose. Plates are incubated at 30° C. for 16 h.
Count cfu the next day.

c. Sequencing

Choose best vector:insert ratio and pick colonies from counting plates (192 in total) into 1 mL 2YT supplemented with 25 µg/mL chloramphenicol and 2% glucose
Incubate at 37° C./800 rpm/35% humidity overnight.
Isolate phagemid DNA and sequence with the M13-RP primer 4. Bulk Ligation a. Ligation Ligation mixture (2×3.5 mL):
15-20 µg SapI-digested pALSphm-dummyT2
X µg SapI-digested library insert (X depends on the determined optimal ligation ratio)
70 µL T4 DNA ligase (2000 U/µL)
350 µL T4 DNA ligase buffer (10×)
add nuclease-free water to 3.5 mL
⇒ split into 14×500 µL aliquots
Incubate at 16° C. overnight.
Inactivate ligase at 65° C. for 10 min.

b. Phenol/Chloroform Extraction

See 1.b c. Re-Buffering with Amicon Filter Units

Add extracted DNA to Amicon filter unit (50 K). Total volume should be 500 µL. It can be added up to 500 µL with nuclease-free water if necessary.
Spin column at 3,000×g for 10-15 min until the liquid volume in the upper column is down to 30-50 µL.
Discard flow-through and top up the concentrated sample with 400 µL nuclease/free water. Mix water and sample and spin again at 3,000×g for 10-15 min until the liquid volume in the upper column is down to 30-50 µL.
Re-buffer the sample with a total of 8×400 µL nuclease-free water.
After the last spinning step carefully transfer the column upside down into a fresh collection tube. Spin at 1,000×g for 2 min and transfer the eluted DNA from the collection tube into a DNA-LoBind tube.
Measure DNA concentration.

5. Big Scale Transformations a. Shooting the Library

Defrost the Recovery Medium at 37° C. and keep it pre-warmed.
Prepare a disposable 125 mL flask with 18-19 mL 2YT media and pre-warm it at 37° C. (19 mL for 1× transformation, 18 mL for 2× transformations)
Place the cuvettes (2 mm) in their bags on ice.
Pre-chill the nuclease-free water on ice.
Defrost the bulk ligation and keep it on ice.
Defrost the TG1 cells on ice for about 10 min.
Add 60 µL pre-chilled nuclease-free water to the cells and 10 µL of the ligation mixture. Mix by flicking.
Transfer the diluted cells/ligation mixture into a pre-chilled cuvette and make sure the cells are at the bottom of the cuvette by gently tapping it onto the bench.
Place the cuvette in the electroporator and apply a pulse (25 µF/200 ohm/2500 V).
No later than 10 s after the pulse add 870 µL Recovery Medium and pipette gently up and down 3 times.
Transfer the transformed cells into the prepared 125 mL flask and incubate them at 37° C./220 rpm for 1 h. (Two consecutive transformations can be pooled in one flask).
Transfer culture into a 50 mL tube and spin at 3,220×g for 5 min. Discard supernatant and resuspend cell pellet in 1 mL 2YT. Remove 10 µL for serial dilutions ($10^{-2/-4/-5/-6/-7}$) and plate the remaining cells on two Bioassay dishes with 2YT agar (25 µg/mL chloramphenicol, 2% glucose) per transformation. Make a note of the volume plated.

Plate 20 µL of the $10^{-5/-6/-7}$ dilutions onto small agar plates (2YT agar with 25 µg/mL chloramphenicol, 2% glucose).

Incubate Bioassay dishes and agar plates at 30° C. overnight.

Repeat transformations until sufficient transformed cells have been collected (~10× than aimed for library size). Bioassay dishes can be sealed with parafilm and stored at 4° C. until all transformations have been finished.

b. QC by Sanger Sequencing

Repeat steps of 3.c c. Pooling Transformed Cells and Making Glycerols

Prepare 2YT media supplemented with 15% (v/v) glycerol (final concentration).

Add 10-15 mL 2YT/glycerol mixture to one Bioassay dish and scrape off colonies.

Once all colonies have been scraped off transfer cell suspension onto next tray and continue scraping off colonies. If suspension gets very viscous it can be topped up with fresh media. However, the final volume shouldn't exceed 14 mL.

Once colonies of all transformations (coming from the same batch) have been pooled, transfer cell suspension into a 15 mL falcon tube.

Measure $OD_{600}$ of each tube and combine cells suspensions depending on diversity calculated from counting plates for each transformation batch.

Aliquots are made of containing cells 15× fold over-representing library diversity and stored at −80° C.

d. Testing Viability of Glycerols

Defrost one aliquot of pooled library glycerols.

Make serial dilutions of pooled glycerol stocks in 2YT ($10^{-6}/10^{-7}$).

Plate 20 µL of each dilution on LB agar plates supplemented with 25 µg/mL chloramphenicol and 2% glucose (duplicates!). Incubate plates at 37° C. overnight.

Cfu numbers indicate actual concentration of viable cells per mL.

6. Phage Propagation a. Calculation of Glycerol Stock Needed

Based on previous calculations regarding the viability of the glycerols, calculate how many glycerols you will need to cover 10× library diversity b. Phage Cultures Inoculate 6×500 ml pre-warmed 2×YT containing 25 µg/ml chloramphenicol and 5% glucose with glycerols to $OD_{600}$=0.08-0.1 in 2 litre disposable flasks to allow good aeration.

Grow at 37° C. with shaking at 250 rpm until $OD_{600}$ is 0.5 (75-90 min).

Option: if calculated amount of cells can't be accommodated in six flasks with an $OD_{600}$=0.08-0.1 then prepare some pre-cultures (same media and sterile flasks), let cultures grow for 1 h and use those pre-cultures to inoculate main six culture flasks Transfer cultures into conical 500 mL centrifuge pots (max. 500 mL) and add 2×10$^{12}$ M13KO7 helper phage per 500 mL culture. Mix well.

Incubate without shaking in a 37° C. water bath for 60 min.

Spin at 3,300×g, 20° C. for 15 min. Check and re-spin if necessary. Resuspend the pellet of each centrifuge tube in 2×YT containing 25 µg/ml chloramphenicol and 50 µg/ml kanamycin (and 0.1% glucose). Use 500 ml per 250 mL of original culture.

Transfer culture to disposable 2 L flasks (max. 500 mL per flask). Flasks from pre-infection step can be re-used.

Incubate shaking (170 rpm) at 25° C. overnight.

c. Phage Purification

Transfer PEG-NaCl aliquots (and 0.5 L or 0.25 L centrifuge pots if available) to the cold room to pre-cool overnight.

The overnight culture is centrifuged at 3,300×g/4° C. for 30 min. The supernatant is recovered and 100 mL pre-chilled PEG/NaCl is added per 400 mL of supernatant. It is advisable to pre-aliquot the PEG/NaCl the day before and leave it in the cold room overnight as this will ensure the tubes and PEG is chilled and will aid the recovery of phage.

The mixture is incubated on ice in the cold room for 2-3 h. Do not incubate with PEG overnight. This will result in larger pellets, but will be mostly due to host DNA and bacterial debris.

The mixture is centrifuged at 3,300×g/4° C. for 30 min and the supernatant is discarded.

The resulting pellets are each resuspended in PBS (8 mL per 400 mL SN+100 mL PEG/NaCl). Once the pellet has been fully resuspended, transfer the phage solution into 50 mL falcon tubes and spin again at 11,600×g/4° C. for 10 min.

Transfer supernatant into new 50 mL tubes and add pre-chilled PEG/NaCl (2 mL per 8 mL PBS). The solution is mixed well by inversion and left on ice for 1 h.

Mixture is centrifuged at 3,300×g/4° C. for 30 min and the supernatant discarded.

The pellet is resuspended in PBS (5 mL per 8 mL PBS used after first precipitation), and centrifuged at 11,600×g for 10 min to remove any remaining bacterial debris.

The supernatant is pooled (not filtered). Glycerol is added to the phage solution (final concentration 15%) and mixed thoroughly.

The phage stocks are now prepared and should be stored in PBS/15% glycerol at 4° C. (not longer than a couple of days until the titre and display levels are determined) and then at −80° C. in working size aliquots (each phage aliquot should have at least 10× over-representation of the library). Use protein LoBind tubes.

It is advisable to determine the titre of the phage by both optical density and *E. coli* infection. Display levels should be determined by western blotting.

d. Contamination/Infectivity Test

Set up a 5 ml culture (2YT medium supplemented 12 µg/ml tetracycline) of ER2738 *E. coli* cells from a single colony in a 14 cm vented tube.

Incubate overnight in an orbital incubator at 37° C., 220 rpm.

Measure the OD600 of a $10^{-1}$ dilution of the overnight ER2738 culture.

If the $OD_{600}$ is <5 this may indicate that they will not be suitable for infection. Discard the overnight culture and prepare a fresh overnight culture.

Prepare a 20 mL culture at $OD_{600nm}$=0.18-0.20 by diluting the ON in 2YT supplemented with 12 µg/mL tetracycline. Check the $OD_{600nm}$.

Incubate at 37° C., 220 rpm for 45-90 mins, until the cells reach an $OD_{600}$ range of 0.50-0.70.

During this incubation prepare the following:

Top agar control (contamination check):

Set a water bath to 45° C. and melt top agar in a microwave.

Aliquot 4×3 ml melted top agar into 14 cm vented tubes and place in the water bath to cool for at least 30 mins prior to use.

Prepare phage samples by serial dilution in PBS and place on ice:

1E10 ph/mL
1E9 ph/mL
1E8 ph/mL

During the second half of the incubation, add 10 µl phage to a 2 ml microfuge tube.

Prepare another 2 ml microfuge tube with 10 µL PBS (this is the negative control).

Leave the tubes at room temperature until required.

Amplified phage control:

Prepare phage samples by serial dilution and place on ice:

2E9 ph/mL
2E8 ph/mL
2E7 ph/mL
2E6 ph/mL
2E5 ph/mL

During the second half of the incubation, add 10 µl of diluted purified phage to 1.5 mL tubes.

Leave the tubes at room temperature until required.

Once the ER2738 cells reach $OD_{600}$=0.50-0.70 add 1 mL cells to each prepared 1.5 and 2 mL tube. Mix all tubes by inversion.

Immediately incubate all tubes at 37° C. for 15 mins without shaking.

After the 15 min incubation:

Amplified phage control: Transfer the 3×2 ml microfuge tubes to a tube shaker at 37° C., 1000 rpm and incubate for a further hour.

Top agar control (eluted phage): Add 300 µl of the cell/phage mixture to the 14 cm vented tubes prepared with top agar. Mix gently by swirling the tube and pour immediately onto LB-agar plates supplemented with 12 µg/ml tetracycline and tilt the plate so that the top agar solution covers the plate. Leave the plates agar-down in a dark place to allow top agar to set.

Amplified phage control: Plate 50 µl from each dilution onto LB-agar plates supplemented with 100 µg/ml carbenicillin or 25 µg/mL chloramphenicol or 50 µg/mL kanamycin.

Incubate all plates agar-up at 37° C. overnight in a static incubator.

Calculate infective phage [pfu/ml].

7. Display Level (Anti-GIIIp Western Blot)

a. SDS-PAGE

Prepare 1E11 phage in 6.5 µL PBS and add 2.5 µL of 4× Loading dye and 1 µL 10× reducing agent. Prepare duplicate samples.

Incubate at 70° C. for 10 min.

Transfer the phage prep into the wells of a 12-well BOLT Bis-Tris gel.

Run the gel at 200 V for 22 min.

b. Blotting

Wet a filter paper (from blue bag) with MilliQ water.

Peel off foil from the NC Mini/Regular Stacks and place stack with the plastic tray in the iBlot2 device.

Lift the copper/gel layer off the stack and place it onto the removed foil.

Remove and discard the thin plastic covering the nitrocellulose membrane of the stack.

Open the cassette holding the SDS gel, remove wells and bottom edge and place it on to the NC membrane (ideally without repositioning). Any bubbles can be removed by carefully streaking over the gel with wetted gloves.

Place previously wetted filter paper on top of the gel and remove any bubbles by rolling across the filter paper with a roller.

Place copper/gel layer back on to the filter paper (gel side facing down) and use roller again.

Take a filter paper with an attached electrode from the NC Mini stacks box and place it on top of the stack with the electrode covering the electronics in the iBlot2 device.

Close the lid of the iBlot2 device and wait for "Start the last run" lighting up on the display. Reposition filter paper with electrode if necessary.

Choose in "templates" the P0 programme (takes 7 min).

c. Detection of gIIIp

Transfer the blotted nitrocellulose membrane into a 50 mL falcon tube and add 5 mL of 3% (w/v) skim milk in TBS pH 7.5 to it.

Incubate on a mixing roller at RT for 1 h.

Discard the blocking solution and wash the membrane by adding 5 mL TBS-T (0.05%).

Mix on a mixing roller at RT for 5 min. Repeat 2 more times.

Primary antibody: Add 5 mL of a 1:1000 dilution of anti-gIIIp antibody in 1% (w/v) skim milk in TBS pH 7.5.

Incubate on a mixing roller at RT for 1 h.

Wash membrane 3× with TBS-T as before.

Secondary antibody: Add 5 mL of a 1:2000 dilution of HRP-coupled anti-mouse antibody in 1% (w/v) skim milk in TBS pH 7.5.

Incubate on a mixing roller at RT for 1 h.

Wash membrane 3× with TBS-T as before.

Detect bound antibodies with 1.5 mL of a chemiluminescence substrate (e.g. ECL). Leave solution on the membrane for 1 min, then tilt the tray and catch any excessive ECL solution with a paper towel.

Image the membrane.

Save the resulting image, quantify the bands and evaluate display levels.

Example 9—Further Exemplary Scaffold Proteins

The invention embraces Stefin A scaffolds with mutations as described above with a certain defined sequence identity with reference to human Stefin A (SEQ ID NO: 1) as mentioned in the claims. Here we provide examples of useful scaffolds according to the present invention illustrating functionality at different levels of sequence identity.

In this example, the polypeptides of the invention comprise amino acid sequence derived from canine SteA.

Mutations relative to canine wild type sequence are underlined (mutations relative to SEQ ID NO: 1 can be identified by sequence alignment).

cSteA3r2: SEQ ID NO: 93
MMPGGLTEAKPATPEVQEIANEVKPQLEKETGKTWQEFEAVEYKTQVDAGLNYYIKVRVN-GKYIHLKIFKGLPGQNPTLTLTGYQTDKSKDDELTGF cSteA3r2 with (GGS)₃ heterologous peptide insertions (boxed):
SEQ ID NO: 94
MMPGGLTEAKPATPEVQEIANEVKPQLEKETGKTWQEFEAVEYKTQVD[GGSGGSGGS]GLNYYIKVRVN-GKYIHLKIFKGL[GGSGGSGGS]PTLTLTGYQTDKSKDDELTGF These have been successfully expressed.
Exemplary Tm measurements are as follows:
cSteA 3r2 Tm=79.2° C.
cSteA 3r2 with (GGS)₃ in loops 2 and 4 Tm=83.6° C.
This demonstrates that heterologous peptides can be inserted in the positions as taught with reference to hSteA.

Further exemplary sequences based on cSteA (changes from wild type cSteA are underlined) include:

```
cSteAtA
                                SEQ ID NO: 95
MIPGGLTEAK PATPEVQEIA NEVKPQLEEK TGETYQEFEA

VEYKTQVDAG INYYIKVRVG DNSYIHLKIF KGLPGQNPTL

TLTGYQTDKS KDDELTGF
``` cSteAtA comprises a minimal set of mutations which have the advantages of preventing possible ambiguous initiation of translation (M2I—reverts to hSteA sequence), removing a glycosylation site (N32G) and minimising domain swap dimerization (V48D—already described). These mutations are useful and may be made individually.

```
cSteAtB
                                SEQ ID NO: 96
MIPGGLTEAK PATPEVQEIA NEVKPQLEEK TGETYQEFEA

VEYKTQVDAG INYYIKVRVG DNSYIHLKIF KSLPGQNEDL

TLTGYQTDKS KDDELTGF
``` cSteAtB includes the minimal mutations and further mutations to advantageously make the "entry" and "exit" of Loop 4 the same as hSteA (G72S, P78E and T79D—all reverting to hSteA sequence)

```
cSteAtC
                                SEQ ID NO: 97
MIPGGLTEAK PATPEVQEIV NEVKPQLEEK TGETYQELEA

VEYKTQVDAG INYYIKVRVG DNSYIHLKIF KGLPGQNPTL

TLTGYQTDKS KDDELTGF
``` cSteAtC includes the minimal mutations and further mutations relative to wild type cSteA to "revert" residues back to the human sequence (which residues were found to be destabilising in hSteA (A20V, F38L—both reverting to hSteA sequence)). This has the advantage of rendering the polypeptide based on cSteA more stable.

```
cSteAtD
                                SEQ ID NO: 98
MIPGGLTEAK PATPEVQEIV NEVKPQLEEK TGETYQELEA

VEYKTQVDAG INYYIKVRVG DNSYIHLKIF KSLPGQNEDL

TLTGYQTDKS KDDELTGF
``` cSteAtD combines includes the minimal mutations and mutations to make the "entry" and "exit" of Loop 4 the same as hSteA (G72S, P78E and T79D—all reverting to hSteA sequence)

```
cSteAt1AL SEQ ID NO: 99
MIPGGLTEAK PATPEVQEIA NEVKPQLEEK TGETYQEFEA VEYKTQVD[GGSGGSGGS]G
INYYIKVRVG DNSYIHLKIF KGL[GGSGGSGGS]PTL TLTGYQTDKS KDDELTGF
```

As cSteAtA but including GGSGGSGGS (SEQ ID NO: 92) heterologous peptide insertions (boxed)—one in place of residue 48 and one in place of residues 74-77

```
cSteAt2BL SEQ ID NO: 100
MIPGGLTEAK PATPEVQEIA NEVKPQLEEK TGETYQEFEA VEYKTQVD[GGSGGSGGS]G
INYYIKVRVG DNSYIHLKIF KSL[GGSGGSGGS]EDL TLTGYQTDKS KDDELTGF
```

As cSteAtA but including GGSGGSGGS (SEQ ID NO: 92) heterologous peptide insertions (boxed)—one in place of residue 48 and one in place of residues 74-77 cSteAt3CL (SEQ ID NO: 101)
MIPGGLTEAK PATPEVQEIV NEVKPQLEEK TGETYQELEA VEYKTQVD GGSGGSGGS G
INYYIKVRVG DNSYIHLKIF KGL GGSGGSGGS PTL TLTGYQTDKS KDDELTGF

As cSteAtC but including GGSGGSGGS (SEQ ID NO: 92) heterologous peptide insertions (boxed)—one in place of residue 48 and one in place of residues 74-77 cSteAt4DL (SEQ ID NO: 102)
MIPGGLTEAK PATPEVQEIV NEVKPQLEEK TGETYQELEA VEYKTQVD GGSGGSGGS G
INYYIKVRVG DNSYIHLKIF KSL GGSGGSGGS EDL TLTGYQTDKS KDDELTGF

As cSteAtD but including GGSGGSGGS (SEQ ID NO: 92) heterologous peptide insertions (boxed)—one in place of residue 48 and one in place of residues 74-77

Additional Exemplary Scaffolds

Wild type cSteA already contains the beneficial residues E42 and I65 and I51 (T51L is most preferred, but T51I is equally as good). The minimal mutant cSteAA (above) is equivalent to 3t5 derived from hSteA sequence.

Here we demonstrate an equivalent to hSteA 3r1 using the canine sequence, which is given below (cSteAr1).

cSteAr1
(SEQ ID NO: 103)
MMPGGLTEAKPATPEVQEIANEVKPQLEKETGKTWQEFEAVEYKTQVD
AGLNYYIKVRVG-NKYIHLKIFKGLPGQNPTLTLTGYQTDKSKDDELT
GF cSteA 3r2 is already presented above (SEQ ID NO: 93).

Example 10: Increased Tm's

Polypeptides having mutation(s) were made as described herein.
In this example, polypeptides were based on the human Ste A sequence (SEQ ID NO: 1) with mutations as described; data relative to wild type human SteA are shown below.

Table of Increasing Stability Substitutions

| Mutation | Effect on Tm (° C.) |
|---|---|
| E29M | +0.7 |
| E29K K30E E33K | +3.9 |
| N32G | +3.5 |
| T34K | +3.0 |
| T34R | +2.6 |
| T34V | +2.2 |
| Q42E | +3.2 |
| T45V | +1.8 |
| T45I | +1.0 |
| T51I | +4.8 |
| T51L | +4.6 |

-continued

Table of Increasing Stability Substitutions

| Mutation | Effect on Tm (° C.) |
|---|---|
| T51V | +4.4 |
| T51F | +1.0 |
| A59V | +3.9 |
| A59I | +3.4 |
| A59L | +1.1 |
| A59L G60N D61G N32K | +0.8 |
| A59V G60 D61N N62K | +1.0 |
| A59 G60N G61G N62K | +1.3 |
| A59 G60N ΔD61 N62G | +2.0 |
| A59 G60 ΔD61 N62 | +2.2 |
| A59L G60N ΔD61 N62G | +3.1 |
| A59V G60N D61G N32K | +3.4 |
| A59I G60N ΔD61 N62G | +3.6 |
| A59I G60N D61G N62K | +3.6 |
| A59V G60N ΔD61 N62G | +3.9 |
| A59V G60 ΔD61 N62 | +4.7 |
| K63R | +1.7 |
| M65I | +5.5 |
| M65V | +3.9 |
| L67I | +1.0 |
| N90T | +1.4 |

Example 11: Decreased Tm's

Polypeptides having mutation(s) were made as described herein.
In this example, polypeptides were based on the human Ste A sequence (SEQ ID NO: 1) with mutations as described; data relative to wild type human SteA are shown below.

Table of Decreasing Stability Substitutions

| Mutation | Effect on Tm (° C.) |
|---|---|
| A12I | -6.5 |
| A12V | -4.5 |
| I16L | -5.7 |
| V20A | -10.6 |
| V20I | -9.1 |
| V20L | -5.2 |
| V20I L38A | -16.7 |

-continued

Table of Decreasing Stability Substitutions

| Mutation | Effect on Tm (° C.) |
|---|---|
| V20L L38A | −15.3 |
| V20L L38V | −11.0 |
| V20I L38V | −10.4 |
| Q26E | −3.2 |
| T31K | −7.4 |
| N32D | −3.8 |
| N32H | −1.6 |
| T34D | −3.7 |
| T34P | −1.9 |
| L38A | −12.8 |
| L38V | −7.8 |
| L38F | −7.2 |
| A40I | −8.0 |
| A40V | −2.8 |
| Q42D | −2.7 |
| V48E | −6.7 |
| V48D | −6.2 |
| V48G | −4.8 |
| V48A | −2.5 |
| V48L | −2.0 |
| G50S | −7.5 |
| T51A | −2.4 |
| Y54D T83D Q86E | −21.0 |
| A59 G60P ΔD61 N62P | −9.7 |
| A59 G60P D61P N62K | −6.9 |
| A59 G60P ΔD61 N62G | −3.8 |
| A59 G60P D61G N62K | −1.4 |
| A59 G60 D61N N62K | −1.1 |
| T83D Q86E | −4.8 |

Figure 13:
FIG. 13 shows a table of output of an iQue assay for binders to Trastuzumab.
Figure 14:
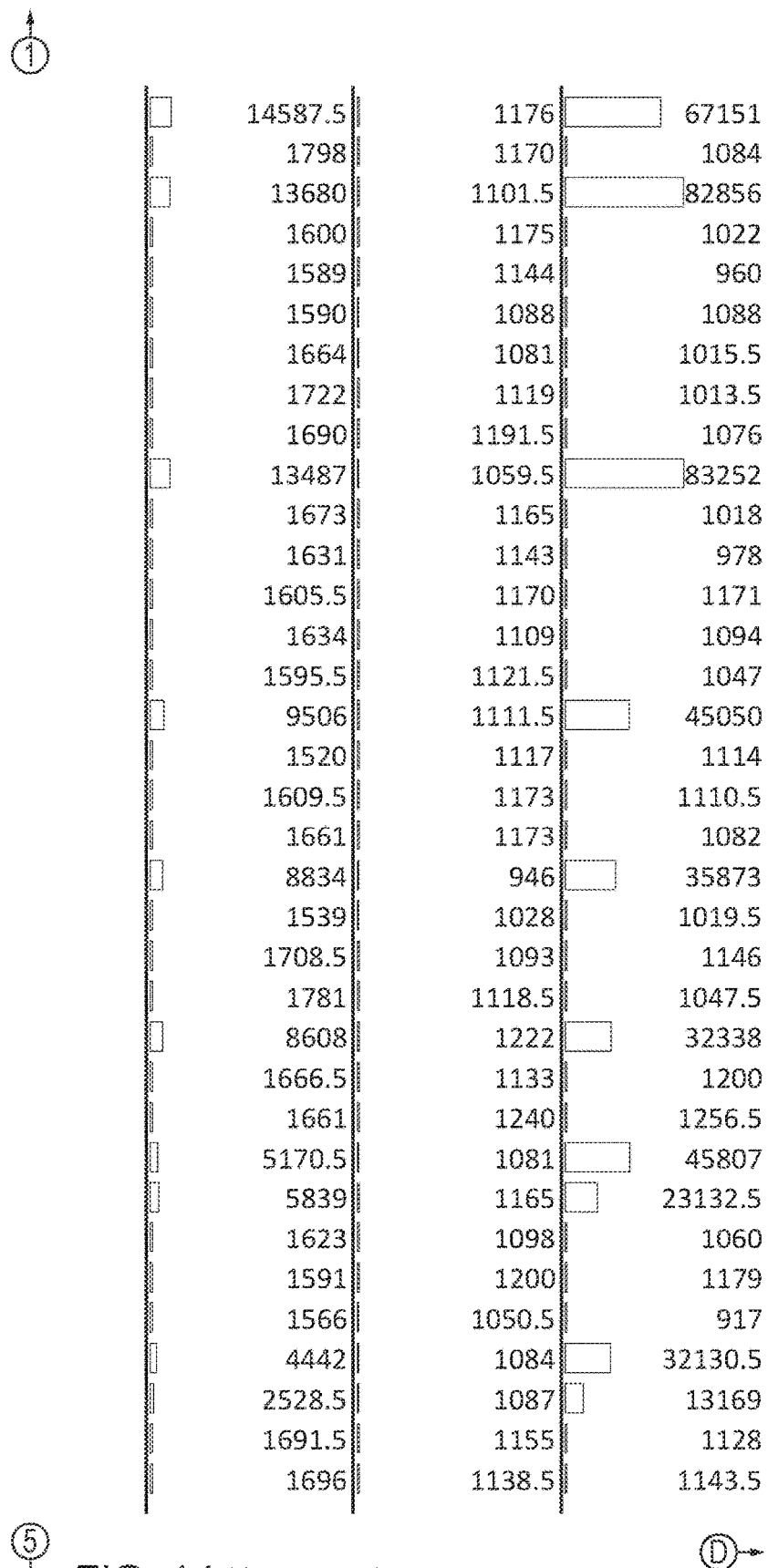
FIG. 14 shows a table of output of an iQue assay for binders to human PD-L1.
Figure 14:
Figure 14:

Example 12: Demonstrations of Various 3r2 Binders and Various Type 4 (Canine) Binders Type 3r2 Library FIGS. 12-14 show that the outputs of selections against human epidermal growth factor receptor 2 (Her2), the humanized monoclonal therapeutic antibody Trastuzumab, and human programmed death-ligand 1 (PD-L1), tested in an "iQue assay". These data show that AFFIMER® reagents can bind tightly and specifically to targets, without cross-reactivity to related and unrelated proteins. These data also show that the results from AFFIMER® reagents are repeatable, as loop sequences are often represented multiple times in an iQue assay, giving similar results.

The Intellicyt iQue Screener is a flow-cytometry based, multiplexed bead assay where the target proteins and relevant controls are immobilised on fluorescently indexed beads. The AFFIMER® reagent is incubated with the beads and binds to the target protein, the complex is then detected with an anti-HA Alexa488 labelled antibody. For screening, iQue assays are used to select the best AFFIMER® reagents based on their affinity and selectivity towards the desired target. Ideally, AFFIMER® reagents will show a strong positive signal to the bead coated in their target, but not to any of the other beads.

In FIGS. 12-14, AFFIMER® Working ID is an internal identifier; heterologous peptides are present (inserted) in the Loop 2 and Loop 4 positions. Amino acid sequence is determined from DNA sequencing data. The targets tested in the iQue assay were EGFR, mIgG2b, hIgGG1 Fc, hPD-L2, Her2 (R&D), hPD-L1, Trastuzumab, hIgG, Her2 (Sino), Her 3, mPD-L1, Avastin, Humira, Rituximab, mPD-L2, Her 4 and a no target control. FL1-A is the measured signal. QSHxx, where xx is a number, refers to a specific type of fluorescently indexed bead.

FIG. 12 shows output of an iQue assay for binders to Her2.

FIG. 13 shows output of an iQue assay for binders to Trastuzumab.

FIG. 14 shows output of an iQue assay for binders to human PD-L1.

Figure 15:
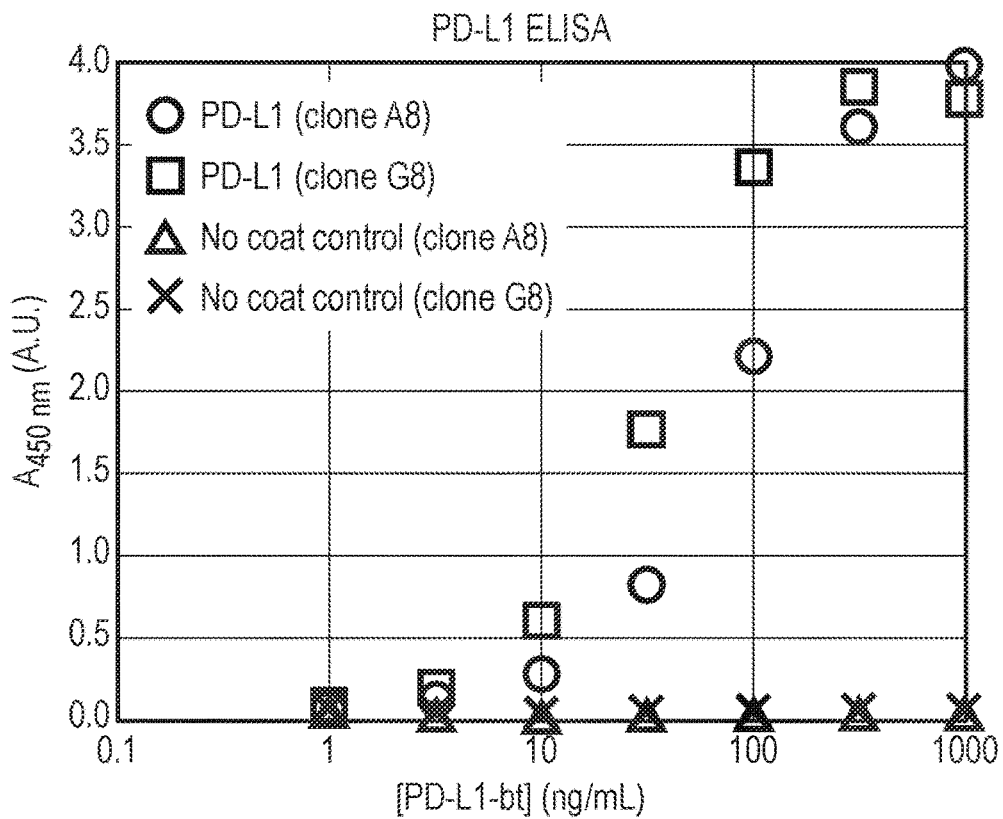
FIG. 15 shows a plot of ELISA data for two different anti-PD-L1 AFFIMER® reagents (clones A8 and G8).
Figure 16:
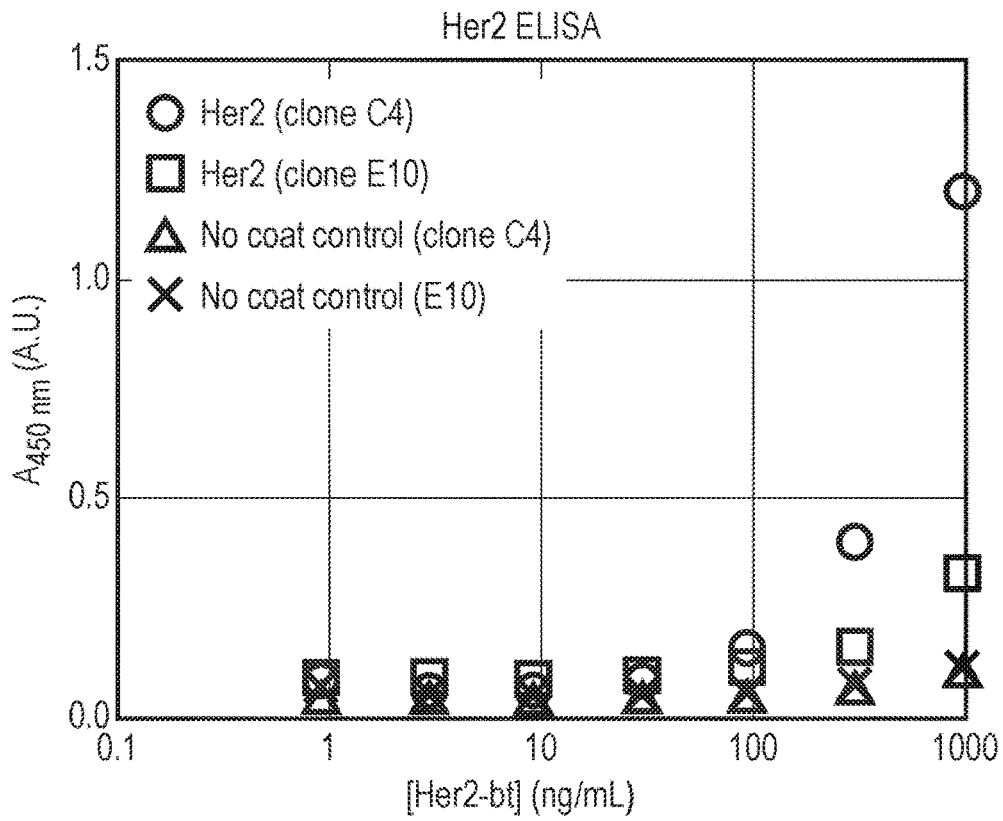
FIG. 16 shows a plot of shows ELISA data for two different anti-Her2 AFFIMER® reagents (clones C4 and E10).

FIGS. 15 and 16 show typical multi-point ELISA data, where an AFFIMER® reagent is coated on to a 96 well plate and is used as a capture reagent. These data show that binders identified in either a phage ELISA (on plates, but with the AFFIMER® reagent attached to a phage) or an iQue assay (on beads, but a purified AFFIMER® reagent) can detect target in a typical ELISA application, that the signal is titratable, and, particularly for PD-L1, a low concentration of target can be detected.

Here, AFFIMER® reagents identified to PD-L1 (FIG. 15) and Her2 (FIG. 16) were coated on ELISA plates at a fixed concentration. After washing and blocking, the appropriate biotinylated targets are titrated and left to bind to the coated AFFIMER® reagents. After a further wash, streptavidin-HRP is used to detect the presence of captured target with the use of an appropriate substrate. Both anti-PD-L1 AFFIMER® reagents bind biotinylated PD-L1 at low concentrations and biotinylated PD-L1 does not bind to the ELISA plate (no coat controls; each clone was on a separate ELISA plate, and each contained its own no coat control). The anti-Her2 AFFIMER® reagents do not perform as well as the anti-PD-L1 AFFIMER® reagents, with lower overall signals, but they do demonstrate a titratable response. Here, biotinylated Her2 does interact slightly with the ELISA plate at the highest concentration tested.

FIG. 15 shows ELISA data for two different anti-PD-L1 AFFIMER® reagents (clones A8 and G8).

FIG. 16 shows ELISA data for two different anti-Her2 AFFIMER® reagents (clones C4 and E10).

Type 4 Library (Canine Scaffold)

The type 4 library, based on the putative canine homologue of Stefin A, has been used to select AFFIMER® reagents against canine PD-L1, specifically those that will inhibit the interaction between canine PD-1 can canine PD-L1. The output of an iQue assay for these reagents (FIG. 17; description of iQue Screener as above) shows that we are also able to use this canine scaffold to find specific binding reagents. Here, the top 6 AFFIMER® reagents are showing cross-reactivity to human Fc, the canine PD-L1 used in the selection process is a canine PD-L1/human Fc fusion protein. Rather than actually binding to canine PD-L1, they are in reality very good binding reagents to the human Fc domain. The use of a scaffold based on a non-human protein such as a canine protein is useful for producing non-human (bio)therapeutics such as canine (bio)therapeutics, which should be much less immunogenic and therefore better tolerated than a therapeutic derived from a different species.

Figure 17:
FIG. 17 shows a table of output of an iQue assay for binders to canine PD-L1 by canine Stefin A-based AFFIMER® reagents.
Figure 17:

FIG. 17 shows output of an iQue assay for binders to canine PD-L1 by canine Stefin A-based AFFIMER® reagents. In FIG. 17, the targets tested in the iQue assay were canine PD-L1, human VEGFR2, SMA(4A6)+BA-peptide, human Fc, canine PD-1, amine PEG11, mIgG2b, fumonisin and SMA (2A9)+BA-peptide, as well as a no target control.

One industrial use for the canine scaffold is to generate canine therapeutic reagents. Suitably the canine AFFIMER® reagents bind to their target, and suitably do so in such a way as to disrupt the binding of the natural ligand to have a biological effect. In this selection, we wanted to find canine AFFIMER® reagents that prevent canine PD-1 binding to canine PD-L1, which would have the potential for use as check-point inhibitors in cancer treatment. Here, eleven of the anti-canine PD-L1 AFFIMER® reagents were tested for their ability to inhibit the interaction of canine PD-L1 with canine PD-1 in a competition ELISA. The results showed that some canine AFFIMER® reagents were able to bind to canine PD-L1 with approximately the same affinity as canine PD-1, and other with a range of lower affinities.

Figure 18:
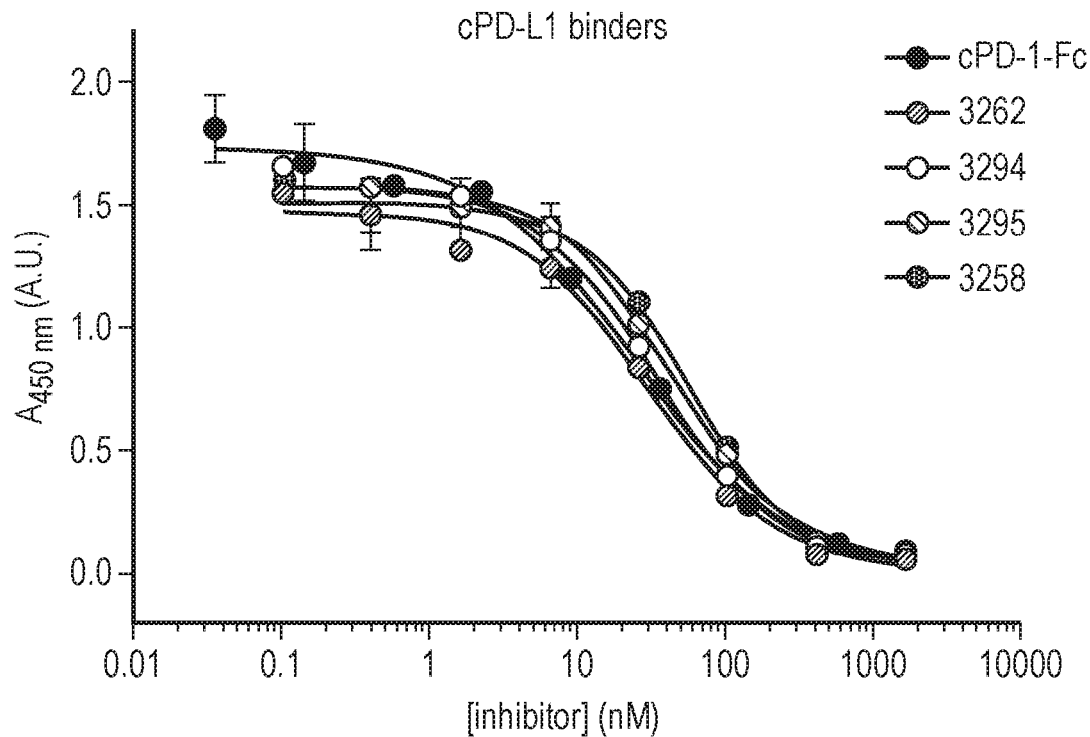
FIG. 18 shows a graph of competition ELISA data for canine AFFIMER® reagents that bind to cPD-L1 with similar affinity to canine PD-1. The curves are fits to a 4-parameter logistic model.

Next, an ELISA plate was coated with canine PD-1. Separately, biotinylated canine PD-L1 is incubated with a titration of the different AFFIMER® reagents, and canine PD-1 as a control (the competition reactions). After incubation, these competition reactions are then incubated with the coated ELISA plate. Where there is no inhibition, the biotinylated PD-L1 will be free to bind the PD-1 on the surface of the plate, and this will give a high signal when detected with a streptavidin-HRP reagent and suitable substrate. If, however, the AFFIMER® reagent binds to canine PD-L1 in such a way as to inhibit binding to PD-1, it will give a low signal. FIG. 18 shows the competition ELISA data for the canine AFFIMER® reagents that affinities similar to PD-1, and FIG. 19 shows the data for canine AFFIMER® reagents that have lower affinities than PD-1.

FIG. 18 shows competition ELISA for canine AFFIMER® reagents that bind to cPD-L1 with similar affinity to canine PD-1. The curves are fits to a 4-parameter logistic model.

Figure 19:
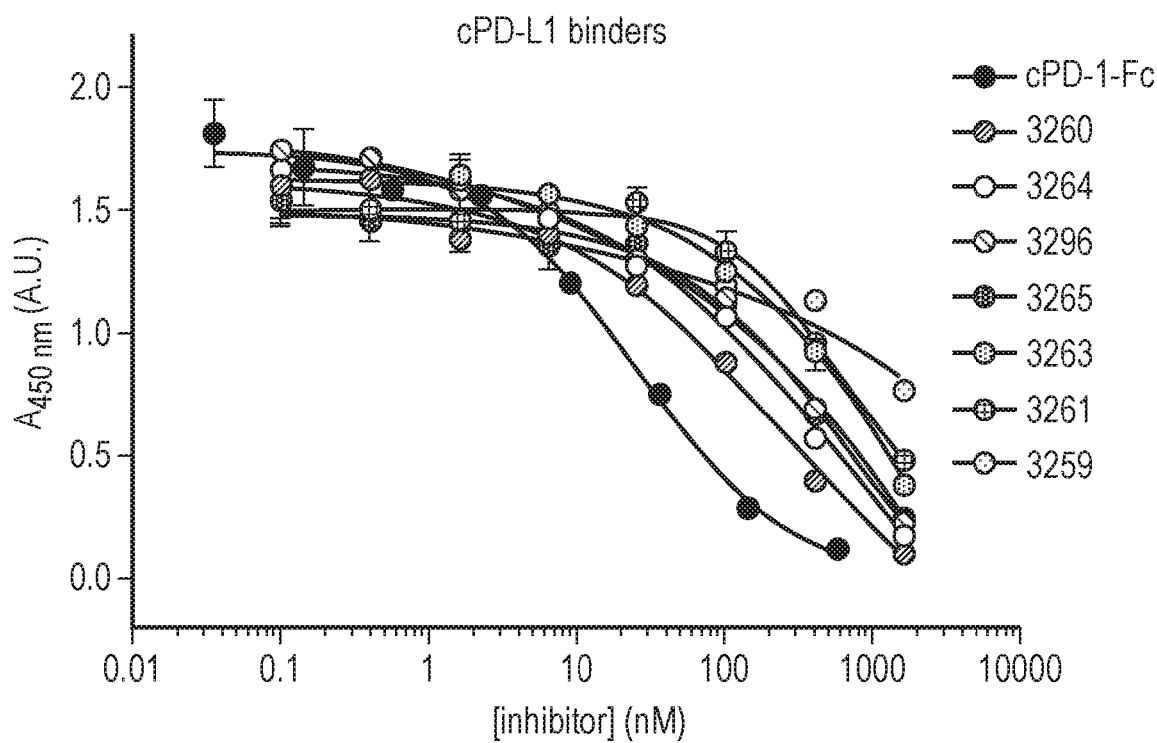
FIG. 19 shows a graph of competition ELISA data for canine AFFIMER® reagents that bind to cPD-L1 with lower affinity to canine PD-1. The curves are fits to a 4-parameter logistic model.

FIG. 19 shows competition ELISA for canine AFFIMER® reagents that bind to cPD-L1 with lower affinity to canine PD-1. The curves are fits to a 4-parameter logistic model.

All the AFFIMER®s in FIGS. 12-14 are 3r2 (SEQ ID NO: 19) except mIgG2b G12 and Zika NS1 C12—see below.

Mouse IgG2b G12 has the adhiron scaffold ("type 2 scaffold", the consensus of plant stefins so unrelated to the human stefin A. The sequence is as follows:

```
                                       (SEQ ID NO: 105)
MSAATGVRAVPGNENSLEIEELARFAVDEHNKKENALLEFVRVVKAKE

QXXXXXXXXXTMYYLTLEAKDGGKKKLYEAKVWVKXXXXXXXXXNFKE

LQEFKPVGDAAAAHHHHHG
```

The canine AFFIMER®s have the mutations M21, N32G and V48D from wildtype cSteA (underlined); the following sequence:

```
                                        (SEQ ID NO: 95)
   MIPGGLTEAK PATPEVQEIA NEVKPQLEEK TGETYQEFEA

VEYKTQVDAG INYYIKVRVG DNSYIHLKIF KGLPGQNPTL

TLTGYQTDKS KDDELTGF
```

In this example, the Zika NS1 C12 is also based on the adhiron scaffold:

```
                                       (SEQ ID NO: 106)
MSAATGVRAVPGNENSLEIEELARFAVDEHNKKENALLEFVRVVKAK

EQXXXXXXXXXTMYYLTLEAKDGGKKKLYEAKVWVKXXXXXXXXXNF

KELQEFKPVGDG
```

The invention claimed is:

1. A polypeptide comprising a scaffold protein sequence, wherein the scaffold protein sequence (a) comprises a N32G mutation relative to the amino acid sequence of SEQ ID NO: 1 and (b) has at least 90% identity to the amino acid sequence of SEQ ID NO: 1, and
the polypeptide further comprises a first heterologous peptide and a second heterologous peptide inserted in the scaffold protein sequence, wherein the first heterologous peptide and second heterologous peptides are excluded from the at least 90% identity calculation.

2. The polypeptide of claim 1, wherein the first heterologous peptide is inserted between amino acid positions 48 and 50 relative to the amino acid sequence of SEQ ID NO: 1.

3. The polypeptide of claim 1, wherein the second heterologous peptide is inserted between amino acid positions 73 and 78 relative to the amino acid sequence of SEQ ID NO: 1.

4. The polypeptide of claim 1, wherein each of the first heterologous peptide and the second heterologous peptide has a length of 3 to 20 amino acids.

5. The polypeptide of claim 4, wherein each of the first heterologous peptide and the second heterologous peptide has a length of 3 to 12 amino acids.

6. The polypeptide of claim 5, wherein each of the first heterologous peptide and the second heterologous peptide has a length of 3 to 9 amino acids.

7. A host cell comprising the polypeptide of claim 1.

8. A fusion protein comprising the polypeptide of claim 1 and one or more additional amino acid sequences.

9. The fusion protein of claim 8, wherein the one or more additional amino acid sequences is selected from signal sequences, peptide linker sequences, affinity tags, and transmembrane domains.

10. The fusion protein of claim 8, wherein the one or more additional amino acid sequences is selected from half-life extension polypeptides.

11. A polypeptide comprising a scaffold protein sequence, wherein the scaffold protein sequence (a) comprises N32G, Y35W, Q42E, V48D, T51 L, and M65I mutations relative to the amino acid sequence of SEQ ID NO: 1 and (b) has at least 80% identity to the amino acid sequence of SEQ ID NO: 1, and the polypeptide further comprises a first heterologous peptide and a second heterologous peptide inserted in the scaffold protein sequence, wherein the first heterologous peptide and second heterologous peptides are excluded from the at least 80% identity calculation.

12. The polypeptide of claim 11, wherein the scaffold protein sequence further comprises A59V, G60N, ΔD61, N62G, E29K, K30E, and E33K mutations relative to the amino acid sequence of SEQ ID NO: 1.

13. The polypeptide of claim 12, wherein the first heterologous peptide is inserted between amino acid positions 48 and 50 relative to the amino acid sequence of SEQ ID NO: 1.

14. The polypeptide of claim 12, wherein the second heterologous peptide is inserted between amino acid positions 73 and 78 relative to the amino acid sequence of SEQ ID NO: 1.

15. The polypeptide of claim 12, wherein each of the first heterologous peptide and the second heterologous peptide has a length of 3 to 20 amino acids.

16. The polypeptide of claim 15, wherein each of the first heterologous peptide and the second heterologous peptide has a length of 3 to 12 amino acids.

17. The polypeptide of claim 16, wherein each of the first heterologous peptide and the second heterologous peptide has a length of 3 to 9 amino acids.

18. A host cell comprising the polypeptide of claim 12.

19. A fusion protein comprising the polypeptide of claim 12 and one or more additional amino acid sequences.

20. The fusion protein of claim 19, wherein the one or more additional amino acid sequences is selected from signal sequences, peptide linker sequences, affinity tags, and transmembrane domains 21. The fusion protein of claim 19, wherein the one or more additional amino acid sequences is selected from half-life extension polypeptides.

22. The polypeptide of claim 11, wherein the scaffold protein sequence further comprises A59V, G60N, ΔD61, and N62G mutations relative to the amino acid sequence of SEQ ID NO: 1.

23. The polypeptide of claim 11, wherein the scaffold protein sequence further comprises E29K, K30E, and E33K mutations relative to the amino acid sequence of SEQ ID NO: 1.

24. The polypeptide of claim 11, wherein the first heterologous peptide is inserted between amino acid positions 48 and 50 relative to the amino acid sequence of SEQ ID NO: 1.

25. The polypeptide of claim 11, wherein the second heterologous peptide is inserted between amino acid positions 73 and 78 relative to the amino acid sequence of SEQ ID NO: 1.

26. The polypeptide of claim 11, wherein each of the first heterologous peptide and the second heterologous peptide has a length of 3 to 20 amino acids.

27. The polypeptide of claim 26, wherein each of the first heterologous peptide and the second heterologous peptide has a length of 3 to 12 amino acids.

28. The polypeptide of claim 27, wherein each of the first heterologous peptide and the second heterologous peptide has a length of 3 to 9 amino acids.

29. A host cell comprising the polypeptide of claim 11.

30. A fusion protein comprising the polypeptide of claim 11 and one or more additional amino acid sequences.

31. The fusion protein of claim 30, wherein the one or more additional amino acid sequences is selected from signal sequences, peptide linker sequences, affinity tags, and transmembrane domains.

32. The fusion protein of claim 30, wherein the one or more additional amino acid sequences is selected from half-life extension polypeptides.

\* \* \* \* \*

UNITED STATES PATENT AND TRADEMARK OFFICE
CERTIFICATE OF CORRECTION

PATENT NO. : 11,952,415 B2
APPLICATION NO. : 16/623680
DATED : April 9, 2024
INVENTOR(S) : Geoffrey William Platt et al.

Page 1 of 1

It is certified that error appears in the above-identified patent and that said Letters Patent is hereby corrected as shown below:

In the Claims

At Column 244, Claim 11, Line 32:
"Y35W, Q42E, V48D, T51 L, and M65I mutations relative to"
Should read:
-- Y35W, Q42E, V48D, T51L, and M65I mutations relative to --

Signed and Sealed this
Twenty-seventh Day of August, 2024

Katherine Kelly Vidal
*Director of the United States Patent and Trademark Office*